United States Patent
Meyerhans et al.

(10) Patent No.: US 10,941,121 B2
(45) Date of Patent: Mar. 9, 2021

(54) HUMAN HELICASE DDX3 INHIBITORS AS THERAPEUTIC AGENTS

(71) Applicant: AZIENDA OSPEDALIERA UNIVERSITARIA SENESE, Siena (IT)

(72) Inventors: Andreas Meyerhans, Barcelona (ES); Miguel Angel Martinez De La Sierra, Vilassar de Mar Barcelona (ES); Annalaura Brai, Siena (IT); Roberta Fazi, Siena (IT); Cristina Tintori, Siena (IT); Maurizio Botta, Siena (IT); Jose Este-Araque, Tiana Barcelona (ES); Javier Martinez, Barcelona (ES)

(73) Assignee: AZIENDA OSPEDALIERA UNIVERSITARIA SENESE, Siena (IT)

(*) Notice: Subject to any disclaimer, the term of this patent is extended or adjusted under 35 U.S.C. 154(b) by 0 days.

(21) Appl. No.: 16/734,788

(22) Filed: Jan. 6, 2020

(65) Prior Publication Data
US 2020/0140398 A1 May 7, 2020

Related U.S. Application Data

(63) Continuation of application No. 15/550,155, filed as application No. PCT/EP2016/052990 on Feb. 12, 2016, now abandoned.

(30) Foreign Application Priority Data

Feb. 13, 2015 (IT) .................. RM2015A000070
May 11, 2015 (EP) ...................... 15167177

(51) Int. Cl.
| | |
|---|---|
| A61K 31/4192 | (2006.01) |
| A61K 31/4245 | (2006.01) |
| A61K 31/433 | (2006.01) |
| A61K 31/4439 | (2006.01) |
| A61K 31/496 | (2006.01) |
| A61K 31/5377 | (2006.01) |
| A61K 31/675 | (2006.01) |
| C07D 249/06 | (2006.01) |
| C07F 9/6518 | (2006.01) |
| C07D 401/12 | (2006.01) |
| C07D 405/12 | (2006.01) |
| C07D 261/08 | (2006.01) |
| C07D 271/06 | (2006.01) |
| C07D 271/10 | (2006.01) |
| C07D 285/12 | (2006.01) |
| C07D 249/04 | (2006.01) |
| C07D 257/04 | (2006.01) |
| A61K 31/42 | (2006.01) |
| A61K 31/7056 | (2006.01) |
| A61K 45/06 | (2006.01) |
| C07D 401/04 | (2006.01) |
| C07H 15/18 | (2006.01) |

(52) U.S. Cl.
CPC ........ *C07D 249/06* (2013.01); *A61K 31/4192* (2013.01); *A61K 31/42* (2013.01); *A61K 31/4245* (2013.01); *A61K 31/433* (2013.01); *A61K 31/4439* (2013.01); *A61K 31/496* (2013.01); *A61K 31/5377* (2013.01); *A61K 31/675* (2013.01); *A61K 31/7056* (2013.01); *A61K 45/06* (2013.01); *C07D 249/04* (2013.01); *C07D 257/04* (2013.01); *C07D 261/08* (2013.01); *C07D 271/06* (2013.01); *C07D 271/10* (2013.01); *C07D 285/12* (2013.01); *C07D 401/04* (2013.01); *C07D 401/12* (2013.01); *C07D 405/12* (2013.01); *C07F 9/6518* (2013.01); *C07H 15/18* (2013.01)

(58) Field of Classification Search
None
See application file for complete search history.

(56) References Cited

U.S. PATENT DOCUMENTS

| 6,344,465 B1 | 2/2002 | Armistead et al. |
|---|---|---|
| 9,533,985 B2 | 1/2017 | Ueno et al. |

FOREIGN PATENT DOCUMENTS

| WO | 2004103980 A1 | 12/2004 |
|---|---|---|
| WO | 2005090297 A1 | 9/2005 |
| WO | 2005090298 A1 | 9/2005 |
| WO | 2006049941 A2 | 5/2006 |
| WO | 2007021941 A2 | 2/2007 |
| WO | 2011039735 A2 | 4/2011 |
| WO | 2012029032 A2 | 3/2012 |
| WO | 2013008162 A1 | 1/2013 |

OTHER PUBLICATIONS

Dosa et al., "Biaryl Sulfonamides from O-Acetyl Arnidoxirnes: 1,2,4-Oxadiazole Cyclization under Acidic Conditions", Journal of Heterocyclic Chemistry, 2011, vol. 48, No. 2, pp. 407-413.
Shi et al., "Identification of a Potent Inhibitor of Human Dual-Specific Phosphatase, VHR, from Computer-Aided and NMR-Based Screening to Cellular Effects", CHEMBIOCHEM, 2007, vol. 8, No. 17, pp. 2092-2099.

(Continued)

*Primary Examiner* — Samantha L Shterengarts
(74) *Attorney, Agent, or Firm* — Lucas & Mercante LLP

(57) ABSTRACT

The present invention refers to compounds endowed with RNA helicase DDX3 inhibitory activity of formula I and II and their therapeutic use, in particular for the treatment of viral diseases.

11 Claims, No Drawings

(56) References Cited

OTHER PUBLICATIONS

Turcotte et al., "Synthesis, Biological Evaluation, and Structure-Activity Relationships of Novel Substituted N-Phenyl Ureidobenzenesulfonate Derivatives Blocking Cell Cycle Progression in S-Phase and Inducing DNA Double-Strand Breaks", Journal of Medicinal Chemistry, 2012, vol. 55, No. 13, pp. 6194-6208.
Kleb, "Neve Umlagerung yom Typ der Smiles-Reaktion", Angewandte Chemie, 1968, vol. 80, No. 7, pp. 284-285.
Laha et al., "Palladium-Catalyzed Intramolecular Oxidative Coupling Involving Double C(sp2)—H Bonds for the Synthesis of Annulated Biaryl Sultams", The Journal of Organic Chemistry, 2014, vol. 79, No. 17, pp. 8010-8019.
International Search Report (annotated) and Written Opinion for PCT International Application No. PCT/EP2016/052990 (dated Apr. 20, 2016) (16 Pages).
Database Registry Chemical Abstracts Service, Accession No. RN 424810-77-5, Entered STN: Jun. 3, 2002, 1 page.
Ito et al., "A medium-term rat liver bioassay for rapid in vivo detection of carcinogenic potential of chemicals", Cancer Sci, 2003, vol. 94, No. 1, pp. 3-8.
Gonzalez-Diaz et al., "QSAR for anti-RNA-virus activity, synthesis, and assay of anti-RSV carbonucleosides given a unified representation of spectral moments, quadratic, and topologic indices", Bioorganic & Medicinal Chemistry Letters, 2005, vol. 15, pp. 1651-1657.
Database Registry Chemical Abstracts Service, Accession No. RN 413604-56-5, Entered STN: May 12, 2002.
Database Registry Chemical Abstracts Service, Accession No. RN 1019180-62-1, Entered STN: May 5, 2008.

ary application of the present invention refers to compounds with RNA
HUMAN HELICASE DDX3 INHIBITORS AS THERAPEUTIC AGENTS

CROSS-REFERENCE TO RELATED APPLICATIONS

This application is a continuation of U.S. application Ser. No. 15/550,155, filed Aug. 10, 2017, which in turn is a 371 of PCT/EP2016/052990, filed Feb. 12, 2016, which claims the benefit of priority from European Patent Application No. 15167177.3, filed May 11, 2015, and Italian Patent Application No. RM2015A000070, filed Feb. 13, 2015, the contents of each of which are hereby incorporated by reference.

FIELD OF THE INVENTION

The present invention refers to compounds with RNA helicase DDX3 inhibitory activity and their therapeutic use, in particular for the treatment of viral diseases.

BACKGROUND ART

DDX3 and Viral Infections

Viruses are obligate intracellular parasites and, as such, they exploit the metabolic mechanisms of their hosts in order to replicate (Alquist et al., 2003, Prussia et al., 2011). Such an extraordinary ability relies on specific interactions between the virus and key components of the cellular machinery. Genome-wide transcriptomic analyses and siRNA screens have revealed that the number of host proteins involved in the response to viral infection and/or important for the viral life cycle, exceeds 1,000 for viruses such as HIV-1 (M. Friedrich et al., 2011) and HCV (Rupp et al., 2014). Among the pathways consistently found to be targeted by viruses are the innate immune response and pathways involved in RNA metabolism. Understanding the complex network of host-pathogen interactions can provide new avenues for the treatment of viral infections, in facts the identification of cellular factors essential for viral replication provides entirely new targets for alternative approaches to treat viral infections. Targeting cellular cofactors of viral infection can, in principle, limit the occurrence of drug resistance, as cellular proteins are less prone to mutate than viral proteins (Garbelli et al., 2011). In order to limit the possibility of serious side effects due to the inhibition of normal cellular functions of the target protein is important to select a protein which is absolutely essential for the virus, but not for the cells, and to target only specific functions of the target protein or directly the viral interaction interface.

Recent studies have revealed that the cellular ATPase/RNA helicase X-linked DEAD-box polypeptide 3 (DDX3) is an essential host factors for the replication of different viruses. Cavignac et al. recently demonstrated that DDX3 is involved in the replication of ssDNA viruses. The study reported that DDX3 represents a proviral cellular factor that is upregulated in Cytomegalovirus infected cells. DDX3 expression seems to be also involved in the life cycle of several ssRNA viruses such as Lassa Virus and Pneumovirus (Easton et al. 2015). Literature clearly showed the role of this human protein in +ssRNA viral replication.

In addition, Jefferson et al recently identified DDX3 such as a N-Terminal Protease, Npro-interacting protein with proviral roles. The interactions described in the paper suggested that many other viruses also target this cellular pathway. Particularly, its functions are known to be exploited by viruses belonging to different families: Human Immunodeficiency Virus 1 (HIV-1, Retroviridae), (Yedavalli et al., 2004), Hepatitis C virus (Owsianka et al., 1999), Japanese Encephalitis virus, Dengue virus (Noble et al., 2010), West Nile virus (respectively HCV, JEV, DV, WNV Flaviviridae), Vaccinia virus (Schroder M et al., 2008), (VACV, Poxviridae), Norovirus (Vashit et al., 2012), (NV, Caliciviridae).

HIV-1 and HCV represent some of the most clinically important and economically relevant human pathogens. HIV-1 is the etiological agent of the Acquired Immunodeficiency Syndrome (AIDS) and is currently responsible for a pandemic affecting >30,000,000 people worldwide. HCV is a causative agent of both acute and chronic hepatitis, infecting over 170 million people worldwide. The majority of HCV infections progress to chronicity ultimately leading in 20% of the cases to liver cirrhosis and hepatocellular carcinoma (HCC). NV has been only recently recognized as the main etiological agent of nonbacterial food-borne gastroenteritis worldwide (Glass et al., 2009). These amount to >20,000,000 cases every year in the US alone with severe complications and even death in around 800 cases per year. NVs are now recognized as the second most common cause of death in the US due to gastrointestinal disease and the number of cases is increasing. NVs have been linked to a number of significant clinical diseases; necrotizing enterocolitis, seizures in infants, encephalopathy, pneumatosis intestinalis and disseminated intravascular coagulation as well as some others. Infection in the elderly and immunocompromised causes long-term chronic infections (>1 year) and can result in death. Clinical data indicate infection of the nervous system. Currently no drugs are available for treatment of NV infections and there is a pressing need to develop treatments for long-term and chronically infected NV patients. HCV treatment is effective in only about 50% of patients infected with genotype 1b, the most widely circulating in Europe. And while the efficacy of current treatment regimens against HCV has recently improved with the addition of new antivirals, these target only one genotype of the virus and have an increased rate of adverse effects, low tolerance and high cost. The problems of antiretroviral therapy for HIV-1 are well known: Despite of over 30 approved drugs, current therapies are still unable to eradicate the virus from the infected patient. Moreover, the efficacy of HIV-1 therapy is often reduced by the development of drug resistance. Thus, there is an urgent need to improve our therapeutic arsenal in order to confront these viruses, which affect millions of people worldwide and put substantial pressure on our healthcare systems. Given the involvement of DDX3 as a common theme in the life cycle of these viruses, it is an exciting target for the development of novel antiviral compounds. Targeting DDX3 might even offer the possibility of simultaneously treating HCV and HIV in the relatively large cohort of co-infected patients.

The first small molecule designed to inhibit the ATPase activity of DDX3 (FE15, Ki=5.4 µm) has been identified by Maga et al. in 2008. Interestingly, FE15 inhibited the replication of HIV-1 (IIIB) in MT4-cells with an EC50 of 86.7 µm, without showing cytotoxicity (CC50>200 µm in MOLT-4 T-lymphocytic). In the same year, Yedavalli et al. identified the ring expanded nucleosides REN as DDX3 ligands by means of a biological screening on a library of known NTPase/helicase inhibitors. REN derivatives were able to inhibit the ATP dependent activity of DDX3 and suppressed HIV-1 replication in T cells and monocyte-derived macrophages. In 2011, a protocol of hit optimization on FE15, led to the identification of a second-generation DDX3 inhibitors endowed with an improved activity profile (as an example FE109 showing a Ki of 0.2 µm). Furthermore, additional inhibitors were identified with a triazine scaffold, with the best one, FE87, which showed a Ki of 0.1 μm on DDX3, an $EC_{50}$ value of 2.0 μm in the inhibition of viral load of peripheral blood mononucleated cells (PBMCs) infected with HIV and a cytotoxicity of 20 μm in HeLa cells (Selectivity Index=10). However, even if some degree of selectivity has been found in in vitro experiments, the major drawbacks of such ATP-mimetics could be represented by a low selectivity in vivo Schutz et al., recently proposed a general mechanism for the opening of the RNA binding site. This observation, coupled with the presence of a conserved residue essential for the helicase activity, suggested that an inhibitor able to target this site could lock the DDX3 helicase in a catalytically inactive conformation. On this basis, the first inhibitors of HIV-1 replication specifically designed to target the DDX3 RNA binding site have been discovered in. Among them, EI01D showed the best activity value being endowed with an $EC_{50}$ of 10 μM in the inhibition of viral load of PBMCs infected with HIV.

The DDX3 Family of RNA Helicases

DEAD-box helicases are involved in all aspects of RNA metabolism. Their role is thought to be the unwinding of RNA, i.e. the removal of secondary structure motifs, the unwinding of short RNA-RNA interactions and also the removal of RNA-bound proteins (Yang et al., 2006), DDX3 is an ATPase/RNA helicase containing all nine conserved motifs that characterize the members of the RNA helicase superfamily including the eponymous Asp-Glu-Ala-Asp (D-E-A-D) motif, within a structurally conserved core element forming two RecA-like domains. The conserved helicase motifs are involved in ATP binding, ATPase activity, RNA substrate binding and unwinding (Linder et al., 2004). The crystal structure of DDX3 shows that these conserved motifs are found in two subdomains connected via a short flexible linker. DDX3 contains a nuclear export signal (NES) at its N-terminus. The amino-terminal domain 1 contains the ATP binding Motifs Q, I (Walker A) and II (Walker B), and the RNA-binding Motifs Ia, Ib and the Motif III. The RNA-binding Motifs IV, V and Motif VI, which may coordinate ATPase and unwinding activities, are found in the carboxyl-terminal domain 2

Cellular Roles of DDX3

DDX3 has been postulated to be involved in many cellular metabolic pathways. Recent evidence suggests that DDX3 is involved in mRNA nuclear export in association with two other shuttle proteins CRM1 and TAP. The proposed mechanism is that DDX3 binds either mRNAs and TAP in the nucleus and subsequently helps to facilitate mRNPs export to the cytoplasm. The interaction with CRM1 seems to be important only for the export of unspliced or incompletely spliced RNAs of HIV (Kohler A, et al., 2007). DDX3 interacts with translation initiation factors eIF4E, eIF4A, eIF4G, PABP and eIF3. Recently Marsden and coworkers, demonstrated a role for DDX3 in enhancing translation of a specific subset of cellular and viral mRNAs carrying specific structural features within their 5'-UTRs.

These RNA structures must be located immediately adjacent to the cap structure to be unwound by DDX3 in order to prepare the mRNA for ribosome binding.

DDX3 and Transcription Regulation

DDX3 downregulates E-Cadherin (Botlagunta et al., 2008) and stimulates interferon (IFN) and p21 expression by interacting with their respective promoters (Schroder et al., 2008). The DDX3 effect on IFN promoter is independent of its ATPase activity or unwinding function, while the ATPase function is required for p21 promoter stimulation.

Innate Immunity

The innate immune system is responsible for early detection of viral infection, by sensing cytoplasmic viral nucleic acids through the endosomal subset of toll-like receptors (TLRs) and the RIG-like helicases (RLHs). Both receptor systems lead to activation of the transcription factors NF-kB and IRF3 and IRF7, thus stimulating production of antiviral type I interferons. DDX3 interact with the protein kinases IKKE and TBK-1, key kinases that phosphorylate and activate IRF3 and IRF7. Interestingly, this function of DDX3 is ATPase-independent (Schroder, et al., 2008). In addition, DDX3 has been found to interact with IPS-1, the adaptor protein that facilitates RLH signalling and to bind directly to the ifnb promoter following its phosphorylation by TBK1. So, while there is strong evidence that human DDX3 contributes to IFNβ induction, its exact placement in the signalling pathways and mechanism of action are unclear. Schroeder et al. suggest that DDX3 directly enhances IKKE activation acting as a downstream scaffolding adaptor that mediates the coordinated activation of IKKE and IRF3. It has been shown that TLR7-mediated IFNα production following HIV infection contributes to excessive immune activation and immunopathology. DDX3 could therefore also be involved in the excessive immune activation that contributes to HIV pathology, suggesting that inhibiting DDX3 might have dual benefit in the context of HIV infection.

DDX3 and Norovirus Replication

The use of a mouse NV as a surrogate model for the genetically closely related human NV, together with the recently developed human NV replicon system, allowed studying the mechanism of NV genome translation and replication in cell culture. Vashist and coworkers have recently demonstrated that DDX3 is associated with the NV RNA genome during replication in cells. Importantly, during NV replication DDX3 redistributes from a largely diffuse cytoplasmic staining into a more punctuate staining which partially overlaps with the site of virus replication and silencing of DDX3 expression significantly reduce virus replication. Quantitative SILAC based proteomics confirmed that DDX3 was enriched in the NV replication complex.

DDX3 and HIV-1 Replication

HIV-1 replication requires the nuclear export and translation of unspliced, singly-spliced and multiply-spliced derivatives of this initial transcript. Fully spliced mRNAs encode the viral regulatory proteins Tat, Rev and Nef. Rev is a sequence-specific nuclear mRNA-export factor which binds to the Rev response element (RRE) to mediate nuclear export of the Rev/RNA complex, through interaction with the cellular export receptor CRM1 and the cellular cofactor DDX3. DDX3 expression was found to be induced in HIV-1 infected cells by the viral transcriptional activator Tat and DDX3 silencing abrogated the export of unspliced/partially spliced HIV-1 transcripts (Yedavalli 2004). However, the molecular details of DDX3 role(s) in this pathway are yet to be fully elucidated. For example, DDX3 was not required for the CRM1-dependent export of cellular endogeneous transcripts, raising the intriguing possibility that this function of DDX3 might be specific for HIV-1 RNAs. In addition to its role in viral RNA export, Ohlmann and coworkers have shown that the knock-down of DDX3 results in the specific inhibition of unspliced genomic RNA translation. Interestingly, as shown for HCV and Norovirus, DDX3 is also found in a cytoplasmic punctuate staining that co-localizes with the HIV-1 genomic RNA.

DDX3 and (−)ssRNA Virus

Involvement of DDX3 in the life cycle of several ssRNA viruses such as Lassa Virus and Pneumovirus (Easton et al. 2015) has been described. Filoviridae family belongs to the same class of virus and includes Ebola and Marburg virus. The 2014-2015 Ebola epidemic in West Africa raised concerns about the risk of a diffuse outbreak and of bioterrorism; in addition although the disease was declared eradicated at the end of 2015, recently new cases have been reported. DDX3 inhibition might contrast the effects of the infection and stop the diffusion via inhibition of the viral replication.

DDX3 and (+)ssRNA Viruses

Group IV viruses are characterized by a positive sense RNA genome, that can be translated directly into protein. The positive RNA strand serves as a template for an RNA-dependent polymerase, yielding a double stranded RNA that serves as template.

Class IV viruses are classified in six subclasses: Picornaviridae, Togaviridae, Coronaviridae, Hepevirdae, Caliciviridae, Flaviviridae and Astroviridae.

Recent studies clearly demonstrate that DDX3 is involved in the replication of +ssRNA viruses.

The Flaviviridae is a large family that consists of three genera: Flavivirus, Pestivirus, and Hepacivirus. Flaviviridae cause significant diseases in human and animal populations. Among them Flavivirus genus comprehends: Yellow Fever virus (YFV), tick-borne encephalitis virus (TBEV), Japanese encephalitis virus (JEV), Dengue virus (DENV), West Nile virus (WNV), Zika virus (ZIKV). Recently an outbreak of Zika virus infection, which is considered to cause birth defect as microcephaly, has exploded in Brazil and cases are reported in other countries. There is the urgent need to contrast the infection and its spread throughout the world with vaccines or treatments; basing on the involvement of DDX3 in +ssRNA virus replication, DDX3 inhibitors can inhibits the intracellular viral replication reducing the infections as well as its spread.

The Pestiviruses are animal pathogens of major economic importance. Pestivirus infect mammals such as bovidae and suidae and are the major cause of hemorrhagic syndromes, abortion, fatal mucosal diseases. Among them Bovine Viral Diarrhea Virus (BVDV), Border Disease Virus (BDV) of sheep, and Classical Swine Fever Virus (CSFV). Jefferson et al recently identified DDX3 such as a Npro-interacting protein that can have proviral roles. The interactions described in the paper suggested that many other viruses also target this cellular pathway. The Hepacivirus genus includes only the hepatitis C virus (HCV).

DDX3 and Hepatitis C Virus Replication

HCV carries a positive-strand RNA genome that replicates in the cytoplasm. The viral RNA replication complexes are associated with the so-called membranous web composed of ER-derived membranes and lipid droplets (LDs). The precise composition of the membranous web is currently unknown, but it is thought to contain a number of host, as well as, viral factors. Owsianka and coworkers have shown that the HCV core protein specifically sequesters DDX3 from its normal diffuse cytoplasmic distribution to virus replication/assembly sites on LDs. Mutation of one of the key residues in core protein that are critical for its interaction with DDX3 (Y35) showed that the core-DDX3 interaction is dispensable for virus growth and morphogenesis, however, DDX3 itself is essential for virus replication. This dual role of DDX3 in the context of HCV infection warrants further investigation. On the other hand, sequestration of DDX3 by HCV is likely to affect cellular functions of DDX3. It will therefore be important to investigate how HCV infection modulates DDX3-dependent gene expression. This will reveal whether HCV manipulates DDX3's role in the antiviral immune response and whether sequestration of DDX3 is linked to the development of hepatocellular carcinoma.

DDX3 and JEV Replication

Japanese encephalitis virus (JEV) belongs to the family Flaviviridae and is transmitted between animals and human host by culex mosquitoes. Japanese encephalitis is prevalent throughout Eastern and Southern Asia and the Pacific Rim. (Usha Kant Misra et al. 2010). Mao and coworkers, recently demonstrated that cellular helicase DDX3 is involved in JEV replication. In facts, DDX3 knockdown inhibits JEV replication suggesting that the helicase activity of DDX3 is crucial for viral replication. GST-pulldown and co-immunoprecipitation experiments demonstrated that DDX3 could interact with JEV non-structural proteins 3 and 5. Co-immunoprecipitation and confocal microscopy analysis confirmed that DDX3 interacts and colocalizes with these viral proteins and viral RNA during the infection. Furthermore, they determined that DDX3 binds to JEV 5' and 3' untranslated regions. Using a JEV-replicon system they demonstrate that DDX3 positively regulates viral RNA translation, which might affect viral RNA replication at the late stage of virus infection.

DDX3 and DENV Replication

The dengue virus (DENV) in one of five serotypes is the cause of dengue fever. It is a mosquito-borne single positive-stranded RNA virus of the family Flaviviridae; genus Flavivirus. All five serotypes can cause the full spectrum of disease. To determine if the cellular proteins were required for DENV infection, Khadka and co-workers used small interfering RNAs to inhibit their expression. Among them DDX3 caused a significant decrease in the replication of a DENV replicon.

DDX3 and WNV Replication

West Nile virus (WNV) is a Flavivirus that can cause serious and potentially fatal infection of the central nervous system, with up to 10% mortality in humans. Virus could be transmitted by mosquitoes and wild birds. Humans are mainly infected through mosquito bites, but infection can occur through organ transplantation and blood.

The majority of clinical cases are mild and present with flu-like symptoms. Severe cases with signs of encephalitis, meningo-encephalitis or meningitis, are most often observed among elderly. As it affects countries in Europe every year, West Nile fever is now recognized as a major cause of public health concern in this region.

Harendra and co-workers, recently demonstrate that several cellular cofactors are involved in WNV replication. In particular, DDX3 is recruited to the viral replication sites, as evidenced by its colocalization at perinuclear region with viral NS3.

DDX3 and Tapeworms

Echinococcosis (hydatid disease) and cysticercosis, caused by the proliferation of larval tapeworms in vital organs, are amongst the most severe parasitic diseases in humans and account for 2 of the 17 Neglected Tropical Diseases prioritized by the World Health Organization2. Larval tapeworms can persist asymptomatically in a human host for decades, eventually causing a spectrum of debilitating pathologies and death. When diagnosed, the disease is often at an advanced stage when surgery is no longer an option. Tapeworm infections are highly prevalent worldwide, and their human disease burden has been estimated at 1 million disability-adjusted life years, comparable with African trypanosomiasis, river blindness and dengue. Tapeworms (Platyhelminthes, Cestoda) are passively transmitted between hosts and parasitise virtually every vertebrate species. Recently, Brindley and coworkers, identified that whereas vasa is absent from the genomes of cestodes and trematodes, three DDX3-like genes, Smvlg1, Smvlg2, and Smvlg3, have been characterized in *S. mansoni*. Expression profiles of these DEAD-box helicases suggest that they perform roles similar to Vasa including functions related to the GMP and to stem cell maintenance. Silencing of Smvlg3 indicated that this DDX3-like enzyme is necessary for proliferation and maintenance of germinal cells in the sporocyst, a population of cells that shares a molecular signature with neoblasts (adult totipotent stem cells) of planarians. Smvlg1, Smvlg2, and Smvlg3 may have assumed the role of vasa and display signatures similar to the GMP of other metazoans together with the neoblasts of planarians. In light of these observations, it is plausible that these DDX3-like RNA helicases in schistosomes could perform the role of Vasa in the piRNA pathway. For these reasons, the development of DDX3 inhibitors, could represent an attractive strategy for the treatment of tapeworms infections.

SUMMARY OF THE INVENTION

The present invention provides compounds able to suppress the enzymatic functions of the cellular protein DDX3 (Dead polypeptide 3; Ref. Seq. NP_001347) namely DNA/RNA unwinding (helicase).

The compounds presented in this invention (Formula I and II) showed:
1. The ability to selectively suppress the enzymatic activity of DDX3 in vitro;
2. The ability to suppress HIV-1 replication in infected cells;
3. The ability to suppress HCV replication in infected cells;
4. The ability to suppress JEV replication in infected cells;
5. The ability to suppress WNV replication in infected cells;
6. The ability to suppress DENV replication in infected cells;
7. The ability to suppress NOROV replication in infected cells;
8. The ability to suppress PRRSV replication in infected cells;
9. The ability to suppress Ebola virus (EBOV) replication in infected cells;

The present invention provides a compound of formula:

wherein

X and Y are each independently C or N;

A is unsubstituted or substituted aryl or unsubstituted or substituted heteroaryl, wherein the one or more substituents on the aryl or heteroaryl are independently selected from unsubstituted or substituted $C_1$-$C_6$ alkyl, unsubstituted or substituted $C_2$-$C_6$ alkenyl, unsubstituted or substituted $C_2$-$C_6$ alkynyl, haloalkyl, halogen, $OR_A$, $SR_A$, $S(=O)(=O)-R_A$, $SO_2NHR_A$, $COOR_B$, $OC(O)R_B$, $C(O)R_B$, $NR_AR_B$, $OP(O)(OR_A)_2$, $NHC(O)R_A$, $COONR_AR_B$, OS or wherein the one or more substituents on the $C_1$-$C_6$ alkyl or on the $C_2$-$C_6$ alkenyl or on the $C_2$-$C_6$ alkynyl are independently selected from $OR_A$, $COOR_B$, $OC(O)R_B$, $C(O)R_B$, $NR_AR_B$, $OP(O)(OR_A)_2$, $NHC(O)R_A$, $NHC(O)OR_A$, $COONR_AR_B$, $SR_A$, $S(=O)(=O)-R_A$, $SO_2NHR_A$;

$R_1$, $R_2$, $R_3$, $R_4$, $R_6$, $R_7$ and $R_{10}$ are each independently selected from H, halogen, alkoxy, $C_1$-$C_6$ alkyl, haloalkyl, $OR_A$, $SR_A$, $S(=O)(=O)-R_A$, $SO_2NHR_A$, $COOR_B$, $OC(O)R_B$, $NR_AR_B$, $OP(O)(OR_A)_2$, $NHC(O)R_A$, $COONR_AR_B$, $NO_2$, CN, $R_2$, $R_4$, $R_7$ and $R_{10}$ are absent when X and/or Y is N;

Z is a heteroaryl group selected from:

wherein $R_5$ is H, unsubstituted or substituted $C_1$-$C_{10}$ alkyl or $C_1$-$C_8$ haloalkyl, unsubstituted or substituted phenyl, wherein the one or more substituents on the $C_1$-$C_{10}$ alkyl are independently selected from halogen, $OR_A$, $COOR_B$, $OC(O)R_B$, $C(O)R_B$, $NR_AR_B$, $OP(O)(OR_A)_2$, $OC(O)NR_AR_B$, $NHC(O)OR_A$, $NHC(O)R_A$, $COONR_AR_B$, $OC(O)CHCHR_C$,

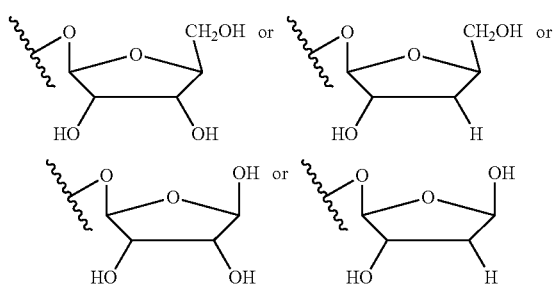

wherein the one or more substituents on the haloalkyl are independently selected from alkoxy, phenyl, OH, $COOR_B$, $OC(O)R_B$, $C(O)R_B$, $NR_AR_B$, $OP(O)(OR_A)_2$, $OC(O)NR_AR_B$, $NHC(O)OR_A$, $NHC(O)R_A$, $COONR_AR_B$, $OC(O)CHCHR_C$, wherein the one or more substituents on the phenyl are independently selected from halogen, haloalkyl, alkoxy, $C_1$-$C_3$ alkyl, OH;

$R_A$ and $R_B$ are each independently selected from H, $C_1$-$C_6$ alkyl, unsubstituted or substituted aralkyl, haloalkyl, or $R_A$ and $R_B$ together with the nitrogen to which they are attached, form a 4-7 membered saturated or partially unsaturated ring optionally containing one or more additional heteroatoms independently selected from N, S and O the ring being optionally substituted by one, two or more groups independently selected from halogen, $C_1$-$C_6$ alkyl, haloalkyl, OH, alkoxy;

$R_C$ is substituted or unsubstituted phenyl, 1,3 benzodioxolyl, wherein the one or more substituent(s) on the phenyl are independently selected from halogen, haloalkyl, alkoxy, $C_1$-$C_3$ alkyl, or OH;

wherein the one or more substituents on the phenyl are independently selected from halogen, haloalkyl, alkoxy, $C_1$-$C_3$ alkyl, OH;

$R_8$ and $R_9$ are each independently selected from H, halogen, alkoxy, COOH, nitro and at least one of $R_8$ and $R_9$ is a heteroaryl group selected from:

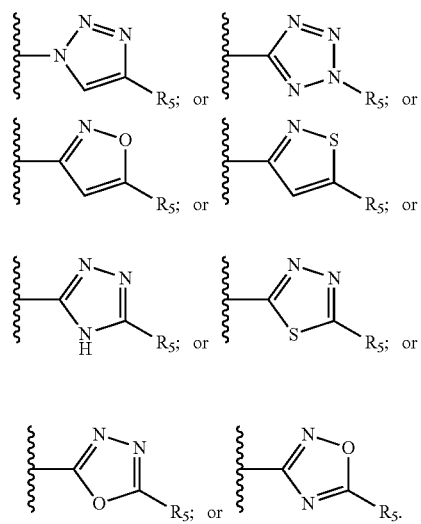

or salt, solvate, stereoisomer thereof, provided that compounds:

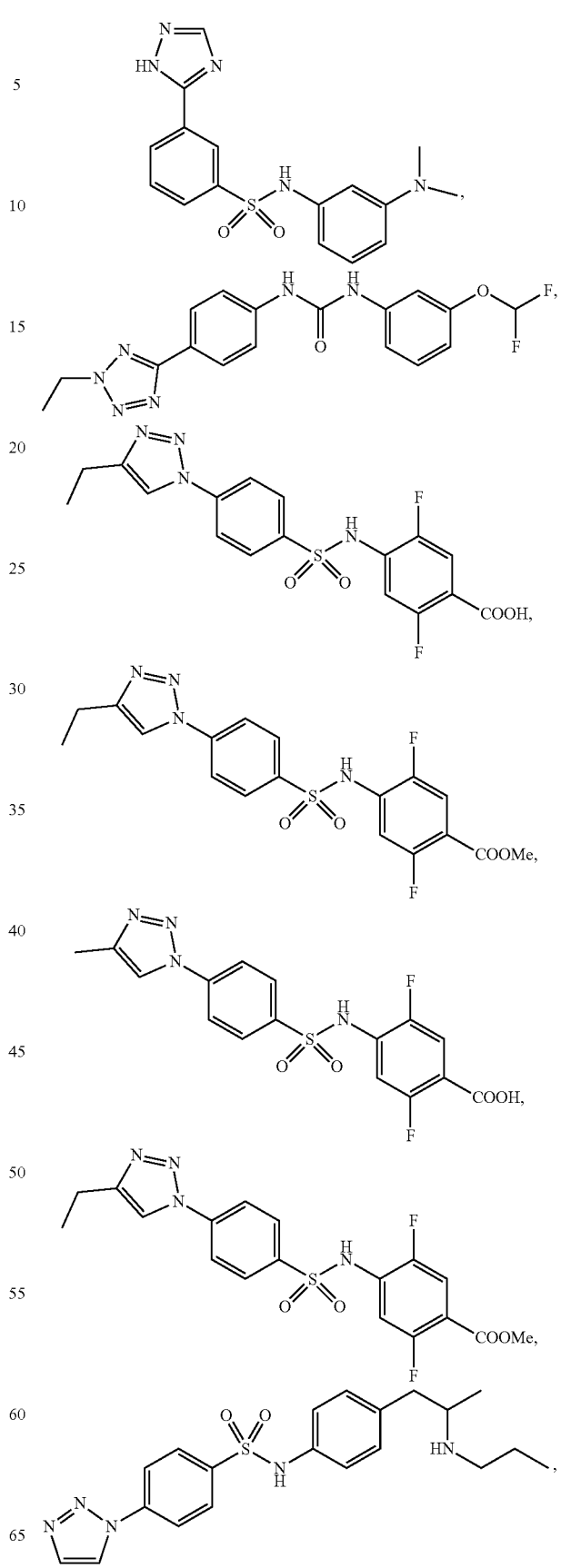

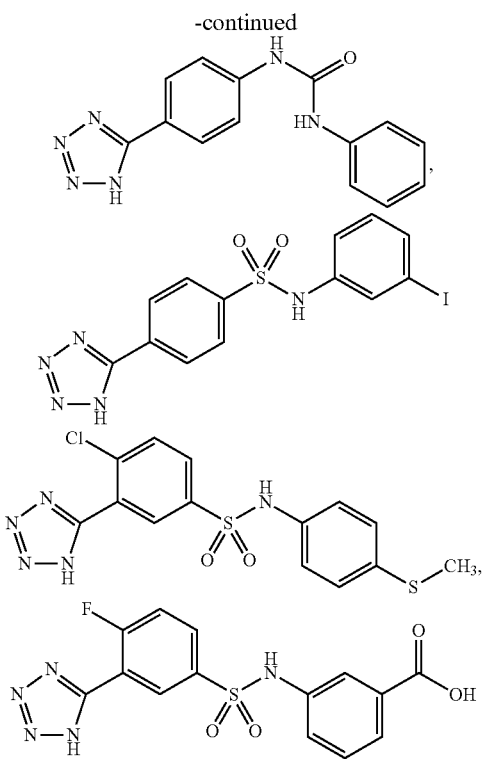

are excluded.

Preferably X and Y are C.

Preferably A is substituted aryl. More preferably X and Y are C and A is substituted aryl.

Still more preferably the substituted aryl is phenyl, preferably substituted by one, two or more groups independently selected from methyl, isopropyl, $CF_3$, F, Cl, OH, OMe.

In another preferred embodiment A is unsubstituted or substituted heteroaryl, preferably the heteroaryl is pyridinyl or isoquinolinyl.

More preferably X and Y are C and A is unsubstituted or substituted heteroaryl, preferably the heteroaryl is pyridinyl or isoquinolinyl.

Preferably the pyridinyl or isoquinolinyl are substituted by one, two or more groups independently selected from methyl, isopropyl, $CF_3$, F, Cl, OH, OMe.

Preferably $R_A$ and $R_B$ together with the nitrogen to which they are attached, form a 6 membered saturated ring containing one or more additional heteroatoms independently selected from N and O the ring being selected form:
morpholinyl
piperazinyl
optionally substituted by one, two or more groups independently selected from $C_1$-$C_6$ alkyl, haloalkyl, OH, alkoxy.

Preferably the compound of the invention is of formula I wherein Z is selected from:

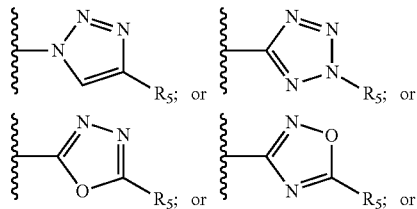

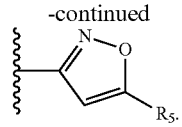

In a preferred embodiment the compound of the invention is of formula I wherein Z is selected from:

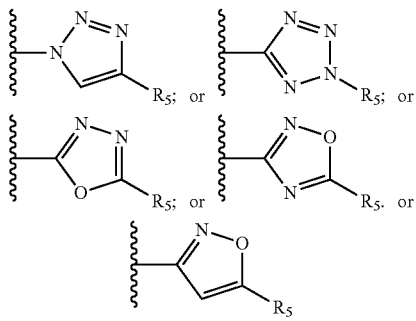

and $R_5$ is butyl, tert-butyl, methyl, ethyl, isopentyl, n-hexanyl, phenyl, $CH_2OH$, $CH_2CH_2OH$, $CH_2CH_2OCH_3$, $CH_2OCH_2CH_3$, $CHOHCH(CH_3)(CH_2CH_2CH_3)$, $CH_2CH_2COOH$, $CH_2CH_2CH_2N(CH_3)_2$, $CH_2NR_AR_B$, $CH_2CH_2NR_AR_B$, $CH_2CH_2CH_2NR_AR_B$, $CH_2CH_2N(CH_3)$ $CH_2C_6H_5$, $CH_2CH_2OP(O)(OCH_3)_2$, $CH_2CH_2OC(O)$ CHCH-(benzo[d][1,3]dioxol-5-yl), $CH_2CH_2OC(O)CH_2CH$ $(CH_3)_2$, $C_4F_9$, $CH_2CH_2CH_2F$ or $CHFCH(CH_3)$ $(CH_2CH_2CH_3)$ or

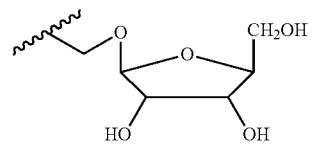 [SMILES: *COC1OC(CO)C(O)C1O]

$R_A$ and $R_B$ together with the nitrogen to which they are attached, form a 6 membered saturated ring selected form:
morpholinyl
piperazinyl
optionally substituted by one, two or more groups independently selected from $C_1$-$C_6$ alkyl, haloalkyl, OH, alkoxy.

Preferably the compound of the invention is of formula I wherein Z is selected from:

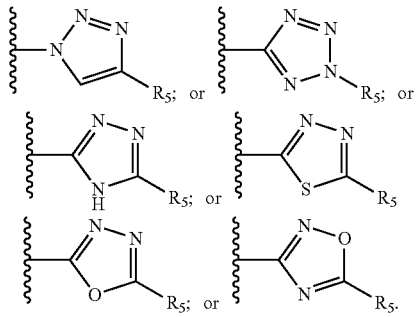

and A is phenyl, pyridinyl or isoquinolinyl, preferably each independently substituted by one, two or more groups independently selected from methyl, isopropyl, $CF_3$, F, Cl, OH or OMe, and $R_5$ is butyl, tert-butyl, methyl, ethyl, isopentyl, n-hexanyl, phenyl, $CH_2OH$, $CH_2CH_2OH$, $CH_2CH_2OCH_3$, $CH_2OCH_2CH_3$, $CHOHCH(CH_3)(CH_2CH_2CH_3)$, $CH_2CH_2COOH$, $CH_2CH_2CH_2N(CH_3)_2$, $CH_2NR_AR_B$, $CH_2CH_2NR_AR_B$, $CH_2CH_2CH_2NR_AR_B$, $CH_2CH_2N(CH_3)CH_2C_6H_5$, $CH_2CH_2OP(O)(OCH_3)_2$, $CH_2CH_2OC(O)CHCH$-(benzo[d][1,3]dioxol-5-yl), $CH_2CH_2OC(O)CH_2CH(CH_3)_2$, $C_4F_9$, $CH_2CH_2CH_2F$, $CHFCH(CH_3)(CH_2CH_2CH_3)$, or

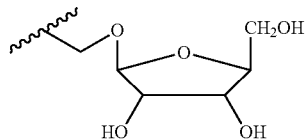 [SMILES: *COC1OC(CO)C(O)C1O]

$R_A$ and $R_B$ together with the nitrogen to which they are attached, form a 6 membered saturated ring selected form:
morpholinyl
piperazinyl
optionally substituted by one, two or more groups independently selected from $C_1$-$C_6$ alkyl, haloalkyl, OH, alkoxy,
and X and Y are C,
and $R_1$, $R_3$, $R_4$ are H,
and $R_2$ is H, F or OMe.

Preferably the compound of the invention has formula II wherein one of $R_8$ or $R_9$ is selected from:

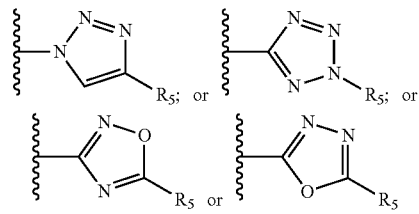

and the other one of $R_8$ or $R_9$ is H.

Preferably the compound of the invention has formula II wherein one of $R_8$ or $R_9$ is selected from:

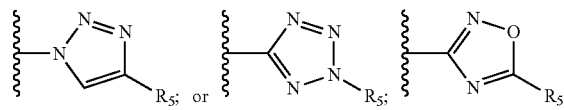

and the other one of $R_8$ or $R_9$ is H,
and A is phenyl, preferably substituted by methyl, isopropyl, $CF_3$, F, Cl, OH or OMe.

Preferably the compound of the invention has formula II wherein one of $R_8$ or $R_9$ is selected from:

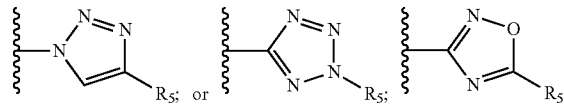

and the other one of $R_8$ or $R_9$ is H,
and A is phenyl, preferably substituted by methyl, isopropyl, $CF_3$, F, Cl, OH, or OMe,
and $R_5$ is H, butyl, isopentyl or $CH_2OCH_2CH_3$,
and X and Y are C,
and $R_6$, $R_7$ and $R_{10}$ are H.

Preferably the compound of the invention has formula II wherein one of $R_8$ or $R_9$ is selected from:

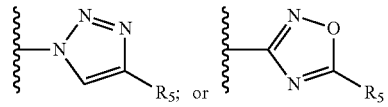

and the other one of $R_8$ or $R_9$ is H,
and A is phenyl, preferably substituted by methyl, isopropyl, $CF_3$, F, Cl, OH or OMe,
and $R_5$ is H, butyl, isopentyl or $CH_2OCH_2CH_3$,
and X and Y are C,
and $R_6$, $R_7$ and $R_{10}$ are H.

Preferably the compound of the invention has formula II wherein one of $R_8$ or $R_9$ is selected from:

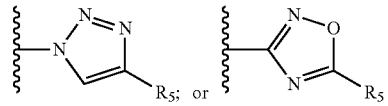

and the other one of $R_8$ or $R_9$ is H,
and A is isoquinolinyl
and $R_5$ is H, butyl, isopentyl or $CH_2OCH_2CH_3$,
and X and Y are C,
and $R_6$, $R_7$ and $R_{10}$ are H.

Preferably the compound of the invention has formula II wherein one of $R_8$ or $R_9$ is selected from:

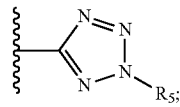

and the other one of $R_8$ or $R_9$ is H,
and A is phenyl, preferably substituted by methyl, isopropyl, $CF_3$, F, Cl, OH or OMe,
and $R_5$ is H,
and X and Y are C,
and $R_6$, $R_7$ and $R_{10}$ are H.

Preferably the compound of formula I or II is selected from the following list:

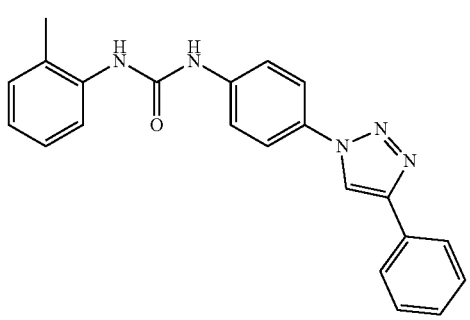

8a

20b
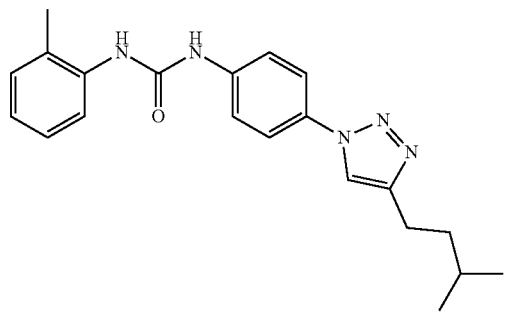
22a
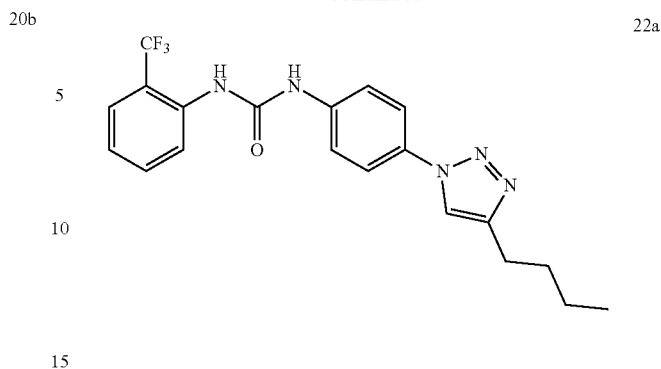
22b
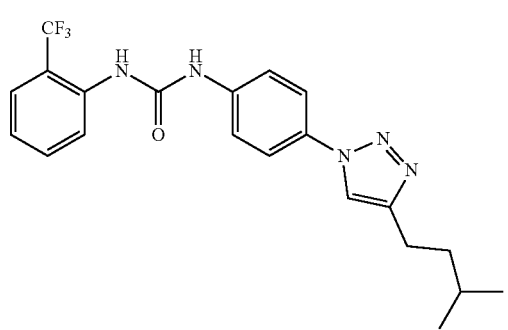
20a
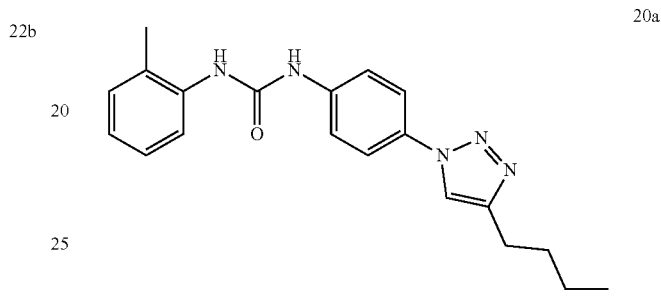
8f
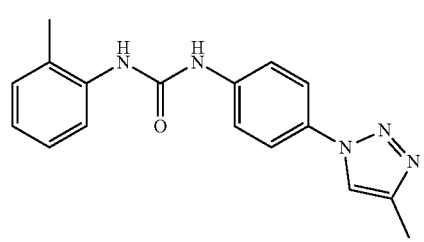
15a
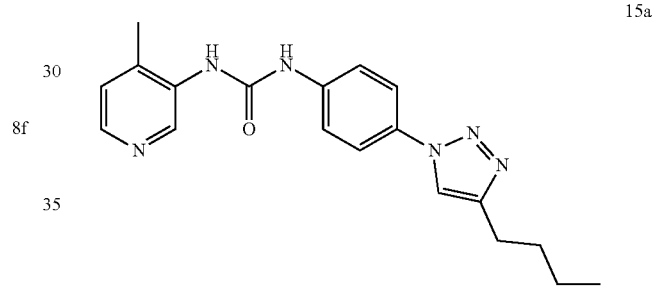
8g
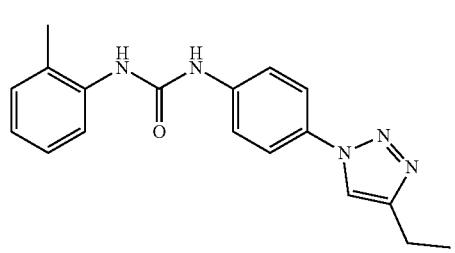
35g
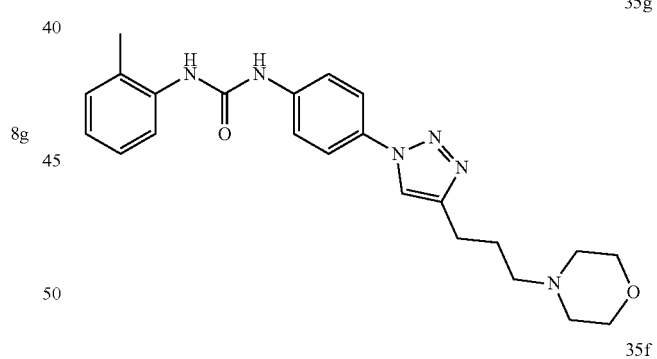
8b
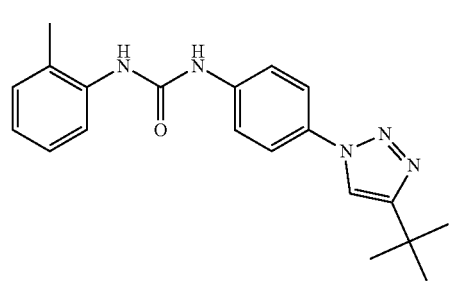
35f
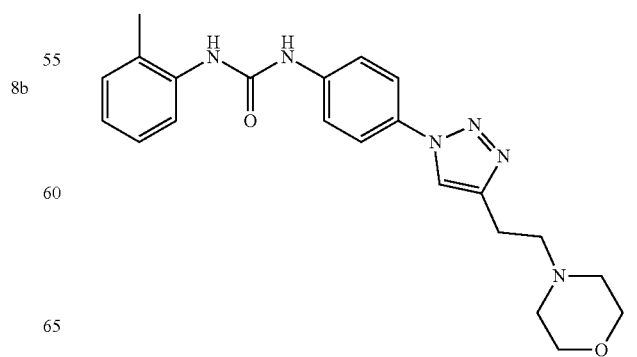

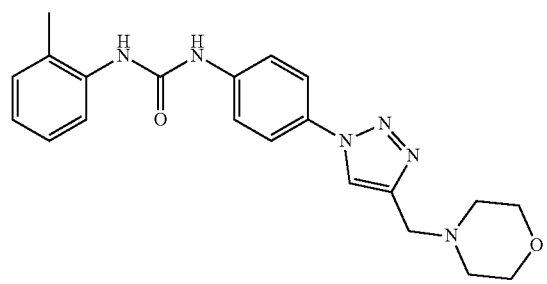
35e
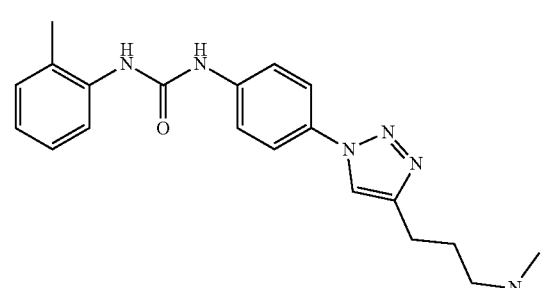
35i
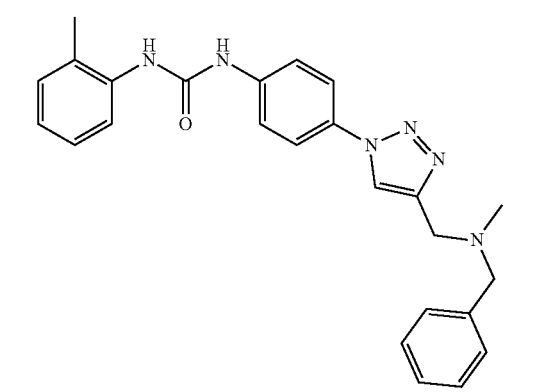
8c
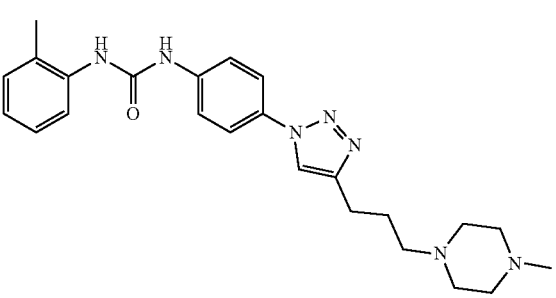
35h
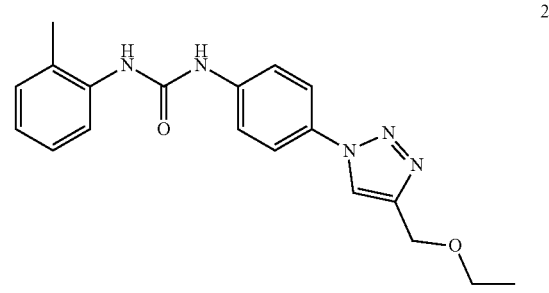
20e
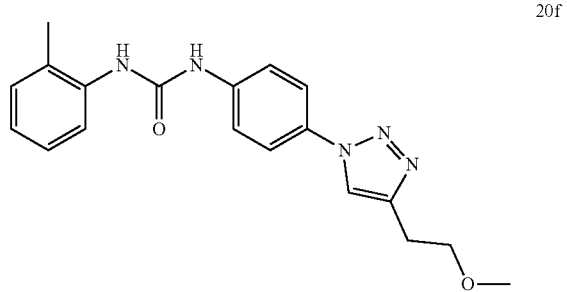
20f
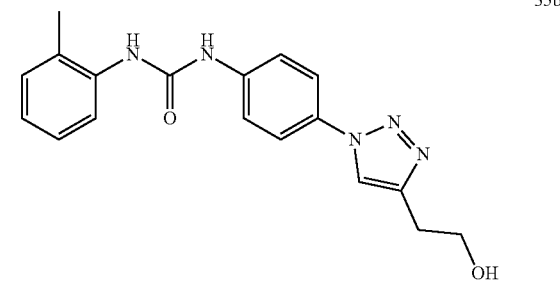
35b
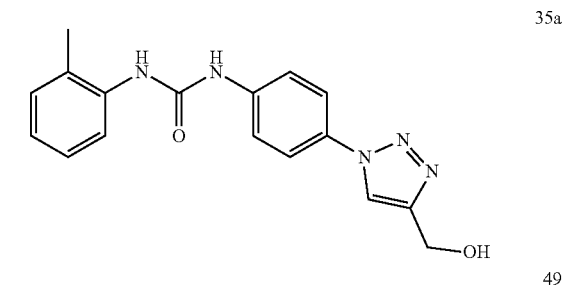
35a
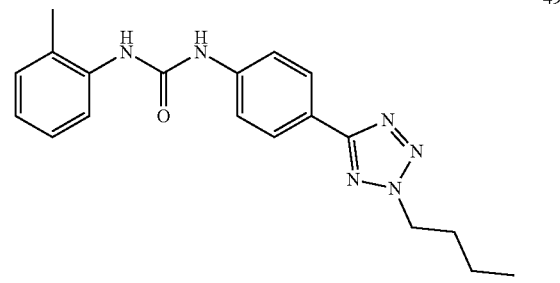
49
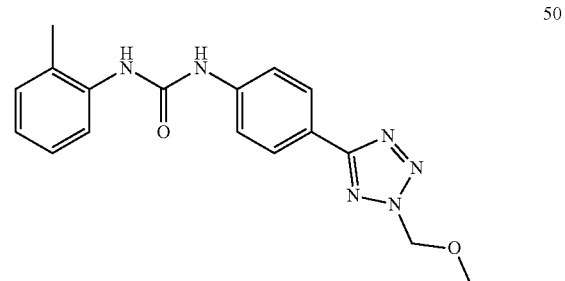
50
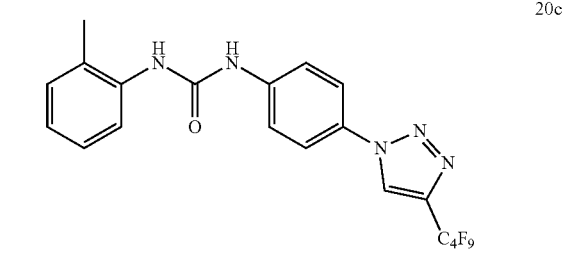
20c

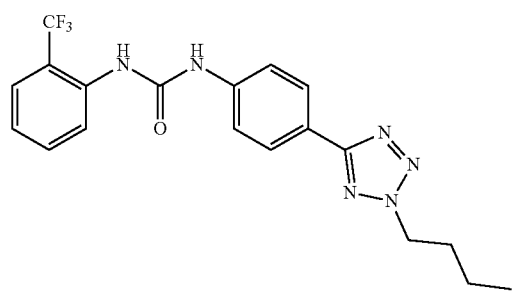
51
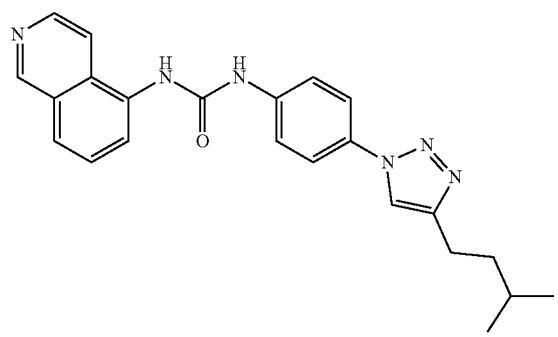
55f
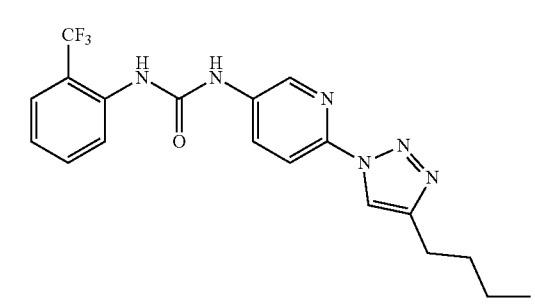
8d
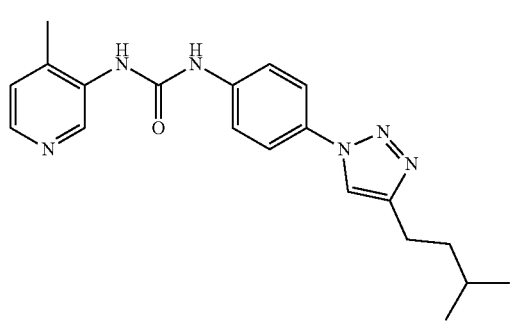
86
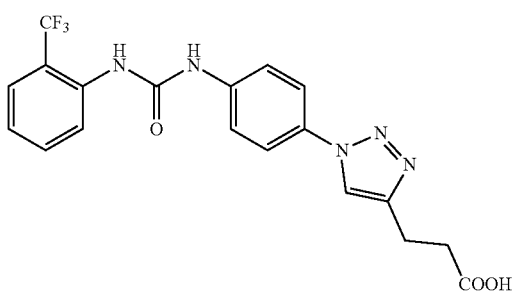
42b
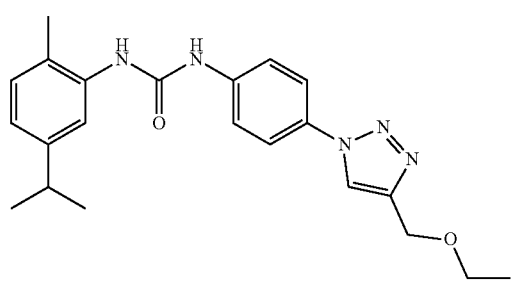
81
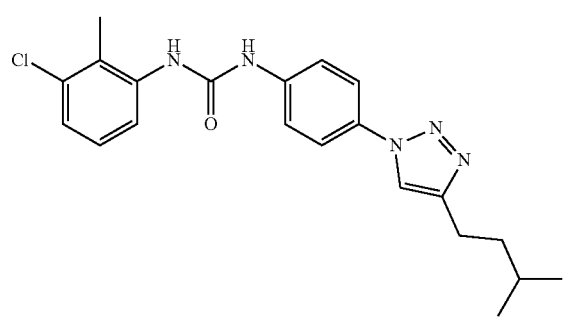
55e
21b
15b
20d

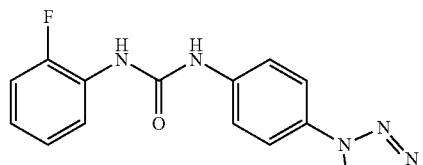
55a
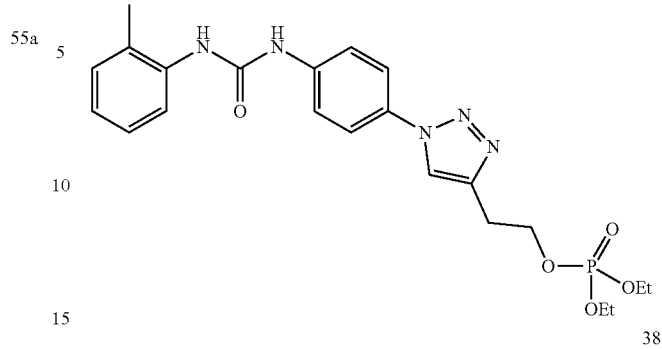
36
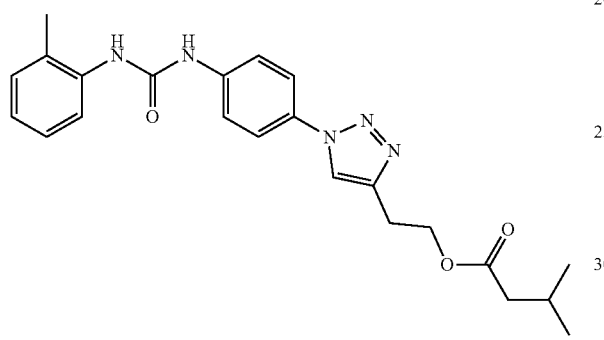
37
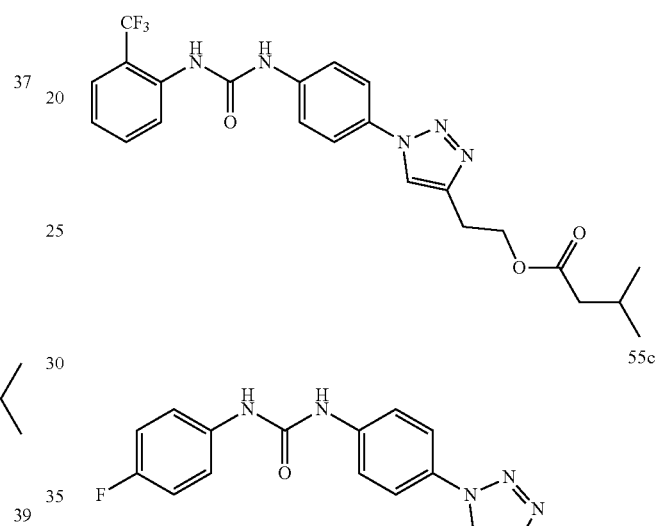
38
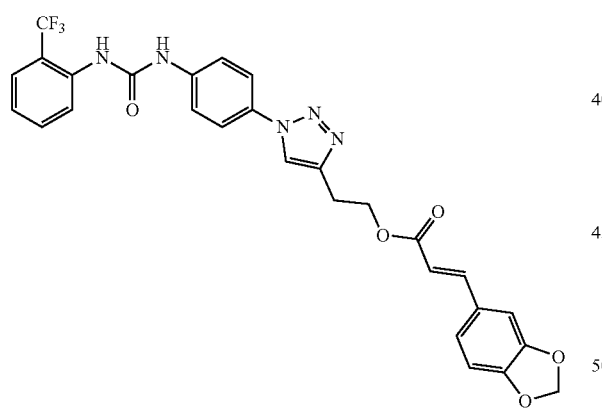
39
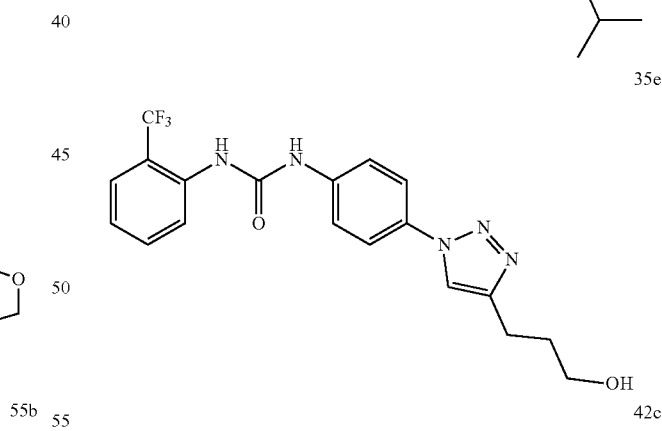
55c
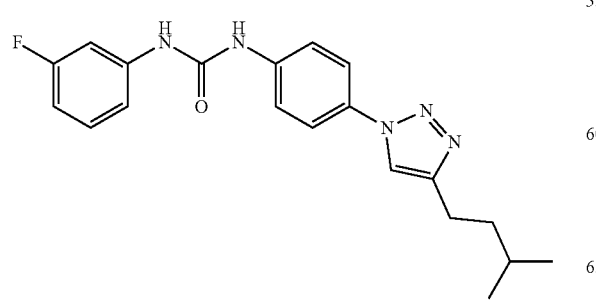
55b
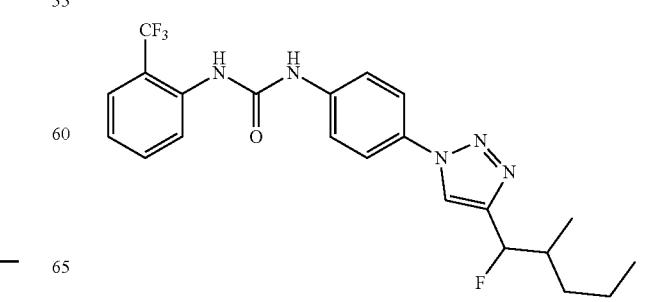
35e
42c

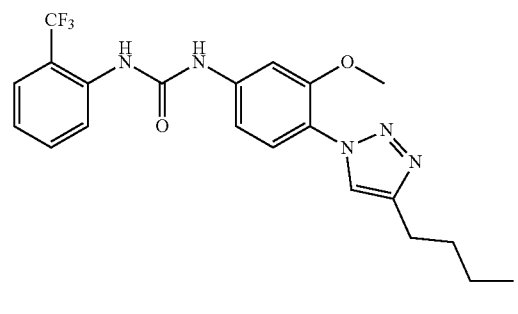
78
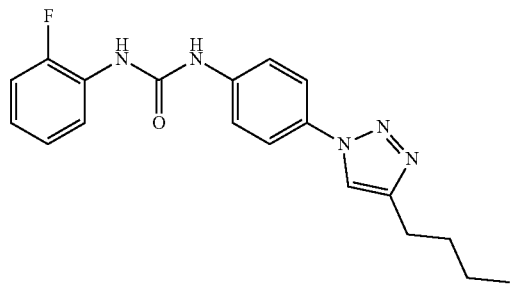
55l
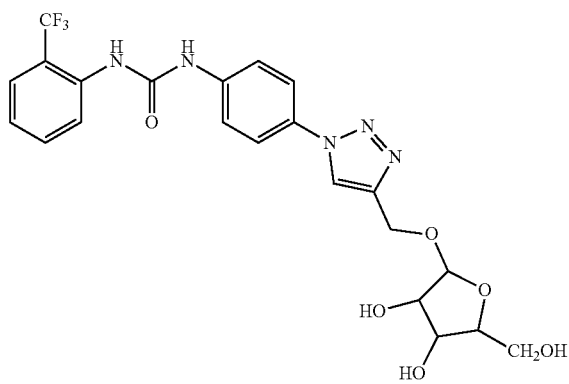
22g
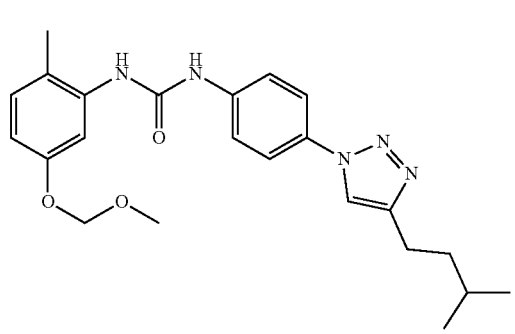
55i
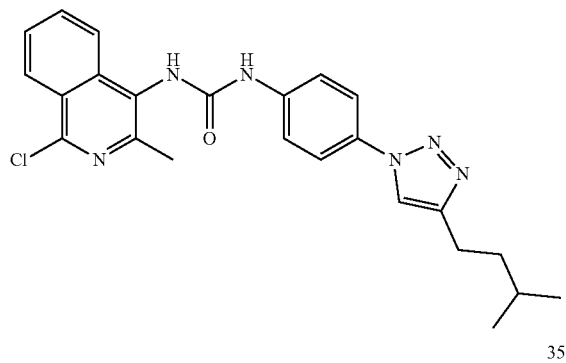
55g
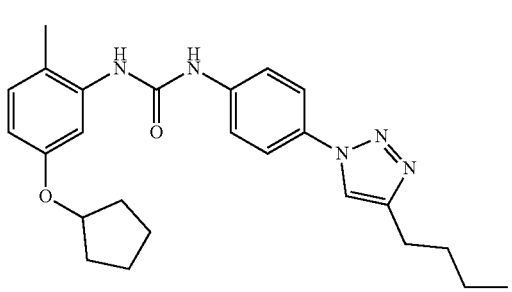
55h
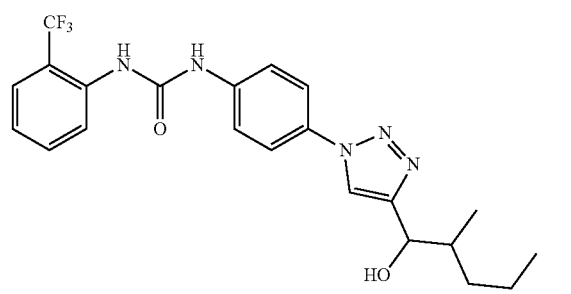
35d
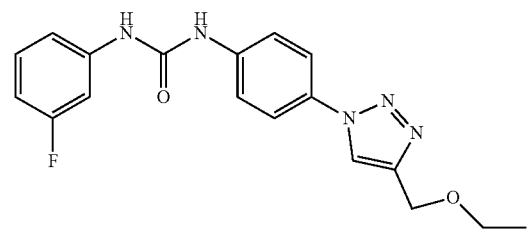
55o
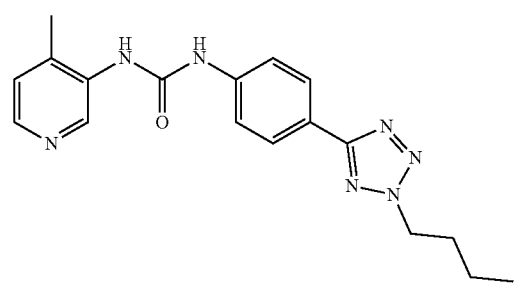
52
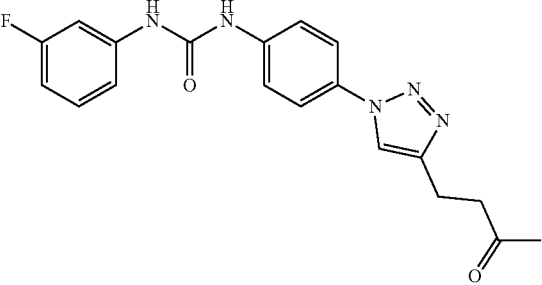
55n -continued
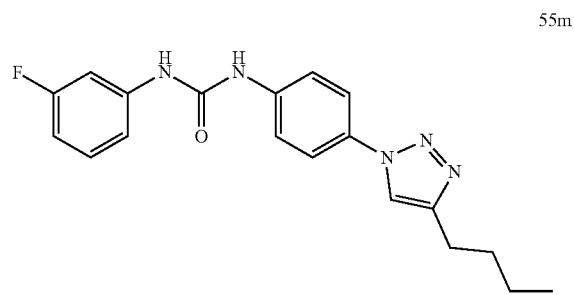
55m
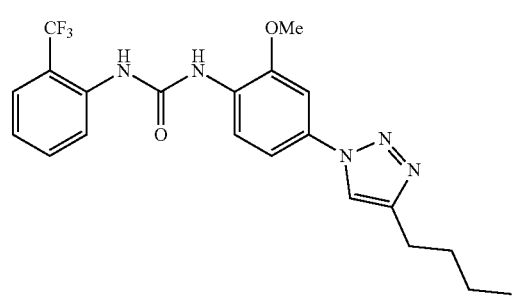
8e
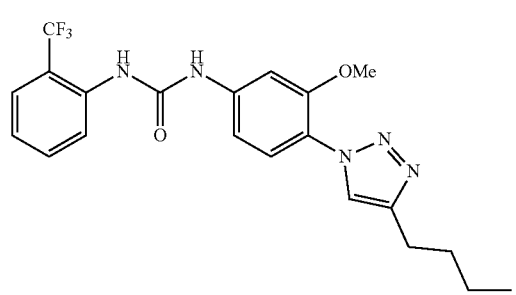
81
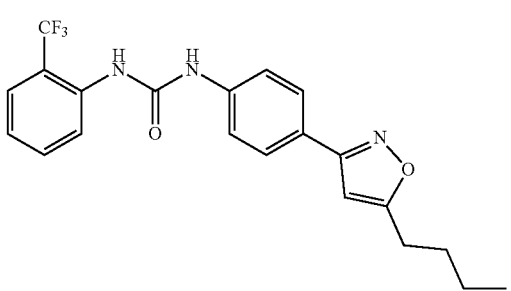
51
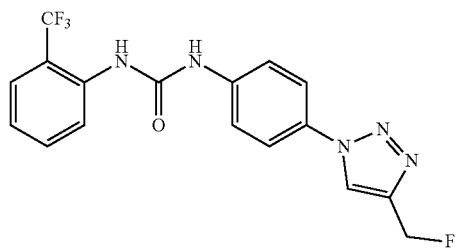
102
-continued
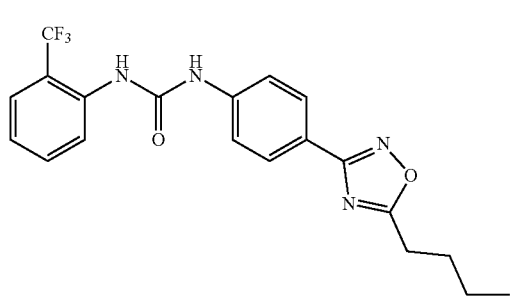
42a
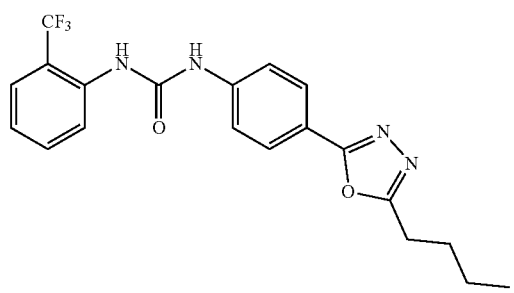
106
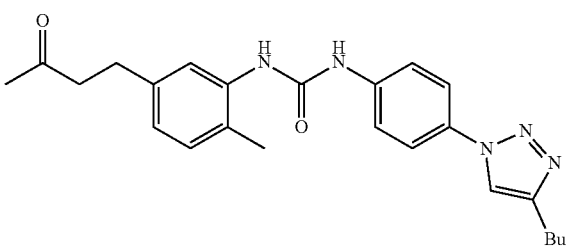
112
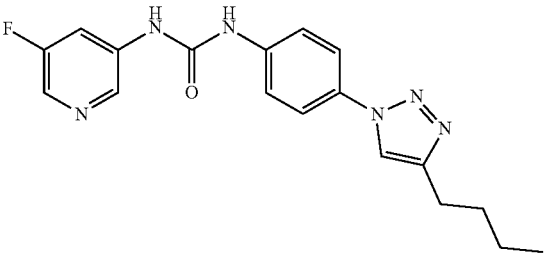
55p
55q

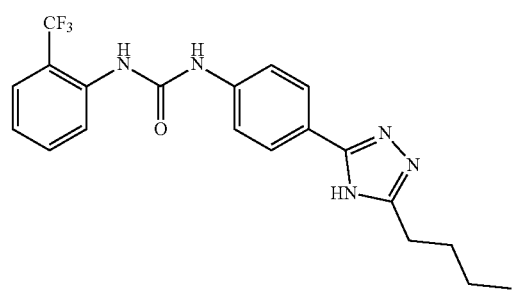
119
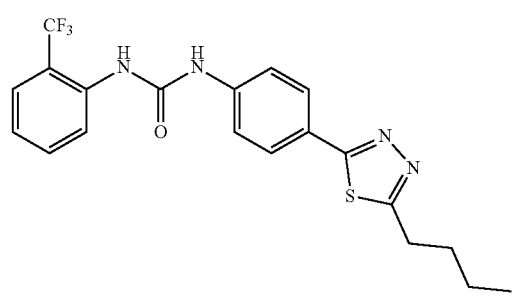
124
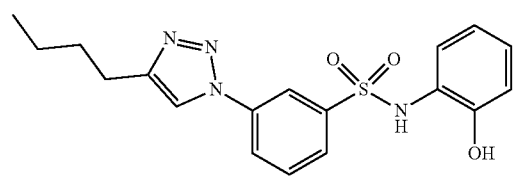
64a
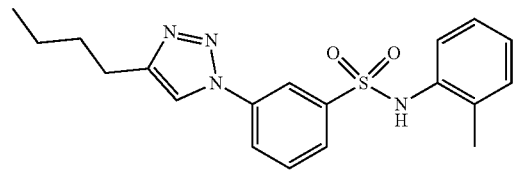
64c
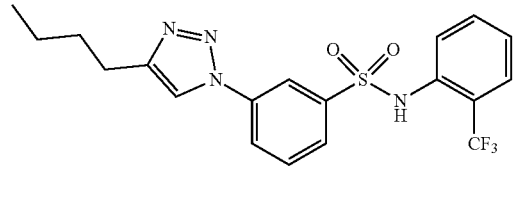
64d
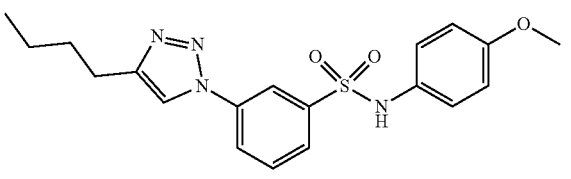
64b
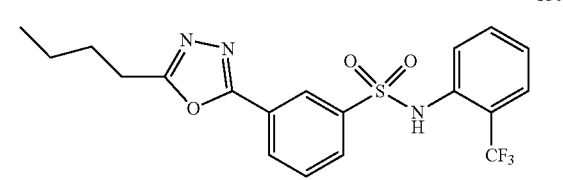
130
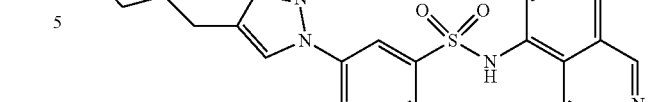
64e
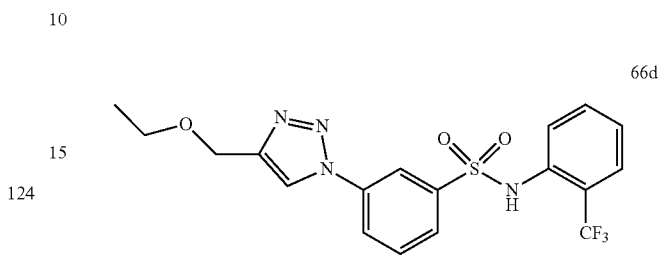
66d
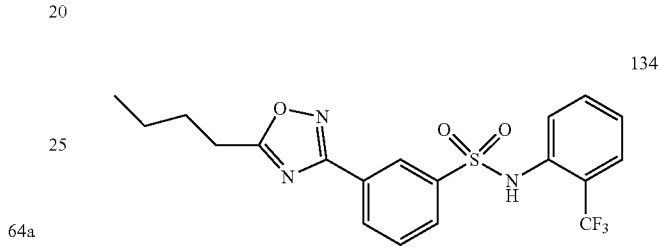
134
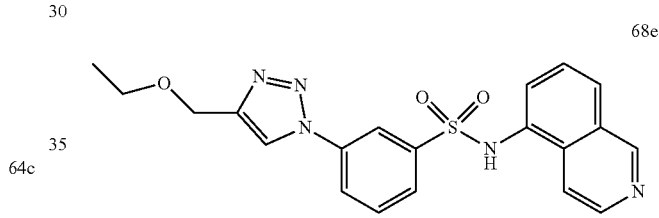
68e
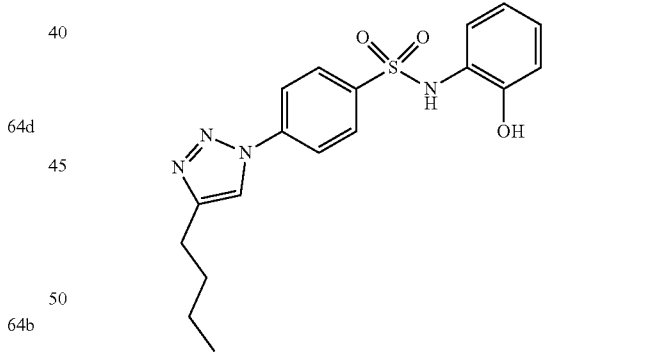
65a
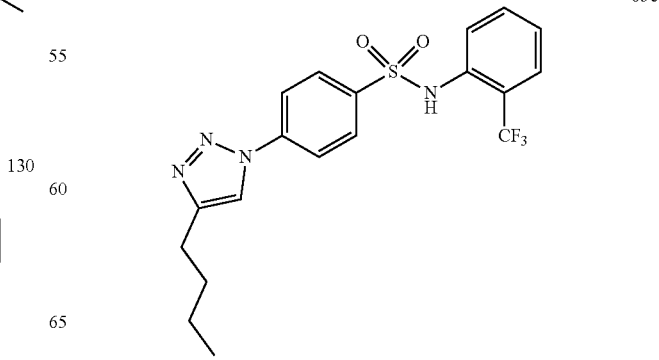
65c -continued
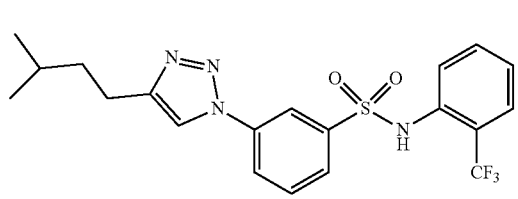
67d
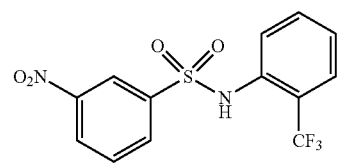
58d
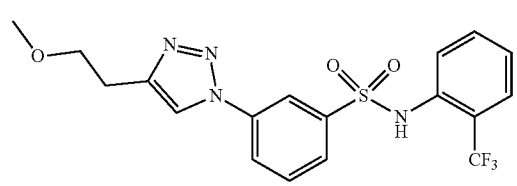
66e
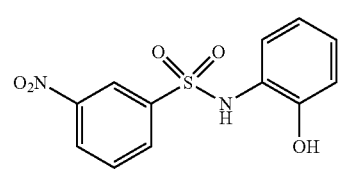
58a
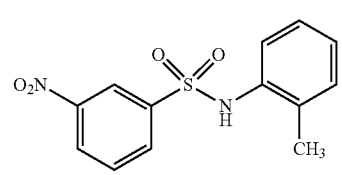
58c
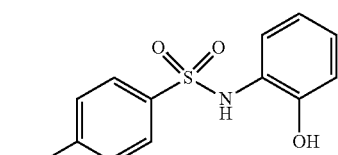
59a
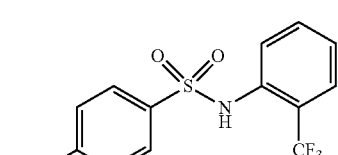
59d
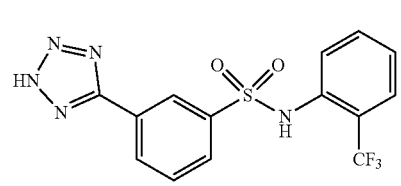
71
or salt, solvate, stereoisomer thereof.
More preferably the compound of formula I or II is selected from the following list:
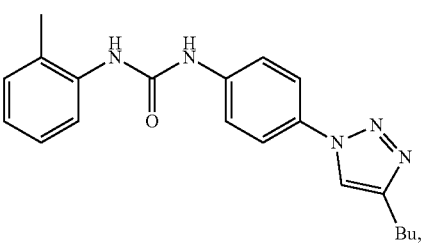
20a
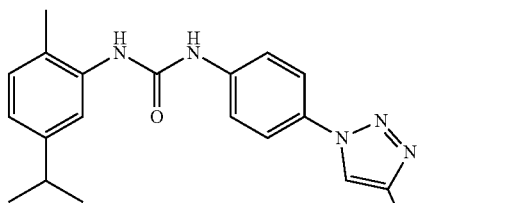
55e
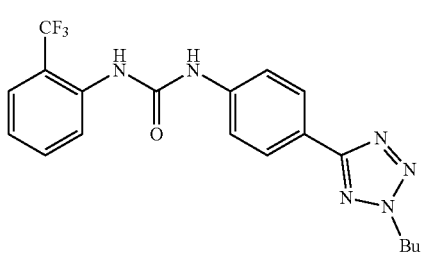
51
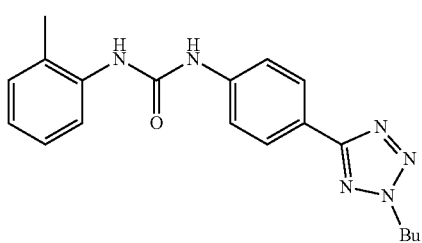
49
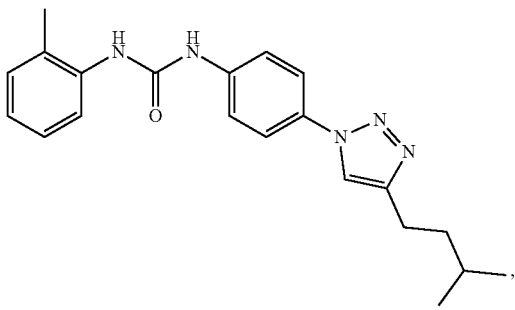
20b
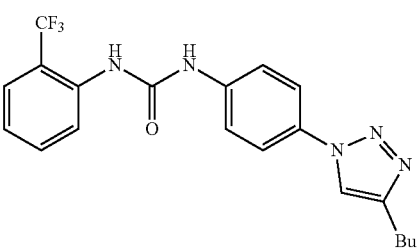
22a -continued

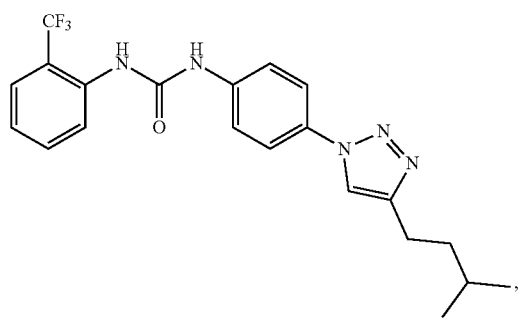
22b

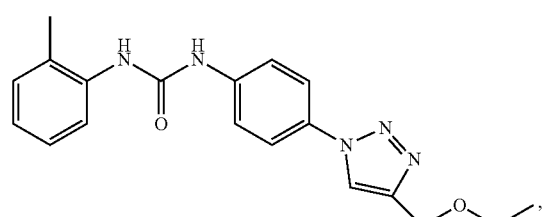
20e

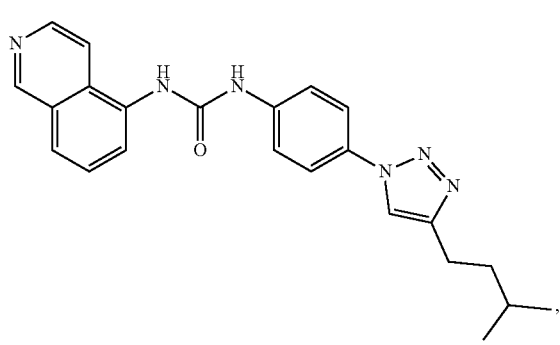
55f

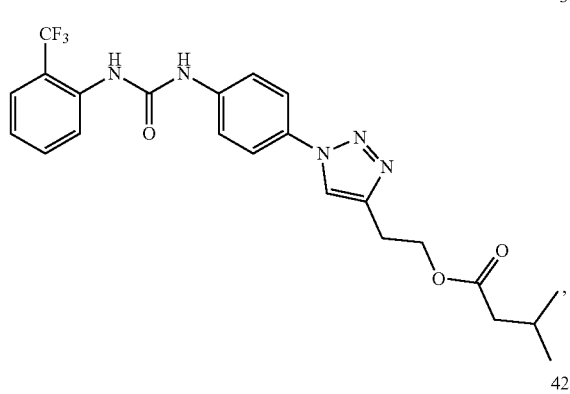
38

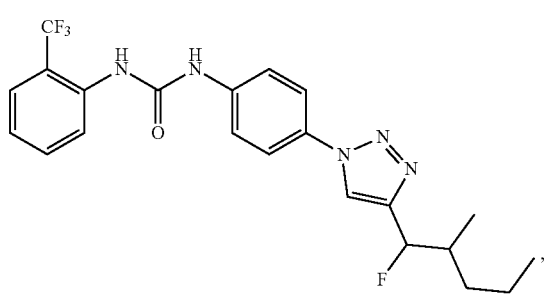
42c

-continued

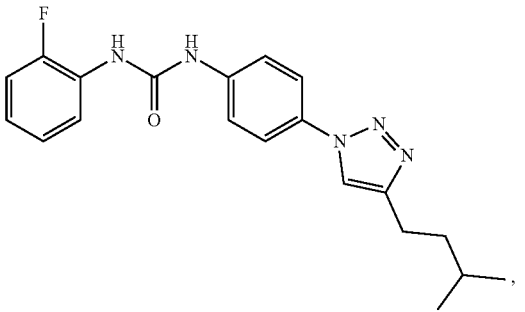
55a

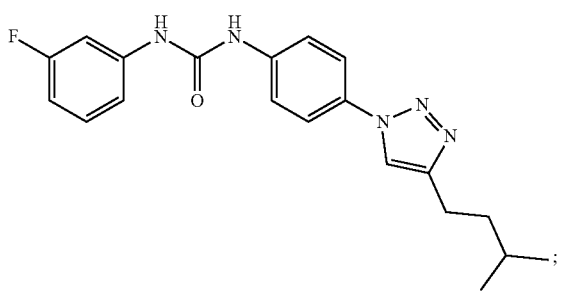
55b

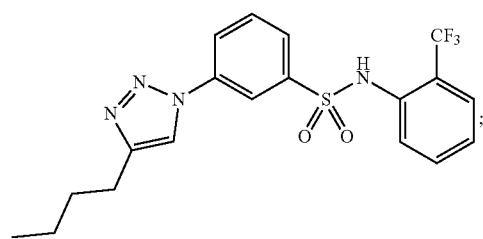
64d

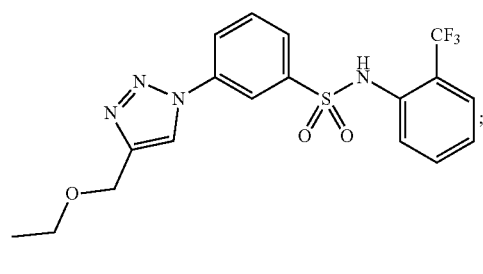
66d

64e or salt, solvate, stereoisomer thereof.

Preferably the compound of formula I or II of the invention is an inhibitor of DDX3.

Preferably the compound of formula I or II as defined herein above is for medical use.

In a preferred embodiment the compound of the invention for medical use has formula II wherein $R_8$ and $R_9$ are each independently selected from H, halogen, alkoxy, COOH, and at least one of $R_8$ or $R_9$ is nitro or heteroaryl group selected from:

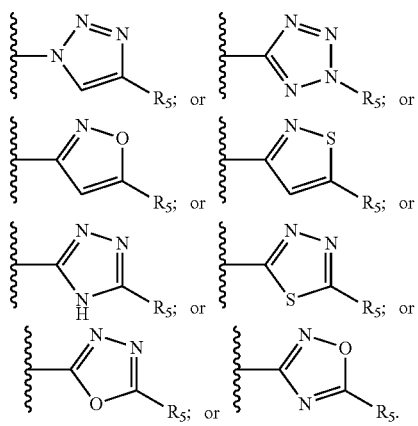

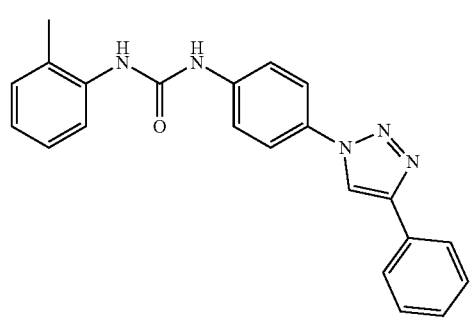

8a

Preferably the compound of the invention for medical use has formula II wherein one of $R_8$ or $R_9$ is nitro.

Preferably the compound of the invention for medical use has formula II wherein $R_8$ is nitro and $R_9$ is H or $R_8$ is H and $R_9$ is nitro and A is phenyl, preferably substituted by methyl, isopropyl, $CF_3$, F, Cl, OH, or OMe.

Preferably the compound of the invention for medical use has formula II wherein $R_8$ is nitro and $R_9$ is H or $R_8$ is H and $R_9$ is nitro and A is phenyl, preferably substituted by methyl, isopropyl, $CF_3$, F, Cl, OH, or OMe, and X and Y are C, and $R_6$, $R_7$ and $R_{10}$ are H.

The present invention further provides a compound of formula I or II as defined herein above or pharmaceutical acceptable salt, solvate, stereoisomer thereof for use in the treatment of a viral disease.

Preferably the viral disease is modulated by DDX3.

Preferably the viral disease is caused by a virus selected from the group consisting of: Human Immunodeficiency Virus 1 (HIV-1), Hepatitis C Virus, Hepatitis B Virus, Western Equine Encephalitis Virus, Venezuelan Equine Encephalitis Virus, Japanese Encephalitis Virus, Tick Borne Encephalitis Virus, Yellow Fever Virus, St. Louis Encephalitis Virus, Murray Valley Encephalitis Virus, Powassan Virus, Dengue Virus, Zika Virus, West Nile Virus, Rubella Virus, Cytomegalovirus, O'nyong'nyong Virus, Mayaro Virus, Ross River Virus, Sindbis Virus, Eastern Equine Encephalitis Virus, Vaccinia Virus, Influenza Virus, Norovirus, SARS Coronavirus, Chikunguya Virus, Lassa Virus, Ebola Virus, Lujo Virus, Pneumovirus, Severe Fever With Thrombocytopenia Syndrome Virus, Porcine Reproductive And Respiratory Syndrome Virus, Poxvirus, Bovine Viral Diarrhea Virus (BVDV), Border Disease Virus (BDV) of sheep, and Classical Swine Fever Virus (CSFV).

Preferably the compound of formula I or II as defined herein above or pharmaceutical acceptable salt, solvate, stereoisomer thereof are for use in the treatment of a viral disease is caused by a virus selected from the group consisting of: Human Immunodeficiency Virus 1 (HIV-1), Hepatitis C Virus, West Nile Virus, Dengue Virus, Japanese Encephalitis Virus, Porcine Reproductive And Respiratory Syndrome Virus, Ebola Virus, Zika Virus. Still preferably for use in the treatment of a viral disease is caused by a virus selected from the group consisting of: Ebola Virus and Zika Virus.

Preferably the compound of formula I or II for use as medicament or for use in the treatment of a viral disease is selected from the following list:

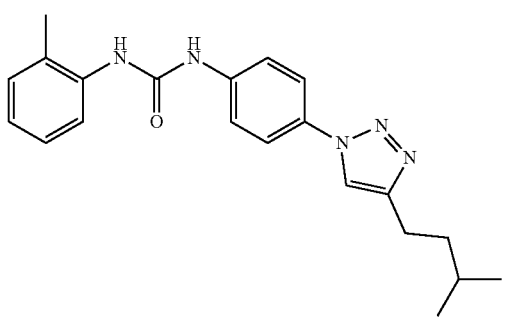

20b

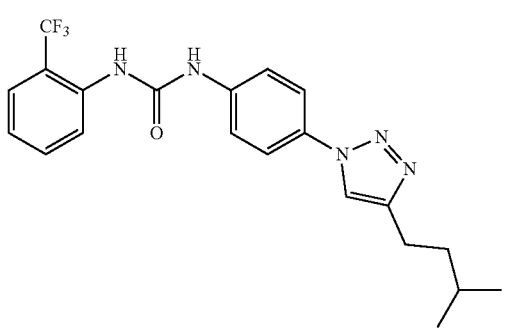

22b

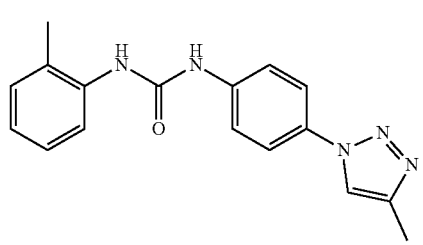

8f

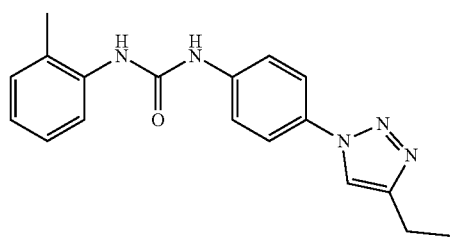

8g

8b
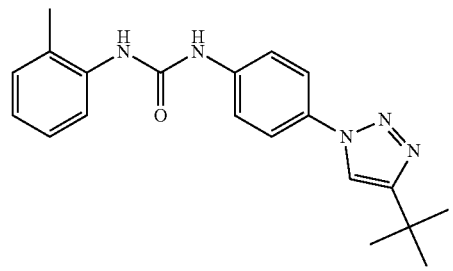
22a
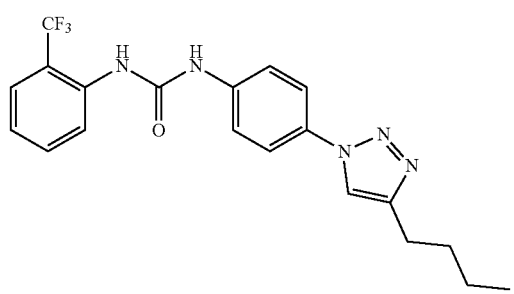
20a
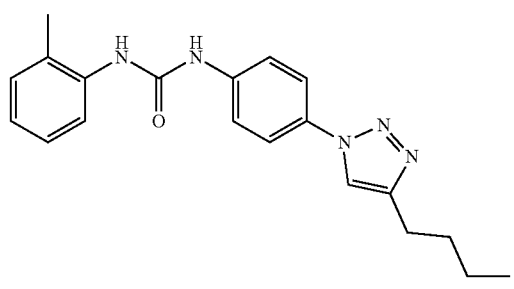
15a
35f
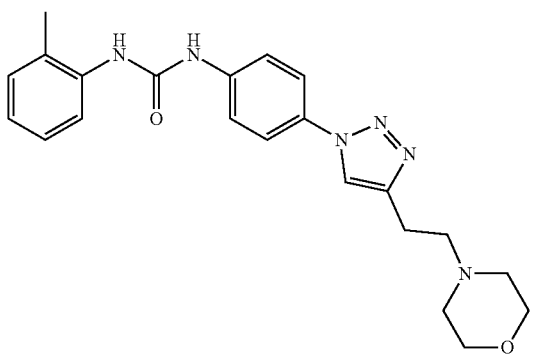
35e
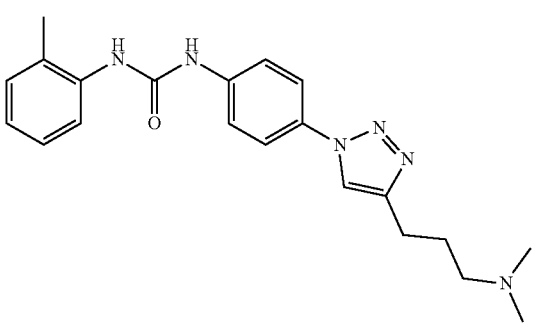
35i
35g
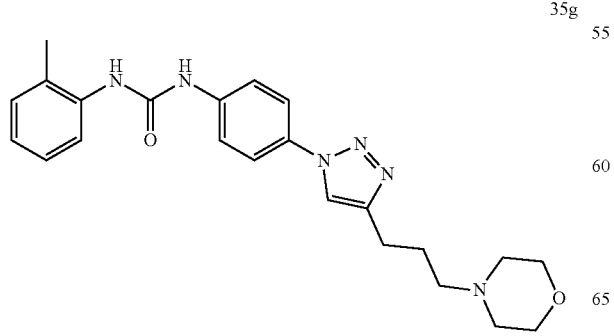
8c 37
-continued
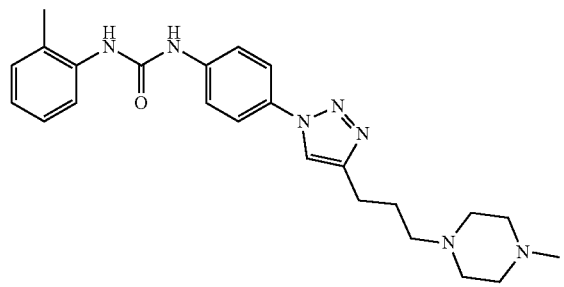
38
-continued
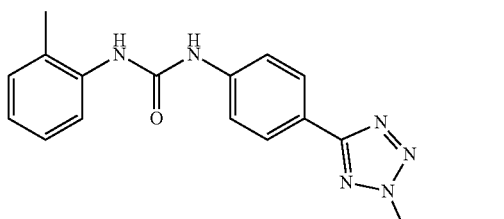
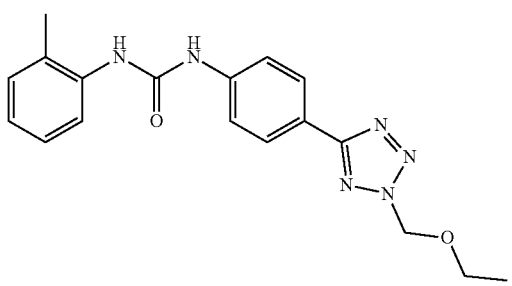
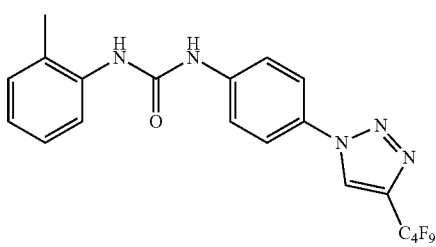
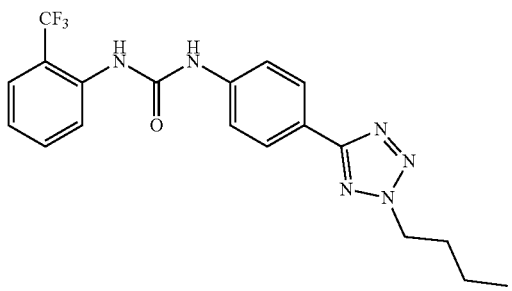
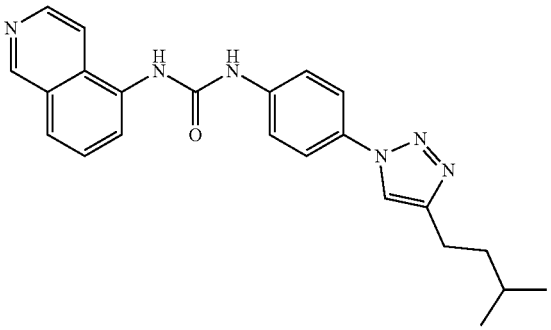

-continued
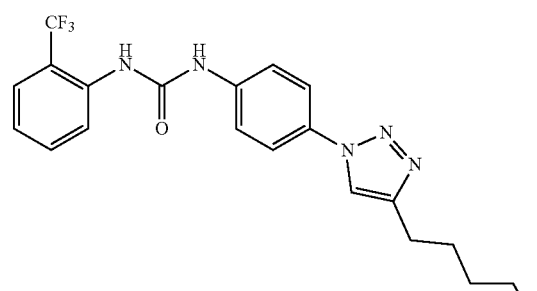
8d
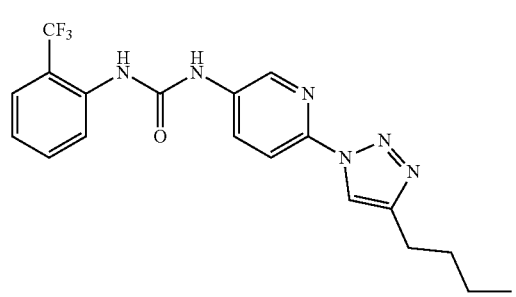
86
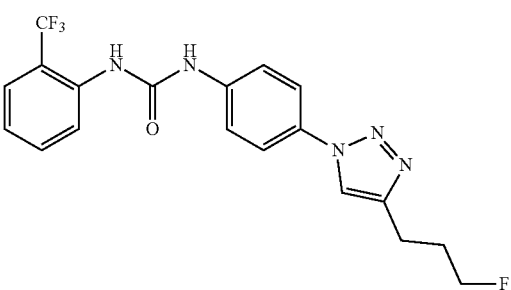
42b
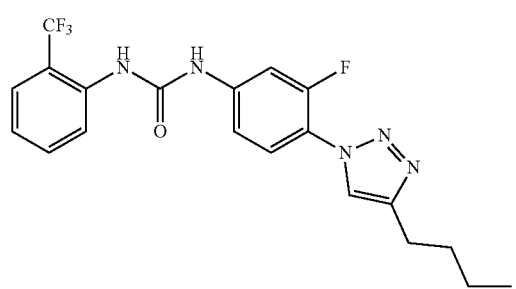
81
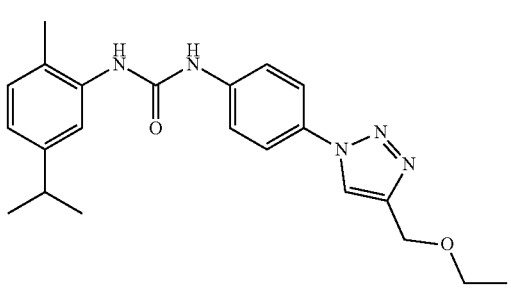
55e
-continued
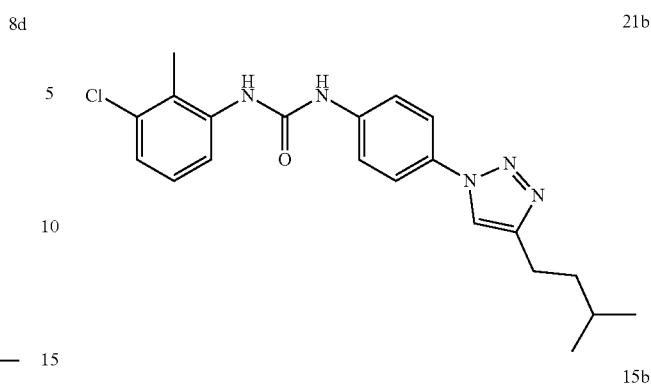
21b
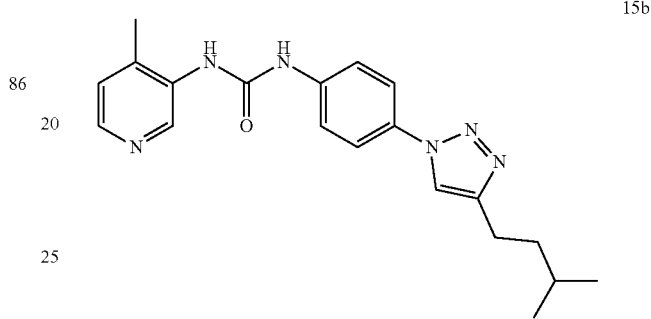
15b
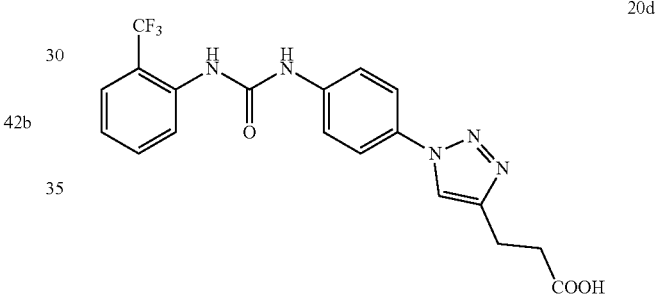
20d
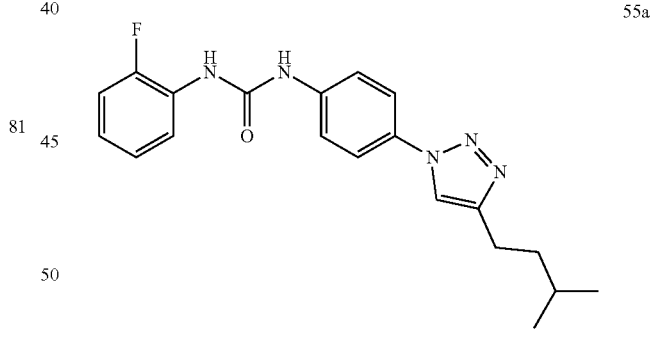
55a
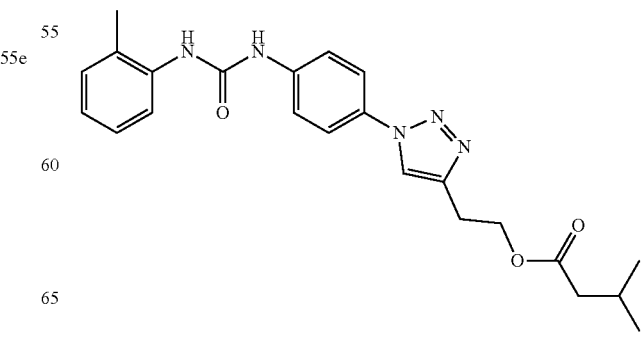
37

39
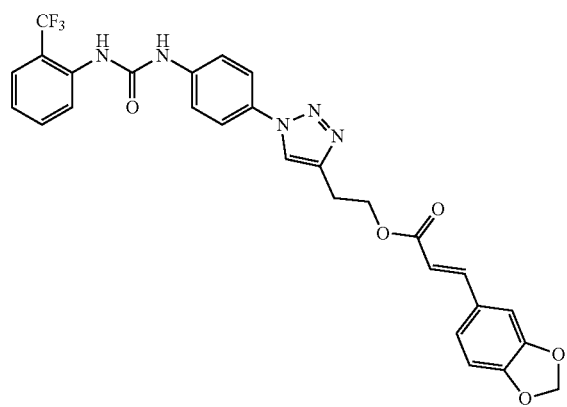
55b
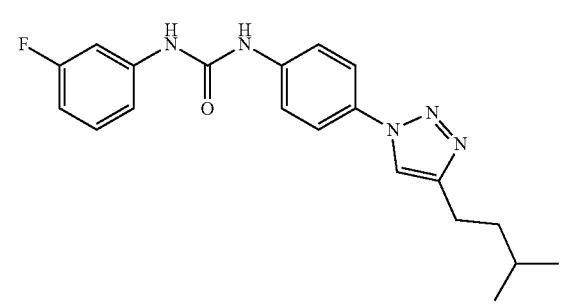
36
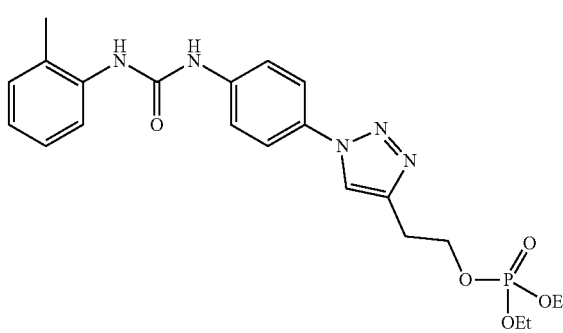
38
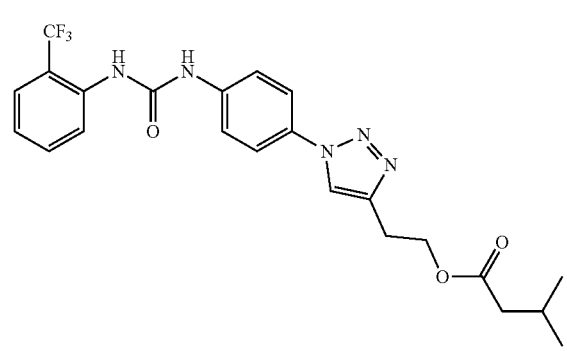
55c
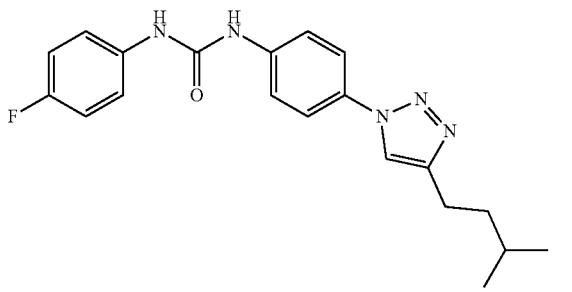
35e
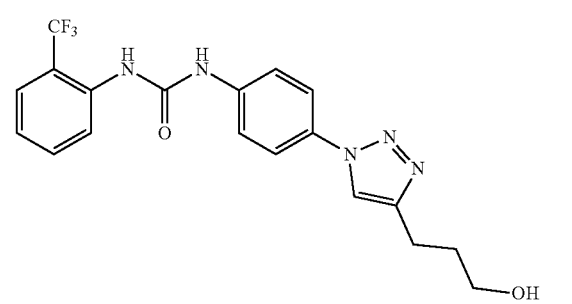
42c
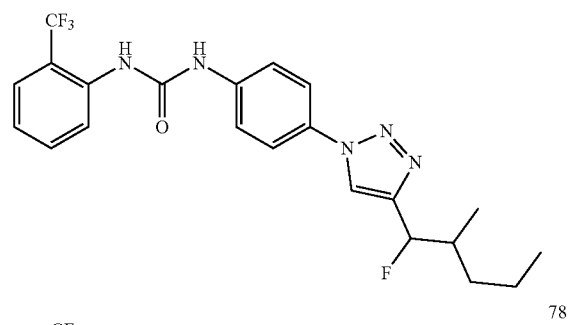
78
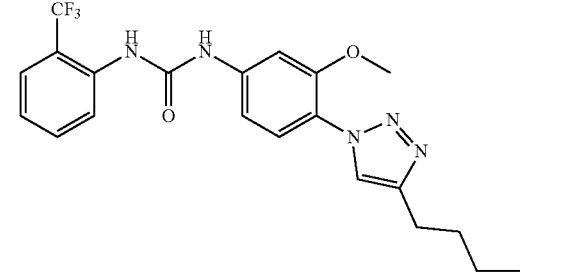
22g
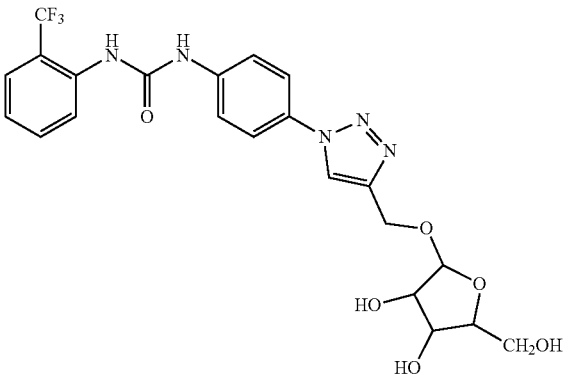

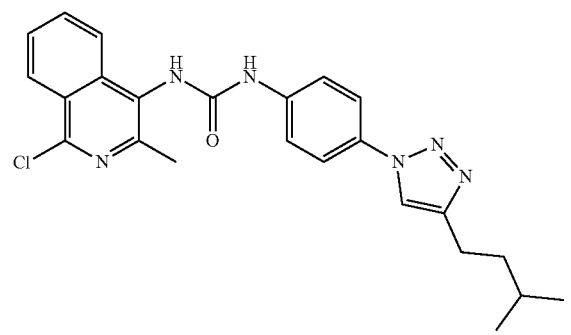
55g
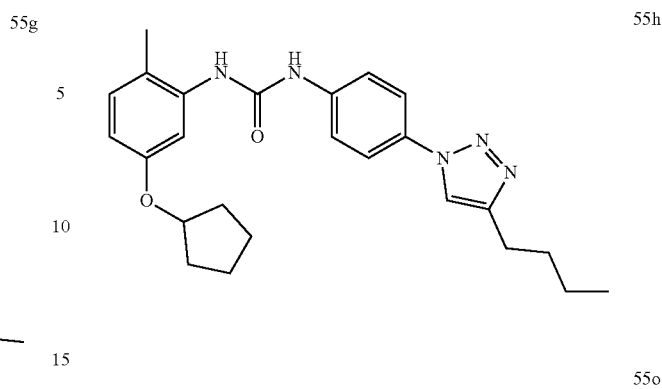
55h
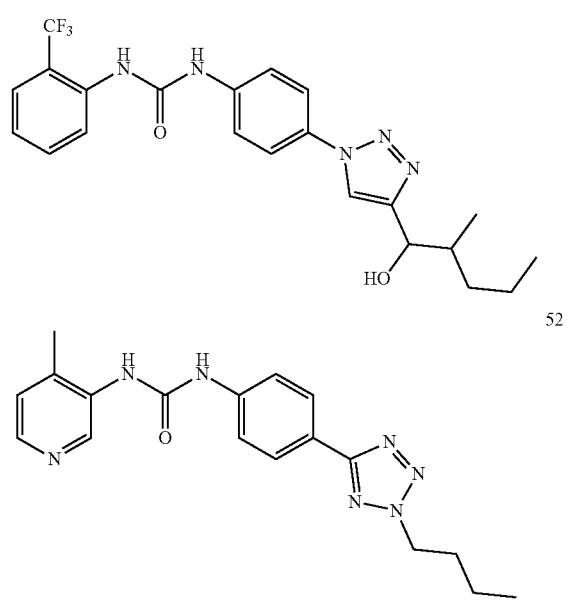
35d
52
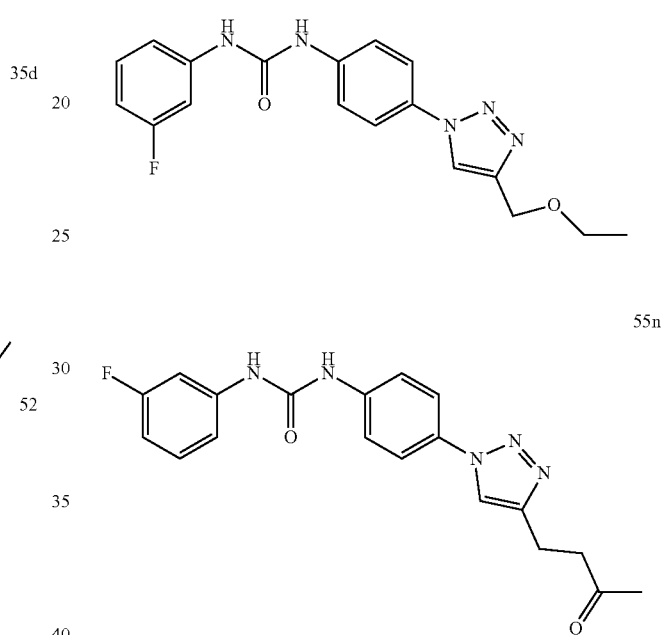
55o
55n
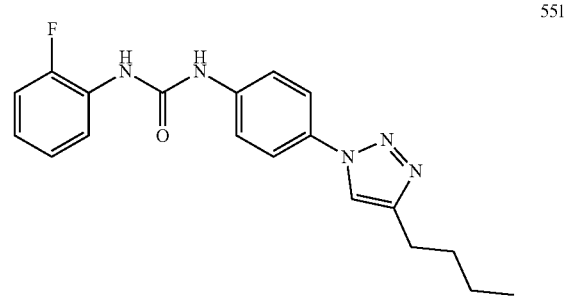
55l
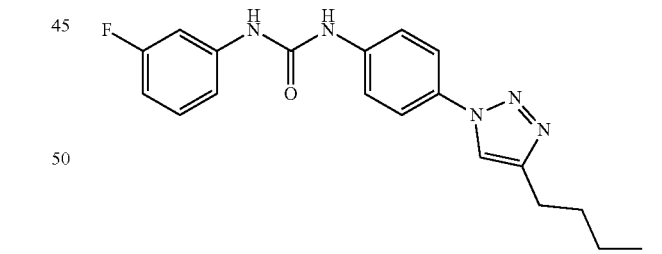
55m
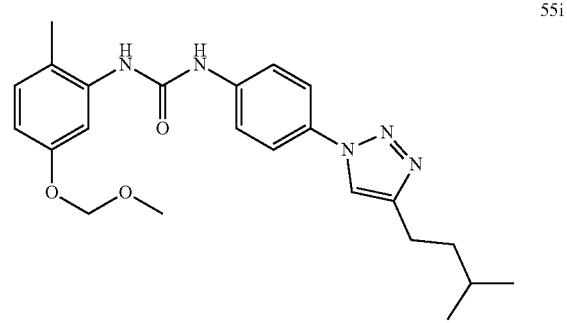
55i
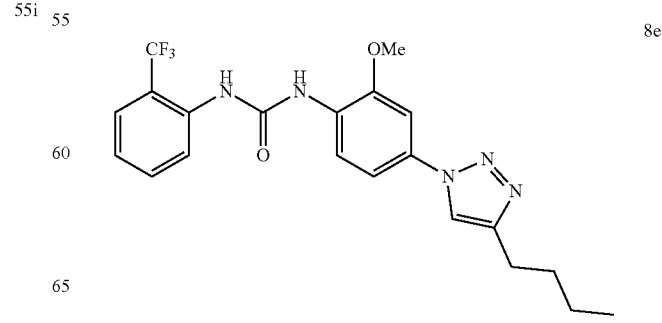
8e

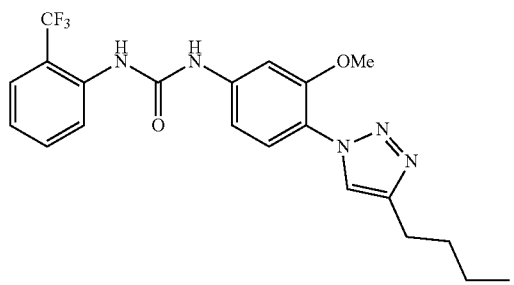
81
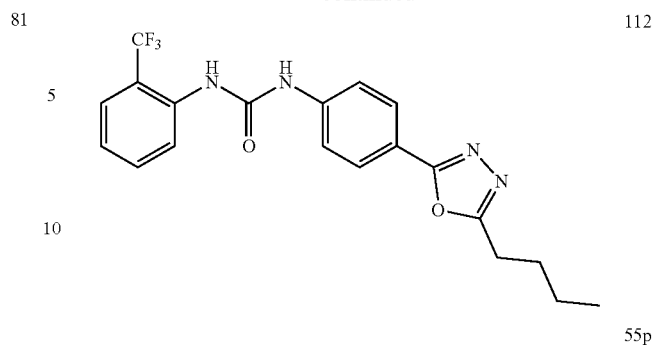
112
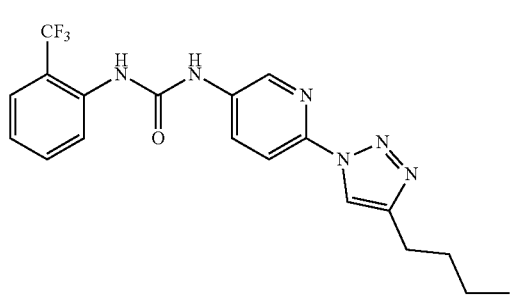
51
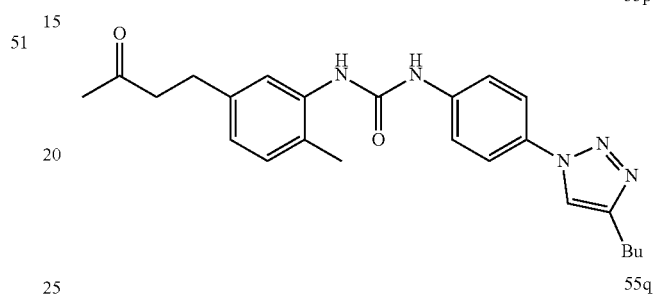
55p
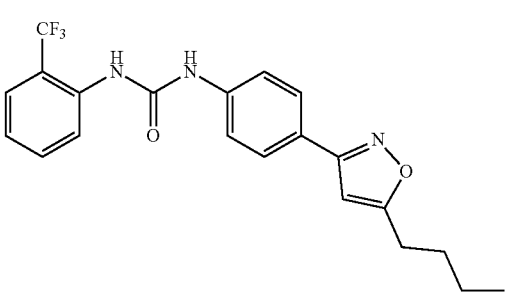
102
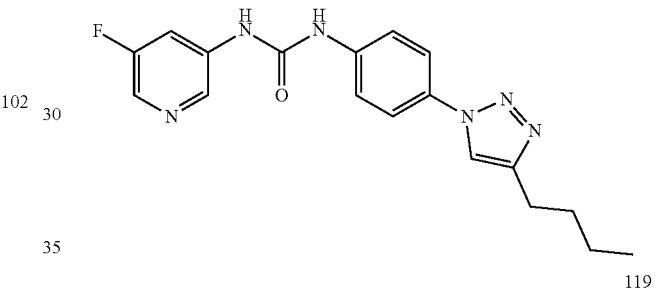
55q
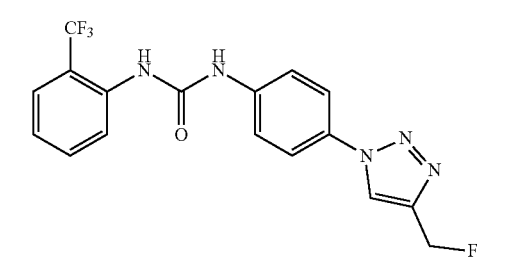
42a
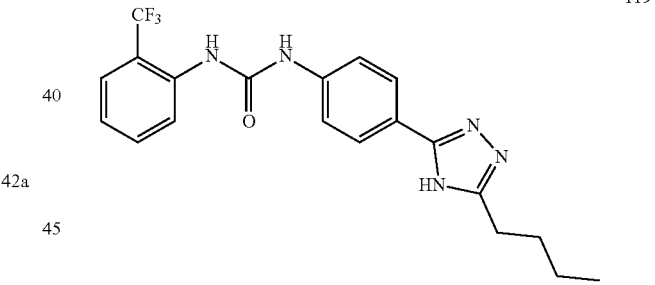
119
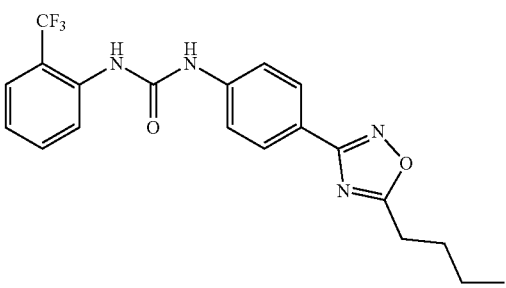
106
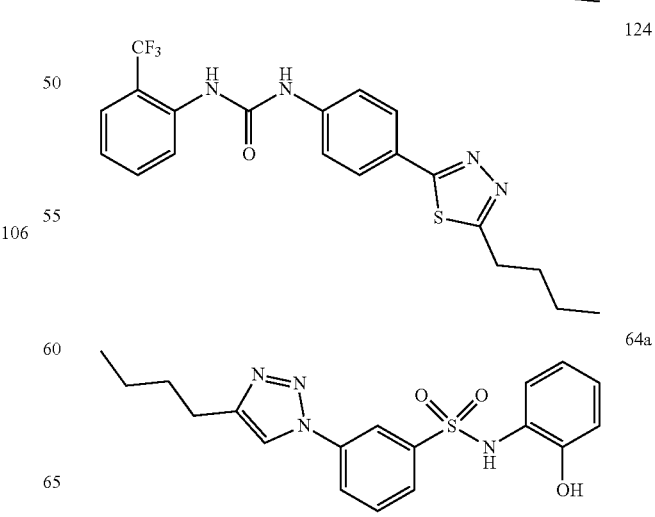
124
64a

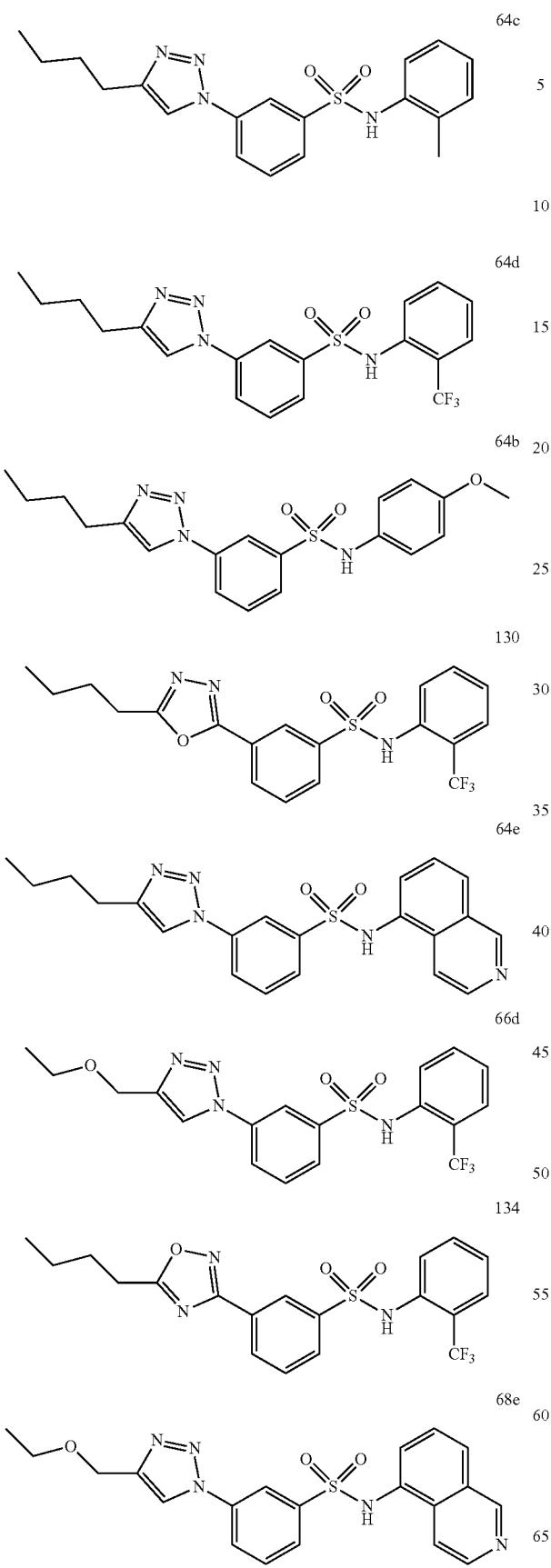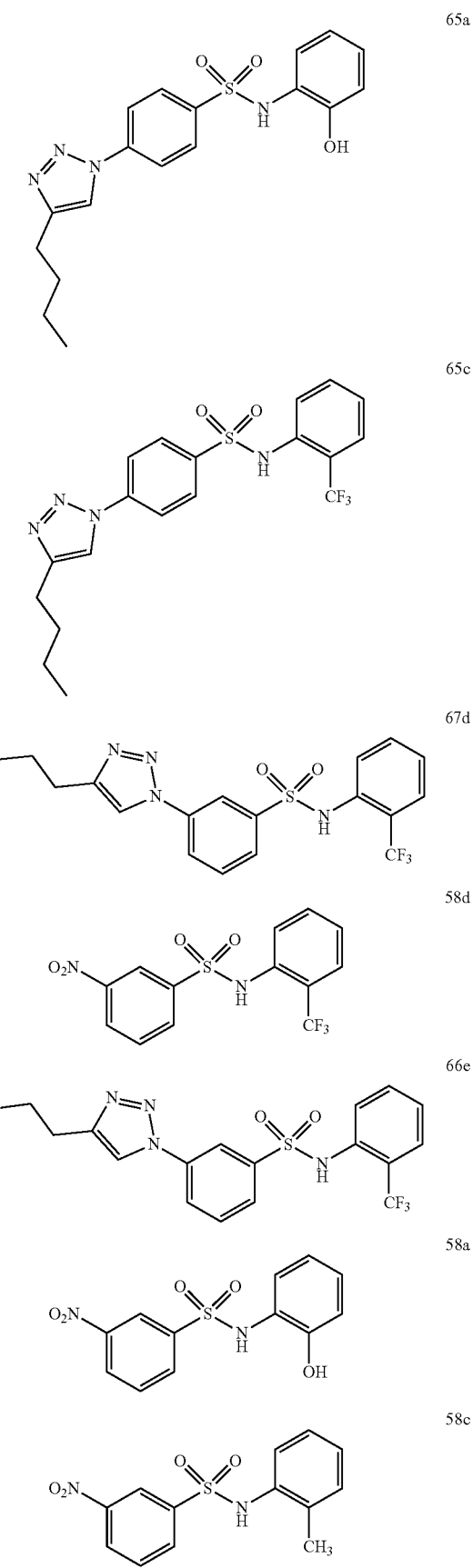

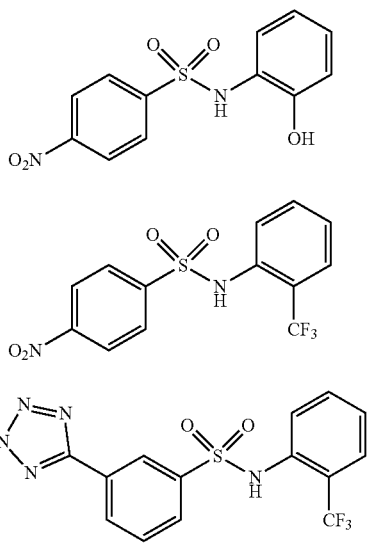

The invention further provides a pharmaceutical composition comprising the compound of formula I or II of the invention and pharmaceutically acceptable excipients.

Preferably the pharmaceutical composition further comprises at least one an antiviral agent.

Still preferably the antiviral agent is selected from the group consisting of: a nucleoside or a non-nucleoside analogue reverse-transcriptase inhibitor, a nucleotide analogue reverse-transcriptase inhibitor, a NS3/4A serine protease inhibitor, a NS5B polymerase inhibitor or interferon alpha.

In the present invention:

The term "substituted" means that the specified group or moiety has any hydrogen atom, on independently each carbon atom, nitrogen atom or other atom, which may be independently replaced by a substituent.

The term "halogen" or "halo" refers to fluoro, chloro, bromo, or iodo.

The term "alkyl" refers to a linear or branched hydrocarbon chain radical, consisting solely of carbon and hydrogen atoms. Suitable examples of said alkyl include but are not limited to methyl, ethyl, n-propyl, isopropyl, butyl, sec-butyl, tert-butyl, pentyl, isopentyl, tert-pentyl, hexyl, heptyl, octyl, nonyl, decanyl, hexadecanyl, eicosanyl, etc.

The term "$C_1$-$C_{10}$ alkyl" refers to a linear or branched hydrocarbon chain radical, consisting solely of carbon and hydrogen atoms, having from one to ten carbon atoms. Suitable examples of $C_{1-10}$ alkyl include but are not limited to methyl, ethyl, n-propyl, isopropyl, butyl, sec-butyl, tert-butyl, pentyl, isopentyl, tert-pentyl, hexyl, heptyl, octyl, nonyl, decanyl.

The term "$C_1$-$C_6$ alkyl" refers to a linear or branched hydrocarbon chain radical, consisting solely of carbon and hydrogen atoms, having from one to six carbon atoms. Suitable examples of $C_1$-$C_6$ alkyl include but are not limited to methyl, ethyl, n-propyl, isopropyl, butyl, sec-butyl, tert-butyl, pentyl, isopentyl, tert-pentyl, hexyl.

The term "$C_1$-$C_3$ alkyl" refers to a linear or branched hydrocarbon chain radical, consisting solely of carbon and hydrogen atoms, having from one to three carbon atoms. Suitable examples of $C_1$-$C_3$ alkyl are methyl, ethyl, n-propyl.

The term "$C_2$-$C_6$ alkenyl" refers to a linear or branched unsaturated hydrocarbon chain radical, containing at least one carbon-carbon double bond, consisting solely of carbon and hydrogen atoms, having from two to six carbon atoms. Suitable examples of $C_2$-$C_6$ alkenyl but are not limited to ethenyl, propenyl, allyl, isobuthenyl, pentenyl, prenyl, esenyl, etc.

The term "$C_2$-$C_6$ alkynyl" refers to a linear or branched unsaturated hydrocarbon chain radical, containing at least one carbon-carbon triple bond, consisting solely of carbon and hydrogen atoms, having from two to six carbon atoms. Suitable examples of $C_2$-$C_6$ alkynyl but are not limited to acetylenyl, ethynyl, propynyl, etc.

The term "haloalkyl" group is a linear or branched alkyl group wherein at least one hydrogen atom on the carbon atom is replaced by halogen and alkyl is as defined herein above.

"Haloalkyl" preferably is a linear or branched $C_1$-$C_{10}$ haloalkyl group, more preferably $C_1$-$C_8$ haloalkyl group, more preferably linear or branched $C_1$-$C_6$ haloalkyl group, also preferably is a linear or branched $C_1$-$C_4$ haloalkyl group, or a $C_1$-$C_2$ haloalkyl group, being in particular, $CHFCH(CH_3)(CH_2CH_2CH_3)$, $CH_2CH_2CH_2F$, $C_4F_9$, $CF_3$, $CHF_2$, $CH_2F$.

The term "$C_1$-$C_{10}$ haloalkyl" refers to linear or branched alkyl group having from one to ten carbon atoms wherein at least one hydrogen on a carbon atom is replaced by halogen and alkyl is as defined herein above. Analogous definition is for $C_1$-$C_8$ haloalkyl, $C_1$-$C_6$ haloalkyl, $C_1$-$C_4$ haloalkyl and $C_1$-$C_4$ haloalkyl having from one to eight, one to six and one to four or one to two carbon atoms respectively.

The term "alkoxy" denotes an organic unit having the general formula —OR, wherein R is an aliphatic. An alkoxy group can be, for example, methoxy and ethoxy. Suitable examples of alkoxy groups include, but are not limited to propoxy, isopropoxy, isobutoxy, and tert-butoxy.

The term "aryl" represents a mono or bicyclic aromatic ring system of, respectively, 6, 9 or 10 atoms, suitable examples of such an aryl are phenyl, indenyl, indanyl and naphthyl.

The term "aralkyl" represents any univalent radical derived from an alkyl radical by replacing one or more hydrogen atoms by aryl groups, wherein the aryl is as defined herein above. Suitable examples of such an aralkyl are benzyl.

"Aralkyl substituted group" means that any hydrogen atom on independently each carbon atom may be independently replaced by a substituent, suitable examples of substituents include but are not limited to F, Cl, Br, $CF_3$, $O$—$C_1$-$C_6$ alkyl, $C_1$-$C_6$ alkyl, OH, $COC_1$-$C_6$ alkyl, $COOC_1$-$C_6$ alkyl.

The term "heteroaryl" means a monocyclic- or polycyclic 5-12 membered aromatic ring comprising carbon atoms, hydrogen atoms, and one or more heteroatoms, preferably, 1 to 3 heteroatoms, independently selected from nitrogen, oxygen, and sulfur. Illustrative examples of heteroaryl groups include, but are not limited to pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, tetrazolyl, furyl, thienyl, isoxazolyl, thiazolyl, isoxazolyl, oxazolyl, indazolyl, indolyl, benzoimidazolyl, quinolyl, isoquinolinyl and the like.

Salts of the compounds of the present invention are also encompassed within the scope of the invention. Because of their potential use in medicine, the salts of the compounds of formula I and II are preferably pharmaceutically acceptable. Suitable pharmaceutically acceptable salts comprise conventional non-toxic salts obtained by salification of a compound of formula I and II with inorganic acids (e.g.

hydrochloric, hydrobromic, sulphuric, or phosphoric acids), or with organic acids (e.g. acetic, propionic, succinic, benzoic, sulfanilic, 2-acetoxy-benzoic, cinnamic, mandelic, salicylic, glycolic, lactic, oxalic, malic, maleic, malonic, fumaric, tartaric, citric, p-toluenesulfonic, methanesulfonic, ethanesulfonic, or naphthalensulfonic acids). For reviews on suitable pharmaceutical salts see (32).

In addition pharmaceutically acceptable base addition salts can be formed with a suitable inorganic or organic base such as triethylamine, ethanolamine, triethanolamine, dicyclohexylamine, ammonium hydroxide, pyridine. The term "inorganic base," as used herein, has its ordinary meaning as understood by one of ordinary skill in the art and broadly refers to an inorganic compound that can act as a proton acceptor. The term "organic base," as used herein, also has its ordinary meaning as understood by one of ordinary skill in the art and broadly refers to an organic compound that can act as a proton acceptor.

Other suitable pharmaceutically acceptable salts include pharmaceutically acceptable alkali-metal or alkaline-earth-metal salts such as sodium, potassium, calcium or magnesium salts; in particular pharmaceutically acceptable salts of one or more carboxylic acid moieties that may be present in the compound of formula I and II.

Other salts, which are not pharmaceutically acceptable, for example the trifluoroacetate salt, may be useful in the preparation of compounds of this invention and these form a further aspect of the invention. The invention includes within its scope all possible stoichiometric and nonstoichiometric forms of the salts of the compounds of formula I and II.

In addition, the compounds of formula I and II may exist in unsolvated as well as in solvated forms with pharmaceutically acceptable solvents such as water, EtOH and the like.

Certain compounds of formula I and II may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula I and II as mixtures with isomers thereof in which one or more chiral centers are inverted. Racemic mixtures may be separated to give their individual enantiomer using preparative HPLC using a column with chiral stationary phase or resolved to yield individual enantiomers utilizing methods known to those skilled in the art. In addition, chiral intermediate compounds may be resolved and used to prepare individual enantiomers.

The compounds of the invention or solvates/hydrates of the compounds of formula I and II or salts, may exist in one or more polymorphic forms. The invention extends to all such forms whether in a pure polymorphic form or when admixed with any other material, such as another polymorphic form.

The compounds of formula I and II may exist in zwirterionic from. Likewise it is understood that compounds of formula I and II may exist in tautomeric forms other than that shown in the formula and these are also included within the scope of the present invention.

It will be appreciated by those skilled in the art that certain protected derivatives of the compounds of the invention, which may be made prior to a final deprotection stage, may not possess pharmacological activity as such, but may, in certain instances, be administered orally or parenterally and thereafter metabolized in the body to form compounds defined in the first aspect which are pharmacologically active. Such derivatives may therefore be described as "prodrugs". All protected derivatives and prodrugs of compounds defined in the first aspect are included within the scope of the invention. Examples of suitable pro-drugs for the compounds of the present invention are described in Drug of Today, Volume 19, Nuber 9, 1983, pp 499-538 and in Topics in Chemistry, Chapter 31, pp 306-316 and in "Design of Prodrugs" by H. Bundgaard, Elsevier, 1985, Chapter1 (the disclosure in which document is incorporated herein by reference). It will be further appreciated by those skilled in the art that certain moieties, known to those skilled in the art as "pro-moieties", for described by H. Bundgaard, in "Design of Prodrugs" (the disclosure in which document is incorporated herein by reference) may be placed on appropriate functionalities when such functionalities are present within the compound defined in the first aspect.

The invention also includes all suitable isotopic variations of a compound of the invention. An isotopic variation of a compound of the invention is defined as one in which at least one atom is replaced by an atom having the same atomic number but an atomic mass different from the atomic mass usually found in nature. Examples of isotopes that can be incorporated into compounds of the invention include isotopes such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively. Certain isotopic variations of the invention, for example, those in which a radioactive isotope such as $^3$H or $^{14}$C is incorporated, are useful in drug and/or substrate tissue distribution studies. Further, substitution with isotopes such as deuterium $^2$H, may afford certain therapeutic advantages resulting from greater metabolic stability. Isotopic variations of the compounds of the invention can generally be prepared by conventional procedures such as by the illustrative methods or by the preparations described in the examples hereafter using appropriate isotopic variations of suitable reagents.

In the present invention a pathology or viral disease modulated by DDX3 is defined a pathology that can be induced, triggered or enhanced by DDX3 protein activity and/or expression. The activity of DDX3 can be measured by techniques known in the art for instance by measuring enzymatic activity of the protein. The expression of DDX3 is also measured by commonly used methods in the art. The compounds of the present invention are particularly suitable for the treatment of patients that are resistant to at least one currently used treatment for HIV infection. For instance, patients resistant to RT inhibitors, PR inhibitors and/or IN inhibitors.

In the present invention the compounds as defined above and suitable excipients or diluents may be administered in combination with pharmaceutical composition of approved drugs for the treatment of the HIV-1 infections as part of the highly active antiretroviral therapy (HAART).

The pharmaceutical composition of the invention may comprise a combination of at least two of the compounds of the invention or a pharmaceutically acceptable salt thereof, and suitable excipients and/or diluents and may be also administered in combination with pharmaceutical compositions of approved drugs for the treatment of the HCV infections as part of combinatorial multidrug anti-HCV therapy.

The pharmaceutical composition of the invention may comprise a combination of at least two of the compounds of the invention or a pharmaceutically acceptable salt thereof, and suitable excipients and/or diluents and may be also administered in combination with pharmaceutical compositions of approved drugs for the treatment of cancers as part of combinatorial multidrug cancer therapy.

Preferably the pharmaceutical composition comprising at least one or two of the compounds of the invention together with at least one approved compound for the treatment of HIV-1 infections are in the same formulation or a pharmaceutically acceptable salt thereof, and suitable excipients and/or diluents to be administered as such. In the present invention the compounds of the invention or their salts may be administered as pure or as pharmaceutical formulations. i.e. suitable for parenteral, oral, or rectal administrations. Each of said formulations may contain excipients and/or fillers and/or additives and/or binders, coatings and/or suspending agents and/or emulsifying agents, preserving and/or control release agents. suitable for the selected pharmaceutical form. It is a further object of the invention a method for inhibiting the human DEAD-box RNA helicases DDX3 comprising contacting the compound of the invention or the composition as defined above with human DDX3, thereby inhibiting the activity of DDX3.

It is a further object of the invention a method for treating a viral disease in a cell, comprising contacting the cell with the compound or the composition of the invention.

The invention also provides pharmaceutical compositions comprising at least one compound of this invention or a pharmaceutical acceptable salt or solvate thereof and one or more pharmaceutically acceptable carriers, excipients and/or diluents.

The pharmaceutical compositions can be chosen based on the treatment requirements. Such compositions are prepared by blending and are suitably adapted to oral or parenteral administration, and as such can be administered in the form of tablets, capsules, oral preparations, powders, granules, pills, injectable, or infusible liquid solutions, suspensions, suppositories, preparation for inhalation. Tablets and capsules for oral administration are normally presented in unit dose form and contain conventional excipients such as binders, fillers (including cellulose, mannitol, lactose), diluents, tableting agents, lubricants (including magnesium stearate), detergents, disintegrants (e.g. polyvinylpyrrolidone and starch derivatives such as sodium glycolate starch), coloring agents, flavoring agents, and wetting agents (for example sodium lauryl sulfate).

The oral solid compositions can be prepared by conventional methods of blending, filling or tableting. The blending operation can be repeated to distribute the active principle throughout compositions containing large quantities of fillers. Such operations are conventional. Oral liquid preparations can be in the form of, for example, aqueous or oily suspensions, solutions, emulsions, syrups or elixirs, or can be presented as a dry product for reconstitution with water or with a suitable vehicle before use. Such liquid preparations can contain conventional additives such as suspending agents, for example sorbitol, syrup, methyl cellulose, gelatin, hydroxyethyl cellulose, carboxymethyl cellulose, aluminium stearate gel, or hydrogenated edible fats; emulsifying agents, such as lecithin, sorbitan monooleate, or acacia; non-aqueous vehicles (which can include edible oils), such as almond oil, fractionated coconut oil, oily esters such as esters of glycerine, propylene glycol, or ethyl alcohol; preservatives, such as methyl or propyl p-hydroxybenzoate or sorbic acid, and if desired, conventional flavoring or coloring agents. Oral formulations also include conventional slow-release formulations such as enterically coated tablets or granules.

Pharmaceutical preparation for administration by inhalation can be delivered from an insufflator or a nebulizer pressurized pack.

For parenteral administration fluid unit dosages can be prepared, containing the compound and a sterile vehicle. The compound can be either suspended or dissolved, depending on the vehicle and concentration. The parenteral solutions are normally prepared by dissolving the compound in a vehicle, sterilising by filtration, filling suitable vials and sealing. Advantageously, adjuvants such as local anaesthetics, preservatives and buffering agents can also be dissolved in the vehicle. To increase the stability, the composition can be frozen after having filled the vials and removed the water under vacuum. Parenteral suspensions are prepared in substantially the same manner, except that the compound can be suspended in the vehicle instead of being dissolved, and sterilized by exposure to ethylene oxide before suspending in the sterile vehicle. Advantageously, a surfactant or wetting agent can be included in the composition to facilitate uniform distribution of the compound of the invention.

In order to increase bioavailability the compounds can be pharmaceutically formulated in liposomes or in nanoparticles. Acceptable liposomes can be neutral, negatively, or positively charged, the charge being a function of the charge of the liposome components and pH of the liposome solution. Liposomes can be normally prepared using a mixture of Phospholipids and cholesterol. Suitable phospholipids include phosphatidylcholine, phosphatidylethanolamine, phosphatidic acid, phosphotidylglycerol, phosphatidylinositol. Polyethylene glycol can be added to improve the blood circulation time of liposomes. Acceptable nanoparticles include albumin nanoparticles and gold nanoparticles.

For buccal or sublingual administration the compositions may be tablets, lozenges, pastilles, or gel.

The compounds can be pharmaceutically formulated as suppositories or retention enemas, e.g. containing conventional suppositories bases such as cocoa butter, polyethylene glycol, or other glycerides, for a rectal administration.

Another means of administering the compounds of the invention regards topical treatment. Topical formulations can contain for example ointments, creams, lotions, gels, solutions, pastes and/or can contain liposomes, micelles and/or microspheres. Examples of ointments include oleaginous ointments such as vegetable oils, animal fats, semisolid hydrocarbons, emulsifiable ointments such as hydroxystearin sulfate, anhydrous lanolin, hydrophilic petrolatum, cetyl alcohol, glycerol monostearate, stearic acid, water soluble ointments containing polyethylene glycols of various molecular weights. Creams, as known to formulation experts, are viscous liquids or semisolid emulsions, and contain an oil phase, an emulsifier and an aqueous phase. The oil phase generally contains petrolatum and an alcohol such as cetyl or stearic alcohol. Formulations suitable for topical administration to the eye also include eye drops, wherein the active ingredient is dissolved or suspended in a suitable carrier, especially an aqueous solvent for the active ingredient.

A further method of administering the compounds of the invention regards transdermal delivery. Topical transdermal formulations comprise conventional aqueous and non-aqueous vectors, such as creams, oils, lotions or pastes or can be in the form of membranes or medicated patches.

A reference for the formulations is the book by Remington (33).

The compounds of the present invention may be employed for use in the treatment and/or prevention of the above mentioned conditions alone as a sole therapy or in combination with other therapeutic agents either by separate administrations, or by including the two or more active principles in the same pharmaceutical formulation. The compounds may be administered simultaneously or sequentially.

The other therapeutic agents may be any antiviral drugs or approved drugs for the treatment of the HIV-1 infections as part of the highly active antiretroviral therapy (HAART). Non-exhaustive examples of suitable additional agents include in particular drugs belonging to the group of: a nucleoside or a non-nucleoside analogue reverse-transcriptase inhibitor, a nucleotide analogue reverse-transcriptase inhibitor.

The other therapeutic agents may be approved drugs for the treatment of the HCV infections as part of combinatorial multidrug anti-HCV therapy. Non-exhaustive examples of suitable additional agents include in particular drugs belonging to the group of: a NS3/4A serine protease inhibitor, a NS5B polymerase inhibitor or interferon alpha.

The combination can be administered as separate compositions (simultaneous, sequential) of the individual components of the treatment or as a single dosage form containing all agents. When the compounds of this invention are in combination with others active ingredients, the active ingredients may be separately formulated into single-ingredient preparations of one of the above-described forms and then provided as combined preparations, which are given at the same time or different times, or may be formulated together into a two- or more ingredients preparation.

Compounds of general formula I and II may be administered to a patient in a total daily dose of, for example, from 0.001 to 1000 mg/kg body weight daily. Dosage unit compositions may contain such amounts of submultiples thereof to make up the daily dose. The compound may also be administered weekly or any other day. The determination of optimum dosages for a particular patient is well known to one skilled in the art. As is common practice, the compositions are normally accompanied by written or printed instructions for use in the treatment in question.

Compounds of the invention may be prepared in a variety of ways. These processes form further aspects of the invention.

The present invention is illustrated by means of non limiting examples.

DETAILED DESCRIPTION OF THE INVENTION

Material and Methods
Synthesis
General

Reagents were obtained from commercial suppliers (for example Sigma-Aldrich). All commercially available chemicals were used as purchased without further purification. CH$_3$CN was dried over calcium hydride, CH$_2$Cl$_2$ was dried over calcium hydride and THF was dried over Na/benzophenone prior to use while DMF was bought already anhydrous. Anhydrous reactions were run under a positive pressure of dry N$_2$ or argon. TLC was carried out using Merck TLC plates silica gel 60 F254. Chromatographic purifications were performed on columns packed with Merk 60 silica gel, 23-400 mesh, for flash technique. $^1$H-NMR and $^{13}$C-NMR spectra were recorded at 400 MHz on a Brucker Avance DPX400 spectrometer. Chemical shifts are reported relative to tetramethylsilane at 0.00 ppm. $^1$H patterns are described using the following abbreviations: s=singlet, d=doublet, t=triplet, q=quartet, quint=quintet, sx=sextet, sept=septet, m=multiplet, br=broad signal, br s=broad singlet.

Mass spectra (MS) data were obtained using an Agilent 1100 LC/MSD VL system (G1946C) with a 0.4 mL/min flow rate using a binary solvent system 25 of 95:5 methyl alcohol/water. UV detection was monitored at 254 nm. Mass spectra were acquired in positive and negative mode scanning over the mass range.

Microwave Irradiation Experiments

Microwave irradiation experiments were conducted using CEM Discover Synthesis Unit (CEM Corp., Matthews, N.C.). The machine consists of a continuous focused microwave power delivery system with operator selectable power output from 0 to 300 W. The temperature of the contents vessels was monitored using calibrated infrared temperature control mounted under the reaction vessel. All the experiments were performed using a stirring option whereby the contents of the vessels are stirred by means of rotating magnetic plate located below the floor of the microwave cavity and a Teflon-coated magnetic stir bar in the vessel.

In the present invention the following abbreviations are used:

| | |
|---|---|
| NMR (Nuclear Magnetic Resonance) | $^1$H (proton) |
| MHz (Megahertz) | $^{13}$C (carbon) |
| $^{19}$F (fluorine) | LC-MS (Liquid Chromatography Mass Spectrum) |
| Hz (Hertz) | HPLC (High Performance Liquid Chromatography) |
| s (seconds) | min (minutes) |
| h (hour(s)) | mg (milligrams) |
| g (grams) | μl (microlitres) |
| mL (millilitres) | mmol (millimoles) |
| nm (nanometers) | μM (micromolar) |
| M (molarity) | SI selectivity index |
| DMEM (Dulbecco's Modified Eagle's Medium) | o.n. (overnight) |
| BOC or boc (tert-butyloxycarbonyl) | DMF (dimethylformamide) |
| DCM (dichloromethane) | ACN (acetonitrile) |
| Pyr Pyridine | RT or rt or r.t. (room temperature) |
| DMF (dimethylformamide) | DMSO (dimethyl sulfoxide) |
| DMSO d-$_6$ (deuterated dimethyl sulfoxide) | MeOH (methanol) |
| MeOD-d$_4$ (deuterated methanol) | CDCl$_3$-d (deuterated chloroform) |
| Et$_2$O (diethyl ether) | EtOAc or EA (ethyl acetate) |
| EtOH (ethanol) | AcOH (acetic acid) |
| iPrOH (isopropanol) | D$_2$O (deuterated water) |
| TEA (triethylamine) | THF (tetrahydrofuran) |
| TMSN$_3$ (Trimethylsilyl Azide) | t-BuONO (tert-Butyl nitrite) |
| PE (petroleum ether) | t-Bu (tert-butyl) |
| t$_R$ (retention time) | Cmpd. (compound) |
| wt wild type | MTBE (methyl tert-butyl ether) |

Except where indicated otherwise, all temperatures are expressed in ° C. (degrees centigrade) or K (Kelvin).

The yields were calculated assuming that products were 100% pure if not stated otherwise.

EXAMPLES

Example 1

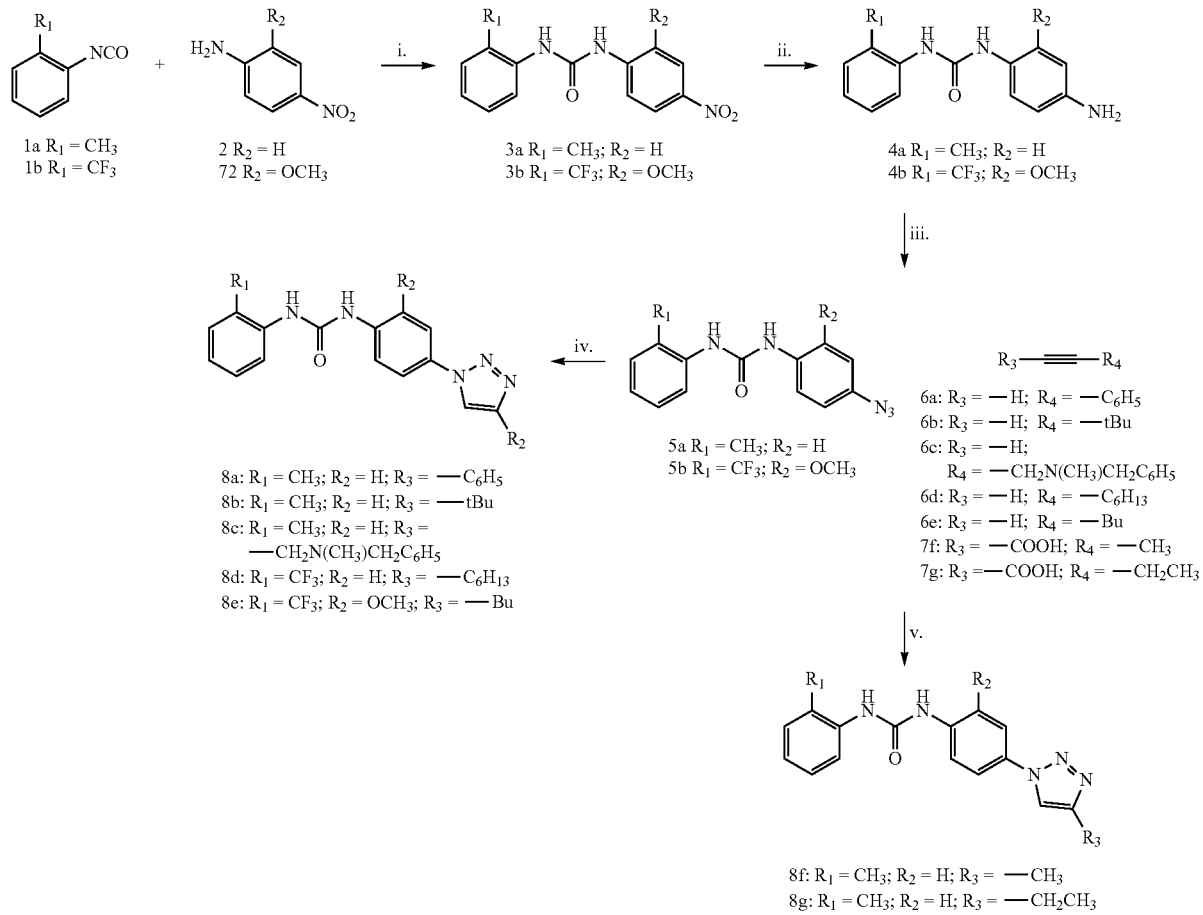

Reagents and conditions: i. o-tolyl-isocyanate CH₂Cl₂, 5 h reflux, ii. H₂, Pd/C, MeOH, 1 h; iii. a) t-BuONO, CH₃CN, 20 min. 0° C; b) TMSN₃, CH₃CN, 2 h r.t.; iv. Alkyne 6a-c, CuSO₄·5 H₂O, sodium ascorbate, H₂O tBuOH (1:1), MW 120° C., 10 min.; v. alkynoic acid 7d-e, CuCl, L-Proline, K₂CO₃, DMSO (dry) MW 65° C., 20 min.

General Procedure for the Synthesis of Compounds 3a and 3b:

The opportune aniline 2 or 72 (3.62 mmol) was added to a solution of the opportune isocyanate 1 or 1a (5.43 mmol) in anhydrous $CH_2Cl_2$ (10 mL) in one portion. The solution was stirred for 4 hours at 60° C. under a nitrogen atmosphere. The yellow precipitate was filtered, washed with cool DCM and petroleum ether and dried under high vacuum to afford the desired product as a white solid.

1-(4-nitrophenyl)-3-o-tolylurea (3a). Yield=63%; $^1$H NMR (400 MHz, DMSO d-$_6$): δ 9.7 (s, 1H, NH), 8.19-8.16 (d, J=9.2 Hz, 2H), 8.13 (s, 1H), 7.78-7.76 (d, J=8.0 Hz, 1H), 7.69-7.66 (d, J=12.0 Hz, 2H), 7.19-7.13 (m, 2H), 7.00-6.97 (t, 1H, J=12.0 Hz), 2.24 (s, 3H) ppm. MS (ESI) m/z 270 [M−H]⁻, 306 [M+Cl]⁻.

1-(2-methoxy-4-nitrophenyl)-3-(2-(trifluoromethyl)phenyl)urea (3b): Yield=56%; $^1$H NMR (400 MHz, MeOD): δ8.40-8.38 (d, J=8.8 Hz, 1H), 7.95-7.91 (m, 2H), 7.74-7.73 (d, J=2.0 Hz, 1H), 7.66-7.64 (d, J=8.0 Hz, 1H), 7.61-7.57 (t, J=7.8 Hz, 1H), 7.45 (s, 1H), 3.97 (s, 3H) ppm. MS (ESI) m/z 354 [M−H]⁻.

General Procedure for the Synthesis of 4a and 4b:

The opportune Urea 3a or 3b (1.10 mmol) was solubilized in 30 mL of anhydrous MeOH, and Palladium on charcoal (50 mg) was added. The reaction mixture was stirred under Hydrogen atmosphere for 1 h, then the mixture was filtered off on a celite pad, the solvent evaporated at reduced pressure and the residue crystallized from acetonitrile.

1-(4-aminophenyl)-3-o-tolylurea (4a). Yield=70%; white solid. $^1$H NMR (400 MHz, DMSO d-$_6$): δ 8.48 (s, 1H), 7.83-7.81 (d, J=8.0 Hz, 2H), 7.67 (s, 1H), 7.15-7.05 (m, 4H), 6.89-6.87 (d J=8.0 Hz, 1H), 6.50-6.48 (d, J=8.0 Hz, 2H), 4.72 (s, 2H), 2.20, (s, 3H) ppm. MS (ESI) m/z 242.0 [M+H]+, 264 [M+Na]⁺, 505 [2M+Na]⁺.

1-(4-amino-2-methoxyphenyl)-3-(2-(trifluoromethyl)phenyl)urea (4b): Yield=70%; white solid. $^1$H NMR (400 MHz, MeOD): δ 8.04-8.02 (d, J=8.0 Hz, 1H), 7.49-7.44 (m, 2H), 7.38-7.36 (d, J=8.0 Hz, 1H), 7.10-7.06 (t, J=7.6 Hz, 1H), 6.27-6.26 (d, J=6.0 Hz, 2H), 3.74 (s, 3H) ppm. MS (ESI) m/z 326 [M+H]⁺.

General Procedure for the Synthesis of 5a and 5b:

The opportune Aniline 4a or 4b (0.41 mmol) was dissolved in $CH_3CN$ and cooled to 0° C. in an ice-salt bath. To this stirred solution, was added tBuONO (0.61 mmol), and the mixture was stirred for 10 min, after this time, TMSN₃ (65 μL, 0.49 mmol) was added dropwise, during 10 minutes, and the resulting brown solution was stirred at r.t. One hour later the solvent was removed at reduced pressure and the residue was purified by flash chromatography on silica gel 1-(4-azidophenyl)-3-o-tolylurea (5a). (Purification Eluent: DCM-MeOH 9:1). Yield 67%. $^1$H NMR (400 MHz, CDCl$_3$-d) δ 9.10 (s, 1H), 7.91 (s, 1H), 7.80-7.78 (d, J=8.0 Hz, 1H), 7.50-7.48 (d, J=8.0 Hz, 2H), 7.16-7.19 (m, 2H), 7.04-7.02 (d, J=8.0 Hz, 2H), 7.95-7.91 (t, J=8.0 Hz, 1H), 2.22 (s, 3H) ppm. MS (ESI) m/z 267 [M+Na]$^+$, 557 [2M+Na]$^+$.

1-(4-azido-2-methoxyphenyl)-3-(2-(trifluoromethyl)phenyl)urea (5b): (Purification Eluent: PE-EA=5:3). Yield=98%; yellow solid. $^1$H NMR (400 MHz, MeOD-d$_4$): δ 8.41 (s, 1H), 8.23-8.18 (t, J=9.0 Hz, 1H), 8.06-8.00 (m, 2H), 7.62-7.55 (m, 2H), 7.24-7.20 (t, J=7.6 Hz, 1H), 3.84 (s, 3H) ppm.

General Procedure for the Preparation of Compounds 8 a-e

The appropriate alkyne (0.10 mmol) and azide 5 (25 mg, 0.09 mmol) were suspended in a 1:1 mixture of water and t-BuOH (1.5 mL each) in a 10 mL glass vial equipped with a small magnetic stirring bar. To this, was added sodium ascorbate (0.1 equiv) and copper(II) sulfate pentahydrate (0.10 mmol). The mixture was then heated for 10 min. at 125° C. under microwave irradiation, using an irradiation power of 300 W. After this time the precipitate was filtered-off and purified on silica, to give final products 8a, 8b, 8c, 8d or 8e.

1-(4-(4-phenyl-1H-1,2,3-triazol-1-yl)phenyl)-3-o-tolylurea (8a). The residue was purified by flash chromatography on silica gel (DCM/MeOH 98:2). Yield 97%, white solid. $^1$H NMR (400 MHz, DMSO d-$_6$): δ 9.42 (s, 1H), 9.18 (s, 1H), 8.08 (s, 1H), 7.93-7.91 (d, J=8.0 Hz, 2H), 7-85-7-80 (m, 3H), 7.70-7.68 (d, J=8.0 Hz, 2H), 7.50-7.46 (m, 3H), 7.38-7.34 (t, J=8.0 Hz, 1H), 7.18-7.14 (m, 2H), 6.97-6.94 (t, J=12.0 Hz, 1H), 2.25 (s, 3H) ppm. $^{13}$C-NMR (100 MHz, DMSO d-$_6$): δ 153.09, 148.24, 140.57, 137.65, 131.33, 130.87, 130.71, 129.45, 128.63, 126.66, 125.79, 123.48, 121.83, 121.35, 119.88, 119.12 ppm. MS (ESI) m/z 368 [M−H]$^−$, 404 [M+Cl]$^−$.

1-(4-(4-tert-butyl-1H-1,2,3-triazol-1-yl)phenyl)-3-o-tolylurea (8b). The residue was purified by flash chromatography on silica gel (DCM/MeOH 98:2). Yield 91%, white solid. $^1$H NMR (400 MHz, DMSO d-$_6$): δ 9.23 (s, 1H), 8.45 (s, 1H), 7.96 (s, 1H), 7.80-7.75 (m, 3H, Ph), 7.63-7.61 (d, J=8.0 Hz, 2H), 7.17-7.11 (m, 2H), 6.96-6.93 (t, J=12.0 Hz, 1H), 2.23 (s, 3H), 1.32 (s, 9H) ppm. $^{13}$C-NMR (100 MHz, DMSO d-$_6$): δ158.38, 155.30, 139.59, 135.73, 131.87, 131.75, 130.66, 126.64, 125.48, 124.84, 121.22, 120.18, 117, 50, 30.33, 17.83 ppm. MS (ESI) m/z 348 [M−H]$^−$, 384 [M+Cl]$^−$.

1-(4-(4-methanamine,N-[(phenyl)methyl]-N-methyl-1H-1,2,3-triazol-1yl)phenyl)-3-o-tolylurea (8c). The residue was purified by flash chromatography on silica gel (DCM/MeOH 98:2). Yield 90%, white solid. $^1$H NMR (400 MHz CDCl$_3$-d): δ 8.43 (s, 1H), 7.80 (s, 1H), 7.57 (s, 1H), 7.51-7.43 (m, 6H), 7.31-7.23 (m, 4H), 7.12-7.07 (m, 2H), 7.00-6.99 (t, J=12.0 Hz 1H), 3.75 (s, 2H), 3.58 (s, 2H), 2.25 (s, 3H), 2.14 (s, 1H) ppm. $^{13}$C-NMR (100 MHz CDCl$_3$-d): δ 154.31, 145.73, 139.98, 137.90, 135.90, 131.48, 130.60, 129.15, 128.39, 127.36, 126.58, 125.26, 124.61, 121.13, 120.08, 61.58, 51.88, 42.11, 17.89 ppm. MS (ESI) m/z 425.0 [M−H]$^−$, 461.1 [M+Cl]$^−$.

1-(4-(4-hexyl-1H-1,2,3-triazol-1-yl)phenyl)-3-(2-(trifluoromethyl)phenyl)urea) (8d). The residue was purified by flash chromatography on silica gel (DCM/MeOH 98:2). Yield 83%, white solid. $^1$H NMR (400 MHz, MeOD): δ 8.16 (s, 1H), 7.93-7.91 (d, J=8.0 Hz, 1H), 7.71-7.69 (dd, J=8.0 Hz 2H), 7.63-7.61 (dd, J=8.0 Hz, 2H), 7.59-7.55 (m, 4H), 7.27-7.23 (t, J=8.0 Hz, 1H), 2.74-2.70 (t, J=8.0 Hz 2H), 1.70-1.65 (m, 2H), 1.37-1.31 (m, 6H), 0.87 (s, 3H) ppm. $^{13}$C-NMR (100 MHz, MeOD): δ 153.58, 148.75, 139.86, 135.97, 132.58, 131.99, 125.99, 125.66, 124.06, 122.64, 120.74, 119.77, 119.30, 31.30, 29.08, 28.57, 24.92, 22.21, 12.98 ppm. MS (ESI) m/z 432 [M+H]$^+$, 454 [M+Na]$^+$.

1-(4-(4-butyl-1H-1,2,3-triazol-1-yl)-2-methoxyphenyl)-3-(2-(trifluoromethyl)phenyl)urea (8e): The residue was purified by flash chromatography on silica gel (PE/EA 7:3). Yield 60%, white solid. $^1$H NMR (400 MHz, CDCl$_3$): δ 8.21-8.19 (d, J=8.8 Hz, 1H), 7.91-7.89 (d, J=8.4 Hz, 2H), 7.63 (s, 1H), 7.50-7.46 (t, J=7.8 Hz, 1H), 7.20-7.15 (m, 2H), 7.04-7.03 (d, J=1.6 Hz, 1H), 3.79 (s, 3H), 2.75-2.71 (t, J=7.6 Hz, 2H), 1.62-1.53 (m, 3H), 0.90-0.88 (d, J=6.0 Hz, 2H) ppm. $^{13}$C-NMR (100 MHz, CDCl$_3$): δ 154.00, 149.16, 135.94, 133.03, 128.55, 125.87, 124.30, 120.04, 118.70, 112.20, 103.47, 56.21, 38.30, 28.00, 23.74, 22.40 ppm. MS (ESI) m/z 448 [M+H]$^+$.

General Procedure for the Preparation of Compounds 8 f and g

L-Proline (1.9 mg, 0.01 mmol), CuCl (8.2 mg, 0.08 mmol), K$_2$CO$_3$, (13.7 mg, azide (20 mg, 0.08 mmol), the appropriate alkynoic acid (0.08 mmol), were sequentially added to a 10 mL glass vial equipped with a magnetic stirrer. The vial was closed with a septum and irradiated at 65° C. After 15 min., the mixture was partitioned between water 20 mL and AcOEt (40 mL), the organic layer was separated, dried (Na$_2$SO$_4$), and solvent removed in vacuo to furnish a brown residue, that was purified by flash chromatography on silica gel (DCM-MeOH 98:2) to give the desired triazole compounds 8e or 8f.

1-(4-(4-methyl-1H-1,2,3-triazol-1-yl)phenyl)-3-o-tolylurea (8f). The residue was purified by flash chromatography on silica gel (DCM/MeOH 98:2). Yield 77%, white solid. Yield $^1$H NMR (400 MHz, MeOD-d$_4$): δ8.15 (s, 1H), 7.72-7.69 (d, J=8.0 Hz, 2H), 7.64-7.62 (m, 3H), 7.21-7.15 (m, 2H), 7.05-7.02 (t, J=8.0 Hz, 1H), 2.38 (s, 1H), 2.30 (s, 3H) ppm. $^{13}$C-NMR (100 MHz, MeOD-d$_4$): δ53.20, 151.00, 141.20, 138.2, 133.01, 131.8, 126.08, 124.23, 123.13, 120.77, 120.28, 119.23, 16.60, 9.06 ppm. MS (ESI) m/z 306 [M−H]$^−$, 342 [M+Cl]$^−$.

1-(4-(4-ethyl-1H-1,2,3-triazol-1-yl)phenyl)-3-o-tolylurea (8g). The residue was purified by flash chromatography on silica gel (DCM/MeOH 98:2). Yield 82%, white solid. $^1$H NMR (400 MHz, MeOD-d$_4$): δ8.21 (s, 1H), 7.73-7.71 (d, J=8.0 Hz, 2H), 7.65-7.63 (m, 3H), 7.21-7.15 (m, 2H), 7.05-7.02 (t, J=8.0 Hz, 1H), 2.82-2.76 (q, J=6.0 Hz, 2H), 2.30 (s, 3H), 1.35-1.31 (t, 8.0 Hz, 3H), ppm. $^{13}$C-NMR (100 MHz, MeOD-d$_4$): δ152.60, 149.76, 140.30, 137.38, 131.86, 130.21, 128.32, 126.25, 123.33, 121.92, 120.59, 118.95, 118.77, 18.75, 17.20, 13.17 ppm. MS (ESI) m/z 320 [M−H]$^−$, 356 [M+Cl]$^−$.

Example 2

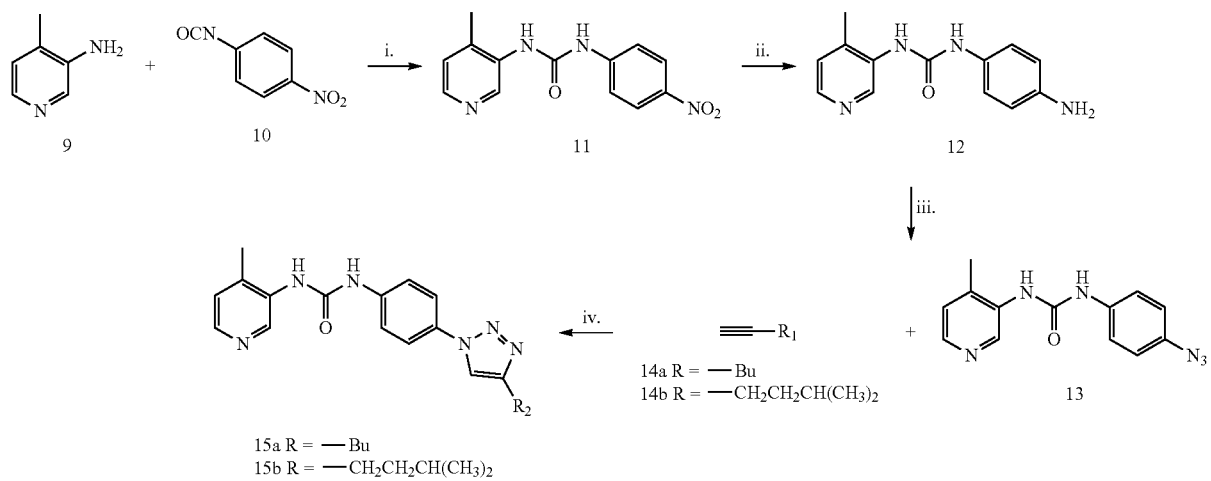

Reagents and conditions: i. CH$_2$Cl$_2$, 6 h reflux ii. H$_2$, Pd/C, MeOH; iii. NaNO$_2$, H$_2$SO$_4$ 25%, 20 min. 0° C.; iv. NaN$_3$ 2 h r.t.; v. alkyne, CuSO$_4$·5 H$_2$O, sodium ascorbate, H$_2$O tBuOH (1:1), MW 80° C., 5 min.

1-(4-methylpyridin-3-yl)-3-(4-nitrophenyl)urea (11). 9 (500 mg, 3.62 mmol) was added to a solution of o-tolyl-isocyanate 10 (673 µL, 5.43 mmol) in anhydrous CH$_2$Cl$_2$ (10 mL) in one portion. The solution was stirred for 6 hours at r.t under a nitrogen atmosphere. The yellow precipitate was filtered, washed with cool DCM and petroleum ether and dried under high vacuum to afford the desired product 11 as a white solid. Yield=93%; $^1$H NMR (400 MHz, DMSO d-$_6$): δ 9.7 (s, 1H, NH), 8.19-8.16 (d, J=9.2 Hz, 2H), 8.13 (s, 1H), 7.78-7.76 (d, J=8.0 Hz, 1H), 7.69-7.66 (d, J=12.0 Hz, 2H), 7.19-7.13 (m, 2H), 7.00-6.97 (t, 1H, J=12.0 Hz), 2.24 (s, 3H) ppm. MS (ESI) m/z 272 [M+H]$^+$, 306 [M+Cl]$^-$.

1-(4-methylpyridin-3-yl)-3-(4-nitrophenyl)urea (12). Urea 11 (500 mg, 1.8 mmol) was solubilized in 30 mL of anhydrous MeOH, and 10% Palladium on charcoal (50 mg) was added. The reaction mixture was stirred under Hydrogen atmosphere for 2 hr, then the mixture was filtered off on a celite pad, and purified by flash chromatography on silica gel (DCM-MeOH 98:2). Yield=80%; white solid. $^1$H NMR (400 MHz, DMSO d-$_6$): δ 8.48 (s, 1H), 7.83-7.81 (d, J=8.0 Hz, 2H), 7.67 (s, 1H), 7.15-7.05 (m, 4H), 6.89-6.87 (d, J=8.0 Hz, 1H), 6.50-6.48 (d, J=8.0 Hz, 2H), 4.72 (s, 2H), 2.20, (s, 3H) ppm. MS (ESI) m/z 242.0 [M+H]+, 264 [M+Na]$^+$, 505 [2M+Na]$^+$.

1-(4-azidophenyl)-3-(4-methylpyridin-3-yl)urea (13). To a stirred suspension of amine 12 (400 mg, 1.6 mmol) in a 25% aq. solution of H$_2$SO$_4$, at 0° C., was added NaNO$_2$ (227.9 mg, 3.3 mmol) in water, dropwise during 20 min. After this time a solution of NaN$_3$ (208 mg, 3.2 mmol) in water (3 mL) was added dropwise during 20 min at 0° C., then the reaction mixture was stirred at r.t. Four hours later a solution of aq. NaOH was added and the pH basified until 10. The reaction mixture was then extracted with EtOAc (3×40 mL), washed with brine, and dried over anhydrous Na$_2$SO$_4$. The solvent was removed at reduced pressure and the residue was purified by flash chromatography on silica gel (DCM-MeOH 9:1). Yield 67%. $^1$H NMR (400 MHz, CDCl$_3$-d) δ 9.10 (s, 1H), 7.91 (s, 1H), 7.80-7.78 (d, J=8.0 Hz, 1H), 7.50-7.48 (d, J=8.0 Hz, 2H), 7.16-7.19 (m, 2H), 7.04-7.02 (d, J=8.0 Hz, 2H), 7.95-7.91 (t, J=8.0 Hz, 1H), 2.22 (s, 3H) ppm. MS (ESI) m/z 267 [M+Na]$^+$, 557 [2M+Na]$^+$.

General Procedure for the Preparation of Compounds 15a-b

The appropriate alkyne (0.10 mmol) and azide 13 (25 mg, 0.09 mmol) were suspended in a 1:1 mixture of water and t-BuOH (1.5 mL each) in a 10 mL glass vial equipped with a small magnetic stirring bar. To this, sodium ascorbate (0.1 equiv) and copper(II) sulfate pentahydrate (0.10 mmol) were added. The mixture was then heated for 5 min. at 80° C. under microwave irradiation, using an irradiation power of 300 W. After this time the precipitate was filtered-off and purified on silica, to give final products 15a or 15b.

1-(4-(4-butyl-1H-1,2,3-triazol-1-yl)phenyl)-3-(4-methylpyridin-3-yl)urea (15a). The residue was purified by flash chromatography on silica gel (DCM/MeOH 98:2). Yield 68%, white solid. $^1$H NMR (400 MHz, MeOD-d$_4$): δ8.87 (s, 1H), 8.20 (s, 1H), 8.15-8.14 (d, J=4 Hz, 1H), 7.74-7.71 (d, J=8.0 Hz, 2H), 7.65-7.63 (J=8.0 Hz, 2H), 7.30-7.29 (d, J=4 Hz, 1H), 4.70-4.67 (t, J=7.0 Hz, 2H), 2.36 (s, 3H), 2.06-1.99 (quint, J=7.0 Hz, 2H), 1.41-1.36 (q, J=6.0 Hz, 2H), 1.00-0.96 (q, J=8.0 Hz, 2H) ppm. $^{13}$C-NMR (100 MHz, MeOD-d$_4$): δ164.69, 153.67, 143.82, 143.19, 141.39, 140.12, 134.50, 127.09, 125.50, 121.37, 118.72, 50.61, 30.06, 18.51, 14.20, 11.30 ppm. MS (ESI) m/z 320 [M−H]$^-$, 356 [M+Cl]$^-$.

1-(4-(4-isopentyl-1H-1,2,3-triazol-1-yl)phenyl)-3-(4-methylpyridin-3-yl)urea (15b). The residue was purified by flash chromatography on silica gel (DCM/MeOH 98:2). Yield 74%, white solid. $^1$H NMR (400 MHz, MeOD-d$_4$): δ8.80 (s, 1H), 8.20 (s, 1H), 8.15-8.14 (d, J=4 Hz, 1H), 7.84-7.81 (d, J=8.0 Hz, 2H), 7.67-7.65 (J=8.0 Hz, 2H), 7.34-7.31 (d, J=4 Hz, 1H), 2.78-2.74 (t, J=8.0 Hz, 2H), 2.35 (s, 3H), 1.63-1.60 (m, 3H), 0.97-0.95 (d, J=8.0 Hz, 2H) ppm. $^{13}$C-NMR (100 MHz, MeOD-d$_4$): δ64.69, 153.67, 143.82, 143.19, 141.39, 140.12, 134.50, 127.09, 125.50, 121.37, 118.72, 38.28, 27.38, 22.87, 21.32, 16.59 ppm. MS (ESI) m/z 363 [M−H]$^-$, 399 [M+Cl]$^-$.

Example 3
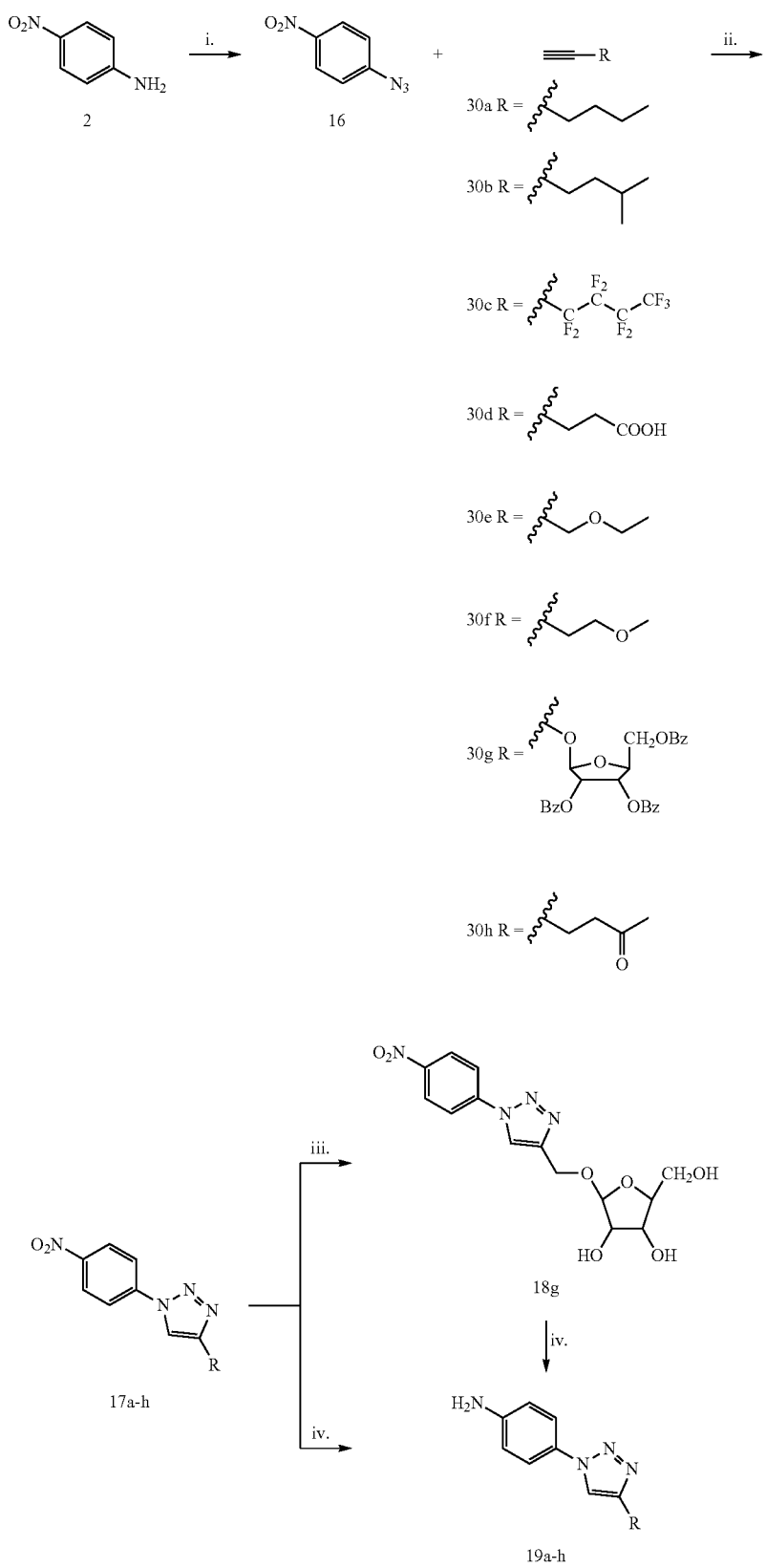

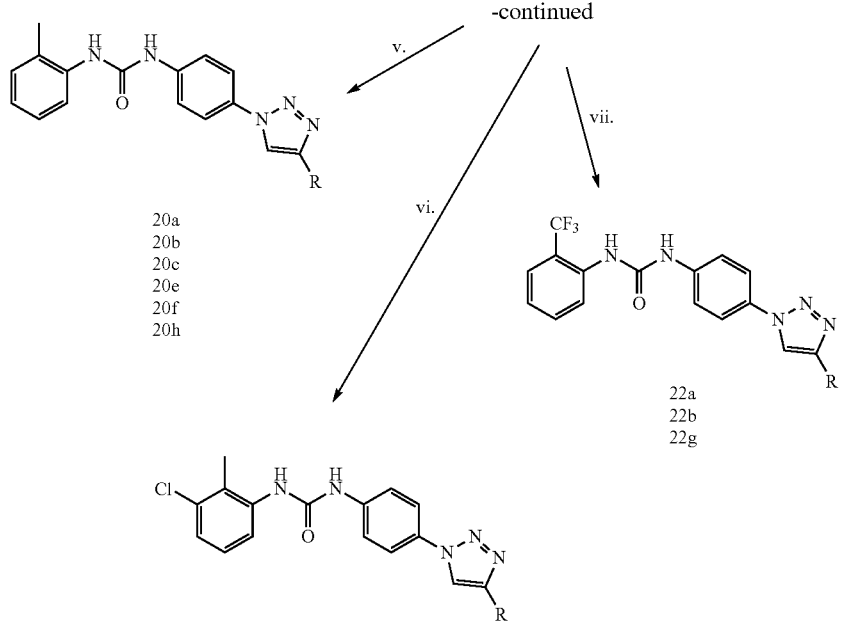

Reagents and conditions: i. a) t-BuONO, CH₃CN, 20 min. 0° C.; b) TMSN₃, CH₃CN, 2 h r.t.; ii. Alkyne 30a-g, CuSO₄•5 H₂O, sodium ascorbate, H₂O tBuOH (1:1). MW 120° C., 10 min.; iii. MeOH/NH₄OH 3:1, r.t., 24 h.; iv. H₂, Pd/C, MeOH, 1 h, v. o-tolyl isocyanate, CH₂Cl₂, 12 h, r.t.; vi. 2-(Trifluoromethyl)phenyl isocyanate, CH₂Cl₂, CH₂Cl₂ 12 h, vii. 5-Chloro-2-methylphenyl isocyanate, CH₂Cl₂, 12 h, r.t.

1-azido-4-nitrobenzene (16). 4-nitroaniline 2 (1000 mg, 7.24 mmol) was dissolved in CH₃CN and cooled to 0° C. in an ice-salt bath. To this stirred solution, was added tBuONO (1033 µL, 8.69 mmol), and the mixture was stirred for 10 min, after this time, TMSN₃ (1441 µL, 10.86 mmol) was added dropwise, during 10 minutes, and the resulting brown solution was stirred at r.t. One hour later the solvent was removed at reduced pressure and the residue was purified by flash chromatography on silica gel (EP-EtOAc 9:1). Yield 99%. ¹H NMR (400 MHz, CDCl₃-d) δ 9.10 (s, 1H), 7.91 (s, 1H), 7.80-7.78 (d, J=8.0 Hz, 1H), 7.50-7.48 (d, J=8.0 Hz, 2H), 7.16-7.19 (m, 2H), 7.04-7.02 (d, J=8.0 Hz, 2H), 7.95-7.91 (t, J=8.0 Hz, 1H), 2.22 (s, 3H) ppm. MS (ESI) m/z 165 [M+H]⁺, 188 [M+Na]⁺.

General Procedure for the Preparation of Compounds 17a-h

The appropriate alkyne 30a-h (4.34 mmol) and azide 16 (594.11 mg, 3.62 mmol) were suspended in a 1:1 mixture of water and t-BuOH (1.5 mL each) in a 10 mL glass vial equipped with a small magnetic stirring bar. To this, was added sodium ascorbate (1.81 mmol) and copper(II) sulfate pentahydrate (1.81 mmol). The mixture was then heated for 10 min. at 120° C. under microwave irradiation, using an irradiation power of 300 W. After this time the precipitate was filtered-off and purified on silica, to give the desired triazole compounds 17a, 17b, 17c, 17d, 17e, 17f, 17g or 17h.

4-butyl-1-(4-nitrophenyl)-1H-1,2,3-triazole (17a). (Purification eluent: DCM/MeOH 98:2). Yield 80%, yellow solid. Yield ¹H NMR (400 MHz, MeOD-d₄): δ8.48 (s, 1H), 8.42-8.44 (d, J=8.0 Hz, 2H), 8.12-8.10 (d, J=8.0 Hz, 2H), 2.80-2.77 (t, –J=7.6 Hz, 2H), 1.74-1.78 (q, J=7.3 Hz, 2H), 1.46-1.40 (q, J=7.3 Hz, 2H), 0.99-0.952 (t, J=7.2 Hz, 3H) ppm. MS (ESI) m/z 245 [M–H]⁻, 281 [M+Cl]⁻.

4-isopentyl-1-(4-nitrophenyl)-1H-1,2,3-triazole (17b). (Purification eluent: PE/EtOAc 9:1). Yield 86%, yellow solid. ¹H NMR (400 MHz, MeOD-d₄): δ8.45-8.39 (m, 3H), 8.11-8.09 (dd, J=8.0 Hz, 2H), 2.81-2.77 (t, 7.6 Hz, 2H), 1.64-1.61 (m, 3H), 0.98-0.96 (d, J=7.4 Hz, 2H) ppm. MS (ESI) m/z 260.9 [M+H]⁺.

1-(4-nitrophenyl)-4-(perfluorobutyl)-1H-1,2,3-triazole (17c). (Purification eluent: PE/EA 95:5). Yield 73%, white solid. ¹H NMR (400 MHz, CDCl₃-d): δ8.48-8.46 (dd, J=8.1 Hz, 2H), 8.42 (s, 1H), 8.05-8.03 (dd, J=8.1 Hz, 2H) ppm. MS (ESI) m/z 442.9 [M+Cl]⁻.

3-(1-(4-nitrophenyl)-1H-1,2,3-triazol-4-yl)propanoic acid (17d). (Purification eluent: DCM/MeOH 98:2). Yield 70%, yellow solid. ¹H NMR (400 MHz, Acetone-d6): δ 8.52 (s, 1H), 8.43-8.41 (dd, J=8.0 Hz, 2H), 8.18-8.16 (dd, J=8.0 Hz, 2H), 3.06-3.03 (t, J=12.0 Hz, 2H), 2.78-2.74 (t, J=8.0 Hz, 2H) ppm. MS (ESI) m/z 261 [M–H]⁻.

4-(2-ethoxymethyl)-1-(4-nitrophenyl)-1H-1,2,3-triazole (17e). (Purification eluent: DCM/MeOH 98:2). Yield 80%, light yellow solid. ¹H NMR (400 MHz CDCl₃-d): δ 8.34-8.31 (d, J=8.8 Hz, 2H), 8.14 (s, 1H), 7.95-7.93 (d, J=8.8 Hz, 2H), 4.65 (s, 2H), 3.61-3.56 (q, J=6.9 Hz, 2H), 1.20-1.16 (t, J=7 Hz, 3H) ppm. MS (ESI) m/z 283.2 [M+Cl]⁻.

4-(2-methoxyethyl)-1-(4-nitrophenyl)-1H-1,2,3-triazole (17f). (Purification eluent: DCM/MeOH 98:2). Yield 78%, pale yellow solid. ¹H NMR (400 MHz, CDCl₃-d): δ 8.40-8.38 (d, J=8.0 Hz, 2H), 7.97-7.95 (d, J=8.4 Hz, 2H), 3.74-3.71 (t, J=6.0 Hz, 2H), 3.38 (s, 3H), 3.10-3.07 (t, J=6.0 Hz, 2H) ppm. MS (ESI) m/z 283.2 [M+Cl]⁻.

2-((benzoyloxy)methyl)-5-((1-(4-nitrophenyl)-1H-1,2,3-triazol-4-yl)methoxy)tetrahydrofuran-3,4-diyl dibenzoate (17g). (Purification eluent: DCM/MeOH 98:2). Yield 86%, foam. ¹H NMR (400 MHz, CDCl₃-d): δ 8.31-8.29 (d, J=8.0 Hz, 2H), 8.12 (s, 1H), 7.99-7.95 (m, 4H), 7.92-7.89 (d, J=8.1 Hz, 2H), 7.85-7.83 (d, J=8.0 Hz, 2H), 7.54-7.29 (m, 5H), 7.29-7.25 (m, 4H), 5.87-5.86 (m, 1H), 5.73-5.72 (m, 1H), 5.43 (s, 1H), 4.99-4.96 (m, J=12 Hz, 1H), 4.84-4.74 (m, 3H), 4.58-4.54 (m, 1H) ppm. MS: m/z 270.9 [M+Na]⁺

4-(1-(4-nitrophenyl)-1H-1,2,3-triazol-4-yl)butan-2-one (17h). (Purification eluent: DCM/MeOH 98:2). Yield 74%, pale yellow solid. $^1$H NMR (400 MHz, CDCl$_3$) δ 8.32 (d, J=9.0 Hz, 1H), 7.91-7.88 (m, 2H), 3.32-2.77 (m, 4H), 2.12 (s, 3H). MS (ESI) m/z 259.1 [M−H]$^−$.

2-(hydroxymethyl)-5-((1-(4-nitrophenyl)-1H-1,2,3-triazol-4-yl)methoxy)tetrahydrofuran-3,4-diol (18g). Compound 17g (155 mg, 0.23 mmol) was dissolved in 4:1 methanol/concentrated ammonium hydroxide (15 mL) and stirred at room temperature for 24 h. The reaction mixture was concentrated in vacuo and azeotroped 3 times with ethanol. The crude product was dissolved in water (5 mL), extracted with methylene chloride (3×50 mL) and the aqueous layer concentrated in vacuo. Yield 99%. $^1$H NMR (400 MHz, MeOD-d$_4$): δ 8.64 (s, 1H), 8.43-8.41 (dd, J=8.0 Hz, 2H), 8.14-8.12 (dd, J=8.0 Hz, 2H), 5.46 (s, 1H), 5.13-5.11 (d, J=8.0 Hz, 1H), 4.70-4.67 (d, J=12 Hz, 1H), 4.13-4.11 (m, 1H), 3.98-3.91 (m, 2H), 3.78-3.66 (m, 1H), 3.60-3.56 (m, 1H) ppm. MS: m/z 375 [M+Na]$^+$ General Procedure for the Preparation of Compounds 19a-h The opportune triazole compound 17 a-f, or 18g (400 mg, 1.60 mmol) was solubilized in 30 mL of anhydrous MeOH, and 10% Palladium on charcoal (25 mg) was added. The reaction mixture was stirred under Hydrogen atmosphere for 1 h, then the mixture was filtered off on a celite pad, the solvent evaporated at reduced pressure and the residue purified by flash chromatography on silica gel with the opportune eluent.

4-butyl-1-(4-aminophenyl)-1H-1,2,3-triazole (19a). (Purification eluent: DCM/MeOH 95:5). Yield 80%, white solid. $^1$H NMR (400 MHz, MeOD-d$_4$): δ7.98 (s, 1H), 7.43-7.41 (d, J=8.0 Hz, 2H), 6.78-6.76 (d, J=8.0 Hz, 2H), 2.72-2.68 (t, −J=7.6 Hz, 2H), 1.70-1.64 (q, J=7.5 Hz, 2H), 1.40-1.35 (q, J=6.7 Hz, 2H), 0.95-0.90 (t, J=7.1 Hz, 3H) ppm. MS (ESI) m/z 217 [M+H]$^+$, 240 [M+Na]$^+$.

4-isopentyl-1-(4-aminophenyl)-1H-1,2,3-triazole (19b). (Purification eluent: DCM/MeOH 98:2). Yield 86%, yellow solid. Yield $^1$H NMR (400 MHz, CDCl$_3$-d): δ7.99 (s, 1H), 7.43-7.41 (dd, J=7.8 Hz, 2H), 6.78-6.76 (dd, J=7.8 Hz, 2H), 4.84 (s, 2H), 2.74-2.70 (t, J=7.6 Hz, 2H), 1.59-1.56 (m, 3H), 0.94-0.92 (d, J=7.4 Hz, 2H) ppm. MS (ESI) m/z 245 [M−H]$^−$, 281 [M+Cl]$^−$.

4-(4-(perfluorobutyl)-1H-1,2,3-triazol-1-yl)aniline (19c). The product was obtained as a pure compound. Yield 99%, white solid. $^1$H NMR (400 MHz, Acetone-d$_6$): δ 8.94 (s, 1H), 7.61-7.59 (dd, J=8.0 Hz, 2H), 6.86-6.84 (dd, J=8.0 Hz, 2H), 5.13 (s, 2H) ppm. $^{13}$C NMR (100 MHz Acetone-d$_6$): δ 150.01, 136.84, 126.31, 123.92, 123.21, 118.89, 114.42, 113.29 ppm. MS (ESI) m/z 377 [M−H]$^−$, 413 [M+Cl]$^−$.

3-(1-(4-aminophenyl)-1H-1,2,3-triazol-4-yl)propanoic acid. (19d) The product was obtained as a pure compound. Yield 99%, white solid. $^1$H NMR (400 MHz, MeOD): δ 8.02 (s, 1H), 7.40-7.39 (dd, J=4.0 Hz, 2H), 6.75-6.74 (dd, J=4.0 Hz, 2H), 3.03-3.00 (t, J=12.0 Hz, 2H), 2.64-2.60 (t, J=8.0 Hz, 2H) ppm. MS (ESI) m/z 233 [M+H]$^+$, 255 [M+Na]$^+$.

4-(2-ethoxymethyl)-1-(4-aminophenyl)-1H-1,2,3-triazole (19e). The product was obtained as a pure compound. Yield 99% white solid. $^1$H NMR (400 MHz, CDCl$_3$-d): δ 7.77 (s, 1H), 7.29-7.28 (d, J=8.4 Hz, 2H), 6.61-6.59 (d, J=8.4 Hz, 2H), 4.57 (s, 2H), 4.06 (s, 2H), 3.55-3.50 (q, J=6.9 Hz, 2H), 1.16-1.12 (t, J=7.0 Hz, 3H) ppm. MS (ESI): m/z 219 [M+H]$^+$.

4-(2-methoxyethyl)-1-(4-aminophenyl)-1H-1,2,3-triazole (19f). The product was obtained as a pure compound. Yield 99% white solid. $^1$H NMR (400 MHz, CDCl$_3$-d): δ 7.66 (s, 1H), 7.40-7.38 (d, J=8.0 Hz, 2H), 6.69-6.67 (d, J=8 Hz, 2H), 3.82 (s, 2H), 3.69-3.66 (t, J=6.4 Hz, 2H), 3.34 (s, 3H), 3.03-3.00 (t, J=6 Hz, 2H) ppm. MS (ESI): m/z 219 [M+H]$^+$.

2-(hydroxymethyl)-5-((1-(4-aminophenyl)-1H-1,2,3-triazol-4-yl)methoxy)tetrahydrofuran-3,4-diol (19g). The product was obtained as a pure compound. Yield 99% Foam. $^1$H NMR (400 MHz, CDCl$_3$-d): δ 8.20 (s, 1H), 7.41-7.39 (dd, J=8.0 Hz, 2H), 6.76-6.74 (dd, J=8.0 Hz, 2H), 5.01 (s, 1H), 4.66-4.63 (d, J=12 Hz, 1H), 4.15, 4.12 (m, 1H), 4.01-3.98 (m, 1H), 3.96-3.95 (m, 1H), 3.79-3.75 (m, 1H), 3.62-3.57 (m, 1H) ppm. MS (ESI): m/z 345 [M+H]$^+$.

4-(1-(4-aminophenyl)-1H-1,2,3-triazol-4-yl)butan-2-one (19h): The product was obtained as a pure compound. Yield 99% white solid. $^1$H NMR (400 MHz, CDCl$_3$-d) δ 7.60 (s, 1H), 7.39 (d, J=8.6 Hz, 2H), 6.71 (d, J=8.6 Hz, 2H), 3.80 (s, 2H), 3.00 (t, J=6.7 Hz, 2H), 2.91 (t, J=6.7 Hz, 3H), 2.14 (s, 3H). ppm. MS (ESI): m/z 231.1 [M+H]$^+$.

General Procedure for the Preparation of Compounds 20-22a-h

The opportune aniline 19 a-h (100 mg, 0.46 mmol) was added to a solution of the appropriate isocyanate (85 µL, 0.65 mmol) in anhydrous CH$_2$Cl$_2$ (10 mL) in one portion. The solution was stirred for 4 hours at r.t. under a nitrogen atmosphere. The solvent was removed, at reduced pressure and the residue purified by flash chromatography using the opportune eluent.

1-(4-(4-butyl-1H-1,2,3-triazol-1-yl)phenyl)-3-o-tolylurea (20a). (Purification eluent: DCM/MeOH 98:2). Yield 85%, white solid. $^1$H NMR (400 MHz, MeOD-d$_4$): δ8.18 (s, 1H), 7.72-7.70 (d, J=8.0 Hz, 2H), 7.63-7.61 (d, J=8.0 Hz, 2H), 7.20-7.16 (m, 2H), 7.05-7.01 (t, J=5.0 Hz, 1H), 2.78-2.74 (t, J=5.0 Hz, 2H), 2.3 (d, J=8.0 Hz, 2H). $^{13}$C-NMR (100 MHz, MeOD-d$_4$): δ 153.09, 140.57, 137.65, 131.33, 130.69, 128.42, 126.62, 123.44, 121.86, 121.09, 120.49, 119.08, 31.41, 25.18, 22.17, 18.34, 14.15 ppm. MS (ESI) m/z 348 [M−H]$^−$, 384 [M+Cl]$^−$.

1-(4-(4-isopentyl-1H-1,2,3-triazol-1-yl)phenyl)-3-o-tolylurea (20b). (Purification eluent: DCM/MeOH 98:2). Yield 89%, white solid. $^1$H NMR (400 MHz, MeOD-d$_4$): δ8.18 (s, 1H), 7.71-7.69 (d, J=8.0 Hz, 2H), 7.64-7.61 (m, 3H), 7.2-7.1 (m, 2H), 7.04-7.01 (t, J=8.0 Hz, 1H), 2.78-2.74 (t, J=8.0 Hz, 2H), 2.29 (s, 3H), 1.63-1.60 (m, 3H), 0.97 (s, 6H), ppm. $^{13}$C-NMR (100 MHz, MeOD-d$_4$): δ155.0, 150.71, 144.20, 140.26, 132.41, 130.09, 128.32, 126.08, 124.22, 123.12, 120.79, 119.76, 119.23, 38.28, 27.38, 22.87, 21.32, 16.59 ppm. MS (ESI) m/z 362 [M−H]$^−$, 398 [M+Cl]$^−$.

1-(4-(4-(perfluorobutyl)-1H-1,2,3-triazol-1-yl)phenyl)-3-(o-tolyl)urea (20c). (Purification eluent: DCM/MeOH 98:2). Yield 70%, white solid. $^1$HNMR (400 MHz, MeOD-d$_4$): δ 9.13 (s, 2H), 7.82-7.79 (dd, J=8.1 Hz, 2H), 7.70-7.68 (dd, J=8.1 Hz, 2H), 7.21-7.15 (m, 3H), 7.06, 7.02 (t, J=8.2 Hz, 1H), 2.30 (s, 3H) ppm. $^{13}$CNMR (100 MHz, MeOD-d$_4$): δ54.16, 141.22, 136.08, 130.84, 130.07, 126.15, 124.43, 123.43, 121.48, 119.03, 115.86, 112.69, 110.20, 107.28, 16.93 ppm. $^{19}$FNMR (280 MHz, MeOD-d$_4$): δ 83.03, 110.64, 124.80, 127.30 ppm MS (ESI) m/z 510 [M−H]$^−$, 545.9 [M+Cl]$^−$.

3-(1-(4-(3-(2-(trifluoromethyl)phenyl)ureido)phenyl)-1H-1,2,3-triazol-4-yl)propanoic acid (20d). The residue was purified by flash chromatography on silica gel (DCM/MeOH 95:5). Yield 65%, white solid. $^1$H NMR (400 MHz, MeOD-d$_4$): δ 8.20 (s, 1H), 7.92-7.90 (d, J=8.0 Hz, 1H), 7.72-7.62 (m, 5H), 7.60-7.57 (t, J=12.0 Hz, 1H), 7.30-7.26 (t, J=8.0 Hz, 1H), 3.05-3.02 (t, J=12.0 Hz, 2H), 2.72-2.69 (t, 2H) ppm. MS (ESI) m/z 418 [M−H]$^−$.

1-(4-(4-(ethoxymethyl)-1H-1,2,3-triazol-1-yl)phenyl)-3-(o-tolyl)urea (20e). (Purification eluent: DCM/MeOH 95:5). Yield 83%, white solid. $^1$HNMR (400 MHz, MeOD-d$_4$): δ 8.41 (s, 1H), 7.73-7.64 (m, 5H), 4.59 (s, 2H), 3.64-3.59 (q, J=6.9 Hz, 2H), 2.30 (s, 3H), 1.23-1.20 (t, J=6.7 Hz, 3H)

ppm. $^{13}$C NMR (100 MHz, MeOD-d$_4$) δ 153.69, 144.40, 140.44, 134.71, 132.83, 131.00, 129.85, 129.41, 125.84, 121.65, 120.1, 115.08, 65.65, 63.12, 16.45, 14.27 ppm. MS (ESI): m/z 351.9[M+H]$^+$ 1-(4-(4-(2-methoxyethyl)-1H-1,2,3-triazol-1-yl)phenyl)-3-o-tolylurea (20f). (Purification eluent: DCM/MeOH 95:5). Yield 78%, white solid. $^1$HNMR (400 MHz, CDCl$_3$-d): δ 8.22 (s, 1H), 7.73-7.67 (d, J=8.0 Hz, 2H), 7.65-7.62 (m, 3H), 7.21-7.15 (d, J=8.0 Hz, 2H), 7.05-7.01 (t, J=8.0 Hz, 1H), 3.72-3.69 (t, J=6.0 Hz, 2H), 3.03-3.0 (t, J=6.0 Hz, 2H), 2.30 (s, 3H), $^{13}$C NMR (100 MHz, CDCl$_3$-d): δ 145.76, 140.09, 130.10, 126.08, 124.24, 123.14, 120.84, 120.68, 119.24, 70.97, 57.42, 25.61, 16.60 ppm. MS (ESI): m/z 351.9 [M+H]$^+$ 1-(4-(4-(3-oxobutyl)-1H-1,2,3-triazol-1-yl)phenyl)-3-(o-tolypurea (20h): (Purification eluent: DCM/MeOH 95:5). Yield 81%, white solid. $^1$H NMR (400 MHz, CDCl$_3$-d) δ 8.08 (s, 1H), 7.85-7.67 (m, 2H), 7.20-7.02 (m, 3H), 6.91 (s, 1H), 6.88-6.69 (m, 2H), 6.38 (d, J=6.8 Hz, 2H), 3.09-2.98 (m, 2H), 2.96-2.85 (m, 2H), 2.22-2.14 (m, 6H) ppm. $^{13}$C NMR (100 MHz, CDCl$_3$-d) δ 206.98, 153.62, 137.21, 136.75, 131.73, 129.47, 127.74, 124.73, 123.07, 123.07, 122.19, 122.17, 121.34, 41.35, 28.57, 20.36, 17.35 ppm. MS (ESI): m/z 362.5 [M−H]$^−$ 1-(3-chloro-2-methylphenyl)-3-(4-(4-isopentyl-1H-1,2,3-triazol-1-yl)phenyl)urea (21b). (Purification eluent: DCM/MeOH 98:2). Yield 80%, white solid. $^1$HNMR (400 MHz, MeOD-d$_4$): δ 7.89 (s, 1H), 7.64-7.57 (m, 4H), 7.08-7.06 (d, J=8.0 Hz, 1H), 6.95-6.93 (d, J=8.0 Hz, 1H), 2.77-2.73 (t, J=7.2 Hz, 2H), 2.23 (s, 3H), 1.60-1.56 (m, 3H), 0.94-0.93 (d, J=6.0 Hz, 6H) ppm. $^{13}$C NMR (100 MHz, CDCl$_3$-d): δ 153.48, 149.08, 139.85, 137.69, 131.73, 131.14, 126.60, 123.47, 121.61, 121.16, 119.74 ppm. MS (ESI): m/z 396 [M−H]$^−$ 1-(4-(4-butyl-1H-1,2,3-triazol-1-yl)phenyl)-3-(2-(trifluoromethyl)phenyl)urea (22a). (Purification eluent: DCM/MeOH 98:2). Yield 78%, white solid. $^1$HNMR (400 MHz, MeOD-d$_4$): δ 8.16 (s, 1H), 7.93-7.92 (d, J=8.0 Hz, 2H), 7.71-7.68 (m, 2H), 7.64-7.61 (m, 3H), 7.59-7.55 (t, J=7.8 Hz, 1H), 7.27-7.23 (t, J=8.0 Hz), 2.75-2.71 (t, J=7.6 Hz), 1.72-1.64 (quint J=7.5 Hz, 2H), 1.42-1.34 (sx J=7.6 Hz, 2H), 0.96-0.92 (t, J=7.6 Hz, 3H) ppm $^{13}$C NMR (100 MHz, CDCl$_3$-d): δ 153.67, 148.70, 139.78, 135.85, 132.39, 131.91, 125.96, 125.62, 124.03, 120.85, 119.82, 119.40, 31.30, 24.60, 21.97, 12.99 ppm. MS (ESI): m/z 402 [M−H]$^−$.

1-(4-(4-isopentyl-1H-1,2,3-triazol-1-yl)phenyl)-3-(2-(trifluoromethyl)phenyl)urea (22b). (Purification eluent: DCM/MeOH 98:2). Yield 72%, white solid. $^1$HNMR (400 MHz, CDCl$_3$-d): δ 9.11 (s, 1H), 7.83-7.81 (m, 2H), 7.654 (s, 1H), 7.48-7.46 (m, 4H), 7.41-7.37 (t, J=8.0 Hz, 1H), 7.10-7.06 (t, J=8.0 Hz, 1H), 2.76-2.72 (t, J=7.2 Hz, 2H), 1.60-1.54 (m, 3H), 0.88-0.87 (d, J=6.0 Hz). $^{13}$C NMR (100 MHz, CDCl$_3$-d): δ 153.78, 149.36, 139.65, 135.58, 132.44, 131.92, 127.93, 126.53, 126.05, 125.22, 124.45, 122.48, 122.16, 121.09, 120.11, 119.37, 38.38, 27.62, 23.43, 22.27 ppm. MS (ESI): m/z 416.2 [M+H]$^+$.

1-(4-(4-(((3,4-dihydroxy-5-(hydroxymethyl)tetrahydrofuran-2-yl)oxy)methyl)-1H-1,2,3-triazol-1-yl)phenyl)-3-(2-(trifluoromethyl)phenyl)urea (22g). (Purification eluent: DCM/MeOH 98:2). Yield 86%, white solid. $^1$HNMR (400 MHz, Acetone-d$_6$): δ 9.05 (s, 1H), 8.43 (s, 1H), 8.13-8.11 (d, J=8.0 Hz, 2H), 7.79-7.72 (m, 5H), 7.67-7.61 (m, 2H), 7.29-7.26 (t, J=7.6 Hz, 1H), 5.03 (s, 1H), 4.85-4.82 (d, J=12 Hz, 1H), 4.69-4.66 (d, J=12 Hz, 1H), 4.23 (s, 2H), 4.08-4.06 (d, J=8.0 Hz, 1H), 3.98-3.94 (m, 2H), 3.81-3.79 (m, 1H), 3.62-3.56 (m, 1H) ppm. $^{13}$C NMR (100 MHz, Acetone d$_6$): δ 152.41, 145.37, 140.16, 136.73, 1332.82, 131.91, 125.92, 125.47, 123.78, 121.56, 121.30, 120.99, 119.27, 114.23, 106.76, 84.67, 75.10, 70.93, 63.07, 60.13 ppm. MS (ESI): m/z 508 [M−H]$^−$, 543 [M+Cl]$^−$.

Compounds 30a and 30b were purchased from Sigma Aldrich and used without further purification.

Example 4

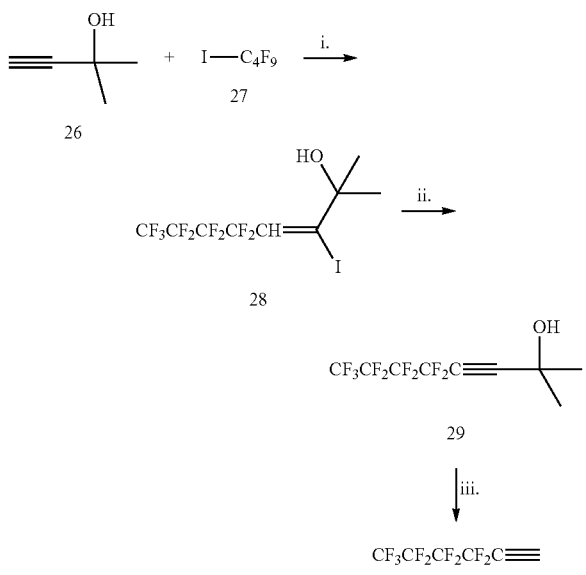

Reagents and conditions: i. Zn hv, CF$_3$COOH, CH$_2$Cl$_2$, 1 h, rt; ii. KOH, H$_2$O, 2 h r.t; iii. NaOH, H$_2$O, 2 h reflux 5,5,6,6,7,7,8,8,8-nonafluoro-3-iodo-2-methyloct-3-en-2-ol (28). Compound 27 (2.04 mL 11.8 mmol) and 3 mL of CH$_2$Cl$_2$ were added to a stirred suspension of Zinc dust (777 mg, 11.8 mmol) in 26 (1.15 mL, 11.8 mmol). To this were added 2 drops of CF$_3$COOH, and the mixture was stirred at r.t under hv irradiation for 1 h. After that time, the reaction mixture was filtered off on a celite pad and the solvent removed at reduced pressure to give a colourless oil. Yield 92%. $^1$HNMR (400 MHz, CDCl$_3$-d): δ 6.85-6.78 (t, J=12 Hz, 1H), 2.85 (s, 1H), 1.52-1.51 (s, 6H) ppm. $^{13}$C NMR (100 MHz, CDCl$_3$-d): δ 126.49, 120.64, 118.77, 115.92, 113.40, 87.36, 71.79, 29.35 ppm. MS (ESI): m/z 429 [M−H]$^−$ 5,5,6,6,7,7,8,8,8-nonafluoro-2-methyloct-3-yn-2-ol (29). To a stirring solution of KOH (434 mg, 7.7 mmol) in a mixture of EtOH (20 mL) and water (5 mL) 28 (3330 mg, 7.7 mmol) was added dropwise. The reaction mixture was stirred at r.t for 2 h, after then HCl was added, and the pH adjusted to 7. Et$_2$O was added and the reaction mixture extracted several times and dried over anhydrous Na$_2$SO$_4$. Yield 90%, yellow oil. $^1$HNMR (400 MHz, CDCl$_3$-d): δ 1.49, (s, 6H) ppm. $^{13}$C NMR (100 MHz, CDCl$_3$-d): δ 120.49, 118.68, 115.88, 113.38, 111.10, 82.10, 76.49, 64.83, 29.10 ppm. MS (ESI): m/z 431 [M−H]$^−$ 3,3,4,4,5,5,6,6,6-nonafluorohex-1-yne (30c). Compound 29 (2114 mg, 7 mmol) was added to a solution of 280 mg of NaOH in water. The mixture was heated and immediately distilled (b.p. 40° C.). Yield 78%. Colourless oil. $^1$HNMR (400 MHz, CDCl$_3$-d): δ 2.16, (s, 1H) ppm. $^{13}$C NMR (100 MHz, CDCl$_3$-d): δ 117.0, 108.12, 107.50, 80.32, 71.63 ppm. MS (ESI): m/z 243 [M−H]$^−$

Example 5

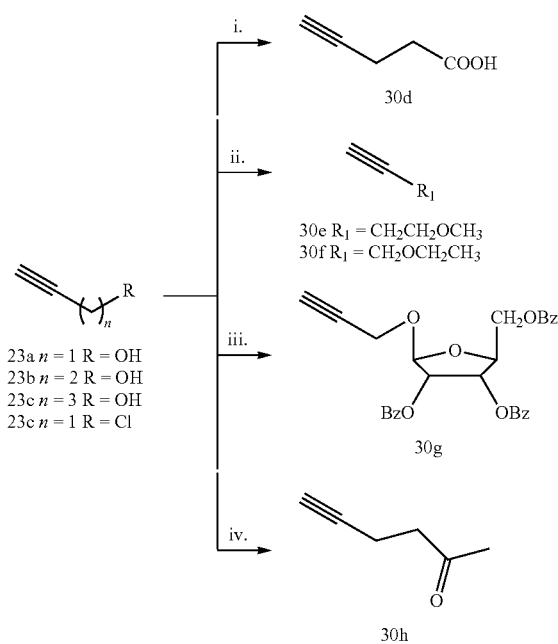

Reagents and conditions: i. Jones reagent, r.t, acetone, 1 h; ii. a) opportune alcohol, NaOH (6M) 20 min. r.t; b) dimethylsulfate or diethylsulfate, 50-55° C.; iii. a) β-D-ribofuranose 1-acetate 2,3-5 tribenzoate, BF$_3$, Et$_2$O 0° C., CH$_2$Cl$_2$, 15 min; b) K$_2$CO$_3$ 15 min; iv. K$_2$CO$_3$, acetylacetone, EtOH, 90° C., 12 h.

pent-4-ynoic acid (30d). 23d (1 mL, 10.7 mmol) was dissolved in Acetone and cooled to 0° C. Jones reagent was added dropwise to the solution, under vigorous stirring, until the reaction mixture remained orange. The mixture was allowed to reach r.t., and more Jones reagent was added to maintain the orange colour. The reaction mixture was stirred at r.t. for 1 h, then water was added, and was extracted with Et$_2$O several times, washed with Brine and dried over anhydrous Na$_2$SO$_4$. The solvent was removed at reduced pressure and the resulting oil purified by flash chromatography on silica gel (Hexane/Et$_2$O 8:2). Yield 82%, colourless oil. $^1$HNMR (400 MHz CDCl$_3$-d): δ 2.61-2.59 (m, 2H), 2.52-2.48 (m, 2H), 1.98-1.95 (m, 1H) ppm.

General Procedure for the Preparation of Compounds 30e and 30f

To a stirring solution of 200 g of NaOH in 300 mL of water (0.3 mol, 16.8 g) was added the opportune alcohol (2.5 mL, 33.02 mmol). To this, was slowly added the corresponding sulfate (15 mmol, 2082 mg) in 2 h dropwise and the mixture was heated at 50° C. The final product was distilled off, the distillation was stopped at 95° C., then the content of the receiver was washed with cold NH$_4$Cl aq solution and separated.

3-ethoxyprop-1-yne (30e). Yield 68% colourless oil. $^1$H NMR (400 MHz, CDCl$_3$-d): δ 4.13-4.13 (d, J=2.4 Hz, 2H), 3.60-3.55 (q, 2H), 2.41-2.40 (t, J=4.8 Hz, 1H), 1.24-1.22 (t, J=4 Hz, 3H) ppm 4-methoxybut-1-yne (30f). Yield 52% colourless oil. $^1$H NMR (400 MHz, CDCl$_3$-d): δ 3.52-3.49 (m, 2H), 3.33 (s, 3H), 2.47-2.43 (m, 2H), 1.99-1.97 (m, 1H) ppm.

1-propynyl-2,3,4-tri-O-benzoyl-ribofuranose (30g): To a solution of 0-D-ribofuranose 1-acetate 2,3-5 tribenzoate (937 mg, 1.8 mmol) in dichloromethane (8 mL) was added propargyl alcohol (129 µl, 2.23 mmol) and BF$_3$.Et$_2$O (344 µL, 2.79 mmol) at 0° C. and the reaction mixture was stirred at room temperature for 2 h. After this time, K$_2$CO$_3$ (450 mg) was added and stirring was continued for further 15 min. Then the reaction mixture was filtered and washed with dichloromethane. The filtrate was washed with water, the aqueous phase was separated and extracted with dichloromethane (3×20 mL) and the combined organic phases were dried (Na$_2$SO$_4$) and concentrated to yield the desired compound 30g as a crystalline solid. Yield 85%. $^1$H NMR (400 MHz CDCl$_3$-d): δ 8.07-7.00 (m, 4H), 7.87-7.85 (d, J=8.1 Hz, 2H), 7.55-7.43 (m, 3H), 7.41-7.34 (m, 4H), 7.29-7.25 (m, 2H), 5.93-5.90 (m, 1H), 5.77-5.76 (d, J=4.2 Hz, 1H), 5.50 (s, 1H), 4.70-4.65 (m, 2H), 4.50-4.46 (m, 1H), 4.20 (s, 2H), 2.45 (s, 1H) ppm. $^{13}$C NMR (100 MHz, CDCl$_3$-d): δ 166.10, 165.26, 165.07, 133.44, 133.33, 133.10, 129.75, 129.67, 129.11, 128.84, 128.43, 128.34, 128.29, 103.30, 79.30, 78.25, 75.48, 75.24, 72.07, 64.42, 54.49 ppm. MS (ESI) m/z: 523 [M+Na]$^+$.

hex-5-yn-2-one (30h): A mixture of propargyl chloride (485 µL, 6.71 mmol), acetylacetone (758 µL, 7.38 mmol) and K$_2$CO$_3$ (1112 mg, 8.0 mmol) was stirred in EtOH (10 mL), at 80° C., for 12 h. After this time, EtOH was partially removed under reduced pressure, water (15 mL) was added, the aqueous phase was separated and extracted with MTBE (3×20 mL). The combined organic phases were dried (Na$_2$SO$_4$). 30 h was finally purified by distillation bp=71° C. $^1$H NMR (400 MHz, CDCl$_3$) δ 2.66 (t, J=7.1 Hz, 1H), 2.41 (t, J=5.9 Hz, 1H), 2.14 (s, 1H), 1.92 (s, 1H) ppm.

Example 6

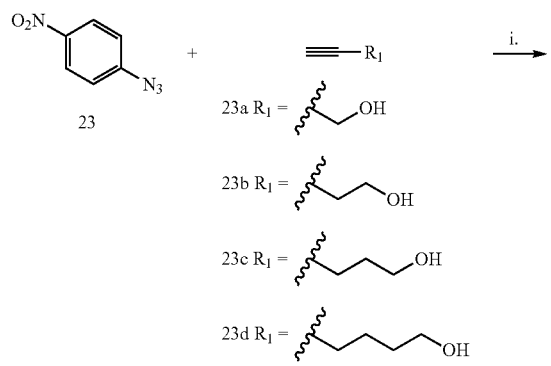

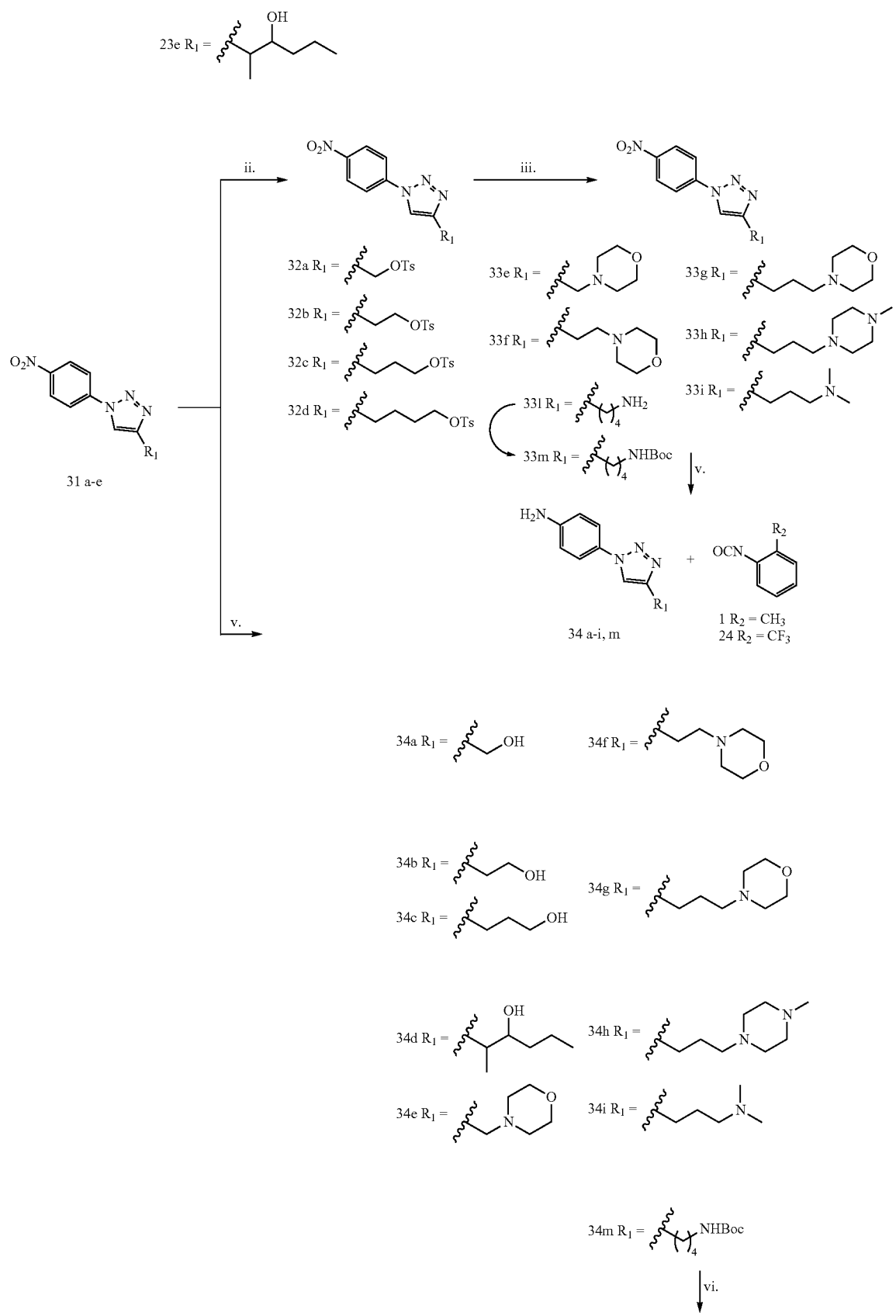

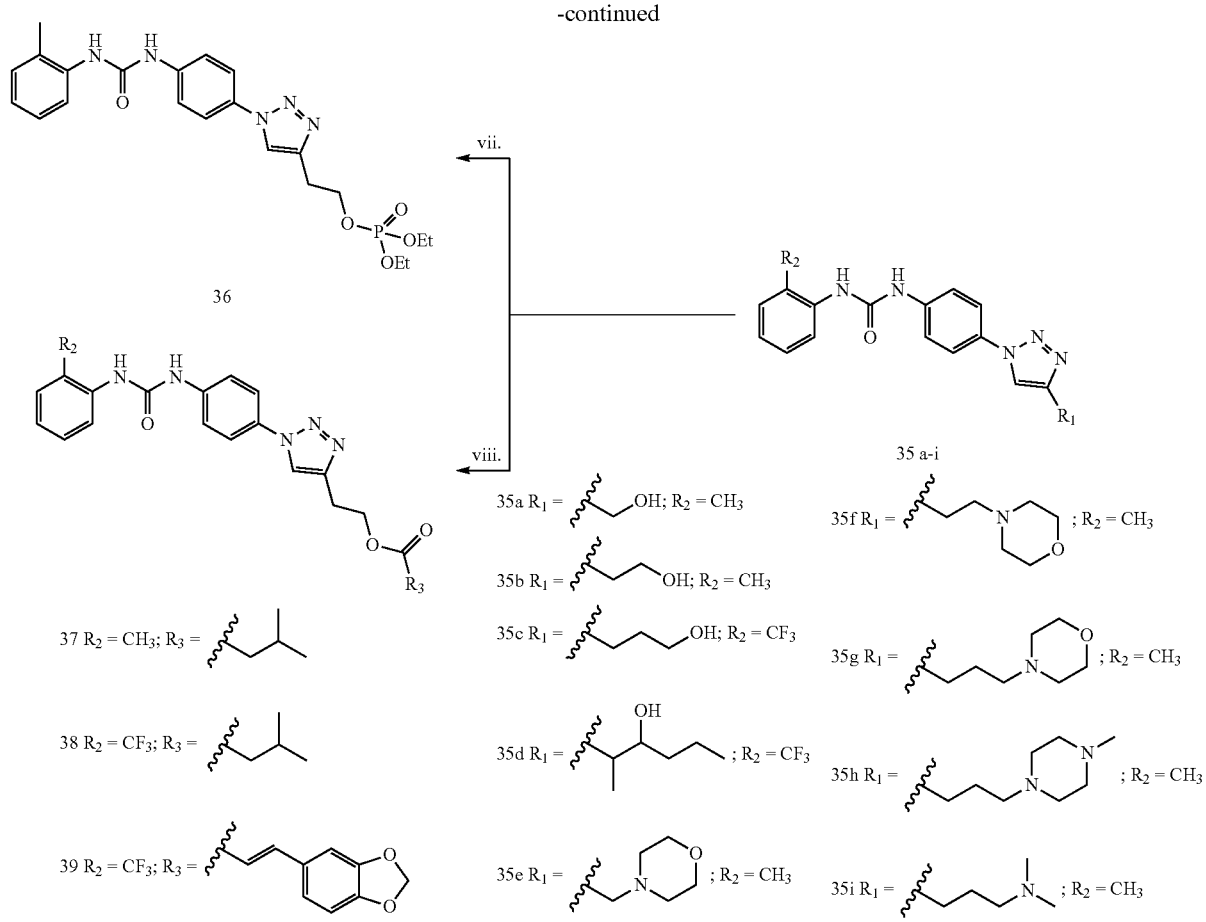

Reagents and conditions: i. alkyne, CuSO$_4$·5 H$_2$O, sodium ascorbate, H$_2$O tBuOH (1:1), MW 10 min, 120° C.; ii. KOH, TsCl, THF (dry) 24 h; iii. opportune amine, DCM, 9 h, 80° C.; iv 5% NaOH (aq), di tert-butyl dicarbonate, THF, rt 12 h v. H$_2$, Pd/C, MeOH, 1 h, vi. opportune isocyanate CH$_2$Cl$_2$, 5 h reflux; vii. titanium isopropoxide; diethyl phosphonate, TEA, CH$_2$Cl$_2$ o.n. r.t.; viii. opportune acid, DCC, DMAP, CH$_2$Cl$_2$, DMF 9 h, r.t.

General Procedure for the Preparation of Compounds 31a-e

The appropriate alkyne (6.08 mmol) and azide 16 (831 mg, 5.07 mmol) were suspended in a 1:1 mixture of water and t-BuOH (1.5 mL each) in a 10 mL glass vial equipped with a small magnetic stirring bar. To this, was added sodium ascorbate (2.5 mmol) and copper(II) sulfate pentahydrate (2.50 mmol). The mixture was then heated for 10 min. at 125° C. under microwave irradiation, using an irradiation power of 300 W. After that time the solvent was removed at reduced pressure water was added and the mixture was extracted with EtOAc (3×20 mL). The organic layers were collected, washed with Brine and dried over Na$_2$SO$_4$. The crude was purified by flash chromatography on silica gel using the opportune eluent to give the desired triazole compounds 31a, 31b, 31c, 31d or 31e.

(1-(4-nitrophenyl)-1H-1,2,3-triazol-4-yl)methanol (31a). (Purification eluent: DCM/MeOH 98:2). Yield 90%, yellow solid. $^1$H NMR (400 MHz, MeOD-d$_4$): δ8.47 (s, 1H), 8.42, 8.40 (d, J=8.0 Hz, 2H), 8.12, 8.09 (d, J=8.0 Hz, 2H), 2.34 (s, 2H) ppm. MS (ESI) m/z 221 [M+H]$^+$, 243 [M+Na]$^+$.

(1-(4-nitrophenyl)-1H-1,2,3-triazol-4-yl)ethanol (31b). (Purification eluent: DCM/MeOH 98:2). Yield 84%, yellow solid. $^1$H NMR (400 MHz, MeOD-d$_4$): δ 8.50 (1H, NCH), δ 8.44-8.42 (d, J=8.0 Hz, 2H), 8.14-8.12 (d, J=8.0 Hz, 2H), 3.90-3.87 (t, J=6.0 Hz, 2H), 3.02-2.99 (t, J=6.0 Hz, 2H) ppm. MS (ESI) m/z 235 [M+H]$^+$, 257 [M+Na]$^+$.

(1-(4-nitrophenyl)-1H-1,2,3-triazol-4-yl)propanol (31c). (Purification eluent: DCM/MeOH 98:2). Yield 88%, yellow solid $^1$H NMR (400 MHz, MeOD-d$_4$): δ8.47 (s, 1H), 8.42, 8.40 (d, J=8.0 Hz, 2H), 8.12, 8.09 (d, J=8.0 Hz, 2H), 3.66-3.63 (t, J=6.0 Hz, 2H), 2.89-2.85 (t, J=8.0 Hz, 2H), 1.98-1.92 (t, J=8.0 Hz, 2H). MS (ESI) m/z 227 [M+H]$^+$, 271 [M+Na]$^+$.

4-(1-(4-nitrophenyl)-1H-1,2,3-triazol-4-yl)butan-1-ol (31d). (Purification eluent: DCM/MeOH 98:2). Yield 85%, yellow solid $^1$H NMR (400 MHz, MeOD-d$_4$) δ 8.43 (s, 1H), 8.35 (d, J=9.0 Hz, 2H), 8.08 (m, Hz, 2H), 3.59 (t, J=6.4 Hz, 2H), 2.79 (t, J=7.6 Hz, 2H), 1.78 (q, J=15.2 Hz, 2H), 1.61 (dt, J=13.1, 6.4 Hz, 2H) ppm. MS (ESI) m/z 361[M−H]$^-$.

2-methyl-1-(1-(4-nitro phenyl)-1H-1,2,3-triazol-4-yl)pentan-1-ol (31e). (Purification eluent: DCM/MeOH 98:2). Yield 88%, yellow solid $^1$H NMR (400 MHz, CDCl$_3$-d): δ 8.39-8.37 (d, J=8.0 Hz, 2H), 8.05 (s, 1H), 7.98-7.96 (d, J=8.0 Hz, 2H), 4.91-4.84 (m, 1H), 2.82 (s, 1H), 2.06-2.03 (m, 1H), 1.51-1.12 (m, 4H), 0.93-0.86 (m, 6H) ppm. $^{13}$C NMR (100 MHz, CDCl$_3$-d): δ 152.24, 147.33, 141.61, 125.52, 124.92, 120.36, 119.28, 71.60, 70.98, 38.88, 38.63, 35.06, 33.80, 20.31, 20.13, 15.25, 14.24, 13.80 ppm. MS (ESI) m/z 325.0 [M+Cl]$^-$.

General Procedure for the Preparation of Compounds 32a-d

Tosyl Chloride, (1.88 mmol, 359.00 mg), KOH (4.28 mmol, 240.39 mg), and the opportune alcohol, were stirred in 15 mL of anhydrous THF in an ice-salt bath, at 0° C. under nitrogen atmosphere. After 30 min. the reaction mixture was stirred at r.t. Twelve hours later the solvent was removed at reduced pressure, water was added and the reaction mixture was extracted with DCM (100 mL×3). The combined organic layers were washed with brine, dried ($Na_2SO_4$), and concentrated. The residue was purified by flash chromatography on silica gel (PE/EtOAc 5:3).

3-(1-(4-nitrophenyl)-1H-1,2,3-triazol-4-yl)methyl 4-methylbenzenesulfonate (32 a). Yield 72%. White solid. $^1$H NMR (400 MHz, $CDCl_3$-d): δ 8.44-8.41 (d, J=9.2 Hz, 2H), 8.17 (s, 1H), 7.96-7.93 (d, J=9.2 Hz, 2H), 7.84-7.82 (d, J=8.4 Hz, 2H), 7.37-7.35 (d, J=8 Hz, 2H), 5.29 (s, 2H), δ 2.45 (s, 3H) ppm. MS (ESI): m/z 397 [M+Na]$^+$ 3-(1-(4-nitrophenyl)-1H-1,2,3-triazol-4-yl)ethyl 4-methylbenzenesulfonate (32 b). Yield 78%. White solid. $^1$H NMR (400 MHz, $CDCl_3$-d): δ 8.42-8.39 (d, J=9.2 Hz, 2H), 7.98 (s, 1H), 7.95-7.93 (d, J=8.8 Hz, 2H), 7.75-7.73 (d, J=8.4 Hz, 2H), 7.32-7.30 (d, J=8 Hz, 2H), 4.37-4.34 (t, J=6.4 Hz, 2H), 3.21-3.18 (t, J=6.4 Hz, 2H), 2.40 (s, 3H) ppm. MS (ESI): m/z 410.8 [M+Na]$^+$ 3-(1-(4-nitrophenyl)-1H-1,2,3-triazol-4-yl)propyl 4-methylbenzenesulfonate (32 c). Yield 83%. White solid. $^1$H NMR (400 MHz, $CDCl_3$-d): δ 8.35-8.33 (d, J=8.8 Hz, 2H), 7.94-7.92 (m, 3H), 7.74-7.72 (d, J=8.0 Hz, 2H), 7.75-7.73 (d, J=8.4 Hz, 2H), 7.31-7.29 (d, J=8 Hz, 2H), 4.09-4.06 (t, J=6.0 Hz, 2H), 2.88-2.84 (t, J=8.0 Hz, 2H), 2.38 (s, 3H), 2.12-2.07 (quint, J=6.0 Hz, 2H ppm. MS (ESI): m/z 402.8 [M+H]$^+$, 424.8 [M+Na]$^+$ 4-(1-(4-nitrophenyl)-1H-1,2,3-triazol-4-yl)butyl 4-methylbenzenesulfonate (32d). Yield 90%. White solid. $^1$H NMR (400 MHz, $CDCl_3$-d): δ 8.38 (d, J=9.0 Hz, 1H), 7.94 (d, J=8.9 Hz, 1H), 7.86 (s, 1H), 7.75 (d, J=8.3 Hz, 1H), 7.32 (d, J=8.0 Hz, 1H), 4.06 (t, J=5.8 Hz, 1H), 2.80 (t, J=7.1 Hz, 1H), 2.42 (s, 2H), 1.89-1.64 (m, 3H). MS (ESI): m/z 417.1 [M+H]$^+$ General Procedure for the Preparation of Compounds 33e-i.

To a solution of the opportune tosylate, was added the corresponding amine, at 0° C. The reaction mixture was stirred at 80° C. in a sealed tube. After 24 h the solvent was removed at reduced pressure and the residue purified by flash chromatography on silica gel.

4-(3-(1-(4-nitrophenyl)-1H-1,2,3-triazol-4-yl)methyl) morphine (33e). (Purification eluent: DCM-methanol 98:2). Yield 95%. White solid. $^1$H NMR (400 MHz, MeOD-$d_4$): δ 8.6 (s, 1H), 8.46-8.44 (d, J=8 Hz, 2H), 8.17-8.14 (d, J=8.0 Hz, 2H), 3.76 (s, 2H), 3.71-3.69 (m, 4H), 2.57-2.55 (m, 4H) ppm. MS(ESI): m/z 412.9 [M+Na]+, 289.9 [M+H]$^+$.

4-(3-(1-(4-nitrophenyl)-1H-1,2,3-triazol-4-yl)ethyl)morpholine (33f). (Purification eluent: DCM-methanol 98:2). Yield 92%. White solid. $^1$H NMR (400 MHz, MeOD-$d_4$): δ 8.51 (s, 1H), 8.43-8.40 (d, J=8 Hz, 2H), 8.13-8.10 (d, J=8 Hz, 2H), 3.72-3.69 (m, 4H), 3.01-2.99 (t, J=2 Hz, 2H) 2.77-2.73 (t, J=8 Hz, 2H), δ 2.57-2.55 (m, 4H). MS (ESI): m/z 303.9 [M+H]$^+$.

4-(3-(1-(4-nitrophenyl)-1H-1,2,3-triazol-4-yl)propyl) morpholine (33g). (Purification eluent: DCM-methanol 98:2). Yield 90%. White solid. $^1$H NMR (400 MHz, Acetone): δ 8.51 (s, 1H), 8.43-8.41 (d, J=8.9 Hz, 2H), 8.19-8.16 (d, J=8.9 Hz, 2H), 3.59-3.57 (m, 4H), 2.83-2.80 (t, J=7.6 Hz, 2H) 2.40-2.36 (m, 4H), δ 2.57-1.93-1.86 (t, J=7.6 Hz, 2H). MS (ESI): m/z 303.9 [M+H]$^+$.

1-methyl-4-(3-(1-(4-nitrophenyl)-1H-1,2,3-triazol-4-yl) propyl)piperazine (33h). (Purification eluent: DCM-methanol 98:2). Yield 69% white solid. $^1$H NMR (400 MHz, $CDCl_3$-d): δ 8.22-8.20 (d, J=8.0 Hz, 2H), 7.85-7.82 (m, 3H), 2.69-2.66 (t, J=6.0 Hz, 2H), 2.31-2.26 (m, 10H), 2.10 (s, 3H), 1.82-1.74 (quint, J=5.9 Hz, 2H) ppm. MS (ESI): m/z 330.9 [M+H]$^+$, 353 [M+Na]$^+$.

4-(3-(1-(4-nitrophenyl)-1H-1,2,3-triazol-4-yl)propyl)dimethylamine (33i). (Purification eluent: DCM-methanol 95:5). Yield 69% white solid. $^1$H NMR (400 MHz, $CDCl_3$-d): δ 8.63 (s, 1H), 8.43-8.41 (d, J=8.8 Hz, 2H), 8.16-8.14 (d, J=8.8 Hz, 2H), 3.14-3.10 (t, J=6.0 Hz, 2H), 2.93-2.90 (t, J=6.0 Hz, 2H), 2.81 (s, 6H), 2.21-2.13 (quint, J=8.0 Hz, 2H) ppm. MS (ESI): m/z 317.9 [M+H]$^+$, 339.9 [M+Na]$^+$.

4-(1-(4-nitrophenyl)-1H-1,2,3-triazol-4-yl)butan-1-amine (33l). 32d (500 mg, 1.2 mmol) was solubilized in anhydrous DCM (2 mL), in a vial. The rxn mixture was cooled to −78° C., and ammonia was bubbled in the solution. The tube was sealed and the resulting mixture was stirred at rt for 12 hrs. After this time the solvent was removed at reduced pressure. HCl 3N was added and the resulting yellow pp was filtered-off and recrystallized from ACN. Yield 80%, white solid $^1$H NMR (400 MHz, MeOD) δ 8.42 (s, 1H), 8.33 (d, J=8.6 Hz, 3H), 8.04 (d, J=8.5 Hz, 3H), 2.77-2.74 (m, 4H), 1.80-1.66 (m, 2H), 1.57-1.55 (m, 2H), 0.81 (m, 2H) ppm. MS (ESI): m/z 262 [M+H]$^+$, 284 [M+Na]$^+$.

tert-butyl (4-(1-(4-nitro phenyl)-1H-1,2,3-triazol-4-yl) butyl)carbamate (33m): 33l (110 mg, 0.42 mmol) and $Boc_2O$ (139 mg, 0.63 mmol), were stirred in a mixture of 5% NaOH(aq) 10 mL, and THF (10 mL) at rt for 8 hrs. After this time the solvent was removed at reduced pressure and the pH adjusted to 6 by addition of 1N HCl. The reaction mixture was extracted with EtOAc (100 mL×3). The combined organic layers were washed with brine, dried ($Na_2SO_4$), and concentrated. The residue was purified by flash chromatography on silica gel (DCM/MeOH 98:2). Yield 93% white solid. $^1$H NMR (400 MHz, $CDCl_3$) δ 8.35 (d, J=7.5 Hz, 1H), 7.95-7.92 (m 2H), 4.61 (s, 1H), 3.13-3.10 (m 2H), 2.78 (m, 2H), 1.75-1.70 (m, 2H), 1.49-1.43 (m, 2H), 1.39 (s, 9H) ppm.

General Procedure for the Preparation of Compounds 34a-i and m.

The opportune triazole compound 31a-d, or 33e-i (400 mg, 1.60 mmol) was solubilized in 30 mL of anhydrous MeOH, and 10% Palladium on charcoal (25 mg) was added. The reaction mixture was stirred under Hydrogen atmosphere for 1 h, then the mixture was filtered off on a celite pad, the solvent evaporated at reduced pressure.

(1-(4-aminophenyl)-1H-1,2,3-triazol-4-yl)methanol (34a). Yield 99%, white solid. $^1$H NMR (400 MHz, MeOD-$d_4$): δ 8.09 (s, 1H), 7.46-7.41 (d, J=8.0 Hz, 2H), 6.81-6.75 (d, J=8.0 Hz 2H), 2.29 (s, 2H) ppm. MS (ESI) m/z 191 [M−H]$^+$, 213 [M+Na]$^+$.

(1-(4-aminophenyl)-1H-1,2,3-triazol-4-yl)ethanol (34b). Yield 99%, white solid. $^1$H NMR (400 MHz, MeOD-$d_4$): δ 8.09 (s, 1H), 7.46-7.41 (d, J=8.0 Hz, 2H), 6.81-6.75 (d, J=8.0 Hz 2H), 3.86-3.83 (t, J=6 Hz, 2H) 2.95-2.93 (t, J=6 Hz, 2H) ppm. MS (ESI) m/z 205 [M+H]$^+$, 227 [M+Na]$^+$.

1-(1-(4-aminophenyl)-1H-1,2,3-triazol-4-yl)-2-methyl-pentan-1-ol (34d). Yield 99%, white solid. $^1$H NMR (400 MHz, MeOD-$d_4$): δ 8.12 (s, 1H), 7.45-7.43 (d, J=8.4 Hz, 2H), 6.79-6.77 (d, J 8.4 Hz, 2H), 4.76-4.62 (m, 1H), 1.98-1.90 (m, 1H), 1.54-1.12 (m, 4H), 0.94-0.88 (m, 6H) ppm. MS (ESI): m/z 261.3 [M+H]$^+$, 282.9 [M+Na]$^+$.

4-(4-(3-morpholinomethyl)-1H-1,2,3-triazol-1-yl)benzenamine (34e). Yield 99%, white solid. $^1$H NMR (MeOD-$d_4$): δ 8.25 (s, 1H), 7.47-7.43 (d, J=8 Hz, 2H), 6.80-6.76 (d, J=8

Hz, 2H), 3.84 (s, 2H) 3.72-3.71 (m, 4H), 2.68-2.67 (m, 4H) ppm. MS (ESI): m/z 259.9 [M+H]+, 281.9 [M+Na]+.

4-(4-(3-morpholinoethyl)-1H-1,2,3-triazol-1-yl)benzenamine (34f). Yield 99%, white solid. $^1$H NMR (400 MHz, MeOD-d$_4$): δ 8.09 (s, 1H), 7.44-7.40 (d, J=8 Hz, 2H), 6.79-6.75 (d, J=8 Hz, 2H), 3.71-3.68 (m, 4H), 2.97-2.93 (t, J=8 Hz, 2H) 2.73-2.69 (t, J=8 Hz, 2H), 2.54-2.53 (m, 4H) ppm. MS: m/z 273.9 [M+H]+.

4-(4-(3-dimethylaminopropyl)-1H-1,2,3-triazol-1-yl)benzenamine (34g). Yield 99%, white solid. $^1$H NMR (400 MHz, MeOD-d$_4$): δ 8.21 (s, 1H), 7.47-7.45 (d, J=8.0 Hz, 2H), 6.82-6.80 (d, J=8.0 Hz, 2H), 3.25-3.21 (t, J=6.0 Hz, 2H), 2.90-2.85 (m, 8H), 2.15-2.18 (quint, J=8.0 Hz, 2H) ppm. MS (ESI): m/z 246.0 [M+H]+.

4-(4-(3-morpholinopropyl)-1H-1,2,3-triazol-1-yl)benzenamine (34h). Yield 99%, white solid. $^1$H NMR (400 MHz, MeOD-d$_4$): δ 8.04 (s, 1H), 7.44-7.42 (d, J=8.0 Hz, 2H), 6.78-6.76 (d, J=8 Hz, 2H), 3.67-3.64, (m, 4H), 2.74-2.72 (t, J=7.6 Hz, 2H), 2.43-2.38 (m, 6H), 1.91-1.84 (quint, J=8.0 Hz, 2H) ppm. MS (ESI): m/z 287.9 [M+H]+, 309.9 [M+Na]+, 4-(4-(3-methylpiperazinopropyl)-1H-1,2,3-triazol-1-yl)benzenamine (34i). Yield 99%, white solid. $^1$H NMR (400 MHz, MeOD-d$_4$): δ 7.56 (s, 1H) 7.37-7.26 (d, J=8.2 Hz, 2H), 6.69-6.67 (d, J=8 Hz, 2H), 2.75-2.72 (t, J=7.6 Hz, 2H), 2.48-2.40 (m, 9H), 2.26 (s, 1H), 1.90-1.86 (quint, J=7.4 Hz, 2H) ppm. MS (ESI): m/z 301.1 [M+H]+, 323.2 [M+Na]+ tert-butyl (4-(1-(4-aminophenyl)-1H-1,2,3-triazol-4-yl)butyl)carbamate (34m): Yield 99%, white solid. $^1$H NMR (400 MHz, CDCl$_3$) δ 7.57 (s, 1H), 7.39 (d, J=8.6 Hz, 2H), 6.70 (d, J=8.7 Hz, 2H), 4.62 (s, 1H), 3.12 (s, 2H), 2.74 (t, J=7.5 Hz, 2H), 1.79-1.61 (m, 2H), 1.61-1.43 (m, 2H), 1.39 (s, 9H). ppm. MS (ESI): m/z 332.4 [M+H]+, 354.1 [M+Na]+

General Procedure for the Preparation of Compounds 35a-i.

The opportune aniline 34a-i (0.10 mmol) was added to a solution of the appropriate isocyanate 1 or 24 (0.15 mmol) in anhydrous MeOH (10 mL) in one portion. The solution was stirred for 9 hours at r.t. under a nitrogen atmosphere. The solvent was removed at reduced pressure and the residue purified on silica to afford the final product 35a, 35b or 35g as white solid. Alternatively the residue was crystallized from MeOH to afford compound 35e or 35f.

1-(4-(4-(hydroxymethyl)-1H-1,2,3-triazol-1-yl)phenyl)-3-o-tolylurea (35a). (Purification eluent: DCM-methanol 95:5). Yield 79% white solid. $^1$H NMR (400 MHz, DMSO d$_6$): δ 9.23 (s, 1H), 8.54 (s, 1H), 7.97 (s, 1H), 7.80-7.76 (d, J=8 Hz, 2H), 7.80-7.76 (m, 3H), 7.64-7.62 (d, J=8.0 Hz, 2H), 7.17-7.12 (m, 2H), 6.96-6.93 (t, J=6.0 Hz, 1H), 4.58 (s, 2H), 2.24 (s, 3H) ppm. $^{13}$C-NMR (100 MHz, DMSO d$_6$): δ 153.09, 140.57, 137.78, 131.50, 131.09, 128.46, 127.04, 123.60, 122.38, 121.27, 120.49, 118.84, 55.44, 18.36 ppm. MS (ESI) m/z 322.1 [M−H]−, 358 [M+Cl]−.

1-(4-(4-(hydroxyethyl)-1H-1,2,3-triazol-1-yl)phenyl)-3-o-tolylurea (35b). (Purification eluent: DCM-methanol 95:5). Yield 75% white solid. $^1$H NMR (400 MHz, DMSO d$_6$): δ 9.23 (s, 1H), 8.54 (s, 1H), 8.04 (1H, s), 7.80-7.76 (d, J=8.0 Hz, 2H), 7.75-7.73 (1H, d, J=8.4 Hz), 7.64-7.62 (d, J=8.0 Hz, 2H), 7.17-7.11 (2H, m), 6.96-6.93 (t, J=6.0 Hz, 1H), 3.71-3.67 (t, 6.4 Hz, 2H), 2.84-2.81 (t, J=6.8 Hz, 2H) 2.24 (s, 3H) ppm. $^{13}$C NMR (100 MHz, DMSO d$_6$): δ 145.80, 140.71, 137.74, 131.44, 130.79, 128.38, 126.71, 123.47, 121.89, 121.15, 119.11, 66.75, 29.68, 18.37 ppm. MS(ESI): m/z 360 [M+Na]+

1-(4-(4-(3-hydroxypropyl)-1H-1,2,3-triazol-1-yl)phenyl)-3-(2-(trifluoromethyl)phenyl)urea (35c). (Purification eluent: DCM/MeOH 98:2). Yield 80%, white solid $^1$H NMR (400 MHz, MeOD-d$_4$): 7.79-7.77 (d, 1H), 7.70 (s, 1H), 7.49-7.47 (m, 3H), 7.43-7.40 (m, 3H), 7.12-7.10 (t, 1H), 3.66-3.63 (t, J=6.0 Hz, 2H), 2.89-2.85 (t, J=8.0 Hz, 2H), 1.98-1.92 (t, J=8.0 Hz, 2H). MS (ESI) m/z 407 [M+H]+, 429 [M+Na]+.

1-(4-(4-(3-hydroxyhexan-2-yl)-1H-1,2,3-triazol-1-yl)phenyl)-3-(2-(trifluoromethyl)phenyl) urea (35d). (Purification eluent: DCM/MeOH 98:2). Yield 77%. $^1$H NMR (400 MHz, MeOD-d$_4$): δ 7.81-7.79 (d, 1H), 7.68 (s, 1H), 7.51-7.49 (m, 3H), 7.42-7.38 (m, 3H), 7.11-7.08 (m, 1H), 4.76-4.62 (m, 1H), 1.98-1.90 (m, 1H), 1.54-1.12 (m, 4H), 0.94-0.88 (m, 6H) ppm. MS (ESI): m/z 446 [M−H]−.

1-(4-(4-(morpholinomethyl)-1H-1,2,3-triazol-1-yl)phenyl)-3-o-tolylurea (35e). The residue was crystallized from MeOH. Yield 69% white crystals. $^1$H NMR (MeOD-d$_4$): δ 8.37 (s, 1H), 7.75-7.73 (d, J=9.2 Hz, 2H), 7.66-7.606 (m, 3H), 7.21-7.17 (m, 2H), 7.06-7.02 t, J=7.6 Hz, 1H), 3.73 (s, 2H)), 3.71-3.69 (m, 4H) 2.565-2.54 (m, 4H), 2.30 (s, 3H) ppm. $^{13}$C NMR (MeOD-d$_4$): δ 144.47, 143.79, 140.39, 131.54, 130.09, 126.08, 124.23, 123.11, 122.06, 120.89, 119.23, 66.20, 52.92, 16.85 ppm. MS: m/z 392.9 [M+H]+

1-(4-(4-(morpholinoethyl)-1H-1,2,3-triazol-1-yl)phenyl)-3-o-tolylurea (35f). The residue was crystallized from MeOH. Yield 75% White solid. $^1$H NMR (400 MHz, DMSO d$_6$): δ 9.24 (s, 1H), 8.44 (s, 1H), 7.97 (s, 1H), 7.80-7.78 (d, J=8 Hz, 2H), 7.75-7.72 (d, J=9.2 Hz, 2H), 7.63-7.61 (d, J=8.8 Hz, 2H), 7.17-7.11 (m, 3H), 6.96-6.92 (t, J=7.2 Hz, 1H), 3.57-3.55 (m, 4H) 2.87-2.83 (t, J=7.6 Hz, 3H), 2.62-2.58 (t, J=8 Hz, 2H), 2.41-2.40 (m, 4H) 2.23 (s, 3H) ppm. $^{13}$C NMR (100 MHz, DMSO d$_6$): δ 145.59, 140.51, 137.64, 131.36, 130.69, 128.36, 126.64, 123.44, 121.81, 121.12, 120.72, 119.09, 66.66, 58.12, 53.62, 23.20, 18.33 ppm. MS (ESI): m/z 421.2 [M+H]+, 443 [M+Na]+.

1-(4-(4-(morpholinopropyl)-1H-1,2,3-triazol-1-yl)phenyl)-3-o-tolylurea (35g). (Purification eluent: DCM-methanol 98:2). Yield 70% white solid. $^1$H NMR (400 MHz, MeOD-d$_4$): δ 8.23 (s, 1H), 7.73-7.71 (d, J=8.0 Hz, 2H), 7.65-7.63 (d, J=7.6 Hz, 2H), 7.21-7.15 (m, 2H), 7.05-7.02 (t, J=7.4 Hz, 1H), 3.70-3.67 (m, 4H), 2.82-2.78 (t, J=8 Hz, 2H), 2.48-2.43 (m, 6H), 2.29 (s, 1H), 1.98-1.90 (quin. J=8.0 Hz, 2H) ppm. $^{13}$C NMR (100 MHz, MeOD-d$_4$) δ 145.61, 140.53, 137.67, 131.38, 130.71, 128.37, 126.66, 123.48, 121.87, 121.21, 120.77, 119.21, 66.21, 58.22, 53.47, 25.78, 22.99, 18.11 ppm. MS (ESI): m/z 406.9 [M+H]+, 428.9 [M+Na]+.

4-(4-(3-(4-methylpiperazin-1-yl)propyl)-1H-1,2,3-triazol-1-yl)benzenamine (35h). (Purification eluent: DCM-methanol 99:1). Yield 69% white solid. $^1$H NMR (400 MHz, MeOD-d$_4$): δ 8.24 (s, 1H), 7.72-7.63 (m, 4H), 7.19-7.14 (m, 2H), 7.04-7.00 (t, J=8 Hz, 1H), 2.81-2.78 (t, J=7.6 Hz, 2H), 2.63-2.60 (m, 8H), 2.52-2.48 (t, J=8 Hz, 2H), 2.36 (s, 1H), 2.30 (s, 1H), 1.98-1.91 (quint, J=7.6 Hz, 2H) ppm. $^{13}$C NMR (100 MHz, MeOD-d$_4$) δ 154.19, 147.95, 140.27, 136.32, 131.61, 130.03, 126.13, 124.15, 123.14, 120.73, 120.14, 120.01, 119.28, 57.08, 53.97, 51.82, 44.18, 25.78, 22.72, 16.78 ppm. MS (ESI): m/z 434 [M+H]+, 457.2[M+Na]+.

1-(4-(4-(dimethylaminopropyl)-1H-1,2,3-triazol-1-yl)phenyl)-3-o-tolylurea (35i). (Purification eluent: DCM-methanol 95:5). Yield 67% white solid. $^1$H NMR (400 MHz, MeOD-d$_4$): δ 8.30 (s, 1H), 7.74-7.72 (d, J=8.0 Hz, 2H), 7.67-7.62 (m, 3H), 7.21-7.15 (m, 2H), 7.06-7.02 (t, J=8.0 Hz, 1H), 3.08-3.04 (t, J=8 Hz, 2H), 2.89-2.85 (t, J=7.4 Hz, 2H), 2.62-2.58 (t, J=8.0 Hz, 2H), 2.77 (s, 6H), 2.3 (s, 3H), 2.15-2.08 (quint, J=7.6 Hz, 2H), ppm. $^{13}$C NMR (100 MHz, MeOD-d$_4$): δ 154.17, 146.69, 140.35, 136.28, 131.54, 130.10, 126.06, 124.2, 123.10, 120.76, 120.34, 119.2, 57.27, 42.5, 29.28, 24.43, 21.97, 16.69 ppm. MS (ESI): m/z 376.9 [M−H]⁻, 412.9 [M+Cl]⁻ diethyl (2-(1-(4-(3-(o-tolyl)ureido)phenyl)-1H-1,2,3-triazol-4-yl)ethyl) phosphate (36). 35b (35 mg, 0.10 mmol), was solubilized in 6 mL of anhydrous CH₂Cl₂, then (Et₂O)₂POCl (17 μL, 0.12 mmol), TEA (42 μL, 0.30 mmol), and Ti(tBuO)₄ were added sequentially via syringe. The reaction mixture was stirred at r.t for 11 h, then the solvent was removed at reduced pressure and the residue purified by flash chromatography on silica gel. (PE-EtOAc 2:1). Yield 75% yellow oil. $^1$H NMR (400 MHz, CDCl₃-d): δ 8.37 (s, 1H), 7.70-7.68 (m, 2H), 7.48-7.38 (m, 5H), 7.20-7.12 (m, 2H), 7.02-6.98 (t, J=8.0 Hz, 1H), 4.40-4.36 (t J=8.0 Hz, 2H), 4.13-4.07 (q, J=7.6 Hz, 4H), 3.18-3.15 (t, J=6.2 Hz, 2H), 2.23 (s, 3H), 1.32-1.29 (t, J=7.0 Hz, 3H) ppm. $^{13}$C NMR (100 MHz, CDCl₃-d): δ 153.60, 143.78, 140.09, 136.29, 131.37, 130.69, 130.42, 129.97, 126.87, 126.62, 124.50, 123.44, 120.95, 120.12, 119.53, 66.42, 66.25, 27.06, 17.90, 16.03 ppm. MS (ESI): m/z 472 [M−H]⁻, 508 [M+Cl]⁻

General Procedure for the Preparation of Compounds 37-39.

The opportune alcohol 35b-c, (25 mg, 0.07 mmol), acid (10 μL, 0.07 mmol), N,N'-dicyclohexylcarbodiimide (22 mg, 0.11 mmol), and DMAP (3 mg, 0.01 mmol), were stirred at 0° C. for 30 min. in a mixture of CH₂Cl₂ 10 mL and DMF 2 mL. After that time, the reaction mixture was allowed to reach r.t. and stirred for 12 h. The solvent was then removed at reduced pressure, EtOAc was added and the mixture was washed with 5% LiCl aq. Solution, dried over anhydrous Na₂SO₄, and concentrated in vacuo. The residue was purified by flash chromatography on silica gel with the opportune eluent.

2-(1-(4-(3-(o-tolyl)ureido)phenyl)-1H-1,2,3-triazol-4-yl)ethyl 3-methylbutanoate (37). (Purification eluent: DCM-methanol 98:2). Yield 74% white solid. $^1$H NMR (400 MHz, CDCl₃-d): δ 7.72 (s, 1H), 7.56-7.48 (m, 5H), 7.25-7.23 (m, 3H), 7.17-7.14 (m, 2H), 6.61 (s, 1H), 4.41-4.38 (t, J=6.6 Hz, 2H), 3.14-3.11 (t, J=6.6 Hz, 2H), 2.28 (s, 3H), 2.18-2.16 (d, J=7.6 Hz, 2H), 0.92-0.89 (d, J=6.8 Hz, 6H) ppm. $^{13}$C NMR (100 MHz, CDCl₃): δ 173.05, 153.62, 144.95, 139.21, 136.93, 135.65, 136.19, 132.73, 132.18, 131.54, 131.00, 127.53, 126.98, 126.62, 125.34, 121.28, 120.30, 119.94, 62.75, 43.32, 25.57, 22.45, 17.88 ppm. MS (ESI): m/z 420 [M−H]⁻, 456 [M+Cl]⁻

2-(1-(4-(3-(2-(trifluoromethyl)phenyl)ureido)phenyl)-1H-1,2,3-triazol-4-yl)ethyl 3-methylbutanoate (38). (Purification eluent: DCM-methanol 98:2). Yield 68% white solid. $^1$H NMR (400 MHz, CDCl₃-d): δ 8.19 (s, 1H), 7.98-7.96 (d, J=8 Hz, 1H), 7.76 (s, 1H), 7.58-7.50 (m, 5H), 7.38 (s, 1H), 7.21-7.17 (t, J=7.6 Hz, 1H), 4.43-4.39 (t, J=6.6 Hz, 2H), 3.16-3.13 (t, J=6.6 Hz, 2H), 2.19-2.17 (d, J=7.2 Hz, 2H), 2.15-2.08 (m, 1H), 0.92-0.90 (d, J=8 Hz, 2H) ppm. $^{13}$C NMR (100 MHz, CDCl₃-d): δ 172.0, 150.9, 139.4, 132.9, 130.1, 129.3, 125.7, 124.7, 124.2, 121.2, 120.7, 118.0, 116.0, 65.7, 46.4, 26.0, 25.0, 20.6 ppm. MS (ESI): m/z 474 [M−H]⁻, 510 [M+Cl]⁻

2-(1-(4-(3-(2-(trifluoromethyl)phenyl)ureido)phenyl)-1H-1,2,3-triazol-4-yl)ethyl 3-(benzo[d][1,3]dioxol-5-yl)acrylate (39). (Purification eluent: DCM-methanol 98:2). Yield 68% white solid. $^1$H NMR (400 MHz, CDCl₃-d): δ 8.12 (s, 1H), 8.02-8.00 (d, J=8 Hz, 1H), 7.60 (s, 1H), 7.58-7.52 (m, 7H), 7.34 (s, 1H), 7.22-7.18 (t, J=8 Hz, 1H), 7.00-6.97 (m, 2H), 6.80-6.78 (d, J=8 Hz, 2H), 6.28-6.24 (d, J=12 Hz, 1H), 5.99 (s, 2H), 4.55-4.52 (t, J=12.4 Hz, 2H), 3.22-3.25 (t, J=12.0 Hz, 2H) ppm. $^{13}$C NMR (100 MHz, CDCl₃-d): δ 167.7, 152.9, 118.6, 117.9, 145.8, 138.4, 133.4, 131.6, 129.7, 127.6, 126.4, 124.9, 121.3, 118.7, 116.2, 115.9, 108.4, 106.7, 103.1, 69.0, 24.2 ppm. MS (ESI): m/z 564.5 [M−H]⁻, 600.3 [M+Cl]⁻

Example 7

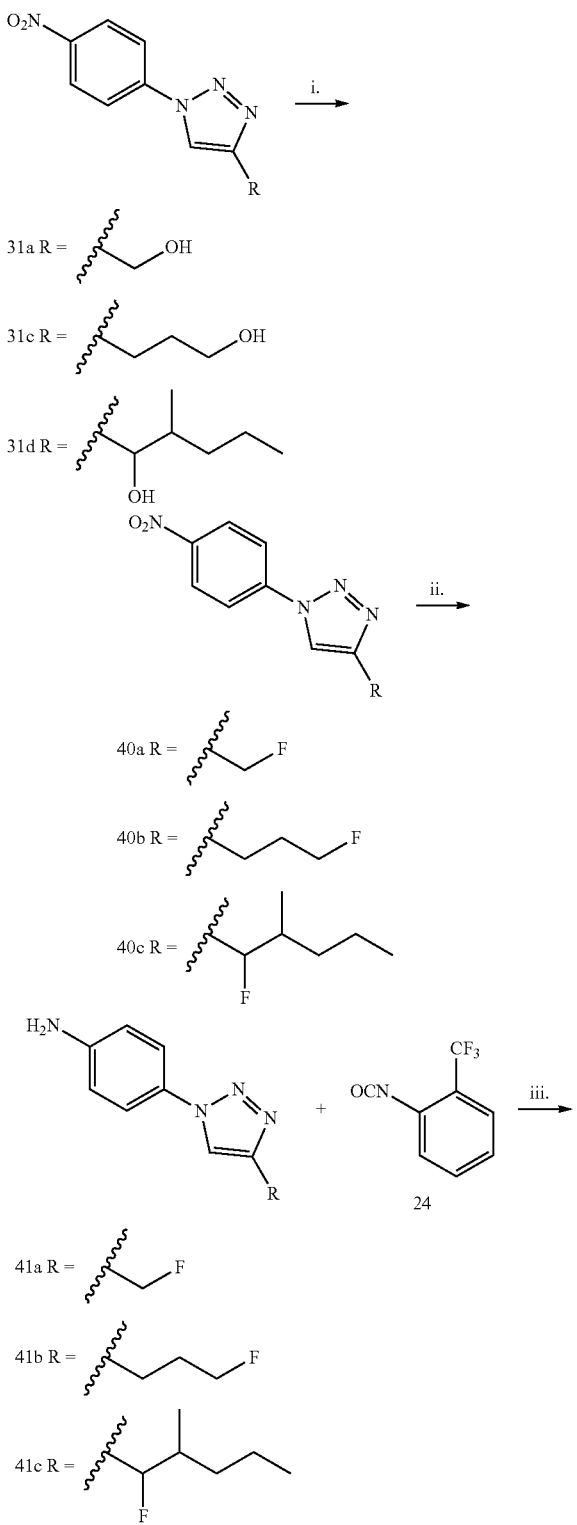

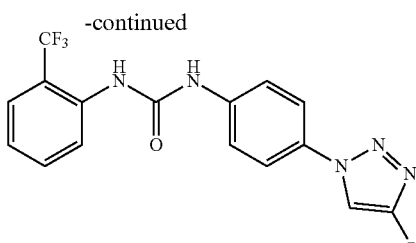

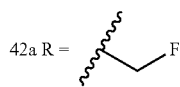
42a R =

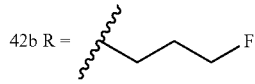
42b R =

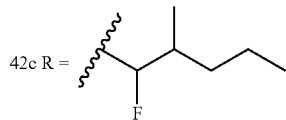
42c R =

Reagents and conditions: i. Deoxo-Fluor®, anhydrous CH$_2$Cl$_2$, 12 h r.t; ii. H$_2$, Pd/C, MeOH, 1 h, iii. 2-(Trifluoromethyl)phenyl isocyanate CH$_2$Cl$_2$, 5 h r.t;

General Procedure for the Preparation of Fluorinated Compounds 40a-c:

The opportune alcohol 31a, 31c, or 31d (400 mg, 1.38 mmol) was dissolved in 15 mL of CH$_2$Cl$_2$, and Deoxo-Fluor® (533 µL, 2.48 mmol), was added at −40° C. After stirring for 2 h at −40° C. the reaction mixture was warmed up to r.t. and stirred overnight. The solvent was removed at reduced pressure and the residue purified by flash chromatography on silica gel.

4-(fluoromethyl)-1-(4-nitrophenyl)-1H-1,2,3-triazole (40a): (Purification Eluent: DCM/MeOH 98:2) Yield: 67%, white solid $^1$H NMR (400 MHz, ACETONE-d$_6$): δ 8.94 (s, 1H), 8.49-8.46 (dd, J=8.8 Hz, 2H), 8.25-8.23 (dd, J=8.8 Hz, 2H), 5.64 (s, 1H), 5.52 (s, 1H) ppm. $^{13}$C-NMR (100 MHz, ACETONE-d$_6$): δ 147.50, 144.31, 141.34, 125.43, 123.38, 120.89, 76.00-74.39 (J$_{CF}$=161.0 Hz) ppm.

4-(3-fluoropropyl)-1-(4-nitrophenyl)-1H-1,2,3-triazole (40 b): (Purification eluent: DCM-methanol 98:2). Yield 57% white solid. $^1$H NMR (400 MHz, CDCl$_3$-d): δ 8.40-8.38 (d, J=9.2 Hz, 2H), 7.97-7.95 (d, J=9.2 Hz, 2H), 7.90 (s, 1H), 4.61-4.59 (t, J=5.7 Hz, 1H), 4.49-4.46 (t, J=5.7 Hz, 1H), 2.98-2.94 (t, J=7.6 Hz, 2H), 2.23-2.10 (m, 2H) ppm. $^{13}$C NMR (100 MHz CDCl$_3$-d): δ 184.54, 147.08, 141.29, 125.53, 120.27, 119.09, 83.73-82.09 (J$_{CF}$=164 Hz), 29.86-29.66 (J$_{CF}$=20 Hz), 21.41 ppm.

4-(1-fluoro-2-methylpentyl)-1-(4-nitrophenyl)-1H-1,2,3-triazole (40c): (Purification eluent: DCM-methanol 98:2). Yield 67% white solid. $^1$H NMR (400 MHz, CDCl$_3$-d): δ 8.38-8.35 (d, J=8.8 Hz, 2H), 5.63-5.45 (m, 1H), 2.22-2.16 (m, 1H), 1.56-1.38 (m, 4H), 0.84-0.92 (m, 3H), 0.79-0.75 (t, J=7.2 Hz, 3H) ppm. MS (ESI) m/z 291 [M−H]$^-$, 327 [M+Cl]$^-$.

General Procedure for the Preparation of Compounds 41a-c

The opportune triazole compound 40a 40b or 40c (100 mg, 0.34 mmol) was solubilized in 10 mL of anhydrous MeOH, and 10% Palladium on charcoal (30 mg) was added. The reaction mixture was stirred under Hydrogen atmosphere for 1 h, then the mixture was filtered off on a celite pad, the solvent evaporated at reduced pressure.

4-(4-(fluoromethyl)-1H-1,2,3-triazol-1-yl)aniline (41a): Yield 99% white solid. $^1$H NMR (400 MHz, ACETONE-d$_6$): δ 7.94 (s, 1H), 7.46-7.44 (dd, J=8.8 Hz, 2H), 6.77-6.75 (dd, J=8.4 Hz, 2H), 5.62 (s, 1H), 5.50 (s, 1H) ppm. MS (ESI) m/z 193 [M+H]$^+$, 215 [M+Na]$^+$.

4-(4-(3-fluoropropyl)-1H-1,2,3-triazol-1-yl)aniline (41b): Yield 99% white solid. $^1$H NMR (400 MHz CDCl$_3$-d): δ 8.51 (s, 1H), 7.84-7.82 (d, J=8.7 Hz, 2H), 7.36-7.34 (d, J=8.6 Hz, 2H), 7.90 (s, 1H), 5.91-4.89 (t, J=5.7 Hz, 1H), 4.99-4.96 (t, J=5.7 Hz, 1H), 2.98-2.94 (t, J=7.6 Hz, 2H), 2.23-2.10 (m, 2H) ppm. MS (ESI) m/z 221 [M+H]$^+$, 243 [M+Na]$^+$.

4-(4-(1-fluoro-2-methylpentyl)-1H-1,2,3-triazol-1-yl) aniline (41c): Yield 99% white solid. $^1$H NMR (400 MHz CDCl$_3$-d): δ 7.83 (s, 1H), 7.42-7.40 (d, J=8.4 Hz, 2H), 6.71-6.69 (d, J=8.4 Hz, 2H), 5.60-5.41 (m, 1H), 4.08 (s, 2H), 2.22-2.18 (m, 1H), 1.60-1.20 (m, 4H), 0.94-0.82 (m, 3H), 0.89-0.85 (t, J=7.2 Hz, 3H) ppm. MS (ESI) m/z 263 [M+H]$^+$, 285 [M+Na]$^+$.

General Procedure for the Preparation of Compounds 42a 42b and 42c

The opportune aniline compound 41-c (100 mg, 0.46 mmol) was added to a solution of the 0-(Trifluoromethyl) phenyl isocyanate 24 (85 µL, 0.65 mmol) in anhydrous CH$_2$Cl$_2$ (10 mL) in one portion. The solution was stirred for 4 hours at r.t. under a nitrogen atmosphere. The solvent was removed, at reduced pressure and the residue purified by flash chromatography using the opportune eluent.

1-(4-(4-(fluoromethyl)-1H-1,2,3-triazol-1-yl)phenyl)-3-(2-(trifluoromethyl)phenyl)urea (42a). (Purification Eluent: DCM/EA 95:5). Yield 79% $^1$H NMR (400 MHz, ACETONE-d$_6$): δ 9.09 (s, 1H), 8.64-8.63 (d, J=2.8 Hz, 1H), 8.15-8.13 (d, J=8.0 Hz, 1H), 7.82-7.64 (m, 5H), 7.31-7.27 (t, J=7.2 Hz, 1H), 5.60 (s, 1H), 5.44 (s, 1H) ppm $^{13}$C-NMR (100 MHz, ACETONE-d$_6$): δ 152.2, 140.56, 140.57, 132.95, 131.72, 125.90, 125.48, 123.78, 122.80, 121.13, 119.28, 76.16-74.53 (J$_{CF}$=163.0 Hz) ppm MS (ESI) m/z 378 [M−H]$^-$, 414 [M+Cl]$^-$.

1-(4-(4-(3-fluoropropyl)-1H-1,2,3-triazol-1-yl)phenyl)-3-(2 (trifluoromethyl)phenyl) urea. (42b). Yield 87% white solid. $^1$H NMR (400 MHz, CDCl$_3$-d): δ 8.80 s (1H), 7.93 (s, 1H), 7.75-7.73 (d, 1H), 7.71 (s, 1H), 7.51-7.49 (m, 3H), 7.42-7.39 (m, 3H), 7.11-7.09 (t, 1H), 5.91-4.89 (m, J=5.7 Hz, 1H), 4.99-4.96 (m, J=5.7 Hz, 1H), 2.98-2.94 (t, J=7.6 Hz, 2H), 2.23-2.10 (m, 2H) ppm. MS (ESI) m/z 408 [M+H]$^+$, 430 [M+Na]$^+$. $^{13}$C NMR (100 MHz CDCl$_3$-d): δ 152.91, 139.44, 132.83, 129.62, 126.77, 121.88, 120.43, 119.13, 115.88, 83.73-82.09 (J$_{CF}$=164 Hz), 32.71-32.51 (J$_{C\text{-}F}$=20 Hz), 27.31 ppm.

1-(4-(4-(1-fluoro-2-methylpentyl)-1H-1,2,3-triazol-1-yl) phenyl)-3-(2-(trifluoromethyl) phenyl) urea (42c): Yield 99% white solid. $^1$H NMR (400 MHz CDCl$_3$-d): δ 8.83 s (1H), 7.90 (s, 1H), 7.79-7.77 (d, 1H), 7.70 (s, 1H), 7.49-7.47 (m, 3H), 7.43-7.40 (m, 3H), 7.12-7.10 (t, 1H), 5.61-5.42 (m, 1H), 2.32-2.10 (m, 1H), 1.42-1.40 (m, 2H), 1.29-1.21 (m, 2H), 0-98-0.86 (m, 6H) ppm. $^{13}$C NMR (100 MHz CDCl$_3$-d): δ 153.85, 147.65, 139.63, 135.31, 132.49, 131.75, 127.90, 126.82, 126.14, 125.17, 124.81, 122.84, 122.54, 121.20, 120.34, 92.81-91.18 (J$_{C\text{-}F}$=164 Hz), 90.72-90.49 (J$_{C\text{-}F}$=23 Hz), 37.64-37.44 (J$_{C\text{-}F}$=20 Hz); 34.45, 33.55, 19.98, 14.07, 13.80 ppm. MS (ESI) m/z 450.1 [M+H]$^+$, 472.1[M+Na]$^+$.

Example 8

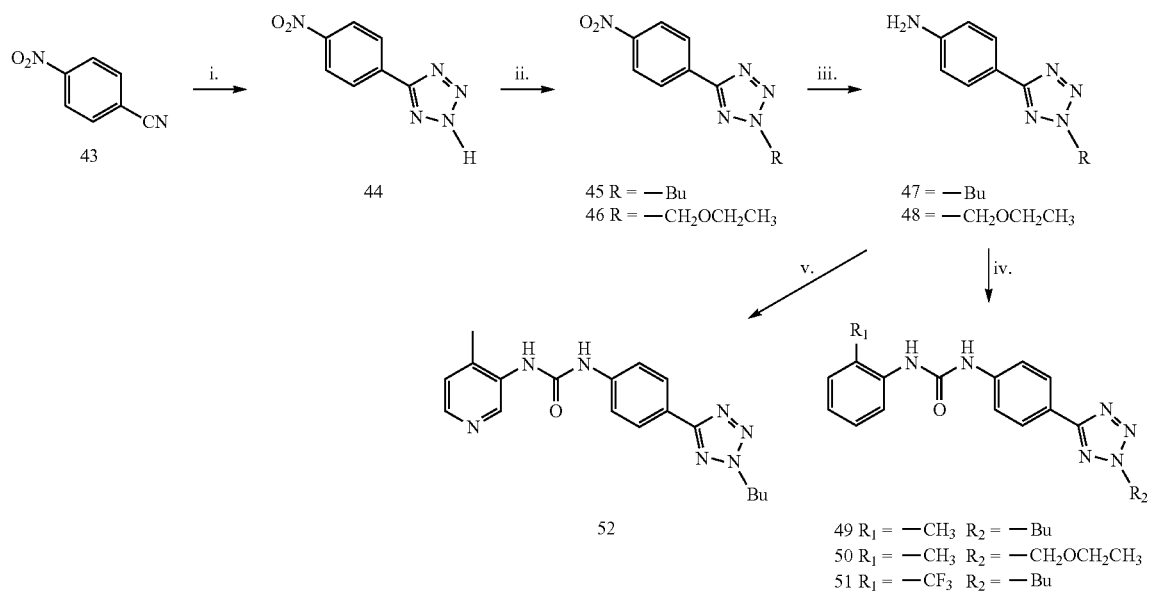

Reagents and conditions: i. NaN₃, NH₄Cl, DMF, 12 h, reflux; ii. K₂CO₃, 1-iodobutane or 1-chloromethylethylether, CH₃CN, 12 h,. r.t; iii. H₂, Pd/C, MeOH 30 min.; iv. Opportune isocyanate CH₂Cl₂, 9 h r.t; v. a) 3-amino,4-methylpyridine, triphosgene, DMAP, CH₂Cl₂, 0° C., b). opportune aniline 9 h r.t CH₂Cl₂, 9 h r.t;

5-(4-nitrophenyl)-2H-tetrazole (44). A mixture of 4-nitrobenzonitrile (600 mg, 4.05 mmol) sodium azide (790 mg, 12.15 mmol) ammonium chloride (867 mg, 16.20 mmol) and DMF (5 mL) was heated at 120° C. for 12 hr. Then the reaction was allowed to cool to r.t., water was added with continuous stirring. The mixture was then acidified to pH 2 with HCl 6N. The reaction mixture was extracted with EtOAc (3×20 mL) and dried over Na₂SO₄, and the solvent was removed under reduced pressure, to give a yellow residue that was crystallized from Ethanol Yield 80% white solid ¹H NMR (MeOD-d₄): δ 8.40-8.38 (d, 2H, J=7.2 Hz), 8.28-8.28 (d, 2H, J=8 Hz) ppm. ¹³C NMR (MeOD-d₄): δ 156.72, 149.46, 131.32, 128.18, 124.07 ppm. MS: m/z 189.9 [M-H]⁻

2-butyl-5-(4-nitrophenyl)-2H-tetrazole (45). A suspension of 44 (200 mg, 1.05 mmol), K₂CO₃ (174 mg, 1.26 mmol) and n-butyliodide (144 μL, 1.26 mmol), in Acetonitrile was refluxed for 4 h. After that time, the reaction mixture was concentrated in vacuo, water was added and the residue was extracted with AcOEt (3×25 mL), washed with brine, and dried over Na₂SO₄. The resulting residue was purified by flash chromatography on silica gel (PE-DCM 1:8). Yield 82%, yellow solid. ¹H NMR (400 MHz CDCl₃-d): δ 8.26 (m, 4H), 4.67-4.63 (t, J=7.6 Hz, 2H), 2.03-1.98 (quint, J=6.8 Hz, 2H), 1.40-1.34 (sx, J=7.2 Hz, 2H) 0.95-0.92 (t, J=7.2 Hz, 3H) ppm. ¹³C NMR (100 MHz CDCl₃-d): δ 163.05, 148.74, 133.42, 127.53, 124.10, 53.20, 31.22, 19.57, 13.30 ppm. MS: m/z 220 [M+H]+

2-(ethoxymethyl)-5-(4-nitrophenyl)-2H-tetrazole (46). A suspension of 44 (50 mg, 0.26 mmol), K₂CO₃ (43 mg, 0.31 mmol) and chloromethylethylether (28 μL, 0.31 mmol), in Acetonitrile was refluxed for 12 h. After that time, the reaction mixture was concentrated in vacuo, water was added and the residue was extracted with AcOEt (3×25 mL), washed with brine, and dried over Na₂SO₄. The resulting residue was purified by flash chromatography on silica gel (PE-DCM 1:7). Yield 66%, yellow solid. A suspension of ¹H NMR (Acetone d-₆): δ 8.42-8.34 (m, 4H), 6.05 (s, 2H), 3.79-3.69 (m, 2H), 1.19-1.09 (m, 3H) ppm; ¹³C NMR (Acetone d-₆): δ 163.80, 149.22, 133.18, 127.83, 123.94, 81.90, 66.35, 14.34 ppm.

4-(2-butyl-2H-tetrazol-5-yl)aniline (47). Compound 45 (100 mg, 0.40 mmol) was solubilized in 30 mL of anhydrous MeOH, and 10% Palladium on charcoal (5 mg) was added. The reaction mixture was stirred under Hydrogen atmosphere for 1 h, then the mixture was filtered off on a celite pad, the solvent evaporated at reduced pressure. Yield 99% ¹H NMR (400 MHz CDCl₃-d): δ 7.90-7.88 (d, J=8.0 Hz, 2H), 6.71-6.69 (d, J=8.0 Hz, 2H), 4.57-4.53 (t, J=7.6 Hz, 2H), 4.03 (s, 2H), 2.00-1.92, (quint, J=8.1 Hz, 2H), 1.38-1.23 (sx, J=8.0 Hz, 2H), 0.93-0.89 (t, 8.0 Hz, 3H) ppm. ¹³C NMR (100 MHz, CDCl₃-d): δ 165.62, 148.77, 128.04, 117.56, 114.87, 113.12, 52.69, 31.38, 19.56, 12.17 ppm MS (ESI): m/z 218 [M+H]+, 239.9 [M+Na]⁺.

4-(2-(ethoxymethyl)-2H-tetrazol-5-yl)aniline (48). Compound 46 (150 mg, 0.60 mmol) was solubilized in 30 mL of anhydrous MeOH, and 10% Palladium on charcoal (5 mg) was added. The reaction mixture was stirred under Hydrogen atmosphere for 1 h, then the mixture was filtered off on a celite pad, the solvent evaporated at reduced pressure. Yield 99%¹H NMR (400 MHz CDCl₃-d): δ 7.97-7.95 (d, 2H, J=7.2 Hz), 6.75-6.73 (d, 2H, J=7.2 Hz), 5.870 (s, 2H), 3.69-68 (m, 2H), 1.241 (s, 3H) ppm. MS: m/z 220 [M+H]+

1-(4-(2-butyl-2H-tetrazol-5-yl)phenyl)-3-(o-tolyl)urea (49). Compound 47 (0.10 mmol) was added to a solution of o-tolyl isocyanate (0.15 mmol) in anhydrous MeOH (10 mL) in one portion. The solution was stirred for 9 hours at r.t. under a nitrogen atmosphere. The solvent was removed at reduced pressure and the residue purified on silica to furnish the final product as white solid. (DCM-MeOH 98:2). Yield 73% ¹H NMR (Acetone d-₆): δ 8.60 (s, 1H), 8.03-8.01 (d, J=8 Hz, 2H), 7.92-7.90 (d, J=8.0 Hz, 2H), 7.55 (s, 1H), 7.18-7.14 (m, 2H), 6.99-6.95 (t, J=7.6 Hz, 1H), 4.71-4.67 (t, J=, 2H), 2.27 (s, 1H), 2.03-1.98 (m, 2H), 1.43-1.34 (sx, J=7.6 Hz, 2H), 0.97-0.94 (t, J=7.4 Hz, 3H) ppm. ¹³C NMR (Acetone): δ 164.91, 152.54, 142.16, 137.33, 130.35, 128.48, 127.64, 126.40, 123.44, 122.20, 121.37, 118.75, 52.47, 31.09, 19.34, 17.17, 12.73 ppm. MS: m/z 351 [M+H]+

1-(4-(2-(ethoxymethyl)-2H-tetrazol-5-yl)phenyl)-3-(o-tolyl)urea (50). Compound 48 (0.10 mmol) was added to a solution of o-tolyl isocyanate (0.15 mmol) in anhydrous MeOH (10 mL) in one portion. The solution was stirred for 9 hours at r.t. under a nitrogen atmosphere. The solvent was removed at reduced pressure and the residue purified on silica to furnish the final product as white solid. (DCM-MeOH 98:2). Yield 62% $^1$H NMR (400 MHz CDCl$_3$-d): δ 8.06-8.04 (d, 2H, J=8 Hz), 7.65-7.62 (m, 3H), 7.21-7.15 (m, 2H), 7.05-7.01 (t, 1H, J=7.6 Hz), 5.95 (s, 2H), 3.74-3.69 (q, 2H), 2.30 (s, 3H), 1.20-1.17 (t, 3H, J=6.8 Hz) ppm. $^{13}$C NMR (100 MHz CDCl$_3$-d): δ 142.06, 136.14, 130.47, 127.51, 126.33, 124.73, 123.05, 120.95, 118.61, 80.93, 66.18, 16.61, 13.32 ppm. MS: m/z 375 [M+Na]+

1-(4-(2-butyl-2H-tetrazol-5-yl)phenyl)-3-(2-(trifluoromethyl)phenyl)urea (51). Compound 47 (0.10 mmol) was added to a solution of o-tolyl isocyanate (0.15 mmol) in anhydrous MeOH (10 mL) in one portion. The solution was stirred for 9 hours at r.t. under a nitrogen atmosphere. The solvent was removed at reduced pressure and the residue purified on silica to furnish the final product as white solid. (DCM-MeOH 98:2). Yield 70%, white solid. $^1$H NMR (400 MHz CDCl$_3$-d): δ 7.93-7.91 (d, J=8 Hz, 2H), 7.82-7.80 (d, J=8.0 Hz, 1H), 7.48-7.39 (m, 2H), 7.36-7.34 (d, J=7.2 Hz, 2H), 7.09-7.05 (t, J=7.2 Hz, 1H), 4.60-4.57 (t, J=6.8 Hz, 2H), 2.01-1.97 (m, 2H), 1.39-1.33 (m, 2H), 0.95-0.91 (t, J=7.2 Hz, 3H) ppm. $^{13}$C NMR (100 MHz, CDCl$_3$-d): δ 153.54, 140.20, 135.38, 132.54, 127.60, 126.29, 126.11, 125.23, 124.54, 122.43, 122.01, 120.07, 52.96, 31.27, 19.60, 13.34 ppm MS (ESI) m/z 405 [M+H]+, 428 [M+Na]+.

1-(4-(2-butyl-2H-tetrazol-5-yl)phenyl)-3-(4-methylpyridin-3-yl)urea (52): A solution of 4-methylpyridin-3-amine (41 mg, 0.3835 mmol) and DMAP (19 mg, 0.1534 mmol) in 5 mL of CH$_2$Cl$_2$ was added dropwise to an ice cold solution of triphosgene in CH$_2$Cl$_2$, during 30 min., then aniline 47 was added in one portion, and the reaction mixture was stirred at rt for 12 h. After this time, 2M HCl was added and the mixture was extracted with CH$_2$Cl$_2$ (3×20 mL). The organic layers were collected, washed with Brine and dried over Na$_2$SO$_4$. The crude was purified by flash chromatography on silica gel (CH$_2$Cl$_2$-MeOH 98:2). Yield 70%. $^1$H NMR (400 MHz, MeOD-d$_4$): δ 8.87 (s, 1H), 8.15 (d, 1H), 8.03-8.61 (d, J=8.0 Hz, 2H), 7.63-7.61 (d, J=8.0 Hz, 2H), 7.30-7.29 (d, J=4 Hz, 1H), 4.71-4.67 (t, J=7.8 Hz, 2H), 2.35 (s, 3H), 2.06-1.99 (q, J=9.3 Hz, 2H), 1.42-1.36, (q, 2H), 1.00-0.97 (t, J=8.0 Hz, 3H) ppm. $^{13}$C NMR (MeOD-d$_4$): δ 164.69, 153.57, 143.82, 143.19, 141.39, 140.12, 134.50, 127.09, 125.50, 121.37, 118.72, 52.64, 31.03, 19.38, 16.20, 12.29 ppm. MS (ESI) m/z 353.2 [M+H]+, 375.2 [M+Na]+.

Example 9

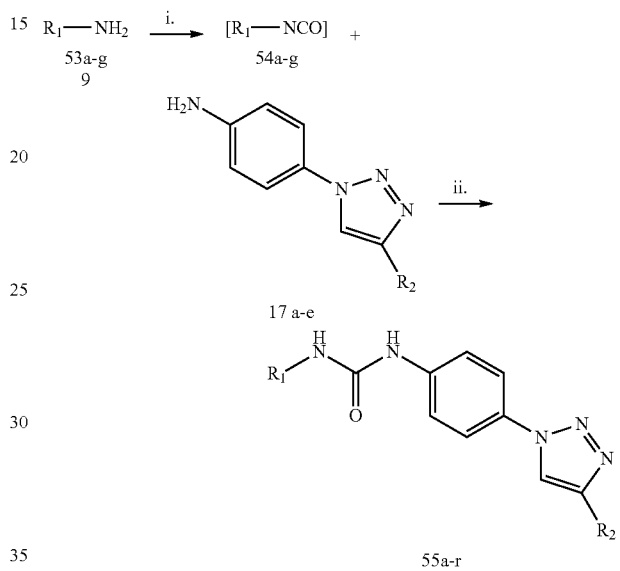

Reagents and conditions: i. triphosgene, opportune aromatic amine, DMAP, CH$_2$Cl$_2$ 0° C. 20 min., ii. opportune aniline r.t CH$_2$Cl$_2$, 9 h r.t;

Urea derivatives 55a-g are reported in Table 1

TABLE 1

List of urea derivatives 55a-r

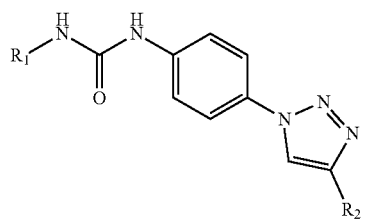

| Entry | Aromatic amine | R$_1$ | Isocyanate | Amine | R$_2$ | Compound |
|---|---|---|---|---|---|---|
| 1 | 53a | 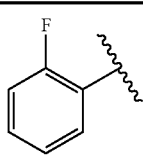 | 54a | 17b | 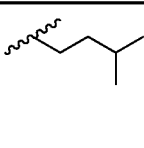 | 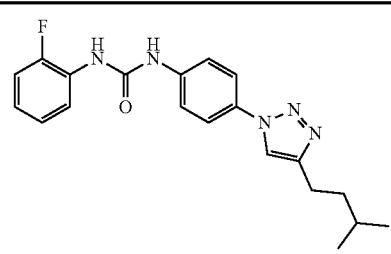 55a |

TABLE 1-continued

List of urea derivatives 55a-r

| Entry | Aromatic amine | R₁ | Iso-cyanate | Amine | R₂ | Compound |
|---|---|---|---|---|---|---|
| 2 | 53b | 3-fluorophenyl | 54b | 17b | isopentyl | 55b |
| 3 | 53c | 4-fluorophenyl | 54c | 17b | isopentyl | 55c |
| 4 | 53d | 3-chloro-2-methylphenyl | 54d | 17b | isopentyl | 55d |
| 5 | 53e | 2-methyl-5-isopropylphenyl | 54e | 17e | ethoxymethyl | 55e |

TABLE 1-continued
List of urea derivatives 55a-r
| Entry | Aromatic amine | R₁ | Iso-cyanate | Amine | R₂ | Compound |
|---|---|---|---|---|---|---|
| 6 | 53f | 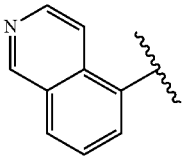 [SMILES: *c1cccc2cnccc12] | 54f | 17b | 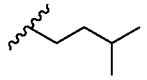 [SMILES: *CCC(C)C] | 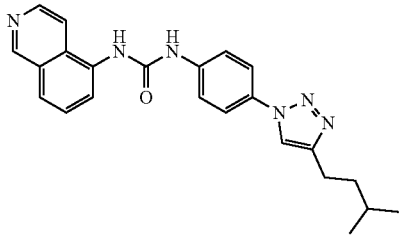 55f |
| 7 | 53g | 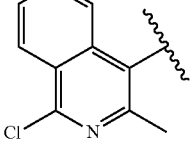 | 54g | 17b | 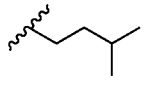 [SMILES: *CCC(C)C] | 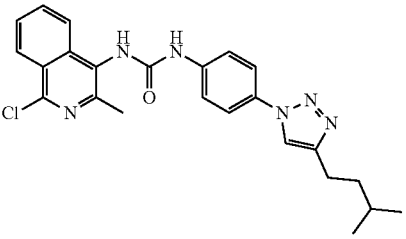 55g |
| 8 | 53h | 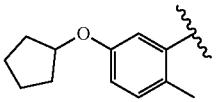 [SMILES: *c1cc(OC2CCCC2)ccc1C] | 54h | 19a | 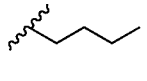 | 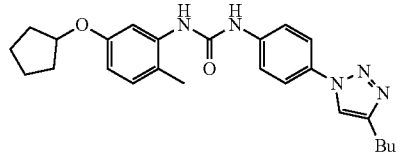 55h |
| 9 | 53i | 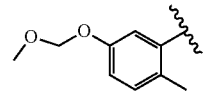 | 54i | 19a | 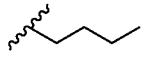 | 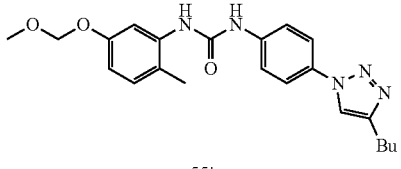 55i |
| 10 | 53a | 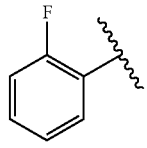 [SMILES: *c1ccccc1F] | 54a | 19a | 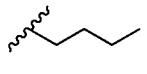 [SMILES: *CCCC] | 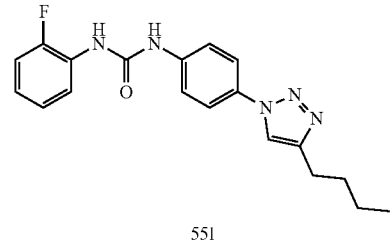 [SMILES: CCCCc1cn(-c2ccc(NC(=O)Nc3ccccc3F)cc2)nn1] 55l |

TABLE 1-continued

List of urea derivatives 55a-r

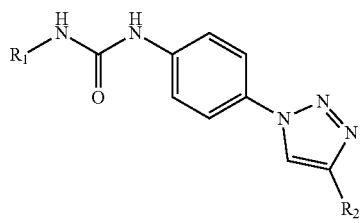

| Entry | Aromatic amine | R₁ | Iso-cyanate | Amine | R₂ | Compound |
|---|---|---|---|---|---|---|
| 11 | 53b | 3-F-phenyl | 54b | 19a | n-butyl | 55m |
| 12 | 53b | 3-F-phenyl | 54b | 55n | -CH₂CH₂C(O)CH₃ | 55n |
| 13 | 53b | 3-F-phenyl | 54b | 19e | -CH₂OCH₂CH₃ | 55o |
| 14 | 53l | 4-methyl-3-(3-oxobutyl)phenyl | 53l | 19a | n-butyl | 55p |
| 15 | 53l | 5-fluoropyridin-3-yl | 54l | 19a | n-butyl | 55q |

General Procedure for the Preparation of 55a-q:

A solution of the opportune aromatic amine (41 mg, 0.3835 mmol) and DMAP (19 mg, 0.1534 mmol) in 5 mL of $CH_2Cl_2$ was added dropwise to an ice cold solution of triphosgene in $CH_2Cl_2$, during 30 min., then the opportune aniline 17a-c was added in one portion, and the reaction mixture was stirred at r.t. for 12 h. After this time, 2M HCl was added and the mixture was extracted with $CH_2Cl_2$ (3×20 mL). The organic layers were collected, washed with Brine and dried over $Na_2SO_4$. The crude was purified by flash chromatography on silica gel using the opportune eluent.

1-(2-fluorophenyl)-3-(4-(4-isopentyl-1H-1,2,3-triazol-1-yl)phenyl)urea (55a): (Purification eluent: DCM/MeOH 98:2). Yield 68%, white solid. $^1$HNMR (400 MHz, MeOD-$d_4$): δ 8.07-8.03 (t, J=8.0 Hz, 1H), 7.64 (s, 1H), 7.56-7.50 (m, 4H), 7.08-6.75 (m, 3H) 2.76-2.72 (t, J=8.0 Hz, 2H), 1.64-1.54 (m, 3H), 0.92-0.90 (d, 6H) ppm. $^{13}$CNMR (MeOD-$d_4$): δ 154.32, 152.91, 139.45, 132.87, 129.94, 129.06, 123.88, 121.63, 119.11, 115.72, 38.37, 27.62, 23.41, 22.29 ppm. MS (ESI) m/z 366 [M−H]$^-$, 402 [M+Cl]$^-$.

1-(3-fluorophenyl)-3-(4-(4-isopentyl-1H-1,2,3-triazol-1-yl)phenyl)urea (55b): (Purification eluent: DCM/MeOH 98:2). Yield 70%, white solid. $^1$HNMR (400 MHz, MeOD-$d_4$): δ 7.74-7.73 (m, 1H), 7.54-7.53 (m, 4H), 7.34-7.32 (m, 1H), 7.25-7.24 (m, 1H), 7.18-7.16 (m 1H), 7.07-7.06 (m, 1H), 6.68-6.65 (t, J=8.0 Hz, 1H), 2.75-2.73 (t, J=8.0 Hz, 2H), 1.62-1.58 (m, 3H), 0.92-0.90 (d, 6H) ppm. $^{13}$CNMR (MeOD-$d_4$): δ 164.10, 153.91, 139.83, 137.51, 133.81, 133.49, 131.51, 129.82, 121.61, 119.17, 117.24, 116.51, 42.71, 29.12, 27.21, 23.27 ppm. MS (ESI) m/z 366 [M−H]$^-$, 402 [M+Cl]$^-$.

1-(4-fluorophenyl)-3-(4-(4-isopentyl-1H-1,2,3-triazol-1-yl)phenyl)urea (55c): (Purification eluent: PE/EA 7:3). Yield 63%, white solid. $^1$H NMR (400 MHz, Acetone-$d_6$): δ 8.48 (s, 1H), 8.34 (s, 1H), 8.15 (s, 1H), 7.71-7.66 (m, 4H), 7.53-7.49 (m, 2H), 7.02-6.97 (m, 2H), 2.72-2.68 (m, 2H), 1.60-1.53 (m, 3H), 0.90-0.88 (d, J=8.0 Hz, 6H) ppm. $^{13}$C-NMR (100 MHz, Acetone-$d_6$): δ 159.71, 152.58, 140.25, 136.40, 131.97, 130.07, 124.70, 120.60, 119.06, 118.60, 115.20, 38.53, 27.36, 23.31, 21.58 ppm. MS (ESI) m/z 366 [M−H]$^-$, 402 [M+Cl]$^-$.

1-(3-chloro-2-methylphenyl)-3-(4-(4-isopentyl-1H-1,2,3-triazol-1-yl)phenyl) urea (55d): (Purification eluent: DCM/MeOH 98:2). Yield 80%, white solid. $^1$HNMR (MeOD-$d_4$): δ 7.89 (s, 1H), 7.64-7.57 (m, 4H), 7.08-7.06 (d, J=8.0 Hz, 1H), 6.95-6.93 (d, J=8.0 Hz, 1H), 2.77-2.73 (t, J=7.2 Hz, 2H), 2.23 (s, 3H), 1.60-1.56 (m, 3H), 0.94-0.93 (d, J=6.0 Hz, 6H) ppm. $^{13}$C NMR (100 MHz CDCl$_3$-d): δ 153.48, 149.08, 139.85, 137.69, 131.73, 131.14, 126.60, 123.47, 121.61, 121.16, 119.74 ppm. MS (ESI): m/z 396 [M−H]$^-$ 1-(4-(4-(ethoxymethyl)-1H-1,2,3-triazol-1-yl)phenyl)-3-(5-isopropyl-2-methyl phenyl) urea (55e): (Purification eluent: DCM/MeOH 98:2). Yield 70%, white solid. $^1$HNMR (400 MHz CDCl$_3$-d): δ 8.39 (s, 1H), 7.85 (s, 1H), 7.46-7.37 (m, 4H), 7.02-7.00 (d, J=8.0 Hz, 1H), 6.89-6.87 (d, J=8.0 Hz, 1H), 4.66 (s, 2H), 3.63-3.58 (q, J=7.8 Hz, 2H), 2.81, 2.75 (m, 1H), 2.10 (s, 1H), 1.23-1.20 (t, J=6.8 Hz, 3H), 1.16-1.14 (d, J=8.0 Hz, 6H) ppm. $^{13}$CNMR (100 MHz CDCl$_3$-d): δ 154.22, 147.65, 145.95, 139.97, 135.57, 131.52, 131.52, 130.54, 128.69, 123.47, 122.80, 121.22, 120.96, 120.01, 66.40, 63.90, 33.66, 23.92, 17.42, 15.09 ppm. MS (ESI) m/z 394.1 [M+H]$^+$, 416.1 [M+Na]$^+$.

1-(4-(4-isopentyl-1H-1,2,3-triazol-1-yl)phenyl)-3-(isoquinolin-5-yl)urea (55f): (Purification eluent: DCM/MeOH 98:2). Yield 63%, white solid. $^1$HNMR (400 MHz CDCl$_3$-d): δ 9.22 (s, 1H), 8.46 (m, 1H), 8.22-8.20 (m, 2H), 7.96 (s, 1H), 7.89-7.87 (d, J=8.0 Hz, 1H), 7.73-7.67 (m, 5H), 2.78-2.74 (t, J=7.2 Hz, 2H), 1.61-1.57 (m, 3H), 0.93-0.92 (d, J=6.0 Hz, 6H) ppm. $^{13}$CNMR (100 MHz CDCl$_3$-d): δ 152.81, 142.11, 140.21, 139.45, 132.84, 129.87, 129.01, 124.88, 121.62, 119.11, 115.75, 114.81, 112.42, 42.66, 30.11, 27.76, 23.21 ppm. MS (ESI) m/z 399.1 [M−H]$^-$, 435.1 [M+Cl]$^-$ 1-(1-chloro-3-methylisoquinolin-4-yl)-3-(4-(4-isopentyl-1H-1,2,3-triazol-1-yl)phenyl)urea (55g): (Purification eluent: DCM/MeOH 98:2). Yield 60%, white solid. $^1$HNMR (400 MHz, MeOD-$d_4$): δ 8.34-8.32 (d, J=8.0 Hz, 1H), 8.21 (s, 1H), 8.08-8.06 (d, J=8.0 Hz, 1H), 7.89-7.84 (t, J=8.0 Hz, 1H), 7.74, 7.20 (m, 3H), 7.67-7.65 (d, J=8.0 Hz, 2H), 2.79-2.75 (t, J=7.2 Hz, 2H), 2.62 (s, 3H), 1.64-1.61 (m, 3H), 0.93-0.92 (d, J=6.0 Hz, 6H) ppm. $^{13}$CNMR (100 MHz CDCl$_3$-d): δ151.88, 148.47, 139.86, 137.05, 134.65, 132.12, 131.84, 128.04, 126.23, 122.63, 121.02, 119.62, 119.1, 114.81, 112.41, 38.27, 29.45, 27.45, 22.84, 21.44, 19.03 ppm. MS (ESI) m/z 447.1 [M−H]$^-$, 483.1 [M+Cl]$^-$.

1-(4-(4-butyl-1H-1,2,3-triazol-1-yl)phenyl)-3-(5-(cyclopentyloxy)-2-methylphenyl)urea (55h)): (Purification eluent: DCM/MeOH 98:2). Yield 76%, white solid. $^1$HNMR (400 MHz, Acetone-d6): δ 8.64 (s, 1H), 8.17 (s, 1H), 7.74-7.65 (m, 5H), 7.48 (s, 1H), 7.01-7.99 (d, J=3.9 Hz, 1H), 6.51-6.48 (dd, J=5.6 Hz, J=5.6 Hz, 0.2 Hz, 1H), 4.75-4.74 (m, 1H), 2.75-2.70 (t, J=7.8 Hz, 2H), 2.16 (s, 3H), 1.91-1.88 (m, 2H), 1.77-1.63 (m, 8H), 1.42-1.38 (m, 2H), 1.01-1.98 (t, J=8 Hz, 3H). $^{13}$CNMR (100 MHz Acetone-d6): δ 154.56, 153.62, 136.75, 136.64, 135.76, 128.05, 125.09, 123.49, 123.07, 123.07, 122.17, 122.17, 109.66, 106.38, 82.15, 33.39, 33.39, 29.99, 27.92, 24.10, 24.10, 22.18, 17.35, 14.02.

1-(4-(4-butyl-1H-1,2,3-triazol-1-yl)phenyl)-3-(5-(methoxymethoxy)-2-methylphenyl)urea (55i): (Purification eluent: DCM/MeOH 98:2). Yield 70%, white solid. $^1$HNMR (400 MHz, Acetone-d6): δ=8.63 (s, 1H), 8.16 (s, 1H), 7.76-7.60 (m, 5H), 7.51 (s, 1H), 7.03 (d, J=8.3 Hz, 2H), 6.64 (dd, J=8.3, 2.6 Hz, 2H), 5.12 (s, 2H), 3.39 (s, 3H), 2.71 (t, J=7.6, 2H), 2.17 (s, 3H), 1.66 (m, 2H), 1.43-1.34 (m, 2H), 0.93-0.89 (t, J=7.8 Hz, 3H). $^{13}$CNMR (100 MHz Acetone-d6): δ 156.07, 152.45, 148.35, 140.15, 138.13, 131.93, 131.11, 129.97, 120.57, 119.10, 118.18, 111.30, 109.96, 109.81, 94.35 55.45, 29.99, 27.92, 22.18, 17.35, 14.02 ppm. MS (ESI) m/z 408.1 [M−H]$^-$, 444.1 [M+Cl]$^-$.

1-(4-(4-butyl-1H-1,2,3-triazol-1-yl)phenyl)-3-(3-fluorophenyl)urea (55l): (Purification eluent: DCM/MeOH 98:2). Yield 80%, white solid. $^1$H NMR (400 MHz, CDCl$_3$-d) δ 7.34 (s, 2H), 7.11-6.93 (m, 4H), 6.66 (s, 2H), 6.48 (s, 2H), 6.25 (d, J=7.5 Hz, 4H), 6.14-6.03 (m, 4H), 5.94 (s, 2H), 5.73 (s, 2H), 2.03-1.98 (m, 4H), 1.00-0.95 (m, 3H), 0.69-0.64 (m, 3H), 0.28-0.22 (m, 6H). $^{13}$C NMR (100 MHz, CDCl$_3$-d) δ: 160.36, 154.56, 154.07, 140.81, 136.75, 135.76, 129.04, 125.09, 123.07, 123.07, 122.17, 122.17, 117.53, 111.81, 110.08, 29.99, 27.92, 22.18, 14.02. ppm. MS (ESI) m/z 352 [M−H]$^-$, 388 [M+Cl]$^-$.

1-(4-(4-butyl-1H-1,2,3-triazol-1-yl)phenyl)-3-(3-fluorophenyl)urea (55m): (Purification eluent: DCM/MeOH 98:2). Yield 80%, white solid. $^1$H NMR (400 MHz, CDCl$_3$-d) δ: 7.78 (s, 1H), 7.59 (m, 4H), 7.37 (d, J=10.6, 1H), 7.22 (dd, J=15.4, 7.2, 1H), 7.08 (d, J=8.0, 1H), 6.71 (t, J=8.2, 1H), 2.77 (t, J=7.6, 2H), 1.77-1.54 (m, 2H), 1.47-1.17 (m, 2H), 0.96-0.93 (t, J=7 Hz 3H) ppm. $^{13}$C NMR (100 MHz, CDCl$_3$-d) δ 160.36, 154.56, 154.07, 140.81, 136.75, 135.76, 129.04, 125.09, 123.07, 123.07, 122.17, 122.17, 117.53, 111.81, 110.08, 29.99, 27.92, 22.18, 14.02 ppm. MS (ESI) m/z 352 [M−H]$^-$, 388 [M+Cl]$^-$.

1-(3-fluorophenyl)-3-(4-(4-(3-oxobutyl)-1H-1,2,3-triazol-1-yl)phenyl)urea (55n): (Purification eluent: DCM/MeOH 98:2). Yield 75%, white solid. $^1$H NMR (400 MHz, Acetone-$d_6$) δ 8.54-8.51 (m, 2H), 8.15 (s, 1H), 7.81-7.56 (m, 4H), 7.58-7.55 (d, J=12 Hz, 1H), 7.22 (m, 1H), 7.28-7.26 (d, J=8 Hz, 1H), 6.73-6.69 (t, J=7.3 Hz, 1H), 2.95-2.88 (m, 4H), 2.12 (s, 3H), ppm. $^{13}$C NMR (100 MHz, Acetone-d6) δ 206.98, 160.36, 154.07, 153.06, 140.81, 136.75, 135.76, 129.04, 123.07, 123.07, 122.17, 122.17, 121.34, 117.53, 111.81, 110.08, 41.35, 28.57, 20.36. ppm. MS (ESI) m/z 366 [M−H]⁻, 402 [M+Cl]⁻.

1-(4-(4-(ethoxymethyl)-1H-1,2,3-triazol-1-yl)phenyl)-3-(3-fluorophenyl)urea (55o): (Purification eluent: DCM/MeOH 98:2). Yield 72%, white solid. ¹H NMR (400 MHz, Acetone-d6) δ: 8.46-8.38 (m, 3H), 7.76-7.70 (m, 4H), 7.58-7.55 (d, J=11 Hz, 1H), 7.27-7.24 (t, J=6 Hz, 1H), 7.17-7.15 (d, J=7 Hz, 1H), 6.74-6.71 (t, J=7 Hz, 1H), 4.59 (s, 1H), 3.57-3.52 (q, J=6.7 Hz, 2H), 1.16-1.13 (t, J=6.6 Hz, 3H) ppm. ¹³C NMR (100 MHz, Acetone d₆) δ 164.26, 161.86, 152.22, 145.85, 140.05, 131.95, 130.14, 121.06, 120.89, 119.35, 114.13, 108.63, 108.42, 105.64, 105.38, 65.30, 63.54, 14.55, −43.88. ppm. MS (ESI) m/z 354 [M−H]⁻, 390 [M+Cl]⁻.

1-(4-(4-butyl-1H-1,2,3-triazol-1-yl)phenyl)-3-(2-methyl-5-(3-oxobutyl)phenyl)urea (55p): (Purification eluent: DCM/MeOH 98:2). Yield 72%, white solid. ¹H NMR (400 MHz, MeOD-d4) δ 8.18 (s, 1H), 7.70 (d, J=9.0 Hz, 2H), 7.62 (d, J=8.9 Hz, 2H), 7.49 (s, 1H), 7.08 (d, J=7.7 Hz, 1H), 6.87 (d, J=6.7 Hz, 1H), 2.79-2.73 (m, 4H), 2.23 (s, 3H), 2.11 (s, 3H), 1.68 (m, 2H), 1.47-1.36 (m, 2H), 0.95 (t, J=7.3 Hz, 3H) ppm. ¹³C NMR (100 MHz MeOD-d4) δ 208.15, 154.56, 139.69, 138.44, 136.75, 135.76, 130.90, 128.16, 125.90, 125.09, 123.54, 123.07, 123.07, 122.17, 122.17, 40.44, 31.99, 29.99, 28.57, 27.92, 22.18, 17.35, 14.02 ppm. MS (ESI) m/z 417.9 [M−H]⁻, 453.8 [M+Cl]⁻.

1-(4-(4-butyl-1H-1,2,3-triazol-1-yl)phenyl)-3-(5-fluoropyridin-3-yl)urea (55q): (Purification eluent: DCM/MeOH 99:2). Yield 67%, white solid. ¹H NMR (400 MHz, MeOD-d₄) δ 9.30 (d, J=1.4 Hz, 1H), 8.10-7.99 (m, 2H), 7.92 (d, J=7.4 Hz, 2H), 7.66-7.57 (m, 3H), 6.52 (d, J=4.8 Hz, 2H), 2.74 (t, J=8.0 Hz, 2H), 1.71 (p, J=7.9 Hz, 2H), 1.48-1.34 (m, 2H), 1.00 (t, J=6.6 Hz, 3H). ppm. ¹³C NMR (100 MHz MeOD-d₄) δ 159.43, 154.56, 154.07, 139.94, 136.75, 135.76, 134.14, 133.93, 125.09, 123.07, 123.07, 122.17, 122.17, 115.14, 29.99, 27.92, 22.18, 14.02 ppm. MS (ESI) m/z 353 [M−H]⁻.

Example 10

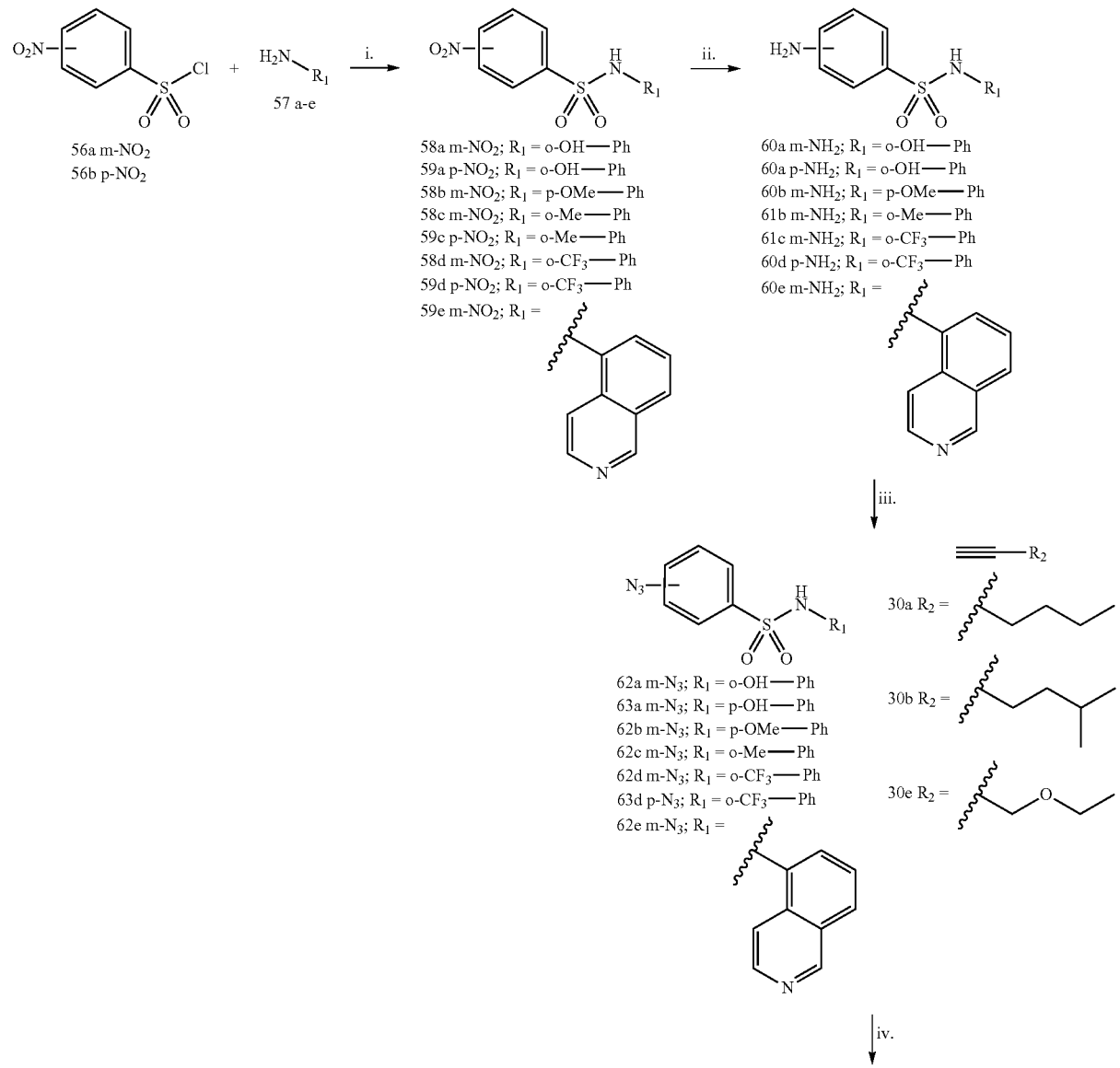

-continued

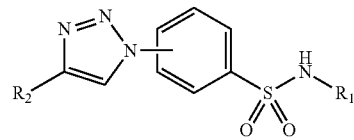

64a m-triazolyl; R₁ = o-OH—Ph; R₂ = butyl;
65a p-triazolyl; R₁ = o-OH—Ph; R₂ = butyl;
64b m-triazolyl; R₁ = p-OMe—Ph; R₂ = butyl;
64c m-triazolyl; R₁ = o-Me—Ph; R₂ = butyl;
64d m-triazolyl; R₁ = o-CF₃—Ph; R₂ = butyl;
66d m-triazolyl; R₁ = o-CF₃—Ph; R₂ =

67d m-triazolyl; R₁ = o-CF₃—Ph; R₂ =

64e m-triazolyl; R₁ = 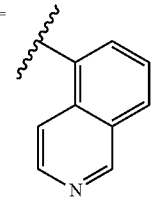 R₂ = butyl;

68e m-triazolyl; R₁ = 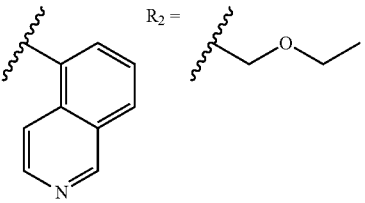 R₂ =

Reagents and conditions: i. Pyr, 5 h r.t. ii. H₂, Pd/C, MeOH; iii. a) t-BuONO, CH₃CN, 20 min. 0° C.; b) TMSN₃, CH₃CN, 2 h r.t.; iii. (for 58e) a) NaNO₂, H₂SO₄ 25%, 20 min. 0° C.; b) NaN₃ 2 h r.t.; v. alkyne, CuSO₄·5 H₂O, sodium ascorbate, H₂O tBuOH (1:1), MW 10 min, 120° C.;

The list of synthesized sulfonamide derivatives is reported in Table 2.

TABLE 2

List of synthesized sulfonamide derivatives

| Entry | Chloryde | Aromatic amine | R₁ | Nitro Cmpd. | Amino- Cmpd. | Azide | Alkyne | R₂ | Compound |
|---|---|---|---|---|---|---|---|---|---|
| 1 | 56a | 57a | o-OH-Phe | 58a | 60a | 62a | 30a | -Butyl | 64a |
| 2 | 56b | 57a | o-OH-Phe | 59a | 61a | 63a | 30a | -Butyl | 65a |

TABLE 2-continued
List of synthesized sulfonamide derivatives
| Entry | Chloryde | Aromatic amine | R₁ | Nitro Cmpd. | Amino- Cmpd. | Azide | Alkyne | R₂ | Compound |
|---|---|---|---|---|---|---|---|---|---|
| 3 | 56a | 57b | p-MeO-Phe | 58b | 60b | 62b | 30a | -Butyl | 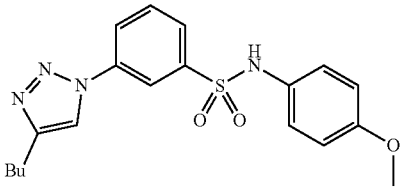 64b |
| 4 | 56a | 57c | o-Me-Phe | 58c | 60c | 62c | 30a | -Butyl | 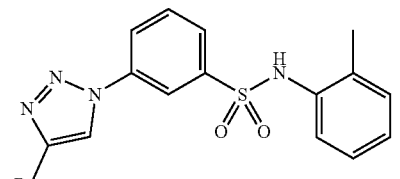 64c |
| 5 | 56a | 57d | o-CF₃-Phe | 58d | 60d | 62d | 30a | -Butyl | 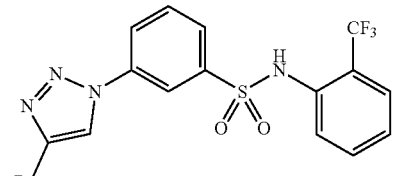 64d |
| 6 | 56a | 57d | o-CF₃-Phe | 58d | 60d | 62d | 30f | —CH₂OCH₂CH₃ | 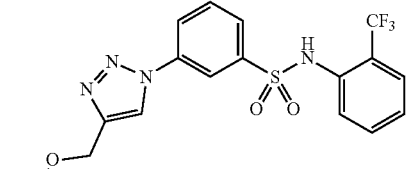 66d |
| 7 | 56a | 57d | o-CF₃-Phe | 58d | 60d | 62d | 30b | Isopentyl | 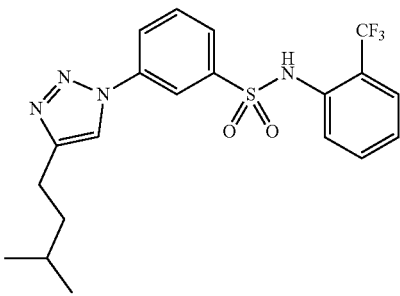 67d |
| 8 | 56b | 57c | o-CF₃-Phe | 59c | 61c | 63c | 30a | -Butyl | 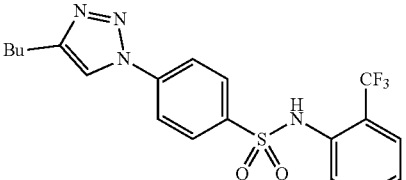 65c |

TABLE 2-continued

List of synthesized sulfonamide derivatives

| Entry | Chloryde | Aromatic amine | R₁ | Nitro Cmpd. | Amino-Cmpd. | Azide | Alkyne | R₂ | Compound |
|---|---|---|---|---|---|---|---|---|---|
| 9 | 56a | 57e | isoquinolin-5-yl | 58e | 60e | 62e | 30a | -Butyl | 64e |
| 10 | 56a | 57e | isoquinolin-5-yl | 58e | 60e | 62e | 30f | —CH₂OCH₂CH₃ | 68e |

General Procedure for the Preparation of Sulfonamides 58-59a-e

To a stirred solution of the opportune aromatic amine (1 eq.) in 5 mL of anhydrous pyridine, was added the corresponding sulphonyl chloride (1.1 eq) at 0° C. The corresponding solution was stirred at r.t. under nitrogen atmosphere, for 5 h. After completion of the reaction the mixture was acidified with 20 mL of 2N HCl, the aqueous phase was extracted with several times and the combined organic phases were dried ($Na_2SO_4$) and concentrated.

N-(2-hydroxy)-3-nitro-phenylbenzenesulfonamide (58a). The residue was purified by flash chromatography on silica gel (Hexane-AcOEt 3:1). Yield 84%. $^1$H NMR (Acetone): δ 8.70 (s, 1H), 8.59, (s, 1H), 8.45-8.42 (d, J=12 Hz, 1H), 8.13-8.12 (d, J=4.3 Hz, 1H), 7.83-7.79 (t, J=8.1 Hz, 1H), 7.36-7.34 (d, J=8.2 Hz, 1H), 7.02-6.98 (t, J=8 Hz, 1H), 6.83-6.76 (m, 2H). MS (ESI): m/z 292.8 [M−H]⁻.

N-(2-hydroxy)-4-nitro-phenylbenzenesulfonamide (59a). $^1$H NMR (MeOD-d₄): δ 8.25-8.22 (dd, 2H, J=8.4 Hz), δ 7.93-7.91 (dd, 2H, J=8.4 Hz), 7.33-7.31 (d, 1H), 6.97-6.94 (t, J=7.6 Hz, 1H), 6.76-6.73 (t, J=7.6 Hz, H), 6.66-6.64 (d, J=8 Hz, 1H) ppm. $^{13}$C NMR (MeOD-d₄): δ 150.36, 150.06, 128.56, 127.06, 125.55, 123.55, 119.29, 115.53 ppm. MS: m/z 292.8 [M−H]⁻

N-(4-methoxy)-3-nitro-phenylbenzenesulfonamide (58b). The residue was purified by flash chromatography on silica gel (Hexane-AcOEt 3:1). Yield 84%. $^1$H NMR (400 MHz CDCl₃-d): δ 8.57 (s, 1H), 8.39-8.37 (d, J=8 Hz, 1H), 7.97-7.95 (d, J=8.0 Hz, 1H), 7.65-7.61 (t, J=7.7 Hz, 1H), 6.99-6.97 (dd, J=8.1 Hz, 2H), 6.78-6.76 (dd, J=8.1 Hz, 2H), 6.69 (s, 1H), 3.75 (s, 3H) ppm. MS (ESI): m/z 309 [M+H]⁺.

N-(2-trifluoromethyl)-3-nitro-phenylbenzenesulfonamide (58c). The residue was purified by flash chromatography on silica gel (Hexane-AcOEt 3:1). Yield 84%. $^1$H NMR (400 MHz CDCl₃-d): δ 8.56 (s, 1H), 8.40-8.38 (d, J=8.4 Hz, 1H), 8.06-8.04 (d, J=8 Hz, 1H), 7.86-7.84 (d, J=8 Hz, 1H), 7.69-7.64 (t, J=8 Hz, 1H), 7.61-7.57 (t, J=7.8 Hz, 1H), 7.52-7.50 (d, J=8.0 Hz, 1H), 7.31-7.27 (t, J=8.1 Hz, 1H), 6.86 (s, 1H). $^{13}$C NMR (100 MHz CDCl₃-d): δ 148.16, 140.78, 133.53, 133.17, 132.66, 130.53, 127.79, 126.83, 126.78, 126.31, 124.91, 122.51, 122.02 MS (ESI): m/z 286.8 [M+Na]⁺.

N-(2-trifluoromethyl)-4-nitro-phenylbenzenesulfonamide (59c) The residue was purified by flash chromatography on silica gel (Hexane-AcOEt 3:1). Yield 84%. $^1$H NMR (400 MHz CDCl₃-d): δ 8.27-8.25 (d, J=8.0 Hz, 1H), 7.91-7.89 (d, J=8.0 Hz, 1H), 7.87-7.85 (d, J=8.0 Hz, 2H), 7.61-7.57 (t, J=8.0 Hz, 1H), 7.53-7.51 (d, J=8.0 Hz, 1H), 7.32-7.25 (t, J=8 Hz, 1H), 6.91 (s, 1H) ppm. $^{13}$C NMR (100 MHz CDCl₃-d): δ 150.80, 144.33, 139.34, 133.61, 128.99, 127.14, 126.03, 124.00 ppm.

N-(2-methyl)-3-nitro-phenylenzenesulfonamide (58d) The residue was purified by flash chromatography on silica gel (Hexane-AcOEt 3:1). Yield 84%. $^1$H NMR (Acetone): δ 8.49-8.47 (m, 2H), 8.09-8.07 (d, J=8 Hz, 1H), 7.87-7.83 (t, J=8 Hz, 1H), 7.17-7.10 (m, 4H) ppm.

N-(isoquinolin-6-yl)-3-nitrobenzenesulfonamide (58e): (Purification eluent: PE-AcOEt: 4-1) Yield 67%. $^1$H NMR (DMSO d-₆): δ 9.56 (s, 1H), 8.52-8.50 (d, J=6.4 Hz, 1H), 8.44-8.41 (m, 2H), 8.21-8.19 (d, J=8.0 Hz, 1H), 8.07-8.05 (d, J=6.4 Hz, 1H), 8.01-7.99 (d, J=7.6 Hz, 1H), 7.79-7.70 (m, 2H), 7.55-7.53 (d, J=7.7 Hz, 1H) ppm.

N-(2-methyl)-4-nitro-phenylenzenesulfonamide (59d) The residue was purified by flash chromatography on silica gel (Hexane-AcOEt 3:1). Yield 84%. $^1$H NMR (400 MHz CDCl₃-d): δ 8.28-8.251 (m, 2H), 7.91-7.88 (m, 2H), 7.27-7.25-(d, J=6.4 Hz, 2H), 7.18-7.12 (m, 2H), 2.02 (s, 3H) ppm. $^{13}$C NMR (100 MHz CDCl₃-d): δ 150.17, 145.28, 133.35, 131.20, 128.45, 127.27, 125.19, 124.30, 17.61 ppm. MS: m/z 314.8 [M+Na]+

General procedure for the preparation of sulfonamides 60a-e and 61 a-d

The opportune sulfonamide (400 mg, 1.35 mmol) was solubilized in 20 mL of anhydrous EtOH, and Palladium on charcoal (60 mg) was added. The reaction mixture was stirred under Hydrogen atmosphere for 1 h. Then the mixture was filtered-off on a celite pad, was concentrated in vacuo and the crude product was purified by flash chromatography on silica gel with the appropriate eluent.

3-amino-N-(2-hydroxyphenyl)benzenesulfonamide (60a) (Purification eluent: Hexane-AcOEt 3:1). Yield 92%. $^1$H NMR (Acetone): δ 8.29 (s, 1H), 7.27-7.24 (d, J=12 Hz, 1H), 7.14-7.09 (m, 2H), 6.99-6.97 (d, J=8 Hz, 1H), 6.95-6.92 (t, J=8 Hz, 1H), 6.82-6.75 (m, 2H), 6.74-6-72 (t, J=4 Hz, 1H), MS (ESI): m/z 286.8 [M+Na]$^+$.

4-amino-N-(2-hydroxyphenyl)benzenesulfonamide (61a) $^1$H NMR (MeOD-d$_4$): δ 7.55-7.53 (dd, J=8.8 Hz, 2H), 7.42-7.40 (dd, J=8.8 Hz, 2H), 7.22-7.18 (m, 1H), 6.90-6.84 (m, 2H), 6.70-6.66 (m, 2H), 6.55-6.53 (d, J=8.8 Hz, 1H) ppm. MS: m/z 286.8 [M+H]+.

3-amino-N-(4-methoxyphenyl)benzenesulfonamide (60b) (Purification eluent: Hexane-AcOEt 3:1). Yield 92%. $^1$H NMR (Acetone): δ 7.3 (s, 1H), 7.26 (s, 1H), 7.17-7.14 (m, 2H), 6.96-6.94 (dd, J=8 Hz, 2H), 6.72-6.70 (dd, J=8.0 Hz, 2H), 3.72 (s, 3H) ppm. MS: m/z 300.8 [M+Na]$^+$.

3-amino-N-(2-(trifluoromethyl)phenyl)benzenesulfonamide (60c) (Purification eluent: Hexane-AcOEt 3:1). Yield 84%. $^1$H NMR (Acetone): δ 7.63-7.61 (d, J=8 Hz, 1H), 7.51-7.58 (m, 2H), 7.24-7.20 (t, J=8 Hz, 1H), 7.19-7.17 (m, 2H), 7.07-7.05 (d, J=8 Hz, 1H), 6.90-6.88 (d, J=8 Hz, 1H), 5.10 (s, 1H). MS (ESI): m/z 338.8 [M+Na]$^+$.

4-amino-N-(2-(trifluoromethyl)phenyl)benzenesulfonamide (61c) (Purification eluent: Hexane-AcOEt 3:1). Yield 84%. $^1$H NMR (Acetone): δ 7.53-7.51 (d, J=8 Hz, 1H), 7.49-7.46 (m, 2H), 7.45-7.43 (d, J=8 Hz, 2H), 7.30-7.28 (t, J=8 Hz, 1H), 6.62-6.60 (d, J=7.4 Hz, 1H), 5.10 (s, 1H). MS (ESI): m/z 338.8 [M+Na]$^+$.

3-amino-N-(o-tolyl)benzenesulfonamide (60d) $^1$H NMR (Acetone): δ 8.14 (s, 1H), 7.2-6.92 (m, 6H), 6.92-6.86 (d, J=8 Hz, 1H), 6.85-6.84 (d, J=8 Hz, 1H), 2.11 (s, 3H) ppm. MS (ESI): m/z 262.9 [M+H]$^+$, 284.8 [M+Na]$^+$.

3-amino-N-(isoquinolin-6-yl)benzenesulfonamide (60e): Compound 59e (400 mg, 1.35 mmol) was solubilized in 20 mL of anhydrous EtOH, and Palladium on charcoal (60 mg) was added. The reaction mixture was stirred under Hydrogen atmosphere for 1 h. Then the mixture was filtered-off on a celite pad, concentrated in vacuo and the crude product was purified by flash chromatography on silica gel (PE-AcOEt: 4-1) Yield 67%. $^1$H NMR (DMSO d$_6$): δ 10.23 (s, 1H), 9.25 (s, 1H), 9.41-9.40 (d, J=6.4 Hz, 1H), 7.95-7.84 (m, 2H), 7.59-7.56 (t, J=8 Hz, 1H), 7.43-7.41 (d, J=8.0 Hz, 1H), 7.09-7.06 (t, J=8.0 Hz, 1H), 6.80-6.78 (d, J=8.0 Hz, 1H), 6.66-6.64 (d, J=8.0 Hz), 5.50 (s, 2H) ppm. MS (ESI): m/z 299.8 [M+H]$^+$, 321.8 [M+Na]$^+$.

General Procedure for the Preparation of Azides 62a-c and 63 a-d

Amine (100 mg, 0.41 mmol) was dissolved in CH$_3$CN and cooled to 0° C. in an ice-salt bath. To this stirred solution, was added tBuONO, and the mixture was stirred for 10 min, after this time, TMSN$_3$ was added dropwise, during 10 minutes, and the resulting brown solution was stirred at r.t. One hour later the solvent was removed at reduced pressure and the residue was purified by flash chromatography on silica gel with the appropriate eluent.

3-azido-N-(2-hydroxyphenyl)benzenesulfonamide (62a). (Purification eluent: Hexane-AcOEt 3:1). $^1$H NMR (Acetone): δ 8.42 (s, 1H), 7.58-7.56 (d, J=8 Hz, 1H), 7.53-7.49 (t, J=8.0 Hz, 1H), 7.44 (s, J=8 Hz, 1H), 7.34-7.32 (d, J=8.0 Hz, 1H), 7.28-7.27 (d, J=4.0 Hz, 1H), 7.00-6.96 (t, J=8.0 Hz, 1H) 6.81-6.77 (m, 2H). MS (ESI): m/z 288.8 [M−H]$^−$.

4-azido-N-(2-hydroxyphenyl)benzenesulfonamide (63a). (Purification eluent: Hexane-AcOEt 3:1). $^1$H NMR (MeOD-d$_4$): δ 7.73-7.72 (dd, J=2.4 Hz, 2H), 7.36-7.35 (d, J=6.4 Hz, 1H), 7.09-7.07 (dd, J=8.8 Hz, 2H), 6.94-6.90 (m, H), 6.73-6.66 (m, 2H) ppm. MS: m/z 312.8 [M+Na]$^+$ 3-azido-N-(2-methoxyphenyl) benzenesulfonamide (62b). (Purification eluent: Hexane-AcOEt 3:1). Yield 92%. $^1$H NMR (Acetone): δ 7.5 (s, 1H), 7.26 (s, 1H), 7.27-7.24 (m, 2H), 7.06-7.04 (dd, J=8 Hz, 2H), 6.74-6.72 (dd, J=8.0 Hz, 2H), 3.73 (s, 3H) ppm. MS: m/z 300.8 [M+Na]$^+$.

3-azido-N-(o-tolyl)benzenesulfonamide (62c). (Purification eluent: Hexane-AcOEt $^1$H NMR (400 MHz CDCl$_3$-d): δ 7.51-7.49 (d, J=8 Hz, 1H), 7.43-7.39 (t, J=8 Hz, 1H), 7.36 (s, 1H), 7.30-7.28 (d, J=8 Hz, 1H), 7.15-7.09 (m, 4H), 6.75 (s, 1H), 2.02 (s, 3H) ppm. MS (ESI): m/z 310.8 [M+Na]$^+$.

3-azido-N-(2-(trifluoromethyl)phenyl)benzenesulfonamide (62d). (Purification eluent: Hexane-AcOEt 4:1). $^1$H NMR (400 MHz CDCl$_3$-d): δ 7.84-7.81 (d, J=8.4 Hz, 1H), 7.56-7.50 (m, 3H), 7.43-7.37 (m, 2H), 7.27-7.23 (t, J=7.6 Hz, 1H), 7.18-7.16 (d, J=8 Hz, 1H), 6.87 (s, 1H) ppm. MS (ESI): m/z 364.8 [M+Na]$^+$.

4-azido-N-(2-(trifluoromethyl)phenyl)benzenesulfonamide (63c). (Purification eluent: Hexane-AcOEt 4:1). $^1$H NMR (400 MHz CDCl$_3$-d): δ 7.81-7.79 (d, J=7.6 Hz, 1H), 7.74-7.71 (d, J=7.4 Hz, 1H), 7.52-7.46 (m, 2H), 7.22-7.18 (t, J=8 Hz, 1H), 7.02-6.98 (m, 3H) ppm. m/z 364.7 [M+Na]$^+$.

3-azido-N-(isoquinolin-6-yl)benzenesulfonamide (62e): The opportune amine (100 mg, 0.41 mmol) was dissolved in CH$_3$CN and cooled to 0° C. in an ice-salt bath. To this stirred solution, was added tBuONO, and the mixture was stirred for 10 min, after this time, TMSN$_3$ was added dropwise, during 10 minutes, and the resulting brown solution was stirred at r.t. One hour later the solvent was removed at reduced pressure and the residue was purified by flash chromatography on silica gel (PE-AcOEt: 4-1) Yield 67%. $^1$H NMR (DMSO d$_6$): δ$^1$H NMR (DMSO d$_6$): δ 9.03 (s, 1H), 8.62 (s, 1H), 8.26 (s, 1H), 7.74-7.33 (m, 6H), 7.09-7.07 (d, J=8.0 Hz, 1H) ppm. MS (ESI): m/z 325.8 [M+H]$^+$, 347.7 [M+Na]$^+$.

General Procedure for the Preparation of Compounds 64a, 64b, 64c, 64d, 64e, 64f 65a, 65c, 66d, 67d and 68.

The appropriate alkyne (6.08 mmol) and the opportune azide (5.07 mmol) were suspended in a 1:1 mixture of water and t-BuOH (1.5 mL each) in a 10 mL glass vial equipped with a small magnetic stirring bar. To this, was added sodium ascorbate (2.5 mmol) and copper(II) sulfate pentahydrate (2.50 mmol). The mixture was then heated for 10 min. at 125° C. under microwave irradiation, using an irradiation power of 300 W. After that time the solvent was removed at reduced pressure water was added and the mixture was extracted with EtOAc (3×20 mL). The organic layers were collected, washed with Brine and dried over Na$_2$SO$_4$. The crude was purified by flash chromatography on silica gel using the opportune eluent to give the desired triazole compounds 64a, 64b, 64c, 64d, 64e, 64f, 65a, 65c, 66d, 67d and 68.

3-(4-butyl-1H-1,2,3-triazol-1-yl)-N-(2-hydroxyphenyl) benzenesulfonamide (64a). (Purification eluent: Hexane-AcOEt 3:1). Yield 82%. $^1$H NMR (400 MHz, Acetone): δ 8.48 (s, 1H), 8.34-8.31 (m, 2H), 8.11-8.09 (d, J=8 Hz, 1H), 7.81-7.79 (d, J=8 Hz, 1H), 7.71-7.67 (t, J=8 Hz, 1H), 7.37-7.35 (d, J=8 Hz, 1H), 6.99-6.95, (t, J=8 Hz, 1H), 6.81-6.77 (m, 2H). $^{13}$C NMR (100 MHz, Acetone): δ 149.88, 142.46, 137.68, 130.44, 137.68, 130.44, 126.66, 126.50, 124.40, 124.19, 123.58, 119.90, 119.47, 118.32, 115.59, 31.30, 24.94, 21.95, 13.19. MS (ESI): m/z 370.7 [M−H]$^−$.

4-(4-butyl-1H-1,2,3-triazol-1-yl)-N-(2-hydroxyphenyl) benzenesulfonamide (65a). (Purification eluent: Hexane-AcOEt 4:1). Yield 80 $^1$H NMR (400 MHz, MeOD-d$_4$): δ 8.34 (s, H), 7.93-7.87 (m, 4H), 7.33-7.31 (d, J=6.8 Hz, 1H), 6.96-6.92 (m, 1H), 6.765-7.727 (t, J=7.6 Hz, 1H), 6.67-6.65

(d, J=8 Hz, 1H), 2.78-2.74 (t, J=7.6 Hz, 2H) 1.74-1.66 (quint, 2H), 1.45-1.36 (sx, 2H), 1.27-1.22 (t, J=7.2 Hz, 3H) ppm. $^{13}$C NMR (100 MHz, MeOD-d$_4$): δ 150.64, 149.22, 140.03, 129.07, 126.59, 125.18, 124.12, 119.86, 115.45, 31.12, 24.93, 22.10, 12.91 ppm. MS: m/z 372.8 [M+H]+, 394.8 [M+Na]$^{-1}$ 3-(4-butyl-1H-1,2,3-triazol-1-yl)-N-(4-methoxyphenyl)benzenesulfonamide (64b). (Purification Eluent: Hexane-AcOEt 3:1). Yield 79%. $^1$H NMR (400 MHz, CDCl$_3$-d): δ 8.10 (s, 1H), 7.95-7.93 (d, J=7.6 Hz, 1H), 7.71 (s, 1H), 7.68-7.66 (d, J=7.7 Hz, 1H), 7.61 (s, 1H), 7.56-7.52 (t, J=7.9 Hz, 1H), 7.07-7.04 (dd, J=8.2 Hz, 2H), 6.77-6.75 (dd, J=8.2 Hz, 2H), 3.73 (s, 3H), 2.78-2.75 (t, J=7.7 Hz, 2H), 1.71-1.64 (quin. J=7.4 Hz, 2H), 1.43-1.36 (sx, J=7.6 Hz, 2H), 0.95-0.91 (t J=7.6 Hz, 3H) ppm. $^{13}$C NMR (100 MHz, MeOD-d$_4$): δ 158.45, 149.70, 141.20, 137.55, 130.75, 127.59, 125.89, 124.43, 119.27, 118.84, 114.46, 55.90, 31.84, 25.52, 21.87, 13.85 ppm. MS: m/z 372.8 [M+H]+, 394.8 [M+Na]$^{-1}$ 3-(4-butyl-1H-1,2,3-triazol-1-yl)-N-(o-tolyl)benzenesulfonamide (64c). (Purification eluent: Hexane-AcOEt 3:1). Yield 90%. $^1$H NMR (400 MHz, Acetone): δ 8.56 (s, 1H), 8.35.8.33 (d, J=8 Hz, 1H), 8.25-8.23 (d, J=8.0 Hz, 1H), 8.14-8.11 (t, J=7.2 Hz, 1H), 7.74-7.72 (m, 2H), 7.17-7.10 (m 4H), 2.77-2.73 (t, J=7.4 Hz, 2H), 1.73-1.65 (q, J=8.0 Hz, 2H), 1.43-1.37 (quint, J=8.0 Hz, 2H), 0.95-0.91 (t, J=8 Hz, 1H) ppm. $^{13}$C NMR (100 MHz, Acetone): 149.06, 142.56, 137.76, 134.78, 134.16, 130.91, 130.72, 126.78, 126.51, 126.37, 126.28, 123.51, 119.46, 118.11 31.22, 24.95, 21.95, 17.18, 13.18 ppm. MS (ESI): m/z 371.7 [M+H]$^+$.

3-(4-butyl-1H-1,2,3-triazol-1-yl)-N-(2-(trifluoromethyl)phenyl)benzenesulfonamide (64d) (Purification eluent: Hexane-AcOEt 3:1). Yield 90%. $^1$H NMR (Acetone): δ 8.78 (s, 1H), 8.41-8.37 (m, 3H), 8.18-8.16 (d, J=8.2 Hz, 1H), 7.89-7.87 (d, J=7.6 Hz, 1H), 7.82-7.78 (t, J=7.8 Hz, 1H), 7.69-7.61 (m 2H), 7.54-7-52 (d, J=8 Hz, 1H), 7.45-7.44 (t, J=7.4 Hz, 1H), 2.77-2.73 (t, J=7.4 Hz, 2H), 1.71-1.67 (q, J=8.0 Hz, 2H), 1.45-1.35 (quint, J=8.0 Hz, 2H), 0.94-0.89 (t, J=8.0 Hz, 1H) ppm. $^{13}$C NMR (Acetone): 149.1, 142.66, 137.89, 134.15, 133.28, 130.93, 127.40, 126.90, 126.28, 124.80, 123.85, 122.29, 119.54, 118.03, 31.22, 24.95, 21.95, 13.18 ppm. MS (ESI): m/z 425 [M+H]$^+$.

4-(4-butyl-1H-1,2,3-triazol-1-yl)-N-(2-(trifluoromethyl)phenyl)benzenesulfonamide (65c). (Purification eluent: Hexane-AcOEt 3:1). Yield 93%. $^1$H NMR (400 MHz, CDCl$_3$-d): δ 8.79-7.81 (m, 4H) 7.75 (s, 1H), 7.57-7.53 (t, J=8 Hz, 1H), 7.51-7.49 (d, J=8 Hz, 1H), 8.41-8.37 (m, 3H), 8.18-8.16 (d, J=8.2 Hz, 1H), 7.89-7.87 (d, J=7.6 Hz, 1H), 7.82-7.78 (t, J=7.8 Hz, 1H), 7.69-7.61 (m 2H), 7.54-7-52 (d, J=8 Hz, 1H), 6.94, (s, 1H), 2.79-2.75 (t, J=7.4 Hz, 2H), 1.73-1.65 (quint, J=8.0 Hz, 2H), 1.43-1.36 (sx, J=8.0 Hz, 2H), 0.95-0.91 (t, J=8.0 Hz, 1H) ppm. $^{13}$C NMR (100 MHz, CDCl$_3$-d): 149.9, 140.8, 137.99, 133.88, 133.56, 129.53, 126.71, 125.70, 124.94, 124.09, 122.27, 120.88, 118.45, 31.32, 25.24, 22.24, 13.76 ppm. MS (ESI): m/z 425 [M+H]$^+$.

3-(4-butyl-1H-1,2,3-triazol-1-yl)-N-(isoquinolin-6-yl) benzenesulfonamide (64e). (Purification Eluent: Hexane-AcOEt 3:1). Yield 77%. $^1$H NMR (400 MHz, CDCl$_3$-d): δ 9.23 (s, 1H), 8.42 (s, 1H), 8.26 (s, 1H), 7.89-7.83 (m, 3H), 7.66-7.62 (m, 3H), 7.55-7.46 (m, 2H), 2.74-2.71 (t, J=7.8 Hz, 2H), 1.66-1.59 (quint, J=8.0 Hz, 2H), 1.39-1.25 (sx, J=8.0 Hz, 2H), 0.90-0.86 (t, J=8.0 Hz, 1H) ppm. $^{13}$C NMR (100 MHz, CDCl$_3$-d): 152.43, 149.84, 142.93, 141.34, 137.68, 132.70, 131.10, 130.51, 129.38, 128.51, 127.38, 126.85, 124.13, 118.81, 115.75, 31.36, 25.25, 22.26, 13.62 ppm. MS (ESI): m/z 408.8 [M+H]$^+$.

3-(4-(ethoxymethyl)-1H-1,2,3-triazol-1-yl)-N-(2-(trifluoromethyl)phenyl) benzenesulfonamide (66d): (Purification eluent: PE/EtOAc 7:2) Yield 85% white solid $^1$H NMR (400 MHz, CDCl$_3$-d): δ 8.09 (1H, s), 7.99-7.97 (d, J=6.8 Hz, 1H), 7.79-7.75 (t, 8.8 Hz, 1H), 7.60-7.47 (m, 3H), 7.26-7.22 (t, J 7.2 Hz, 1H), 4.66 (s, 2H), 3.63-3.58 (q, 2H), 1.24-1.20 (t, J=6.8 Hz, 3H) ppm. $^{13}$C NMR (100 MHz, CDCl$_3$-d): 146.95, 140.78, 137.44, 133.39, 130.80, 126.99, 126.07, 125.84, 124.87, 124.69, 122.09, 120.58, 118.71, 66.39, 63.99, 15.07 ppm. MS (ESI): m/z 427 [M+H]$^+$.

3-(4-isopentyl-1H-1,2,3-triazol-1-yl)-N-(2 (trifluoromethyl)phenyl) benzene sulfonamide (67d): (Purification eluent: PE/EtOAc 7:2), Yield 78%, yellow solid. $^1$H NMR (CDCl$_3$): δ 8.06 (s, 1H), 8.01-8.00 (d, J 7.6 Hz, 1H), 7.84-7.82 (d, J=8.0 Hz, 1H), 7.76-7.74 (d, J=7.6 Hz, 1H), 7.69 (1H, s), 7.60-7.56 (t, J=8.4 Hz, 1H), 7.53-7.49 (t, J 7.6 Hz, 2H), 7.27-7.25 (d, J=8.0 Hz, 1H), 2.80-2.78 (m, 2H), 1.62 (m, 3H), 0.99-0.94 (m, 6H) ppm. $^{13}$C NMR (CDCl$_3$): δ 149.95, 145.96, 143.95, 137.71, 133.39, 160.71, 126.68, 125.29, 124.91, 124.15, 118.51, 38.27, 27.62, 23.51, 22.36 ppm. MS: m/z 438.8 [M+H]$^+$ 3-(4-(ethoxymethyl)-1H-1,2,3-triazol-1-yl)-N-(isoquinolin-6-yl)benzenesulfonamide (68e): (Purification eluent: Hexane-AcOEt 3:1). Yield 74%. $^1$H NMR (400 MHz, CDCl$_3$-d): δ 8.22 (s, 1H), 7.93 (s, 1H), 7.90-7.17 (m, 3H), 7.70-7.67 (d, J 8.0 Hz, 1H), 7.63-7.61 (d, J=8.0 Hz, 1H), 7.56-7.48 (m, 2H), 4.66 (s, 2H), 3.62-3.57 (q, J 7.4 Hz, 2H), 1.22-1.18 (t, J=7.8 Hz, 3H) ppm. $^{13}$C NMR (100 MHz, CDCl$_3$-d): 152.57, 146.93, 143.22, 141.49, 137.46, 132.52, 130.90, 128.22, 127.44, 124.33, 120.66, 119.97, 66.51, 63.97, 15.11 ppm. MS (ESI): m/z 425 [M+H]$^+$.

Example 11

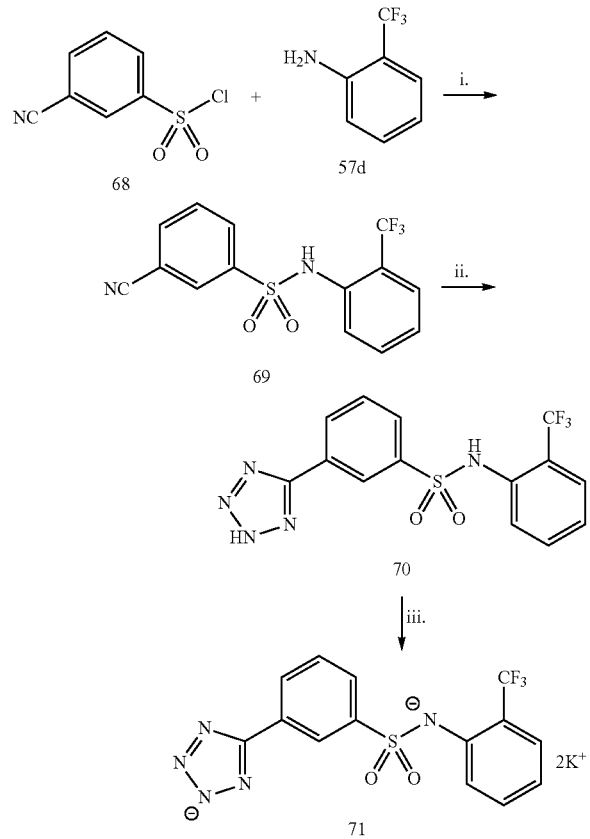

Reagents and conditions: i. Pyr, 5 h r.t.; ii. NaN$_3$, NH$_4$Cl, DMF, 12 h, reflux; iii. K$_2$CO$_3$, H$_2$O, 15 min. reflux.

3-cyano-N-(2-(trifluoromethyl)phenyl)benzenesulfonamide (69) To a stirred solution of 68 (1 eq.) in 5 mL of anhydrous pyridine, was added sulphonyl chloride 57 d (1.1 eq) at 0° C. The corresponding solution was stirred at r.t. under nitrogen atmosphere, for 5 h. After completion of the reaction the mixture was acidified with 1N HCl, the aqueous phase was extracted with several times and the combined organic phases were dried ($Na_2SO_4$) and concentrated. (PE-AcOEt 7:3). Yield 75%, white solid. $^1H$ NMR (400 MHz, $CDCl_3$-d): δ 7.99-7.94 (m, 2H), 7.82-7.80 (m, 2H), 7.60-7.51 (m, 3H), 7.30-7.26 (t, J=8 Hz, 1H), 6.97 (s, 1H) ppm. MS (ESI): m/z 425 $[M+H]^+$.

3-(2H-tetrazol-5-yl)-N-(2-(trifluoromethyl)phenyl)benzenesulfonamide benzenesulfonamide potassium salt (71). 70 (50 mg, 0.13 mmol) and $K_2CO_3$ (37.42 mg, 0.26 mmol) were dissolved in 1.5 mL of water. After the evolution of $CO_2$ ceased, the solution was refluxed for 15 minutes and afterwards evaporated to dryness. The resulting solid was recrystallized from ACN. Mp 224-226 Yield 82% white solid $^1$HNMR (400 MHz, $CDCl_3$-d): δ 8.02 (s, 1H), 7.81-7.79 (d, J=7.6 Hz, 1H), 7.56-7.54 (d, J=8.0 Hz, 1H), 7.44-7.40 (t, J=7.6 Hz, 1H), 6.44-6.40 (t, J=7.9 Hz, 1H) ppm.

Example 12

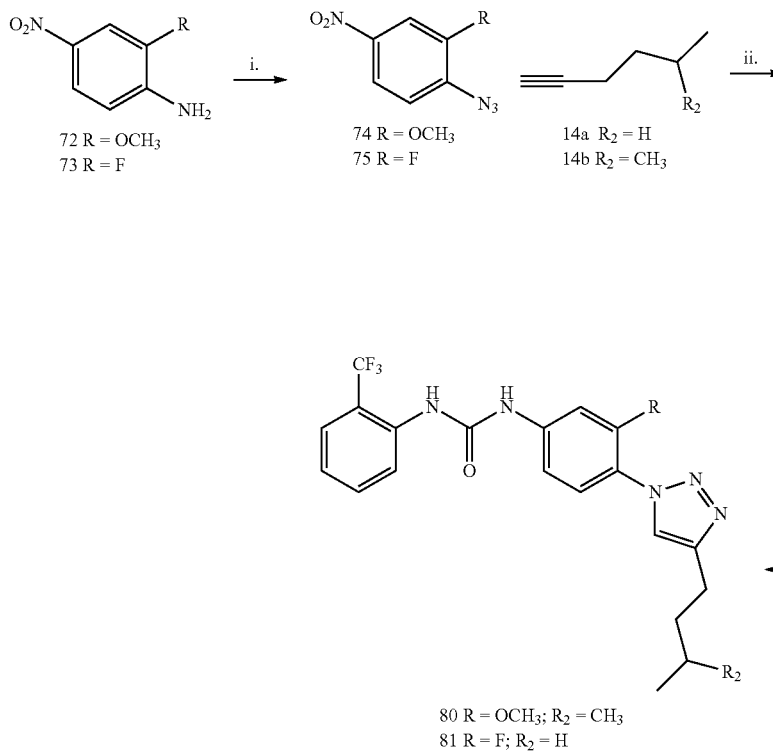
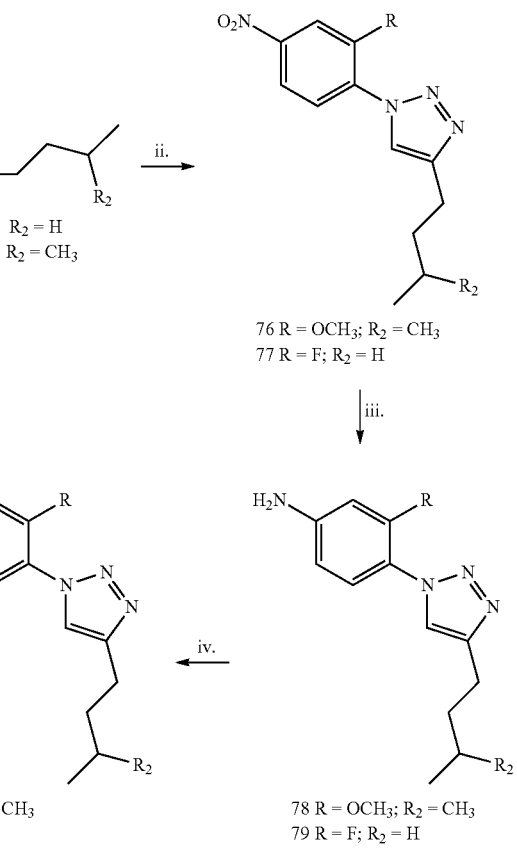

Reagents and conditions: i. a) t-BuONO, $CH_3CN$, 20 min. 0° C.; b) $TMSN_3$, $CH_3CN$, 2 h r.t.; ii. $CuSO_4$·5 $H_2O$, sodium ascorbate, $H_2O$ tBuOH (1:1), MW 120° C., 10 min, iii. $H_2$, Pd/C, MeOH, 1 h, iv. 2-(Trifluoromethyl)phenyl isocyanate, $CH_2Cl_2$, 5 h r.t.

3-(2H-tetrazol-5-yl)-N-(2-(trifluoromethyl)phenyl)benzenesulfonamide (70) A mixture of 69 (500 mg, 1.53 mmol), $NaN_3$ (299 mg, 4.60 mmol), $NH_4Cl$ (328 mg, 6.12 mmol) in DMF (5 mL), was heated at 130° C. for 6 h. After that time the rxn was allowed to r.t. water was added with continuous stirring. The mixture was then acidified to pH 2. The mixture was extracted with DCM (3×25 mL) and washed with aq 5% solution of LiCl, then dried over anhydrous $Na_2SO_4$. The solvent was removed at reduced pressure and the residue purified by flash chromatography on silica gel (DCM-MeOH 94:6). Yield 95%, white solid. mp 138.40° C. $^1$HNMR (400 MHz, $CDCl_3$-d): δ 8.47 (s, 1H), 8.20-8.18 (d, J=7.6 Hz, 1H), 7.88 (s, 1H), 7.75-7.73 (d, J=8.0 Hz, 1H), 7.48-7.40 (m, 2H), 7.31-7.28 (m, 2H), 7.07-7.03 (t, J=7.6 Hz, 1H) ppm. $^{13}$CNMR (100 MHz, $CDCl_3$-d): δ 163.42, 140.86, 133.70, 133.01, 131.54, 130.13, 130.00, 129.15, 127.37, 126.62, 126.10, 125.85, 124.65, 123.08, 119.22 ppm MS General Procedure for the Preparation of Compounds 74 and 75.

Opportune 4-nitroaniline (7.24 mmol) was dissolved in $CH_3CN$ and cooled to 0° C. in an ice-salt bath. To this stirred solution, was added tBuONO (8.69 mmol), and the mixture was stirred for 10 min, after this time, $TMSN_3$ (10.86 mmol) was added dropwise, during 10 minutes, and the resulting brown solution was stirred at r.t. One hour later the solvent was removed at reduced pressure and the residue was purified by flash chromatography on silica gel 1-azido-2-methoxy-4-nitrobenzene (74): (Purification eluent: PE/AcOEt 7:3). Yield 88%, white solid. $^1$HNMR (400 MHz, $CDCl_3$-d): δ 7.74-7.72 (d, J=8.0 Hz, 2H), 7.65 (s, 1H), 6.96-6.94 (d, J=8.0 Hz, 2H), 3.91 (s, 3H) ppm. $^{13}$CNMR (100 MHz, $CDCl_3$-d): δ 152.03, 144.93, 153.31, 120.03, 117.03, 106.97, 56.42 ppm. MS (ESI) m/z 195.1 $[M+H]^+$, 218.1 $[M+Cl]^-$.

1-azido-2-fluoro-4-nitrobenzene (75): (Purification eluent: PE/EA 9:1). Yield 60%, yellow solid. $^1$H NMR (400 MHz, CDCl$_3$): δ 8.02-7.92 (m, 2H), 7.19-7.15 (t, J=16 Hz, 1H) ppm.

General Procedure for the Preparation of Compounds 76 and 77.

The appropriate alkyne 14a or 14b (0.10 mmol) and the opportune azide (0.09 mmol) were suspended in a 1:1 mixture of water and t-BuOH (1.5 mL each) in a 10 mL glass vial equipped with a small magnetic stirring bar. To this, was added sodium ascorbate (0.1 equiv) and copper(II) sulfate pentahydrate (0.10 mmol). The mixture was then heated for 10 min. at 125° C. under microwave irradiation, using an irradiation power of 300 W. After this time the precipitate was filtered-off and purified on silica, to give final products 76 or 77.

4-isopentyl-1-(2-methoxy-4-nitrophenyl)-1H-1,2,3-triazole (76): (Purification eluent: PE/EA 8:3). Yield 94%, white solid. $^1$H NMR (400 MHz, CDCl$_3$): δ 8.24 (s, 1H), 8.00-7.98 (d, J=8.0 Hz, 1H), 7.84-7.80 (m, 2H), 2.76-2.72 (t, J=7.2 Hz, 2H), 1.60-1.54 (m, 3H), 0.88-0.87 (d, J=6.0 Hz) ppm. MS (ESI) m/z 291.32 [M−H]$^+$ 4-butyl-1-(2-fluoro-4-nitrophenyl)-1H-1,2,3-triazole (77). (Purification eluent: PE/EA 7:3). Yield 63%, yellow solid. $^1$H NMR (400 MHz, CDCl$_3$-d): δ 8.24-8.20 (t, J=8.0 Hz, 1H), 8.12-8.10 (m, 2H), 7.91-7.90 (d, J=4.0 Hz, 1H), 2.72-2.69 (t, J=12.0 Hz, 2H), 1.65-1.58 (m, 2H), 1.36-1.27 (m, 2H), 0.86-0.82 (m, 3H) ppm.

General Procedure for the Preparation of Compounds 78 and 79

The opportune triazole compound 76, or 78 (1.60 mmol) was solubilized in 30 mL of MeOH, and 10% Palladium on charcoal (25 mg) was added. The reaction mixture was stirred under Hydrogen atmosphere for 1 h, then the mixture was filtered off on a celite pad, the solvent evaporated at reduced pressure to obtain 78 or 79 as pure compounds.

4-isopentyl-1H-1,2,3-triazol-1-yl)-3-methoxyaniline (78): The product was obtained as a pure compound. Yield 99%, yellow solid. Yield $^1$H NMR (400 MHz, CDCl$_3$-d): δ 7.58 (s, 1H), 7.27-7.25 (dd, J=8.0 Hz, 2H), 6.28 (s, 1H), 6.22-6.20 (dd, J=8.0 Hz, 2H), 4.14 (s, 2H), 3.64 (s, 3H), 2.73-2.69 (t, J=7.6 Hz, 2H), 1.57-1.54 (m, 3H), 0.89-0.88 (d, J=5.6 Hz, 6H) ppm.

4-(4-butyl-1H-1,2,3-triazol-1-yl)-3-fluoroaniline (79). The product was obtained as a pure compound. Yield 99%, white solid. $^1$H NMR (400 MHz, CDCl$_3$-d): δ 7.57 (s, 1H), 7.41-7.39 (d, J=8.0 Hz 1H), 6.44-6.42 (d, J=8.0 Hz, 2H), 4.25 (s, 2H), 1.65-1.62 (d, J=6.0 Hz, 2H), 1.65-1.62 (m, 2H), 1.35-1.32 (m, 2H), 0.89-0.85 (m, 3H) ppm. MS (ESI) m/z 235 [M+H]$^+$.

General Procedure for the Preparation of Compounds 80 and 81.

The opportune aniline 78 or 79 (0.10 mmol) was added to a solution of 2-(Trifluoromethyl)phenyl isocyanate (0.15 mmol) in anhydrous DCM (15 mL) in one portion. The solution was stirred for 9 hours at r.t. under a nitrogen atmosphere. The solvent was removed at reduced pressure and the residue purified on silica to afford the final product 80 or 81.

1-(4-(4-isopentyl-1H-1,2,3-triazol-1-yl)-3-methoxyphenyl)-3-(2-(trifluoromethyl) phenyl)urea (80): (Purification eluent: DCM/MeOH 98:2). Yield 78%, white solid. $^1$H NMR (400 MHz, CDCl$_3$-d): δ 8.12-8.06 (m, 2H), 7.92 (s, 1H), 7.61-7.54 (m, 3H), 7.26-7.21 (m, 2H), 7.18 (s, 1H), 3.97 (s, 3H), 2.83-2.80 (t, J=7.8 Hz, 2H), 1.71-1.63 (m, 3H), 0.98-0.97 (d, J=7.8 Hz, 6H) ppm. $^{13}$C NMR (100 MHz, CDCl$_3$): δ 153.05, 152.05, 148.40, 136.61, 134.63, 132.90, 127.92, 126.70, 126.17, 124.85, 124.78, 122.62, 122.53, 121.46, 121.08, 114.12, 56.43, 38.52, 27.77, 23.66, 22.52 ppm. MS (ESI) m/z 448.3 [M−H]$^+$ 1-(4-(4-butyl-1H-1,2,3-triazol-1-yl)-3-fluorophenyl)-3-(2-(trifluoromethyl)phenyl)urea (81). (Purification eluent: DCM/MeOH 98:2). Yield 70%, yellow solid. $^1$H NMR (400 MHz, CDCl$_3$-d): δ 7.99-7.97 (d, J=12.0 Hz, 1H), 7.91-7.89 (d, J=8.0, 1H), 7.86-7.79 (m, 2H), 7.75 (s, 1H), 7.72-7.68 (t, J=8.0, 1H), 7.60-7.53 (m, 2H), 7.27-7.20 (m, 2H), 2.79-2.75 (t, J=8.0 Hz, 2H), 1.71-1.67 (t, 16.0 Hz, 2H), 1.42-1.37 (m, 2H), 0.94-0.90 (t, 16.0 Hz, 3H) ppm. MS (ESI) m/z 420 [M−H]$^−$.

Example 13

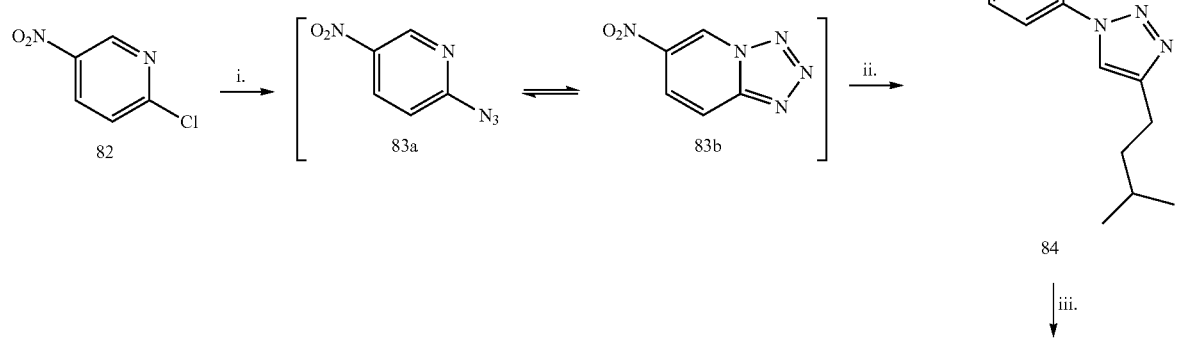

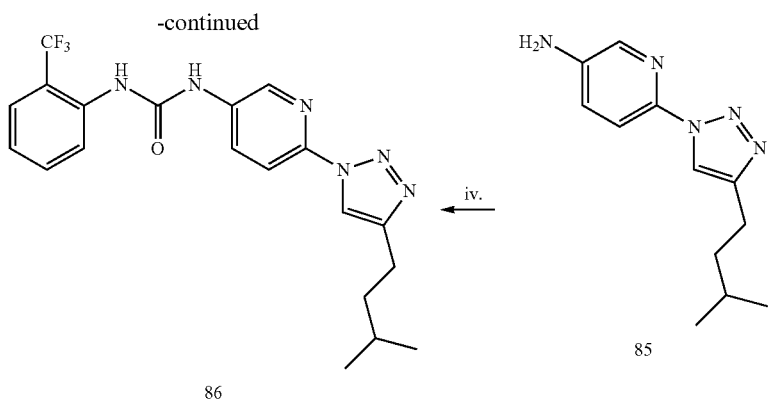

-continued

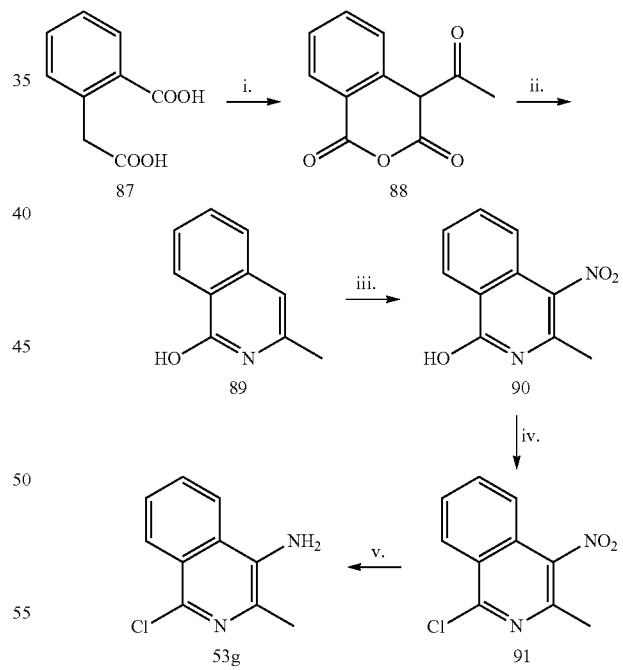

Reagents and conditions: i. NaN₃, HCl, EtOH: H₂O, reflux, 12 h; ii. CuSO₄·5 H₂O, sodium ascorbate, H₂O—THF (1:1), rt, 5 h; iii. H₂, Pd/C, MeOH, 1 h; iv. 2-(Trifluoromethyl) phenyl isocyanate, CH₂Cl₂, 5 h r.t.

2-(4-isopentyl-1H-1,2,3-triazol-1-yl)-5-nitro pyridine (84). A solution of 2-chloro-5-nitropyridine 82 (100 mg, 0.63 mmol) in a mixture of ethanol (8 mL) and water (3 mL) was carefully treated with NaN₃ (81 mg, 1.26 mmol). Concentrated HCl (0.8 mL) was added dropwise at rt. The reaction was stirred at reflux on, then cooled to rt. After that time saturated NaHCO₃ was added and the pH adjusted to 7. DCM (15 mL) was added and the rxn was washed with water. The organic layers were dried over Na₂SO₄ and concentrated to afford a yellow residue. The residue and the appropriate alkyne (90 µL, 0.75 mmol) were suspended in a 1:1 mixture of water and THF (1.5 mL each). To this, was added sodium ascorbate (1.0 equiv) and copper(II) sulfate pentahydrate (1.0 mmol). The mixture was stirred at r.t. for 5 h. After that time the reaction was partitioned between sat. aq. solution of NH₄Cl and AcOEt, and stirred for 15 min. The organic layer was separated, dried over Na₂SO₄ and the solvent removed in vacuo. The residue was purified by flash chromatography on silica gel (DCM/MeOH 98:2). Yield 75%, yellow solid. $^1$H NMR (400 MHz, CDCl₃): δ 9.28 (s, 1H), 8.67-8.64 (m, 1H), 8.36-8.32 (m, 2H), 2.80-2.76 (t, J=7.8 Hz, 2H), 1.67-1.58 (m, 3H), 0.84-0.82 (d, J=8.0 Hz, 6H) ppm. $^{13}$C NMR (100 MHz, CDCl₃-d): δ 152.24, 150.03, 144.99, 143.23, 134.59, 118.55, 114.44, 113.60, 38.08, 27.56, 23.48, 22.32 ppm. MS (ESI) m/z 260.3 [M−H]⁻

6-(4-isopentyl-1H-1,2,3-triazol-1-yl)pyridin-3-amine (85): 84 (1.60 mmol) was solubilized in 30 mL of anhydrous MeOH, and 10% Palladium on charcoal (25 mg) was added. The reaction mixture was stirred under Hydrogen atmosphere for 1 h, then the mixture was filtered off on a celite pad, the solvent evaporated at reduced pressure. The product was obtained as a pure compound. Yield 99%, yellow solid. Yield $^1$H NMR (400 MHz, CDCl₃-d): δ 8.14 (s, 1H), 7.92-7.90 (m, 2H), 7.17-7.14 (m, 1H), 3.89 (s, 2H), 2.80-2.76 (t, J=7.8 Hz, 2H), 1.74-1.58 (m, 3H), 0.95-0.93 (d, J=8.0 Hz, 6H) ppm. MS (ESI) m/z 232.3 [M+H]⁺.

1-(6-(4-isopentyl-1H-1,2,3-triazol-1-yl)pyridin-3-yl)-3-(2-(trifluoromethyl)phenyl)urea (86). Aniline 85 (0.10 mmol) was added to a solution of 2-(Trifluoromethyl)phenyl isocyanate (0.15 mmol) in anhydrous CH₂Cl₂ (15 mL) in one portion. The solution was stirred for 9 hours at r.t. under a nitrogen atmosphere. The solvent was removed at reduced pressure and the residue purified on silica to furnish the final product as white solid. (Purification eluent: DCM-MeOH 98:2). Yield 61%, white solid. $^1$H NMR (400 MHz, Acetone-d₆): δ 9.14 (s, 1H), 8.66 (s, 1H), 8.37 (s, 1H), 8.28-8.24 (d, J=8.0 Hz, 1H), 8.14-8.12 (d, J=8.0 Hz, 1H), 8.06-8.04 (d, J=8.0 Hz, 1H), 7.81 (s, 1H), 7.70-7.64 (m, 2H), 7.33-7.30 (t, J=8.0 Hz, 1H), 2.80-2.75 (t, J=7.7 Hz, 2H), 1.64-1.61 (m, 3H), 0.96-0.94 (d, J=8.0 Hz, 6H) ppm. $^{13}$C NMR (100 MHz, Acetone-d₆): δ 152.31, 148.41, 144.17, 138.61, 138.26, 136.46, 132.84, 128.80, 125.95, 125.65, 123.96, 117.98, 117.71, 113.35, 38.34, 27.33, 23.23, 21.91, 21.64 ppm. MS (ESI) m/z 419.3 [M+H]⁺.

Example 14

Reagents and conditions: i. Ac₂O, pyr, 0° C. to rt; ii. NH₄OH, 95° C., 5 h; iii. HNO₃, CH₃COOH, 0° C. to rt, 3 h; iv. POCl₃, 110° C., 1 h; v. H₂, Pd/C, MeOH, 1 h; vi. SnCl₂·2H₂O, HCl rt, 18 h.

4-acetylisochroman-1,3-dione (88): Pyridine (2 mL) was slowly added to a slurry of homophtalic acid (1000 mg, 5.55 mmol) in acetic anhydride at 0° C. with stirring. The resulting solution was stirred at room temperature for 5 h. After that time Et₂O was added and the resulting white solide was collected by filtration and rinsed twice with ether.

Yield 75% white solid. ¹H NMR (400 MHz, CDCl₃ d): δ 8.25-8.23 (d, J=8.0 Hz, 1H), 7.70-7.68 (d, J=8.0 Hz, 1H), 7.60-7.58 (d, J=8.0 Hz, 1H), 7.39-7.37 (d, J=8.0 Hz, 1H), 2.64 (s, 3H), 2.62 (s, 1H), 3-methylisoquinolin-1-ol (89): To 4-acetyl isochroman-1,3-dione (1000 mg, 4.90 mmol) was added slowly sat aq. NH₄OH (9 mL). The resulting bright yellow suspension was heated in a sealed tube at 95° C. for 5 h. Then the reaction mixture was cooled to r.t and diluted with water. The resulting white solid was collected by filtration at reduced pressure and dried. Yield 99%. White solid. ¹H NMR (400 MHz, CDCl₃ d): δ 11.61 (br s, 1H), 8.39-8.37 (d, J=8.0 Hz, 1H), 7.62-7.58 (t, J=8.0 Hz, 1H), 7.46-7.39 (m, 2H), 6.30 (s, 1H), 2.40 (s, 3H) ppm.

3-methyl-4-nitroisoquinolin-1-ol (90): To a solution of 89 (800 mg, 5.02 mmol), in acetic acid (7 mL), was slowly added 90% nitric acid (fuming) (2 mL), at 0° C. with stirring. The reaction mixture is allowed to warm to rt and stirred for 3 h. Water was added and the resulting solid was collected by filtration and dried. Yield 90% yellow solid ¹H NMR (400 MHz, CDCl₃ d): δ 12.03 (br s, 1H), 8.21-8.19 (d, J=8.0 Hz, 1H), 7.82-7.78 (t, J 8.0 Hz, 1H), 7.73-7.17 (d, 1H), 7.58-7.54 (t, J=8.0 Hz, 1H), 2.42 (s, 3H) ppm.

1-chloro-3-methyl-4-nitroisoquinoline (91): A mixture of 90 (100 mg, 0.49 mmol), and POCl₃ (5 mL) was heated with stirring at 110° C. for 1 h. POCl₃ was removed by distillation, and the resulting residue was neutralized with aq NaHCO₃ and extracted with AcOEt (3×25 mL). The organic layers were collected and washed with brine, dried over anhydrous Na₂SO₄ filtered and evaporated under reduced pressure to obtain pure compound. Yield 99% ¹H NMR (400 MHz, CDCl₃ d): δ 8.31-8.29 (d, J=8.0 Hz, 1H), 7.84-7.80 (t, J=8.0 Hz, 1H), 7.71-7.68 (m, 1H), 2.65 (s, 3H) ppm.

1-chloro-3-methylisoquinolin-4-amine (53g). To a solution of 91 (800 mg, 3.59 mmol) in concentrated HCl (15 mL), was added SnCl₂ 2H₂O. The reaction mixture was stirred for 18 h at rt. After that time was poured into ice-water and the pH adjusted to 8 by addition of 1N NaOH. The rxn mixture was extracted with AcOEt (3×25 mL) and the combined organic layers were dried over Na₂SO₄ to obtain a residue that was crystallized from Ethanol to obtain pure compound. Yield 84% ¹H NMR (400 MHz, CDCl₃ d): δ 8.23-8.20 (d, J=8.0 Hz, 1H), 7.75-7.73 (d, J=8.0 Hz, 1H), 7.73-7.64 (t, 1H), 7.59-7.55 (t, J=8.0 Hz, 1H), 3.95 (s, 2H), 2.53 (s, 3H) ppm. MS (ESI) m/z 193.0 [M+H]⁺.

Example 15

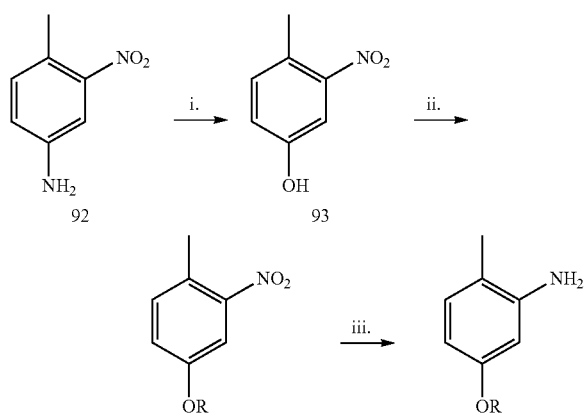

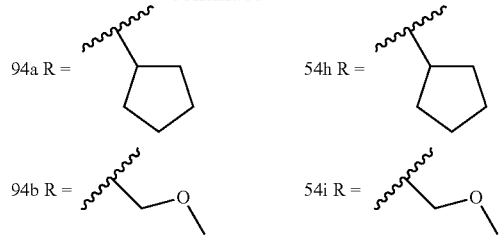

Reagents and conditions: i. a) H₂SO₄—H₂O (3:1), 100° C., 30 min.; b) NaNO₂ 0° C. to rt; ii. a) NaH, DMF 0° C. to rt b) cyclopentyl iodide (for 94a) or MOM—Cl (for 94b) 65° C., 1 h; iii. H₂, Pd/C, MeOH, 1 h.

4-methyl-3-nitrophenol (93): 92 (200 mg, 1.31 mmol) was dissolved in a 3:1 mixture of H₂SO₄—H₂O. The resulting mixture was heated to 100° C. for 30 minutes. After that time, rxn was cooled to 0° C. and a solution of NaNO₂ was added dropwise. After 1 hr the mixture was heated to reflux. After completion of the reaction the mixture was extracted with EtOAc several times and the combined organic phases were dried (Na₂SO₄) and concentrated. The resulting mixture was purified by flash chromatography (Purification eluent: PE-AcOEt 9:1). Yellow solid, Yield 70%. ¹H NMR (400 MHz, CDCl₃) δ 7.48 (s, 1H), 7.17 (d, J=8.4 Hz, 1H), 7.01 (dd, J=8.4, 2.4 Hz, 1H), 5.84 (s, 1H), 2.48 (s, 3H) ppm.

General Procedure for the Synthesis of 94a and 94b:

93 (500 mg, 3.26 mmol) was dissolved in anhydrous DMF (3 mL) under nitrogen atmosphere. To this, NaH (86 mg, 3.58 mmol) was added at 0° C., in one portion. After 20 minutes, a solution of the opportune halogen derivative (3.9 mmol) in DMF (1 mL) (cyclopentyl iodide for 94a or chloromethyl methyl ether for 94b) was added via cannula. The resulting solution was stirred at rt for 2 hrs. After completion of the reaction a water was added, and the mixture was extracted with EtOAc several times, washed with 5% LiCl(aq), and the combined organic phases were dried (Na₂SO₄) and concentrated.

4-(cyclopentyloxy)-1-methyl-2-nitrobenzene (94a): (Purification eluent: PE-AcOEt 95:5). Yield 70%. yellow liquid, ¹H NMR (400 MHz, CDCl₃) δ 7.44-7.43 (m, 1H), 7.16 (d, J=8.4 Hz, 1H), 6.98 (dd, J=8.4, 2.5 Hz, 1H), 4.81-4.68 (m, 1H), 2.48 (s, 3H), 1.98-1.69 (m, 6H), 1.67-1.52 (m, 2H) ppm. MS (ESI) m/z 222.0 [M+H]⁺.

4-(methoxymethoxy)-1-methyl-2-nitrobenzene (94b): 94b was obtained as a pure compound. Yield 99%. yellow liquid, ¹H NMR (400 MHz, CDCl₃) δ 7.62 (s, 1H), 7.34-6.90 (m, 2H), 5.16 (s, 2H), 3.45 (s, 3H), 2.49 (s, 3H). ppm. MS (ESI) m/z 198.2 [M+H]⁺.

General Procedure for the Synthesis of 54a and 54b:

The opportune nitro compound 94a or 94b (0.40 mmol) was solubilized in 30 mL of MeOH, and 10% Palladium on charcoal (5 mg) was added. The reaction mixture was stirred under Hydrogen atmosphere for 1 h, then the mixture was filtered-off on a celite pad and the solvent was evaporated at reduced pressure to furnish 54a or 54b as a pure compound.

5-(cyclopentyloxy)-2-methylaniline (54a): yellow solid, Yield 99%. ¹H NMR (400 MHz, CDCl₃) δ 6.92 (d, J=8.0 Hz, 1H), 6.31-6.24 (m, 2H), 4.93-4.49 (m, 1H), 3.57 (s, 2H), 2.10 (s, 3H), 1.86-1.78 (m, 6H), 1.61 (s, 2H) ppm. MS (ESI) m/z 192.3[M+H]⁺.

5-(methoxymethoxy)-2-methylaniline (54b): yellow solid, Yield 99%. ¹H NMR (400 MHz, CDCl₃-d) δ 6.93 (d, J=8.8 Hz, 1H), 6.40 (m, 2H), 5.11 (s, 2H), 3.59 (s, 2H), 3.47 (s, 3H), 2.09 (s, 3H). MS (ESI) m/z 168.1[M+H]⁺.

Example 16

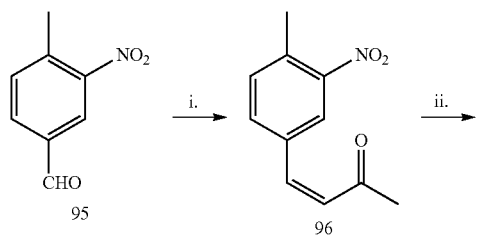

Example 17

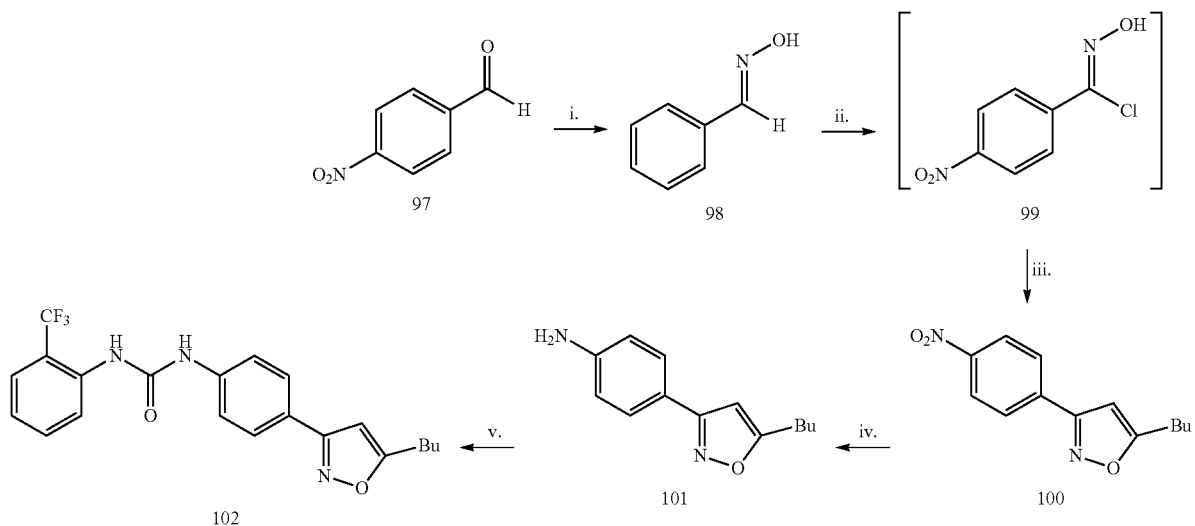

Reagents and conditions: i. NH₂OH•HCl/NaOH, EtOH/H₂O, rt., 1 h; ii. N-chlorosuccinimide, DMF dry, rt., 3 h; iii. 1-hexyne, CuSO₄•5 H₂O, sodium ascorbate, H₂O tBuOH (1:1), KHCO₃, MW 80° C., 15 min,; iv. Zinc, DCM, CH₃COOH, rt., 7 min; v. 2-(trifluoromethyl)-phenyl-isocyanate, CH₂Cl₂ dry, rt., 12 h.

-continued

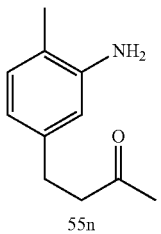

55n

Reagents and conditions: i. NaOH, H₂O 40° C., 20 min.; ii. H₂, Pd/C, MeOH, 12 h.

4-(4-methyl-3-nitrophenyl)but-3-en-2-one (96): To a mixture of 3-nitro-4-methylbenzaldehyde (300 mg, 1.8 mmol), acetone (20 mL) and water (10 mL) 5% aqueous NaOH (1 mL) was slowly added at 40° C. After 20 minutes, acetone was removed under reduced pressure. The residue was extracted with ethyl acetate. The organic layer was separated, washed with brine, dried (Na₂SO₄) and concentrated under reduced pressure. (yield 76%) yellow oil. ¹H NMR (400 MHz, CDCl₃) δ 7.93 (s, 1H), 7.51 (s, 1H), 7.33 (d, J=16.0 Hz, 1H), 6.60 (d, J=15.9 Hz, 1H), 2.42 (s, 4H), 2.24 (s, 3H) ppm.

4-(3-amino-4-methylphenyl)butan-2-one (55n): Compound 95 (0.40 mmol) was solubilized in 30 mL of MeOH, and 10% Palladium on charcoal (5 mg) was added. The reaction mixture was stirred under Hydrogen atmosphere for 12 h, then the mixture was filtered off on a celite pad and the solvent was evaporated at reduced pressure. Yield 99% ¹H NMR (400 MHz, CDCl₃) δ 7.02-6.86 (m, 1H), 6.55-6.40 (m, 1H), 3.93 (s, 2H), 3.38 (s, 1H), 2.73 (d, J=6.8 Hz, 1H), 2.65 (dd, J=21.6, 14.4 Hz, 1H), 2.10 (s, 1H), 2.08 (s, 1H). MS (ESI) m/z 178.0 [M+H]⁺.

benzaldehyde oxime (98): Hydroxylamine hydrochloride (1103 mg, 15.8 mmol) was dissolved in water (10 mL) and neutralized with a 10% NaOHaq solution. A solution of 97 (2000 mg, 13.2 mmol) in ethanol was added slowly to this mixture with stirring at rt for 1 hr. After this time ethanol was evaporated at reduced pressure. Water was added and the rxn mixture was extracted with dichloromethane (3×40 mL). The combined organic phase was washed with brine and dried with anhydrous sodium sulfate. 98 was used for further reactions without additional purification. ¹HNMR (400 MHz, CDCl₃-d): δ 8.25 8.23 (d, J=7.2 Hz, 2H), 8.23 (s, 1H), 7.75 (s, 1H), 7.73-7.72 (t, J=7.2 Hz, 2H) ppm. MS (ESI) m/z 164.9 [M−H]⁻

N-hydroxy-4-nitrobenzimidoyl chloride (99): 98 (100 mg, 0.60 mmol) was dissolved in dry DMF (2 mL) under nitrogen atmosphere. To this stirring solution, N-chlorosuccinimide was added (96.5 mg, 0.72 mmol). Initiation of the reaction was accelerated by use of UV light for 20 min. After 3 hrs the mixture was poured onto crushed ice, and extracted three times with Et₂O. The organic layers were collected, dried over anhydrous Na₂SO₄ and the solvent was evaporated. 99 was used for further reactions without additional purification.

5-butyl-3-(4-nitrophenyl)isoxazole (100): 1-hexyne (28 µL, 0.25 mmol), 99 (50 mg, 0.25 mmol), KHCO₃ (119 mg, 1.08 mmol) were suspended in a 1:1 mixture of water and t-BuOH (1.5 mL each) in a 10 mL glass vial equipped with a small magnetic stirring bar. To this, was added sodium ascorbate (2 mg, 0.02 mmol) and copper(II) sulfate pentahydrate (2 mg, 0.02 mmol). The mixture was then heated for 7 min. at 80° C. under microwave irradiation, using an irradiation power of 300 W. After this time the solvents were partially removed, the residue was stirred with NH₄Cl ss (10 mL), and NH₄OH (0.5 mL) for 15 min, then extracted with EtOAc. The residue was finally purified on silica gel, to give final products (PE/EtOAc 98:2). Yield 76% ¹HNMR (400 MHz, CDCl₃-d): δ 8.31-8.29 (d, J=8.4 Hz, 2H), 7.97-7.95 (d, J=8.4 Hz, 2H), 6.35 (s, 1H), 2.84-2.80 (t, J=7.2 Hz, 2H), 1.77-1.70 (m, 2H), 1.46-1.41 (q, J=7.2 Hz, 2H), 0.98-0.94 (t, J=7.2 Hz, 3H) ppm.

4-(5-butylisoxazol-3-yl)aniline (101): 99 (100 mg, 0.40 mmol) was dissolved in DCM and cooled to 0° C. Zinc dust (392 mg, 6 mmol) and AcOH (366 μL) were added and the reaction mixture was stirred at rt for 30 min. After this time the mixture was filtered off on a celite pad. The pH was adjusted to 7 by addition of NaHCO₃(ss), and the mixture was extracted several times. The organic layers were collected, washed with Brine and dried over anhydrous Na₂SO₄ Yield 70%. ¹HNMR (400 MHz, CDCl₃-d): δ 7.59-7.57 (m, 2H), 6.72-6.71 (d, J=7.2 Hz, 2H), 6.18 (s, 1H), 3.84 (s, 2H), 2.77-2.73 (t, J=7.6 Hz, 3H), 1.74-1.67 (m, 2H), 1.46-1.37 (m, 2H), 0.96-0.93 (t, J=7.6 Hz, 3H) ppm. MS (ESI) m/z 216.9 [M–H]⁺

1-(4-(5-butylisoxazol-3-yl)phenyl)-3-(2-(trifluoromethyl)phenyl)urea (102): 100 (100 mg, 0.46 mmol) was added to a solution of the 1-(Trifluoromethyl)phenyl isocyanate 24 (85 μL, 0.65 mmol) in anhydrous CH₂Cl₂ (10 mL) in one portion. The solution was stirred for 4 hours at r.t. under a nitrogen atmosphere. The solvent was removed, at reduced pressure and the residue purified by flash chromatography (PE/EtOAc 95:5) Yield 73% ¹HNMR (400 MHz, CDCl₃-d): δ 7.99-7.97 (d, J=7.6 Hz, 2H), 7.71-7.69 (d, J=7.6 Hz, 2H), 7.58-7.56 (d, J=7.2 Hz, 2H), 7.51-7.18 (m, 2H), 7.03 (s, 2H), 2.78-2.77 (d, J=6.8 Hz, 2H), 1.71-1.61 (m, 2H), 1.42-1.40 (d, J=6.4 Hz, 2H), 0.96-0.87 (t, J=6.8 Hz, 3H) ppm ¹³C-NMR (100 MHz, CDCl₃-d): δ 174.66, 163.30, 152.83, 139.94, 136.25, 134.15, 133.10, 128.10, 126.20, 125.37, 124.86, 124.63, 124.22, 120.74, 98.30, 29.99, 26.83, 22.62, 13.94 ppm. MS (ESI) m/z 402.2 [M–H]⁻

Example 18

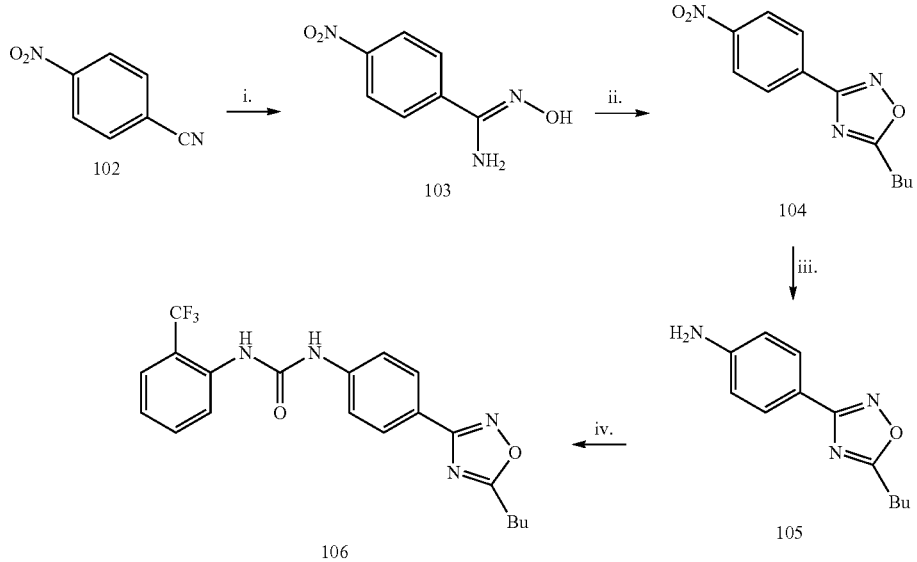

Reagents and conditions: i. NH₂OH•HCl/NaOH, EtOH/H₂O, rt., 12 h; ii. valeric acid, EDC•HCl, HOBT, DMAP, CH₂Cl₂ dry, DMF dry, rt., 12 h; iii. Fe⁰, NH₄Cl, EtOH, H₂O, 80° C., 30 min; v. 2-(trifluoromethyl)-phenylisocyanate, CH₂Cl₂ dry, rt., 12 h.

N'-hydroxy-4-nitrobenzimidamide (103): hdroxylamine hydrochloride (469 mg, 6.75 mmol) was dissolved in water and neutralized with NaOH 2N. A solution of 102 (500 mg, 3.37 mmol) in ethanol was added with continuous stirring. The reaction mixture was stirred at rt for 12 hrs, then was extracted with DCM. The combined organic phase was washed with brine and dried. Yield 88.3%¹H NMR (400 MHz, CDCl₃-d): δ 8.26-8.24 (d, J=8.4 Hz, 2H), 7.82-7.80 (d, J=8.2 Hz, 2H), 4.89 (s, 2H), 1.57 (s, 1H) ppm. MS (ESI) m/z 181.9 [M+H]+MS (ESI) m/z 182.1 [M+H]⁺

5-butyl-3-(4-nitrophenyl)-1,2,4-oxadiazole (104): EDC HCl (1587 mg, 8.28 mmol), HOBt (373 mg, 2.76 mmol) and DIPEA (1.44 mL), were dissolved in a 10:1 mixture of DCM and DMF (22 mL) at 0° C. Valeric acid (300 μL, 8.28 mmol) was added, and the mixture was stirred under nitrogen atmosphere for 1 h at rt. After this time 103 (4.1 mmol) was added and the mixture was stirred at rt for 1 h, then at 110° C. for 12 h. After this time the solvent was removed at reduced pressure, and extracted with EtOAc. The organic phase was washed with 5% LiCl(aq) solution, and dried over Na₂SO₄. The residue was purified by flash chromatography on silica gel. (PE/EtOAc 9:1). Yield 73% ¹HNMR (400 MHz, CDCl₃-d): δ 8.20-8.18 (d, J=8.4 Hz, 2H), 8.13-8.11 (d, J=8.8 Hz, 2H), 2.91-2.87 (t, J=7.6 Hz, 2H), 1.82-1.74 (m, 2H), 1.44-1.34 (m, 2H), 0.91-0.88 (t, J=7.6 Hz, 3H) ppm.

4-(5-butyl-1,2,4-oxadiazol-3-yl)aniline (105): 104 (95 mg, 0.38 mmol) was solubilized in a mixture of EtOH (30 mL) and water 2.5 mL. To this Iron powder (107.2 mg, 1.92 mmol) and NH₄Cl (11 mg, 0.19 mmol) were added. The reaction mixture was heated at 80° C. and stirred for 30 min.

After this time the reaction was warmed to rt and filtered on a celite pad. The mixture was concentrated and water (15 mL) was added, followed by extraction with EtOAc. The organic layers were washed with Brine and dried over $Na_2SO_4$. Yield 95% $^1$H NMR (400 MHz, $CDCl_3$-d): δ 7.84-7.83 (d, J=7.2 Hz, 2H), 6.70-6.68 (d, J=7.2 Hz, 2H), 3.82 (s, 2H), 2.90-2.86 (t, J=6.8 Hz, 2H), 1.82-1.79 (t, J=6.8 Hz, 2H), 1.43-1.41 (d, J=7.2 Hz, 2H), 0.95-0.92 (t, J=6.4 Hz, 3H) ppm.

1-(4-(5-butyl-1,2,4-oxadiazol-3-yl)phenyl)-3-(2-(trifluoromethyl)phenyl)urea (106): 105 (0.46 mmol) was added to a solution of the 1-(Trifluoromethyl)phenyl isocyanate 24 (85 μL, 0.65 mmol) in anhydrous $CH_2Cl_2$ (10 mL) in one portion. The solution was stirred for 4 hours at r.t. under a nitrogen atmosphere. The solvent was removed, at reduced pressure and the residue purified by flash chromatography (PE/EtOAc 9:1) Yield 76% $^1$HNMR (400 MHz, $CDCl_3$-d): δ 7.58-7.56 (d, J=7.6 Hz, 2H), 7.44-7.41 (m, 3H), 7.25 (s, 1H), 7.18 (s, 1H), 7.08 (s, 1H), 1.86-1.82 (t, J=7.2 Hz, 2H), 1.48-1.42 (m, 2H), 0.96-0.94 (t, J=7.6 Hz, 3H) ppm $^{13}$C-NMR (100 MHz, ACETONE-$d_6$): δ 180.10, 152.51, 142.51, 136.56, 132.78, 127.87, 125.98, 125.32, 123.81, 120.98, 118.33, 25.69, 21.82, 13.03 ppm.

Example 19

2-butyl-5-(4-nitrophenyl)-1,3,4-oxadiazole (110): A solution of valeraldehyde (58.7 μL, 0.55 mmol) and 109 (100 mg, 0.55 mmol) in EtOH, was heated at reflux for 12 h. After this time, the solvent was removed at reduced pressure. The resulting residue was redissolved in DMSO (3 mL) and $K_2CO_3$ (228.04 mg, 1.65 mmol) and 12 (155.63 mg, 0.66 mmol) were added. The reaction mixture was stirred at 100° C. for 12 h. After completion of the reaction the mixture was cooled and treated with $Na_2S_2O_3$, then extracted with EtOAc (3×25 mL), washed with Brine and dried over $Na_2SO_4$. The residue purified by flash chromatography. (PE/EtOAc 9:1). Yield: 70%: $^1$HNMR (400 MHz, $CDCl_3$-d): δ 8.35-8.33 (d, J=8.4 Hz, 2H), 8.22-8.20 (d, J=8.4 Hz, 2H), 2.97-2.93 (t, J=7.6 Hz, 2H), 1.86-1.82 (t, J=7.2 Hz, 2H), 1.49-1.44 (m, 2H), 0.99-0.95 (t, J=6.8 Hz, 3H) ppm.

4-(5-butyl-1,3,4-oxadiazol-2-yl)aniline (111): Compound 110 (0.40 mmol) was solubilized in 30 mL of MeOH, and 10% Palladium on charcoal (5 mg) was added. The reaction mixture was stirred under Hydrogen atmosphere for 1 h, then the mixture was filtered off on a celite pad and the solvent was evaporated at reduced pressure. Yield 99% Eluente. DCM/MeOH 98:2, Yield: 72%, $^1$HNMR (400 MHz, $CDCl_3$-d): δ 7.80-7.78 (d, J=8.4 Hz, 2H), 6.71-6.69 (d, J=8.8 Hz, 2H), 4.07 (s, 2H), 2.88-2.84 (t, J=7.6 Hz, 2H), 1.82-1.75 (m, 2H), 1.48-1.39 (m, 2H), 0.96-0.93 (t, J=7.6 Hz, 3H) ppm.

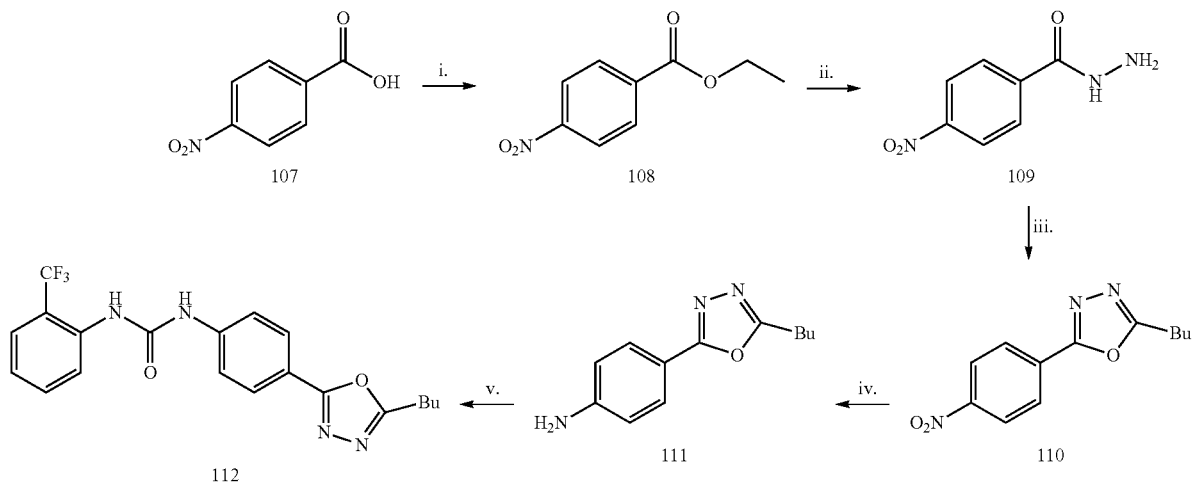

Reagents and conditions: i. $H_2SO_4$/EtOH, 100° C., 3 h; ii. $N_2H_4 \cdot H_2O$, EtOH, 100° C., 48 h; iii. Valeraldehyde, EtOH, 100° C., 12 oh; iv. $I_2$, $K_2CO_3$, DMSO, 100° C., 12 h; v. $H_2$, Pd/C (10%), $CH_3OH$, 4 h; vi. 2-(trifluoromethyl)-phenylisocyanate, $CH_2Cl_2$ dry, rt., 12 h.

ethyl 4-nitrobenzoate (108): 107 (200 mg, 1.19 mmol), was solubilized in a mixture of $H_2SO_4$ (4 mL) and EtOH (10 mL). The mixture was stirred at 100° C. for 1 h. After this time the solvent was partially evaporated at reduced pressure and the pH adjusted to 6 with $NaHCO_3$. The reaction was extracted with EtOAc, washed with Brine and dried over $Na_2SO_4$. Yield: 90% $^1$HNMR (400 MHz, $CDCl_3$-d): δ 8.26-8.24 (d, J=8.8 Hz, 2H), 8.19-8.17 (d, J=8.8 Hz, 2H), 4.43-4.38 (m, 2H), 1.41-1.38 (t, J=7.2, 3H) ppm.

4-nitrobenzohydrazide (109): To a solution of 108 (180 mg, 0.92 mmol) in EtOH (20 mL), $N_2H_4.H_2O$ (236 μL) was added. The resulting solution was heated to refluc for 48 h. After this time the mixture was warmed at rt, and the volatiles were removed in vacuo. The residue was crystallized in ACN. Yield 85% $^1$HNMR (400 MHz, MeOD-d): δ 8.31-8.29 (d, J=8.8 Hz, 2H), 7.99-7.97 (d, J=8.8 Hz, 2H) ppm.

1-(4-(5-butyl-1,3,4-oxadiazol-2-yl)phenyl)-3-(2-(trifluoromethyl)phenyl)urea (112): Aniline 111 (31 mg, 0.14 mmol) was added to a solution of 2-(Trifluoromethyl)phenyl isocyanate (22 μL, 0.15 mmol) in anhydrous $CH_2Cl_2$ (15 mL) in one portion. The solution was stirred for 9 hours at r.t. under a nitrogen atmosphere. The solvent was removed at reduced pressure and the residue purified on silica to furnish the final product as white solid. (Purification eluent: PE/EtOAc 7:3). Yield 71%, white solid. $^1$HNMR (400 MHz, MeOD-d): δ 7.95-7.93 (d, J=8.4, 2H), 7.67-7.65 (d, J=8.8, 2H), 7.63-7.59 (m, 2H), 7.31-7.27 (m, 2H), 2.96-2.92 (d, J=7.6, 2H), 1.86-1.78 (m, 2H), 1.51-1.42 (m, 2H), 1.00-0.97 (t, J=7.2, 3H) ppm. $^{13}$C-NMR (100 MHz, ACETONE-$d_6$): δ 166.35, 164.11, 152.03, 142.81, 136.48, 132.79, 127.35, 125.90, 125.55, 123.65, 118.51, 29.30, 29.11, 28.92, 28.73, 28.54, 24.56, 21.82, 12.95 ppm.

Example 20

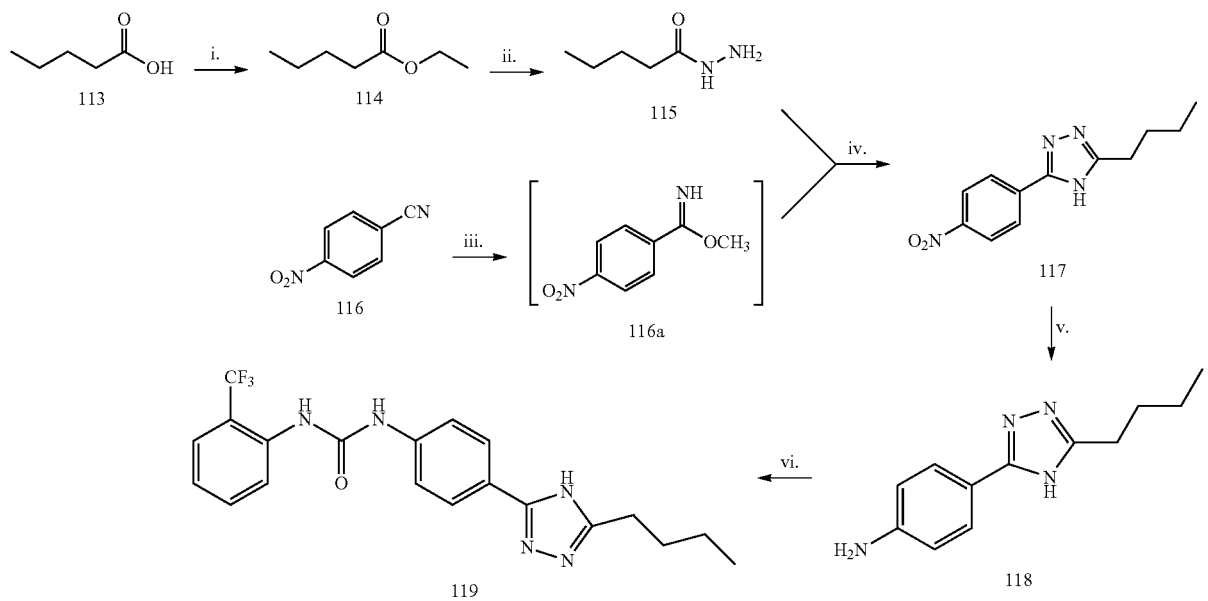

Reagents and conditions: i. EtOH/H$_2$SO$_4$, 100° C., 3 h; ii. N$_2$H$_4$·H$_2$O, EtOH, 100° C., 12 h; iii. CH$_3$ONa, dry CH$_3$OH, rt., 1 h; iv., CH$_3$COOH, 0° C., 2 h; v. H$_2$, Pd/C (10%), CH$_3$OH, 3 h; v. 2-(trifluoromethyl)-phenylisocyanate, CH$_2$Cl$_2$ dry, rt., 12 h.

4-nitrobenzohydrazide (109): To a solution of 108 (180 mg, 0.92 mmol) in EtOH (20 mL), N$_2$H$_4$·H$_2$O (236 µL) was added. The resulting solution was heated to refluc for 48 h. After this time the mixture was warmed at rt, and the volatiles were removed in vacuo. The residue was crystallized in ACN. Yield 85% $^1$HNMR (400 MHz, MeOD-d): δ 8.31-8.29 (d, J=8.8, 2H), 7.99-7.97 (d, J=8.8, 2H) ppm.

ethyl pentanoate (114): 113 (1000 mg, 9.79 mmol), was solubilized in a mixture of H$_2$SO$_4$ (4 mL) and EtOH (10 mL). The mixture was stirred at 100° C. for 3 h. After this time the solvent was partially evaporated at reduced pressure and the pH adjusted to 6 with NaHCO$_3$. The reaction was extracted with EtOAc, washed with Brine and dried over Na$_2$SO$_4$. Yield 99%. $^1$HNMR (400 MHz, CDCl$_3$-d): δ 4.12-4.07 (q, J=7.2, 2H), 2.29-2.25 (t, J=8.0 Hz, 2H), 1.62-1.54 (m, 2H), 1.37-1.30 (q, J=8.0 Hz, 2H), 1.28-1.18 (t, J=8.0 Hz, 3H) ppm.

pentanehydrazide (115): To a solution of 114 (420 mg, 3.22 mmol) in EtOH (20 mL), N$_2$H$_4$·H$_2$O (783 µL) was added. The resulting solution was heated to refluc for 12 h. After this time the mixture was warmed at rt, and the volatiles were removed in vacuo. 115 was used for further reactions without additional purification. Yield: 99% $^1$HNMR (400 MHz, CDCl$_3$-d): δ 7.25 (s, 1H), 2.15-2.119 (d, J=7.6, 2H), 1.64-1.57 (m, 2H), 1.37-1.28 (m, 2H), 0.92-0.88 (t, J=7.2, 3H) ppm.

3-butyl-5-(4-nitrophenyl)-4H-1,2,4-triazole (117): A 30% solution of MeONa (2.36 mmol) in anhydrous Methanol, was added dropwise to a solution of 116 (3.98 mmol) in CH$_3$OH. The reaction mixture was stirred at rt for 1 h. The pH was adjusted to 6 with CH$_3$COOH at 0° C. then 115 (4.3 mmol) was added. The rxn was stirred at rt for 2 h, then the solvent was removed at reduced pressure. Toluene (10 mL) was added and the reaction was heated at reflux with a Dean-Stark trap for 12 h. After this time the reaction was cooled and water and EtOAc were added. The mixture was stirred at rt for 30 min, then extracted, washed with Brine and dried over Na$_2$SO$_4$. The solvent was removed at reduced pressure and the residue was purified by flash chromatography. (PE/EtOAc 6:4). Yield 60%, $^1$H NMR (400 MHz, CDCl$_3$-d: δ 8.37-8.35 (d, J=8.4, 2H), 8.29-8.24 (d, J=7.6, 2H), 1.84-1-76 (m, 2H), 1.46-1.39 (m, 2H), 0.98-0.946 (t, J=7.2 Hz, 3H) ppm. $^{13}$C-NMR (100 MHz, ACETONE-d$_6$): δ 160.05, 159.25, 148.07, 136.95, 127.13, 124.00, 77.39, 77.08, 76.76, 29.98, 26.36, 22.29, 13.58 ppm.

4-(5-butyl-4H-1,2,4-triazol-3-yl)aniline (118): 117 (0.40 mmol) was solubilized in 30 mL of MeOH, and 10% Palladium on charcoal (5 mg) was added. The reaction mixture was stirred under Hydrogen atmosphere for 1 h, then the mixture was filtered off on a celite pad and the solvent was evaporated at reduced pressure. The residue was purified by flash chromatography (PE/EtOAc/TEA 6:4:0.5). Yield 70% $^1$HNMR (400 MHz, CDCl$_3$-d): δ 7.77-7.75 (d, J=6.8 Hz, 2H), 6.68-6.66 (d, J=6.8 Hz, 2H), 4.13 (s, 1H), 2.77-2.75 (d, J=7.6 Hz, 2H), 1.72-1.71 (d, J=7.2 Hz, 2H), 1.38-1.34 (d, J=8.0 Hz, 2H), 0.91-0.88 (m, 3H) ppm.

1-(4-(5-butyl-4H-1,2,4-triazol-3-yl)phenyl)-3-(2-(trifluoromethyl)phenyl)urea (119): Aniline 118 (25 mg, 0.11 mmol) was added to a solution of 2-(Trifluoromethyl)phenyl isocyanate (18 µL, 0.11 mmol) in anhydrous CH$_2$Cl$_2$ (15 mL) in one portion. The solution was stirred for 12 hours at r.t. under a nitrogen atmosphere. The solvent was removed at reduced pressure and the residue purified on silica to furnish the final product as white solid. (Purification eluent: PE/EtOAc 7:3). Yield 70%, white solid. $^1$HNMR (400 MHz, MeOD-d): δ 7.95-7.89 (m, 4H), 7.66-7.56 (m, 4H), 7.29-7.25 (m), 2.81-2.77 (d, J=7.6 Hz, 2H), 1.79-1.72 (m, 2H), 1.45-1.36 (m, 2H), 0.98-0.94 (t, J=7.6 Hz, 3H) ppm. $^{13}$C-NMR (100 MHz, MeOD-d$_6$): δ153.58, 146.64, 140.81, 135.86, 132.40, 126.77, 126.01, 125.67, 124.01, 121.78, 121.44, 118.53, 30.00, 29.31, 25.76, 21.88, 12.61 ppm.

Example 21

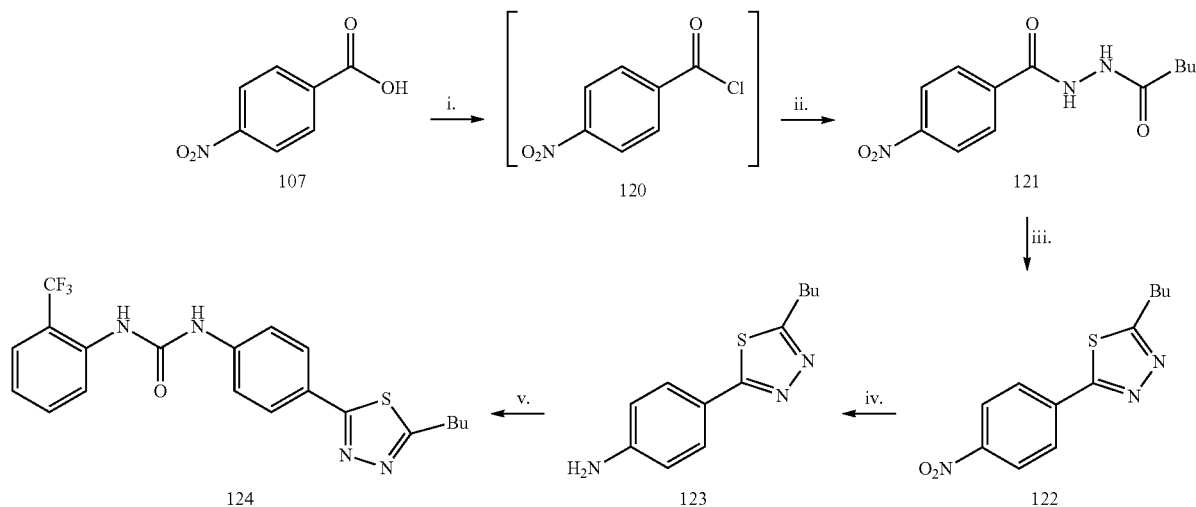

Reagents and conditions: i. SOCl$_2$, 100° C., 1 h; ii. 115, DMAP, CH$_2$Cl$_2$, 0° C., 12 h; iii. Lawesson's reagents, dioxane, 80° C., 12 h; iv. Fe$^0$, NH$_4$Cl, EtOH, H$_2$O, 80° C., 1 h; v. 2-(trifluoromethyl)-phenylisocyanate, CH$_2$Cl$_2$ dry, rt., 12 h.

4-nitrobenzoyl chloride (120): 107 (719.8 mg, 4.30 mmol), was stirred with 1 mL of anhydrous SOCl$_2$, at 100° C., for 1 h. The excess of SOCl$_2$ was removed by distillation. 120 was used for further reactions without additional purification.

4-nitro-N'-pentanoylbenzohydrazide (121): A solution of 120 (500 mg, 4.30 mmol) and DMAP (525 mg, 4.30 mmol) in dry DCM (5 mL) was added dropwise to a solution of 120 in anhydrous DCM. The resulting mixture was stirred at rt on. The solvent was removed at reduced pressure and the residue purified by flash chromatography (DCM/MeOH/TEA 98:2:0.5), Yield: 67%, $^1$H NMR (400 MHz, MeOD-d): δ 8.34-8.31 (d, J=8.8, 2H), 8.08-8.06 (d, J=8.8, 2H), 2.34-2.30 (q, J=7.2, 2H), 1.71-1.57 (q, 2H), 1.47-1.35 (t, J=7.7 Hz, 3H) ppm.

2-butyl-5-(4-nitrophenyl)-1,3,4-thiadiazole (122): Lawesson's reagent (458 mg, 1.31 mmol) was added to a stirring solution of 121 in anhydrous dioxane (20 mL). The reaction mixture was stirred at 80° C. for 24 h. Dioxane was removed under reduced pressure, and the residue obtained was dissolved in water. The pH was basified to 9 by adding of NaHCO$_{3(aq)}$ and the organic phases were washed with brine and dried over Na$_2$SO$_4$. The residue was purified by flash chromatography (PE/EtOAc 8:2), Yield 60% $^1$HNMR (400 MHz, CD$_3$OD): δ 8.39-8.37 (d, J=8.8 Hz, 2H), 8.26-8.24 (d, J=8.8 Hz, 2H), 3.22-3.18 (t, J=7.6 Hz, 2H), 1.87-1.79 (m, 2H), 1.51-1.42 (m, 2H), 0.98-0.94 (t, J=7.2 Hz, 3H) ppm.

4-(5-butyl-1,3,4-thiadiazol-2-yl)aniline (123): 122 (58 mg, 0.22 mmol) was solubilized in a mixture of EtOH (30 mL) and water 2.5 mL. To this Iron powder (62 mg, 1.1 mmol) and NH$_4$Cl (6 mg, 0.11 mmol) were added. The reaction mixture was heated at 80° C. and stirred for 30 min. After this time the reaction was warmed to rt and filtered on a celite pad. The mixture was concentrated and water (15 mL) was added, followed by extraction with EtOAc. The organic layers were washed with Brine and dried over Na$_2$SO$_4$. Yield 75% $^1$HNMR (400 MHz, CDCl$_3$-d): δ 7.72-7.70 (d, J=8.0, 2H) 6.70-6.68 (d, J=8.0, 2H), 3.96 (s, 2H), 3.10-3.06 (t, J=8.0, 2H), 1.82-1.75 (q, J=7.6 Hz, 2H), 1.49-1.40 (q, J=7.6 Hz, 2H), 0.97-0.93 (t, J=8.0 Hz, 3H) ppm. MS (ESI) m/z 234.1 [M+H]$^+$ 1-(4-(5-butyl-1,3,4-thiadiazol-2-yl)phenyl)-3-(2-(trifluoromethyl)phenyl)urea (124): Aniline 123 (25 mg, 0.11 mmol) was added to a solution of 2-(Trifluoromethyl)phenyl isocyanate (17 μL, 0.11 mmol) in anhydrous CH$_2$Cl$_2$ (15 mL) in one portion. The solution was stirred for 12 hours at r.t. under a nitrogen atmosphere. The solvent was removed at reduced pressure and the residue purified on silica to furnish the final product as white solid. (Purification eluent: PE/EtOAc 7:3). Yield 68%, white solid. $^1$H NMR (400 MHz, CDCl$_3$-d) δ 7.57 (m 5H), 7.31-7.22 (m, 2H), 7.18 (dd, J=7.5, 1.6 Hz, 1H), 6.97 (td, J=7.5, 1.6 Hz, 1H), 4.18 (s, 1H), 2.75 (t, J=5.5 Hz, 2H), 1.65 (dq, J=7.7, 5.6 Hz, 2H), 1.46-1.32 (m, 2H), 1.32-1.07 (m, 3H) ppm.

Example 22

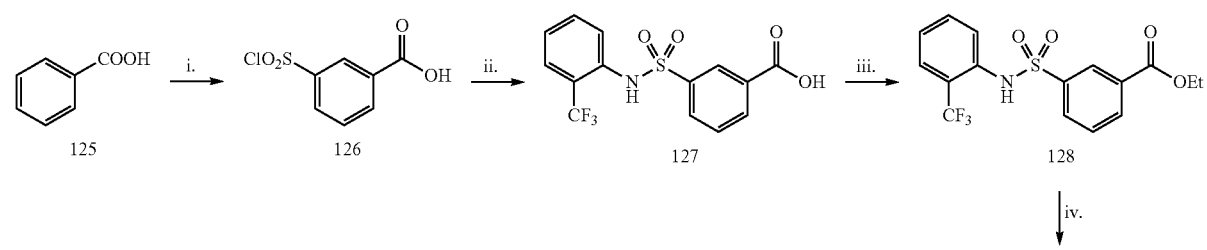

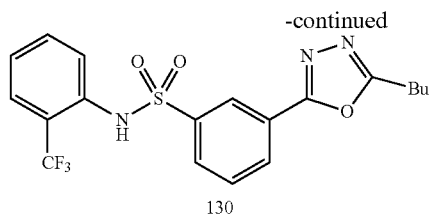
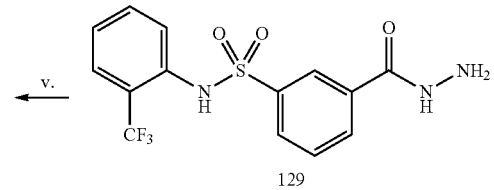

Reagents and conditions: i. HSO₃Cl, 2 h, 120° C. (82%); ii. Pyr, 5 h, rt; iii. H₂SO₄/EtOH, 100° C., 3 h; iv. N₂H₄·H₂O, EtOH, 100° C., 48 h; v. a) EtOH, 100° C., 12 oh; b). I₂, K₂CO₃, DMSO, 100° C., 12 h;

3-(Chlorosulfonyl)benzoic acid, (126): Chlorosulfonic acid (2 mL, 300.4 mmol) was added to 125, (500 mg, 40.9 mmol) and the mixture was stirred at 120° C. for 2 h. After this time the mixture was added dropwise to a mixture of EtOAc (200 mL) and crushed ice. The resulting precipitate was collected, dissolved in ethyl acetate, washed with water (3×25 mL) and Brine, dried over Na₂SO₄, and the solvent was removed under reduced pressure. ¹H-NMR (400 MHz, DMSO-d6): δ=8.80 (t, J=1.4 Hz, 1H), 8.40 (m 1H), 8.19 (m, 1H), 7.69 (t, J=7.5 Hz, 1H). ppm.

3-(N-(2-(trifluoromethyl)phenyl)sulfamoyl)benzoic acid (127): To a stirred solution of 2-trifluoromethyl-phenylaniline (1 eq.) in 5 mL of anhydrous pyridine, was added sulphonyl chloride 126 (1.1 eq) at 0° C. The corresponding solution was stirred at r.t. under nitrogen atmosphere, for 5 h. After completion of the reaction the mixture was acidified with 1N HCl, the aqueous phase was extracted with several times and the combined organic phases were dried (Na₂SO₄) and concentrated. (PE-AcOEt 95:5). Yield 75%, white solid. ¹H NMR (400 MHz, CDCl₃-d): δ 9.44 (s, 1H), 8.72 (s, 1H), 8.39 (s, 1H), 8.23 (s, 1H), 7.71 (s, 1H), 7.35 (s, 1H), 7.20 (s, 1H), 6.82 (s, 1H), 6.71 (s, 1H), 6.08 (s, 1H). ppm. MS (ESI): m/z 344 [M−H]⁻.

ethyl 3-(N-(2-(trifluoromethyl)phenyl)sulfamoyl)benzoate (128): 127 (200 mg, 1.19 mmol), was solubilized in a mixture of H₂SO₄ (4 mL) and EtOH (10 mL). The mixture was stirred at 100° C. for 1 h. After this time the solvent was partially evaporated at reduced pressure and the pH adjusted to 6 with NaHCO₃. The reaction was extracted with EtOAc, washed with Brine and dried over Na₂SO₄. Yield: 87% ¹H NMR (400 MHz, CDCl₃-d): δ 8.41 (s, 1H), 8.20 (d, J=7.8 Hz, 1H), 7.91 (d, J=7.9 Hz, 1H), 7.83 (d, J=8.3 Hz, 1H), 7.60-7.44 (m, 2H), 7.25 (t, J=7.7 Hz, 1H), 6.74 (t, J=7.9 Hz, 1H), 4.36 (q, J=7.6 Hz, 2H), 1.38 (t, J=7.5 Hz, 3H). ppm.

3-(hydrazinecarbonyl)-N-(2-(trifluoromethyl)phenyl) benzenesulfonamide (129): To a solution of 128 (90 mg, 0.24 mmol) in EtOH (20 mL), N₂H₄.H₂O (58 μL) was added. The resulting solution was heated to refluc for 48 h. After this time the mixture was warmed at rt, and the volatiles were removed in vacuo. The residue was crystallized in ACN. Yield 85% ¹HNMR (400 MHz, Acetone-d₆): δ 7.39 (dd, J=7.5, 1.4 Hz, 1H), 7.18 (ddd, J=19.2, 12.6, 1.0 Hz, 2H), 6.84 (td, J=7.5, 1.4 Hz, 1H), 6.71 (dd, J=7.5, 1.5 Hz, 1H), 6.07-6.01 (m, 2H), 5.79 (d, J=2.0 Hz, 1H), 5.64 (s, 1H), 2.05 (s, 1H), 2.00 (d, J=0.8 Hz, 3H), 1.66 (s, 1H). ppm.

2-butyl-5-(4-nitrophenyl)-1,3,4-oxadiazole (130): A solution of valeraldehyde (15 μL, 0.14 mmol) and 129 (50 mg, 0.14 mmol) in EtOH, was heated at reflux for 12 h. After this time, the solvent was removed at reduced pressure. The resulting residue was redissolved in DMSO (3 mL) and K₂CO₃ (58 mg, 0.42 mmol) and 12 (43 mg, 0.16 mmol) were added. The reaction mixture was stirred at 100° C. for 12 h. After completion of the reaction the mixture was cooled and treated with Na₂S₂O₃, then extracted with EtOAc (3×25 mL), washed with Brine and dried over Na₂SO₄. The residue purified by flash chromatography. (PE/EtOAc 8:2). Yield: 73% ¹HNMR (400 MHz, CDCl₃-d): δ 8.21 (s, 2H), 8.04 (s, 2H), 7.86 (s, 2H), 7.65 (s, 2H), 7.33 (s, 2H), 7.17 (s, 2H), 6.81 (s, 2H), 6.69 (s, 2H), 6.19 (s, 2H), 2.73-2.68 (m, 4H), 1.67-1.62 (m, 3H), 1.40-1.35 (m, 3H), 1.01-0.96 (m, 6H). ppm. ¹³C NMR (100 MHz, CDCl₃-d) δ 166.44, 162.20, 144.51, 139.07, 135.27, 133.84, 132.13, 131.76, 128.46, 128.22, 127.97, 127.75 123.87, 27.52, 26.97, 22.18, 14.02 ppm.

Example 23

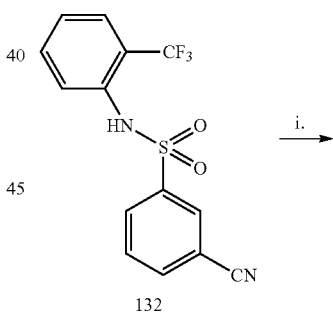

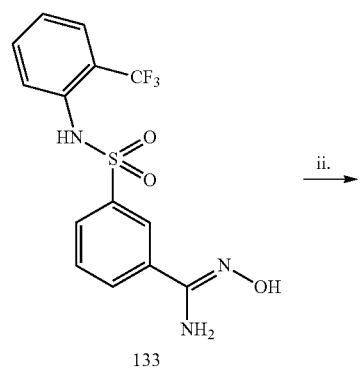

-continued

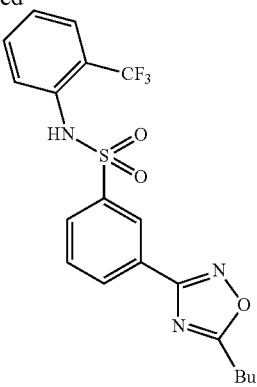

134

Reagents and conditions: i. NH$_2$OH•HCl/NaOH, EtOH/H$_2$O, r.t., 12 h; ii. valeric acid, EDC•HCl, HOBt, DMAP, CH$_2$Cl dry, DMF dry, rt., 12 h.

hydroxy-3-(N-(2-(trifluoromethyl)phenyl)sulfamoyl)benzimidamide (133): hydroxylamine hydrochloride (469 mg, 6.75 mmol) was dissolved in water and neutralized with NaOH 2N. A solution of 132 (3.37 mmol) in ethanol was added with continuous stirring. The reaction mixture was stirred at rt for 12 hrs, then was extracted with DCM. The combined organic phase was washed with brine and dried. Yield 99% $^1$HNMR (400 MHz, Acetone): δ 8.23 (s, 1H), 7.98 (d, J=7.7 Hz, 1H), 7.83 (d, J=7.8 Hz, 1H), 7.66 (d, J=8.2 Hz, 1H), 7.58 (d, J=7.3 Hz, 2H), 7.47 (d, J=8.1 Hz, 1H), 7.39 (t, J=7.2 Hz, 1H). MS (ESI) m/z 362.1 [M+H]$^+$ 3-(5-butyl-1,2,4-oxadiazol-3-yl)-N-(2-(trifluoromethyl) phenyl)benzenesulfonamide (134): EDC HCl (1587 mg, 8.28 mmol), HOBt (373 mg, 2.76 mmol) and DIPEA (1.44 mL), were dissolved in a 10:1 mixture of DCM and DMF (22 mL) at 0° C. Valeric acid (300 µL, 8.28 mmol) was added, and the mixture was stirred under nitrogen atmosphere for 1 h at rt. After this time 133 (4.1 mmol) was added and the mixture was stirred at rt for 1 h, then at 110° C. for 12 h. After this time the solvent was removed at reduced pressure, and extracted with EtOAc. The organic phase was washed with 5% LiCl(aq) solution, and dried over Na$_2$SO$_4$. The residue was purified by flash chromatography on silica gel. (PE/EtOAc 7:3). Yield 73% $^1$H NMR (400 MHz, Acetone) δ 8.29 (s, 1H), 8.07 (d, J=7.8 Hz, 1H), 7.92 (d, J=7.8 Hz, 1H), 7.70-7.53 (m, 2H), 7.43 (dd, J=15.2, 7.8 Hz, 2H), 6.47 (s, 2H), 2.47 (t, J=7.4 Hz, 2H), 1.63 (dd, J=15.1, 7.5 Hz, 2H), 1.38 (dd, J=14.9, 7.5 Hz, 2H), 0.92 (t, J=7.4 Hz, 3H). ppm. $^{13}$C NMR (101 MHz, Acetone) δ 169.93, 154.59, 141.46, 134.45, 133.19, 130.93, 129.43, 128.77, 127.07, 126.88, 126.64, 125.30, 32.17, 26.90, 22.02, 13.12. MS (ESI) m/z 426.3 [M+H]$^+$ Example 24

In Vitro ADME Studies

ADME properties of compounds are actually of primary importance. Poor solubility and poor permeability are among the main causes of failure during drug-development. In general, it is important try to find a good balance between lipid bilayer permeability, that affect gastrointestinal absorption by passive diffusion after oral dosing, and solubility. For these reasons, physicochemical properties of our compounds were predicted, starting from the first phases, using QikProp (QP) prediction program (QikProp, version 3.3, Schrödinger, LLC, New York, N.Y., 2010).

A few in vitro experiments were conducted to quickly establish the absorption/stability of drug candidates in the early phase: aqueous solubility, parallel artificial membrane permeability (PAMPA) assay and human liver microsome (HLM) stability determination.

Materials and Methods

Chemicals. All solvents, reagents, were from Sigma-Aldrich Srl (Milan, Italy). Dodecane was purchased from Fluka (Milan, Italy). Pooled Male Donors 20 mg mL$^{-1}$ HLM were from BD Gentest-Biosciences (San Jose, Calif.). Milli-Q quality water (Millipore, Milford, Mass., USA) was used. Hydrophobic filter plates (MultiScreen-IP, Clear Plates, 0.45 µm diameter pore size), 96-well microplates, and 96-well UV-transparent microplates were obtained from Millipore (Bedford, Mass., USA).

Parallel Artificial Membrane Permeability Assay (PAMPA). Donor solution (0.5 mM) was prepared by diluting 1 mM dimethylsulfoxide (DMSO) compound stock solution using phosphate buffer (pH 7.4, 0.025 M). Filters were coated with 5 µL of a 1% (w/v) dodecane solution of phosphatidylcholine prepared from CHCl$_3$ solution 10% w/v, for intestinal permeability. Donor solution (150 µL) was added to each well of the filter plate. To each well of the acceptor plate were added 300 of solution (50% DMSO in phosphate buffer). All compounds were tested in three different plates on different days. The sandwich was incubated for 5 h at room temperature under gentle shaking. After the incubation time, the plates were separated, and samples were taken from both receiver and donor sides and analyzed using LC with UV detection at 280 nm.

LC analysis were performed with a Varian Prostar HPLC system (Varian Analytical Instruments, USA) equipped with a binary pump with a manual injection valve and model Prostar 325 UV-VIS Detector. Chromatographic separations were conducted using a Polaris C18-A column (150-4.6 mm, 5 µm particle size) at a flow rate of 0.8 mL min$^{-1}$ with a mobile phase composed of 60% ACN/40% H$_2$O Permeability (Papp) for PAMPA was calculated according to the following equation, obtained from Wohnsland and Faller and Sugano et al. equation with some modification in order to obtain permeability values in cm s$^{-1}$, $$P_{app} = \frac{V_D V_A}{(V_D + V_A)At} - \ln(1-r)$$

where $V_A$ is the volume in the acceptor well, $V_D$ is the volume in the donor well (cm$^3$), A is the "effective area" of the membrane (cm$^2$), t is the incubation time (s) and r the ratio between drug concentration in the acceptor and equilibrium concentration of the drug in the total volume ($V_D + V_A$). Drug concentration is estimated by using the peak area integration.

Membrane retentions (%) were calculated according to the following equation:

$$\% \, MR = \frac{[r - (D+A)]100}{Eq}$$

where r is the ratio between drug concentration in the acceptor and equilibrium concentration, D, A, and Eq represented drug concentration in the donor, acceptor and equilibrium solution, respectively.

Water Solubility Assay. Each solid compound (1 mg) was added to 1 mL of water. The samples were shaken in a shaker bath at room temperature for 24-36 h. The suspensions were filtered through a 0.45 μm nylon filter (Acrodisc), and the solubilized compound determined by LC-MS-MS assay. For each compound the determination was performed in triplicate.

For the quantification was used an LC-MS system consisted of a Varian apparatus (Varian Inc) including a vacuum solvent degassing unit, two pumps (212-LC), a Triple Quadrupole MSD (Mod. 320-LC) mass spectrometer with ES interface and Varian MS Workstation System Control Vers. 6.9 software. Chromatographic separation was obtained using a Pursuit C18 column (50×2.0 mm) (Varian) with 3 μm particle size and gradient elution: eluent A being ACN and eluent B consisting of water. The analysis started with 0% of eluent A, which was linearly increased up to 70% in 10 min, then slowly increased up to 98% up to 15 min. The flow rate was 0.2 mL min$^{-1}$ and injection volume was 5 μL. The instrument operated in positive mode and parameters were: detector 1850 V, drying gas pressure 25.0 psi, desolvation temperature 300.0° C., nebulizing gas 40.0 psi, needle 5000 V and shield 600 V. Nitrogen was used as nebulizer gas and drying gas. Collision induced dissociation was performed using Argon as the collision gas at a pressure of 1.8 mTorr in the collision cell.

Microsomal Stability Assay. Each compound in DMSO solution was incubated at 37° C. for 60 min in 125 mM phosphate buffer (pH 7.4), 5 of human liver microsomal protein (0.2 mg mL$^{-1}$), in the presence of a NADPH-generating system at a final volume of 0.5 mL (compound final concentration, 50 μM); DMSO did not exceed 2% (final solution). The reaction was stopped by cooling on ice and adding 1.0 mL of acetonitrile. The reaction mixtures were then centrifuged, and the parent drug and metabolites were subsequently determined by LC-UV-MS.

Chromatographic analysis was performed with an Agilent 1100 LC/MSD VL system (G1946C) (Agilent Technologies, Palo Alto, Calif.) constituted by a vacuum solvent degassing unit, a binary high-pressure gradient pump, an 1100 series UV detector, and an 1100 MSD model VL benchtop mass spectrometer.

Chromatographic separation was obtained using a Varian Polaris C18-A column (150-4.6 mm, 5 μm particle size) and gradient elution: eluent A being ACN and eluent B consisting of water. The analysis started with 2% of eluent A, which was rapidly increased up to 70% in 12 min, then slowly increased up to 98% in 20 min. The flow rate was 0.8 mL min$^{-1}$ and injection volume was 20 μL.

The Agilent 1100 series mass spectra detection (MSD) single-quadrupole instrument was equipped with the orthogonal spray API-ES (Agilent Technologies, Palo Alto, Calif.). Nitrogen was used as nebulizing and drying gas. The pressure of the nebulizing gas, the flow of the drying gas, the capillary voltage, the fragmentor voltage, and the vaporization temperature were set at 40 psi, 9 L/min, 3000 V, 70 V, and 350° C., respectively. UV detection was monitored at 280 nm. The LC-ESI-MS determination was performed by operating the MSD in the positive ion mode. Spectra were acquired over the scan range m/z 100-1500 using a step size of 0.1 u. The percentage of not metabolized compound was calculated by comparison with reference solutions.

TABLE 3

| | | PAMPA Papp *10$^{-6}$ (cm/s) GI (RM %) | Aq. Solub. (μg/mL) | LogS | QP Pred. Log S |
|---|---|---|---|---|---|
| Cmpd ID | Structure | | | | |
| 20a | | 2.86 (19.1) | 0.135 | −7.05 | −6.4 |
| 20b | | 1.93 (26.7) | <0.001 | <−8.6 | <−6.7 |

TABLE 3-continued

ADME properties of selected compounds

| Cmpd ID | Structure | PAMPA Papp *10⁻⁶ (cm/s) GI (RM %) | Aq. Solub. (µg/mL) | LogS | QP Pred. Log S |
|---|---|---|---|---|---|
| 21b | 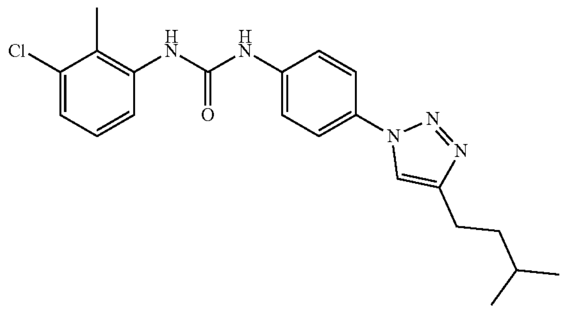 [SMILES: Cc1c(Cl)cccc1NC(=O)Nc1ccc(-n2cc(CCC(C)C)nn2)cc1] | 2.51 (59.1) | <0.001 | <−8.6 | −7.3 |
| 81 | 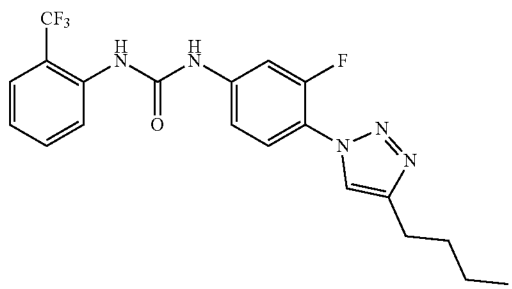 [SMILES: CCCCc1cn(-c2ccc(NC(=O)Nc3ccccc3C(F)(F)F)cc2F)nn1] | 7.22 (30.4) | 80.11 | −6.4 | −7.3 |
| 22a | 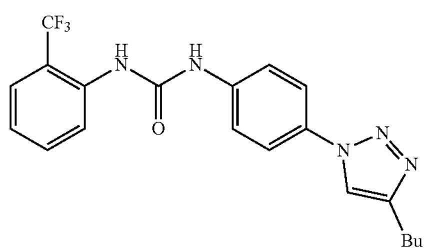 | 7.47 (23.9) | 0.107 | −7.43 | −7.1 |
| 22b | 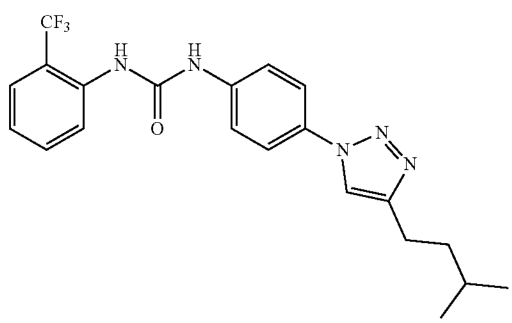 [SMILES: CC(C)CCc1cn(-c2ccc(NC(=O)Nc3ccccc3C(F)(F)F)cc2)nn1] | 7.41 (24.8) | 0.002 | <−8.6 | −7.5 |
| 49 | 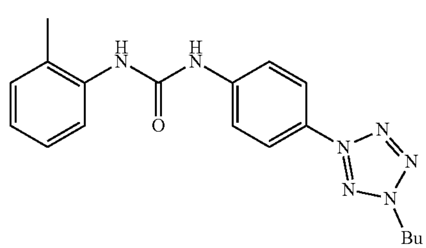 | 7.57 (24.8) | <0.001 | <−8.5 | −5.74 |

TABLE 3-continued

ADME properties of selected compounds

| Cmpd ID | Structure | PAMPA Papp *10⁻⁶ (cm/s) GI (RM %) | Aq. Solub. (μg/mL) | LogS | QP Pred. Log S |
|---|---|---|---|---|---|
| 20f | 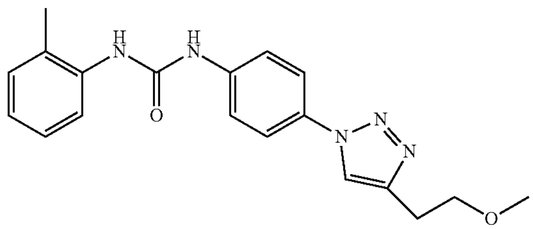 [SMILES: COCCc1cn(-c2ccc(NC(=O)Nc3ccccc3C)cc2)nn1] | 0.69 (7.4) | 26.27 | −4.3 | −5.12 |
| 64e | 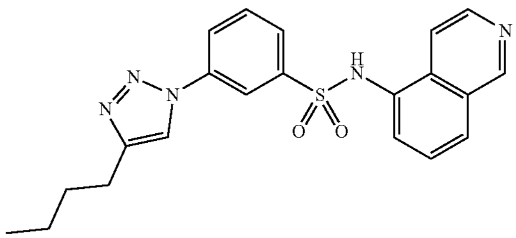 [SMILES: CCCCc1cn(-c2cccc(S(=O)(=O)Nc3cccc4cnccc34)c2)nn1] | 0.68 (0) | 1.37 | −5.57 | −5.47 |
| 68c | 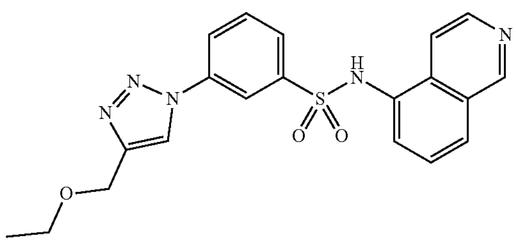 [SMILES: CCOCc1cn(-c2cccc(S(=O)(=O)Nc3cccc4cnccc34)c2)nn1] | 0.44 (0) | 45.35 | −4.26 | −4.7 |

TABLE 4

Metabolic stability of selected compounds

| Cmpd ID | Structure | Sability % |
|---|---|---|
| 20a | 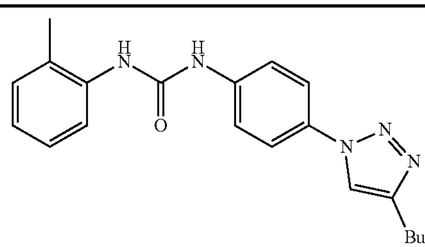 | 99 |
| 81 | 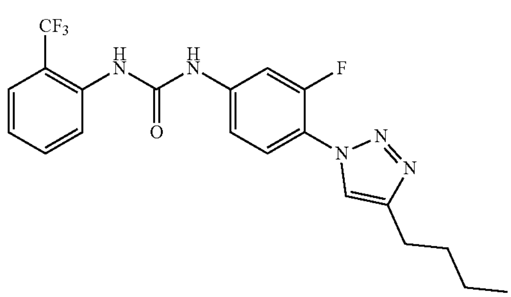 [SMILES: CCCCc1cn(-c2ccc(NC(=O)Nc3ccccc3C(F)(F)F)cc2F)nn1] | 94 |

TABLE 4-continued

Metabolic stability of selected compounds

| Cmpd ID | Structure | Sability % |
|---|---|---|
| 49 | [structure: 2-methylphenyl urea linked to phenyl-tetrazole with N-Bu] | 95.6 |
| 64d | [structure: butyl-triazole-phenyl sulfonamide with 2-CF3-phenyl] | 99 |
| 64e | [structure: butyl-triazole-phenyl sulfonamide with isoquinolin-5-yl] | 98 |
| 68e | [structure: ethoxymethyl-triazole-phenyl sulfonamide with isoquinolin-5-yl] | 95.7 |

Example 25

Biology

Enzymatic Assays

Helicase Assays

The helicase activity of DDX3 wt was monitored by measuring the conversion of a double stranded (ds) RNA (labelled at the 5'-end of one strand with a 6-FAM fluorescent) into single stranded (ss) nucleic acid. A final concentration of 25 nM RNA substrate was used in the experiments, unless otherwise stated. Reactions were performed in 50 mM TrisHCl pH 7.5, 1 mM DTT, 0.2 mg/ml BSA, 5% glycerol and 100 µM ATP, 10 mM $MgCl_2$ at 37° C. degrees for 10' and stopped by adding EDTA 50 mM pH 8. Products were separated through non-denaturating 8% PAGE at 5 W for 4 hours in TBE buffer at 4° C. Substrates and products were quantified by laser scanning densitometry (Thyphoon-TRIO, GE Healthcare).

Proteins

Human recombinant DDX3 was cloned, expressed and purified as described (Franca et al. *Proteins* 2007, 67, 1128-37).

Antiviral Assays

In Vitro Antiviral Activity ($EC_{50}$) and Cytotoxicity ($CC_{50}$) of Dengue Virus (DENY) and West Nile Virus (WNV).

Around $10^4$ Huh7 cells (provided by Apath, LLC) cultured in Dulbecco's Modified Eagle Medium (DMEM) (Invitrogen, Carlsbad, Calif.) supplemented with 10% fetal bovine serum, 1% nonessential amino acids, 100 units/ml penicillin and 100 units/ml streptomycin (DMEM complete) per well were infected for 1 h with Dengue virus type 2 (DENV-2; New Guinea-C Strain, NCPV ref 0006041v) or West Nile virus New York 99 strain (WNV-NY99; NCPV ref 0209291v) at MOI (multiplicity of infection) of 0.5 in 96 well plates in. After washing viral input, 10 fold serial dilutions of DMSO control or DDX3 inhibitors were immediately added in duplicates to the corresponding wells together with fresh DMEM complete medium (final concentrations of 100, 10, 1, 0.1 and 0.01 µM). 48 h after initial infection, cells were fixed with 4% PFA and immunostained against the viral E protein (envelope) using specific Anti E protein primary antibodies (Anti-DENV: Abcam Cat. Num. ab41349; Anti-WNV: Abcam Cat. Num. ab156843) and an AlexaFLuor488 secondary antibody (Invitrogen, Cat. Num. A11029). DAPI was used for nuclei staining. Plates were analyzed with the ImageXpress automated microscope, using the 20× Plan Fluor objective. The microscope was set for two channels (FITC and DAPI). Between 4 and 9 images were taken per well per condition at arbitrary objective fields. Between 500 and 1000 images were analysed using the CellProfiler Software (Broad Institute of MIT, http://www.cellprofiler.org/). Images were thresholded for background subtraction and target fluorescent dot sizes and intensities were analysed. Positive green counts and nuclei blue counts were estimated per image per condition.

Relative % infectivity and toxicity for each compound was estimated by normalizing the number of green signals (positive counts) and blue signals (nuclei counts) to DMSO treated controls, respectively. EC50 and CC50 values were calculated in GraphPad (http://www.graphpad.com/) by applying a nonlinear regression with log dose vs. normalized response to the CellProfiler data.

Evaluation of the In Vitro Antiviral Activity ($EC_{50}$) and Cytotoxicity ($CC_{50}$) in the HCV Replicon System.

Antiviral activity was carried out in white-clear bottom 96-well plates, and cytotoxicity assays were performed in clear 96-well plates. LucUbiNeo-ET Cells were seeded at a density of $10^4$/well in 100 µL D-MEM without selection of antibiotics. After 24 h, nine fold serial dilution of compounds, with 3 replicates at each dilution, were prepared in D-MEM and added to the appropriate wells, yielding concentrations of 125 to 0,00032 µg/mL in a final volume of 100 µL of D-MEM. After 2 days of incubation, the inventors determined the antiviral activity ($EC_{50}$) by quantifying the luciferase with the BriteLite Plus luciferase (Perkin Elmer). Briefly, LucUbiNeo-ET cells were harvested with the addition of 50 µL of luciferase per well, and after 2 minutes of shaking, the light was read in a Luminometer Fluoroskan Ascent FL.

Toxicity ($CC_{50}$) was analysed in the Lunet/HuH7 cells by the addition of 10 µL of MTT (3-(4,5-dimethylthiazol-2-yl)-2,5-diphenyltetrazolium bromide) per well. After 4 h of incubation at 37° C. in a humidified atmosphere with 5% $CO_2$, the amount of formazan produced was quantified spectrophotometrically at 550/620 nm (C. Pannecouque et al, Nature protocol 2008; 3 (3): 427-434). The $EC_{50}$ and $CC_{50}$ values were calculated for each compound in GraphPad by applying a non-linear regression with log dose vs. normalized response to the CellProfiler data. These assays were done in duplicate.

Evaluation of the In Vitro Antiviral Activity ($EC_{50}$) and Cytotoxicity ($CC_{50}$) in the HCV Infectious Cell Culture System.

Naive Huh-7.5/RFP(TagRFP)-NLS-IPS/mitoEGFP cells were seeded in clear 96-well plates the previous day at a concentration of 6400 cells/well. The next day, cells were infected with the HCV chimera Jc1 (genotype 2a) infectious supernatant at a multiplicity of infection (MOI) of 0.02. After 24 h, the cells were washed with PBS and the medium was replaced with complete growth medium with or without compounds. Nine fold serial dilution of compounds, with 3 replicates at each dilution, were prepared in D-MEM and added to the appropriate wells, yielding concentrations of 125 to 0,00032 µg/mL in a final volume of 100 µL of D-MEM. After 2 days of incubation, the cultures were immunostained for NS5A 9E10 monoclonal antibody as described by Lindenbach (Lindenbach B. D. et al. Complete Replication of Hepatitis C Virus in Cell Culture. Science 2005; 309: 623-626). Single HCV NS5A+ cells were manually counted for each well.

Toxicity ($CC_{50}$) was analysed in the nave Huh-7.5/RFP (TagRFP)-NLS-IPS/mitoEGFP cells by the addition of 10 µL of MTT (3-(4,5-dimethylthiazol-2-yl)-2,5-diphenyltetrazolium bromide) per well. After 4 h of incubation at 37° C. in a humidified atmosphere with 5% $CO_2$, the amount of formazan produced was quantified spectrophotometrically at 550/620 nm (C. Pannecouque et al, Nature protocol 2008; 3 (3): 427-434). The $EC_{50}$ and $CC_{50}$ values were calculated for each compound in GraphPad by applying a non-linear regression with log dose vs. normalized response to the CellProfiler data. These assays were done in duplicate.

Evaluation of the In Vitro Antiviral Activity ($EC_{50}$) and Cytotoxicity ($CC_{50}$) in the HIV Infectious Cell Culture System.

HeLa cell viability in the presence of the compounds has been determined by standard MTT assays. The susceptibility of HIV-1 recombinant strains to drugs was performed as previously reported (Paolucci et al., 2004). In detail, 0.5 µg of each HIV-1 plasmid construct was transfected into CD4+ HeLa cells by using the lipofectin reagent, according to the recommendations of the manufacturer (Invitrogen, Groningen, The Netherlands). After 3 days of incubation at 37° C., the cell supernatants, which contained reconstituted viable recombinant viruses, were collected. Quantification of the newly produced recombinant strains was obtained by determination of the HIV RNA copy number in the cell culture supernatants. In detail, transfected HeLa CD4+ cell culture supernatants containing $1 \times 10^9$/mL RNA copies were used to infect aliquots of $20 \times 10^6$ phytohemagglutinin-stimulated peripheral blood mononuclear cells (PBMC) obtained from HIV-seronegative blood donors. After 4 h of incubation, supernatants were removed and infected PBMC were incubated at 37° C. in 10 mL of RPMI 1640 medium (Eurobio, Les Ulis Cedex B, France) supplemented with 20% fetal calf serum (Life Technologies, Ltd., Paisley, UK), 2 mM Lglutamine, 100 U/mL penicillin, 100 µg/mL streptomycin, 50 U/mL interleukin-2 (Roche Diagnostics, Mannheim, Germany), 5 µg/mL hydrocortisone (Sigma Chemical Co., St. Louis, Mass.) and with fourfold dilutions of antiretroviral drugs. "No-drug" control for each drug dilution was included in each assay. The HIV-1 RNA in the cell culture supernatant was quantified after 72 h post infection. Recombinant HIV-1 strains from treatment-naive patients were assayed. The degree of inhibition of viral replication was measured by determining the HIV-1 RNA level in the supernatants of cell cultures and was expressed as the fold increase in the 50% inhibitory concentrations ($IC_{50}$) for resistant recombinant HIV-1 variants, compared with the $IC_{50}$ for the wild type recombinant variant. Each test was performed in triplicate.

Toxicity ($CC_{50}$) was analysed in human primary PBMCs. Increasing doses of the tested compounds were added to $2 \times 10^6$ cells. Culture medium supplemented with fresh compound was replaced every 24 hours. After 72 hours of continuous exposure of the cells to the compounds at 37° C., cell viability was measured with the CellTiter 96® (Promega) viability assay, which contains MTS [3-(4,5-dimethylthiazol-2-yl)-5-(3-carboxymethoxyphenyl)-2-(4-sulfophenyl)-2H-tetrazolium, inner salt] and an electron coupling reagent (phenazine ethosulfate). Assays are performed by adding 20 µL of the Cell Titer 96® reagent directly to culture wells, incubating for 4 hours and then recording absorbance at 490 nm with a 96-well plate reader. The quantity of formazan product as measured by the amount of 490 nm absorbance is directly proportional to the number of living cells in culture. Determinations for each compound dose were in quadruplicate. The $CC_{50}$ values were calculated from dose-response curves using the mean values of each set of determinations.

Evaluation of the In Vitro Antiviral Activity ($EC_{50}$) and Cytotoxicity ($CC_{50}$) in the JEV Infectious Cell Culture System.

Baby hamster kidney (BHK)-21 cells (C-13, American Type Culture Collection) were maintained in Dulbecco's minimal essential medium (Invitrogen) supplemented with 10% fetal calf serum (FCS) (GIBCO), penicillin (100 μg/ml) and streptomycin (100 U/ml) at 37° C. and 5% $CO_2$. JEV strain (NJ2008, GenBank Accession ID: GQ918133 was propagated in BHK-21 cells, the viral titer was determined by plaque formation assay in BHK-21 cells. In first experiment the drugs (20 μM) were first incubated with the cells for 3 h, then the cells were washed three times with PBS (10 mM $Na_2HPO_4$, 2 mM $KH_2PO_4$, pH7.4, 137 mM NaCl, 2.7 mM KCl) and then the drugs (20 μM) were inoculated simultaneously with the virus (MOI=0.01) for 2 h at 37° C. The cells were washed with PBS for three times and the drugs (20 μM) were added back to the cells with the same concentration (20 μM, diluted with 2% FCS DMEM). The cells were cultured for 48 h. The supernatant was harvested, diluted and inoculated in BHK-21 cells (1.2×106 cells/well) in a 6-well plate for 2 h at 37° C. The excess virus inocula were removed by rinsing the wells with PBS for three times. Subsequently, overlay medium (2% low melting-point agarose with DMEM medium containing 2% FBS) was added to each well and the plates were further incubated at 37° C. with 5% $CO_2$ for 3 days. The cells were stained with 0.5% crystal violet. Determinations for each compound dose were in quadruplicate. The $CC_{50}$ values were calculated from dose-response curves using the mean values of each set of determinations.

Evaluation of the In Vitro Antiviral Activity ($EC_{50}$) in the PRRSV (Porcine Reproductive and Respiratory Syndrome Virus) Infectious Cell Culture System.

According to the requirement of different experiments, MARC-145 cells were either infected with PRRSV at MOIs of 0.1, 1 or 10, or mock infected with phosphate-buffered saline (PBS). After 1 h incubation at 37° C., unbounded viruses were removed by washing thrice with PBS and cultured in DMEM supplemented with 8% FBS at 37° C. for various lengths of time. For the autophagy induction and inhibition experiments, MARC-145 cells were pretreated with varying concentrations of rapamycin or 3-MA for 4 h before viral infection. MARC-145 cells were then infected with PRRSV at MOI of 1. After 1 h incubation at 37° C., unbounded viruses were removed by washing thrice with PBS and cultured in DMEM supplemented with 2% FBS containing varying concentrations of compound, 3-MA or the corresponding amount of dimethyl sulfoxide (DMSO, control) at 37° C. for 24 h. Determinations for each compound dose were in quadruplicate. The $CC_{50}$ values were calculated from dose-response curves using the mean values of each set of determinations.

Results

Anti-Enzymatic Activity

The anti-enzymatic activity of representative compounds against the DDX3 helicase is reported in Table 5.

TABLE 5

Activity of representative compounds of the invention against DDX3 Helicase.

| Compound ID | Structure | $ID_{50}$ (μM)[a] |
|---|---|---|
| EI01D published reference compound[6] | 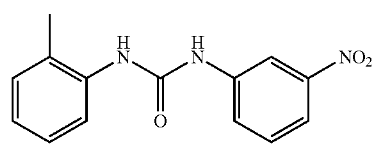 [SMILES: Cc1ccccc1NC(=O)Nc1cccc([N+](=O)[O-])c1] | 1 |
| 8a | 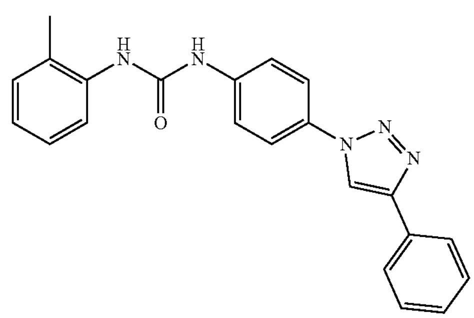 [SMILES: Cc1ccccc1NC(=O)Nc1ccc(-n2cc(-c3ccccc3)nn2)cc1] | nd |
| 20a | 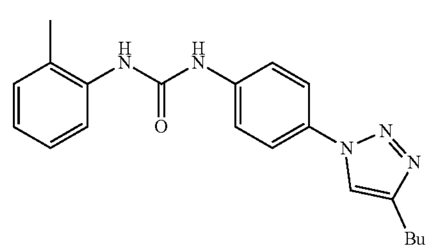 | 0.3 |

TABLE 5-continued
Activity of representative compounds of the invention against DDX3 Helicase.
| Compound ID | Structure | $ID_{50}$ (μM)[a] |
|---|---|---|
| 8b | 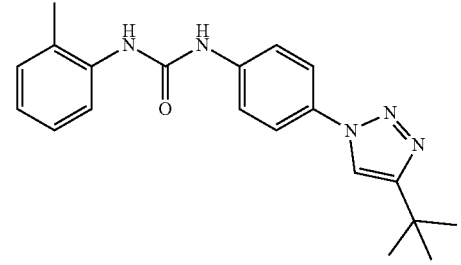 [SMILES: Cc1ccccc1NC(=O)Nc1ccc(-n2cc(C(C)(C)C)nn2)cc1] | 3.36 |
| 8c | 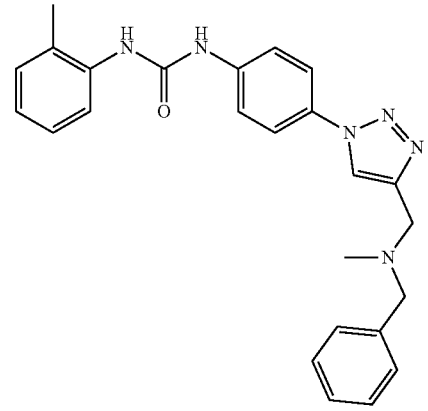 [SMILES: Cc1ccccc1NC(=O)Nc1ccc(-n2cc(CN(C)Cc3ccccc3)nn2)cc1] | 22.8 |
| 8f | 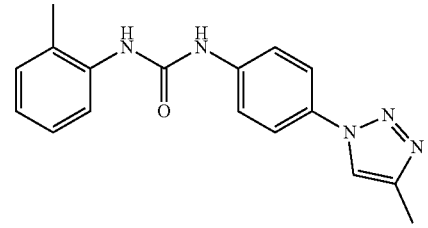 [SMILES: Cc1cn(-c2ccc(NC(=O)Nc3ccccc3C)cc2)nn1] | n.a |
| 8g | 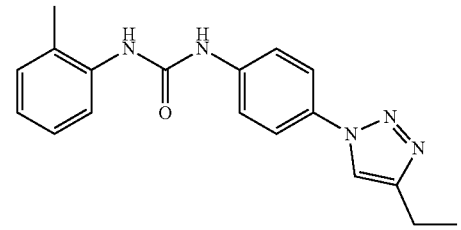 [SMILES: CCc1cn(-c2ccc(NC(=O)Nc3ccccc3C)cc2)nn1] | 0.98 |
| 20b | 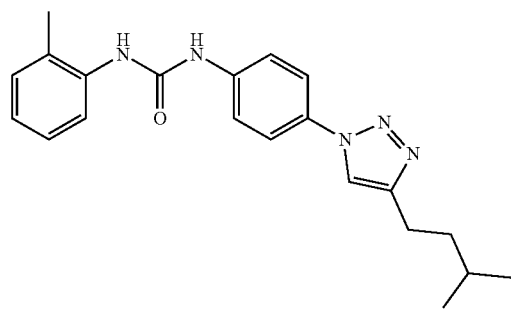 [SMILES: Cc1ccccc1NC(=O)Nc1ccc(-n2cc(CCC(C)C)nn2)cc1] | 0.5 |

TABLE 5-continued

Activity of representative compounds of the invention against DDX3 Helicase.

| Compound ID | Structure | ID$_{50}$ (μM)$^a$ |
|---|---|---|
| 20e | 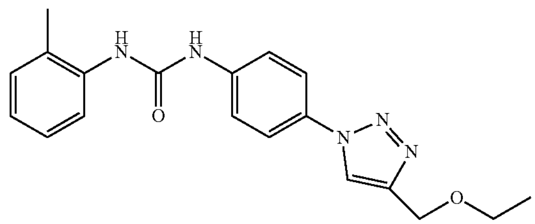 [SMILES: CCOCc1cn(-c2ccc(NC(=O)Nc3ccccc3C)cc2)nn1] | 0.94 |
| 20f | 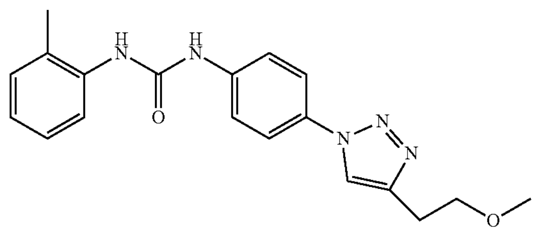 [SMILES: COCCc1cn(-c2ccc(NC(=O)Nc3ccccc3C)cc2)nn1] | 1 |
| 22a | 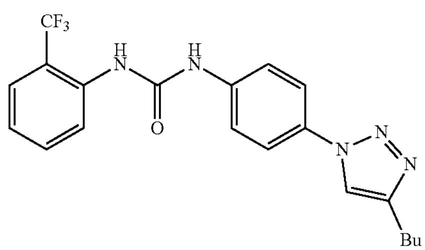 | 0.3 |
| 22b | 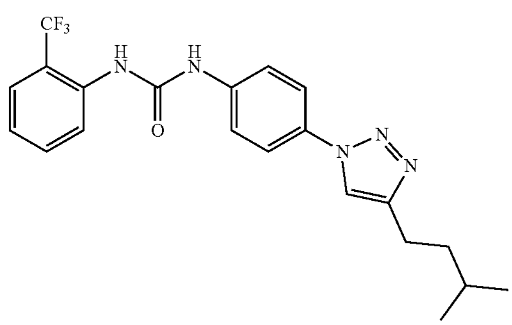 | 0.17 |
| 20d | 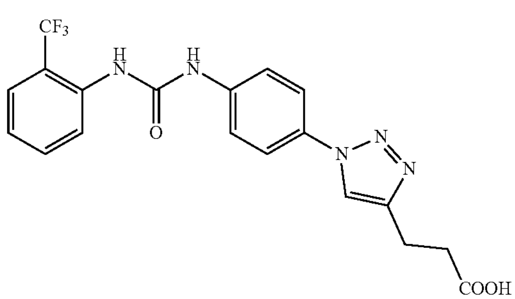 [SMILES: O=C(O)CCc1cn(-c2ccc(NC(=O)Nc3ccccc3C(F)(F)F)cc2)nn1] | n.a |

TABLE 5-continued

Activity of representative compounds of the invention against DDX3 Helicase.

| Compound ID | Structure | ID$_{50}$ (μM)$^a$ |
|---|---|---|
| 22g | 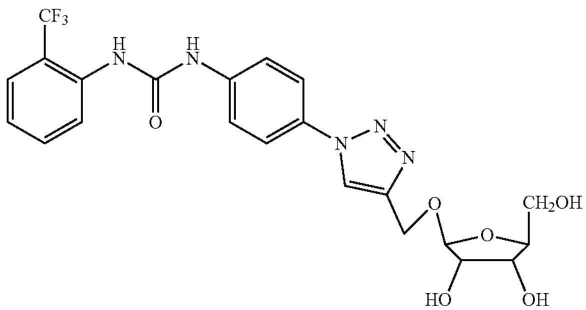 [SMILES: O=C(Nc1ccc(-n2cc(COC3OC(CO)C(O)C3O)nn2)cc1)Nc1ccccc1C(F)(F)F] | n.a |
| 35a | 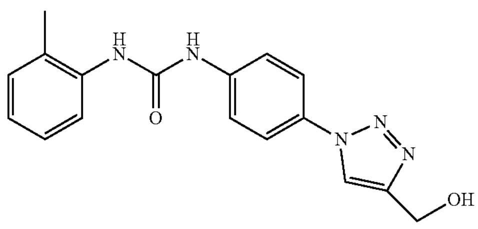 [SMILES: Cc1ccccc1NC(=O)Nc1ccc(-n2cc(CO)nn2)cc1] | 17.5 |
| 35b | 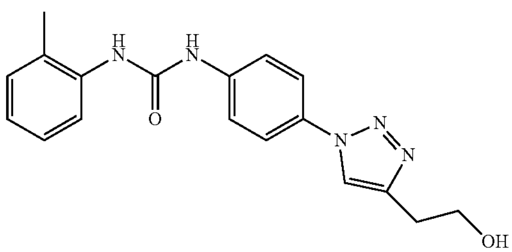 [SMILES: Cc1ccccc1NC(=O)Nc1ccc(-n2cc(CCO)nn2)cc1] | 20 |
| 35e | 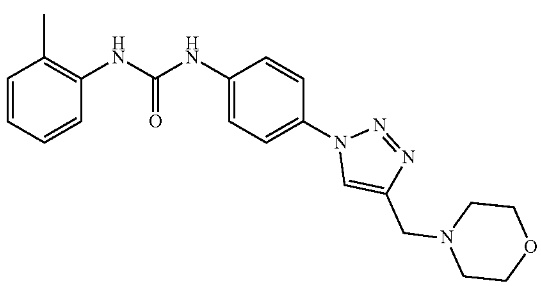 [SMILES: Cc1ccccc1NC(=O)Nc1ccc(-n2cc(CN3CCOCC3)nn2)cc1] | n.a |
| 35h | 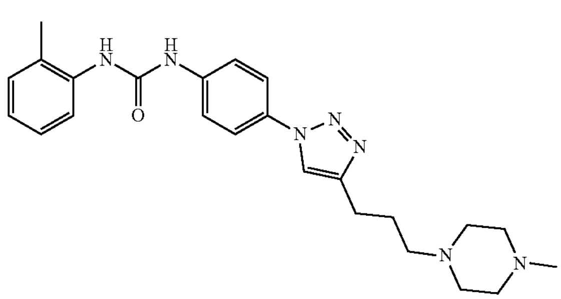 [SMILES: Cc1ccccc1NC(=O)Nc1ccc(-n2cc(CCCN3CCN(C)CC3)nn2)cc1] | 40 |

TABLE 5-continued

Activity of representative compounds of the invention against DDX3 Helicase.

| Compound ID | Structure | ID$_{50}$ (μM)$^a$ |
|---|---|---|
| 35i | 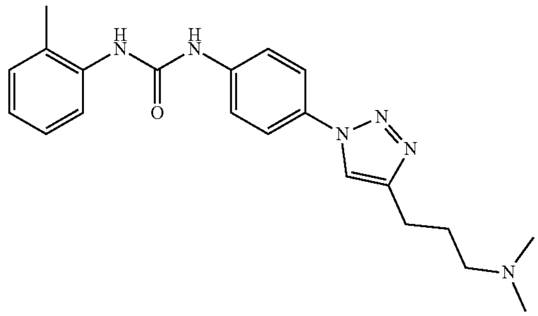 [SMILES: Cc1ccccc1NC(=O)Nc1ccc(-n2cc(CCCN(C)C)nn2)cc1] | 2.9 |
| 36 | 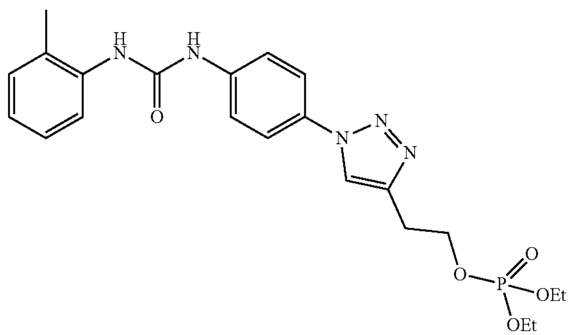 [SMILES: CCOP(=O)(OCC)OCCc1cn(-c2ccc(NC(=O)Nc3ccccc3C)cc2)nn1] | 0.9 |
| 37 | 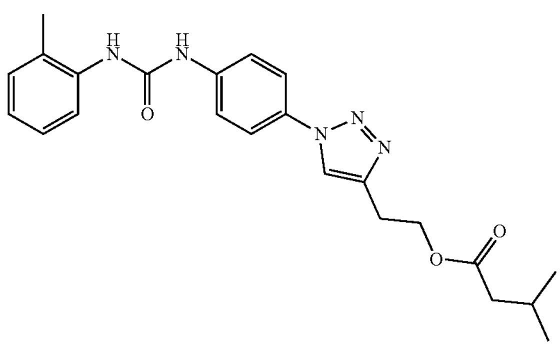 [SMILES: Cc1ccccc1NC(=O)Nc1ccc(-n2cc(CCOC(=O)CC(C)C)nn2)cc1] | 1.3 |
| 38 | 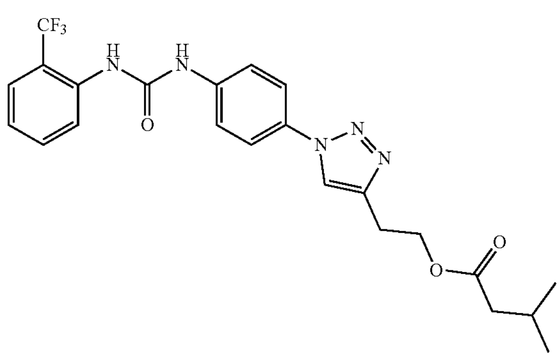 [SMILES: CC(C)CC(=O)OCCc1cn(-c2ccc(NC(=O)Nc3ccccc3C(F)(F)F)cc2)nn1] | 0.4 |

TABLE 5-continued

Activity of representative compounds of the invention against DDX3 Helicase.

| Compound ID | Structure | ID$_{50}$ (μM)$^a$ |
| --- | --- | --- |
| 39 | 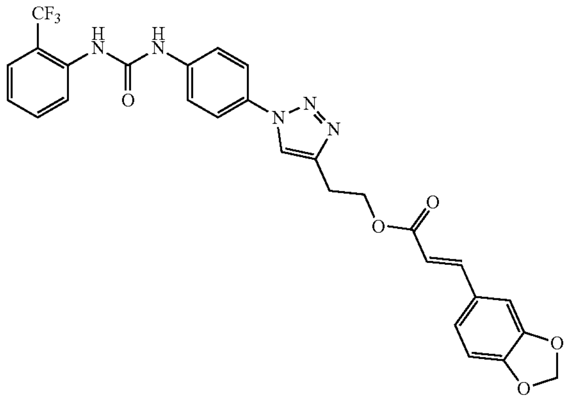 [SMILES: O=C(Nc1ccc(-n2cc(CCOC(=O)/C=C/c3ccc4c(c3)OCO4)nn2)cc1)Nc1ccccc1C(F)(F)F] | 5.1 |
| 42c | 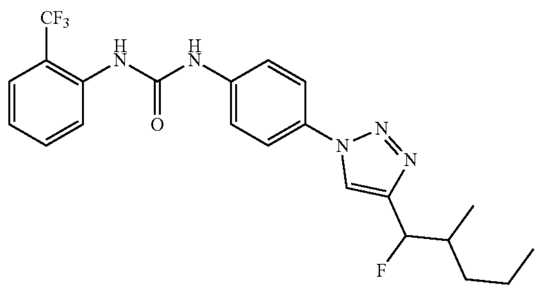 [SMILES: CCCC(C)C(F)c1cn(-c2ccc(NC(=O)Nc3ccccc3C(F)(F)F)cc2)nn1] | 0.3 |
| 20c | 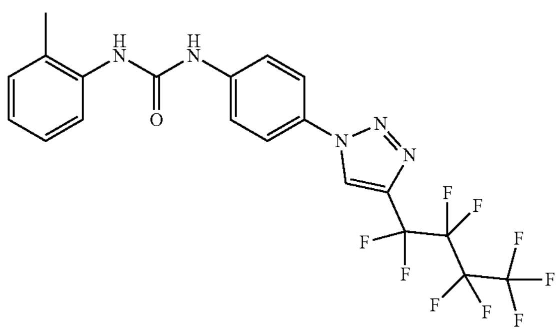 [SMILES: Cc1ccccc1NC(=O)Nc1ccc(-n2cc(C(F)(F)C(F)(F)C(F)(F)C(F)(F)F)nn2)cc1] | 6 |
| 81 | 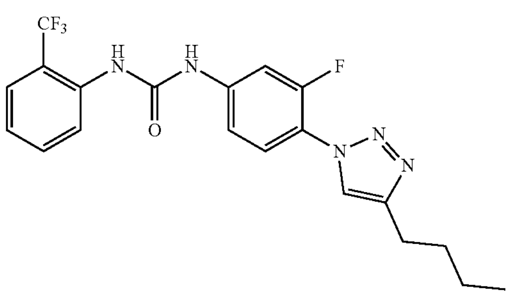 [SMILES: CCCCc1cn(-c2ccc(NC(=O)Nc3ccccc3C(F)(F)F)cc2F)nn1] | 1 |
| 49 | 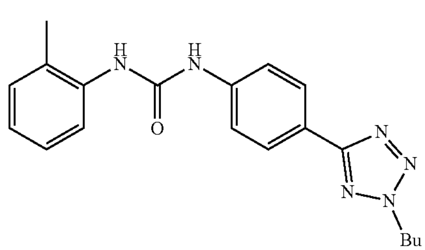 | 4.9 |

TABLE 5-continued

Activity of representative compounds of the invention against DDX3 Helicase.

| Compound ID | Structure | ID$_{50}$ (μM)$^a$ |
| --- | --- | --- |
| 50 | 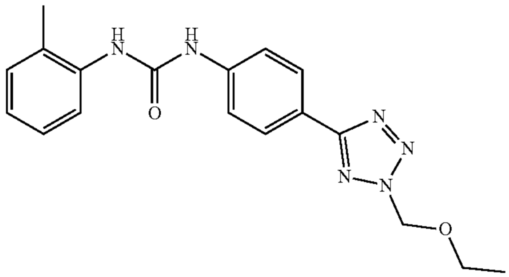 [SMILES: CCOCn1nnc(-c2ccc(NC(=O)Nc3ccccc3C)cc2)n1] | 14 |
| 51 | 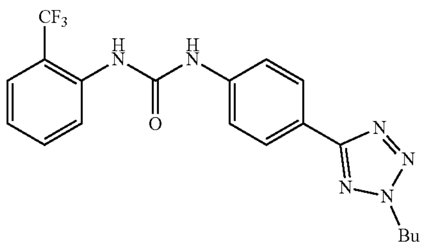 | 0.8 |
| 52 | 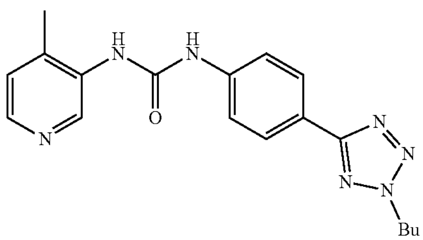 | 2.49 |
| 55a | 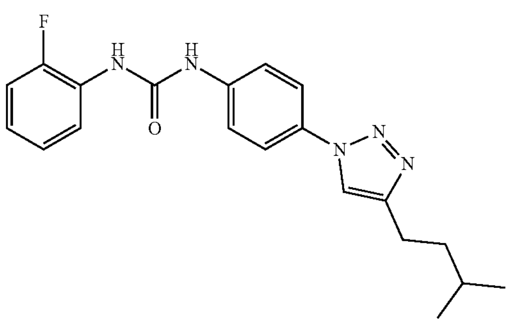 [SMILES: CC(C)CCc1cn(-c2ccc(NC(=O)Nc3ccccc3F)cc2)nn1] | 0.12 |
| 55b | 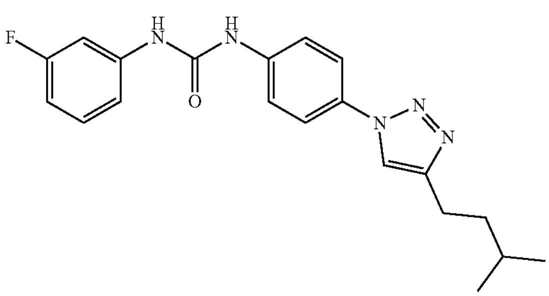 [SMILES: CC(C)CCc1cn(-c2ccc(NC(=O)Nc3cccc(F)c3)cc2)nn1] | 0.2 |

TABLE 5-continued

Activity of representative compounds of the invention against DDX3 Helicase.

| Compound ID | Structure | ID$_{50}$ (μM)$^a$ |
|---|---|---|
| 55e | 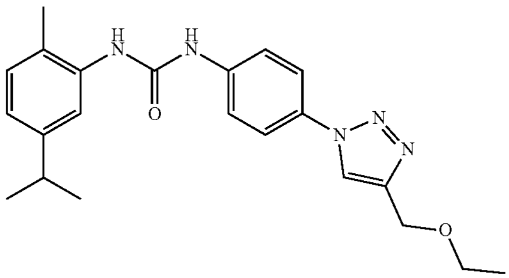 [SMILES: CCOCc1cn(-c2ccc(NC(=O)Nc3cc(C(C)C)ccc3C)cc2)nn1] | 0.9 |
| 55f | 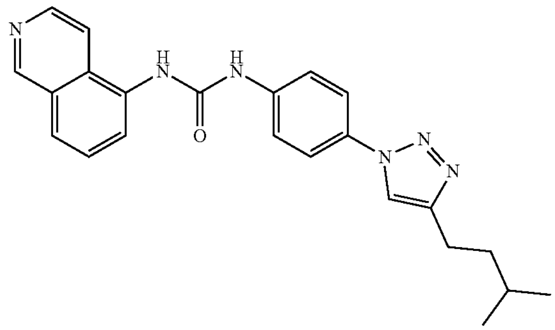 [SMILES: CC(C)CCc1cn(-c2ccc(NC(=O)Nc3cccc4cnccc34)cc2)nn1] | 0.5 |
| 55g | 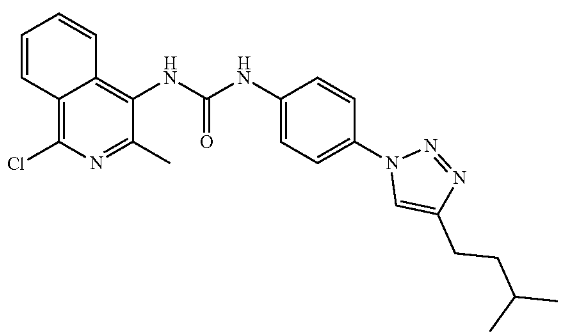 [SMILES: Cc1nc(Cl)c2ccccc2c1NC(=O)Nc1ccc(-n2cc(CCC(C)C)nn2)cc1] | 10 |
| 15a | 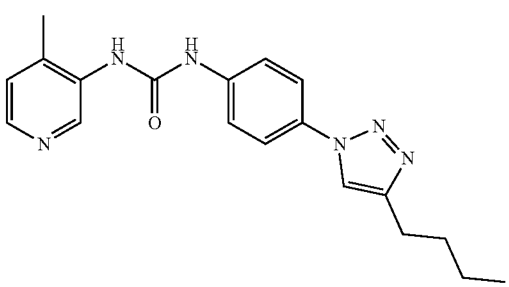 [SMILES: CCCCc1cn(-c2ccc(NC(=O)Nc3cnccc3C)cc2)nn1] | 1.47 |
| 15b | 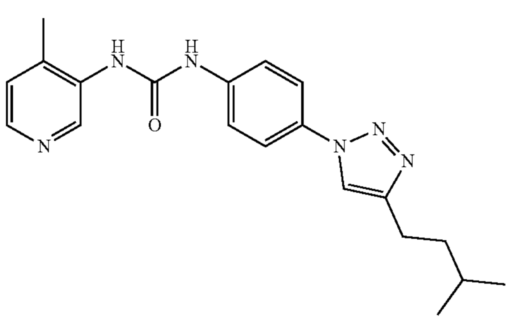 [SMILES: Cc1ccncc1NC(=O)Nc1ccc(-n2cc(CCC(C)C)nn2)cc1] | 2.0 |

TABLE 5-continued
Activity of representative compounds of the invention against DDX3 Helicase.
| Compound ID | Structure | ID$_{50}$ (μM)$^a$ |
|---|---|---|
| 58a | 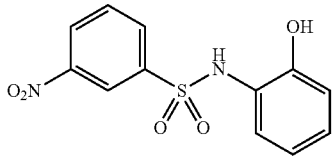 [SMILES: O=[N+]([O-])c1cccc(S(=O)(=O)Nc2ccccc2O)c1] | 0.37 |
| 64a | 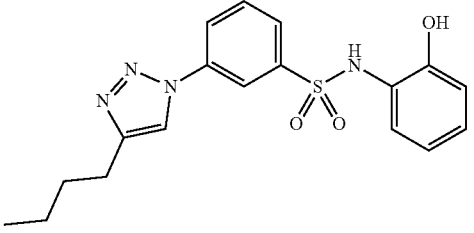 [SMILES: CCCCc1cn(-c2cccc(S(=O)(=O)Nc3ccccc3O)c2)nn1] | n.a |
| 64b | 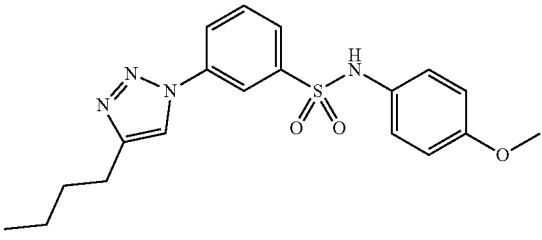 [SMILES: CCCCc1cn(-c2cccc(S(=O)(=O)Nc3ccc(OC)cc3)c2)nn1] | 52.2 |
| 64d | 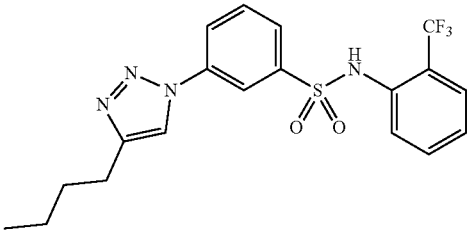 [SMILES: CCCCc1cn(-c2cccc(S(=O)(=O)Nc3ccccc3C(F)(F)F)c2)nn1] | 0.4 |
| 66d | 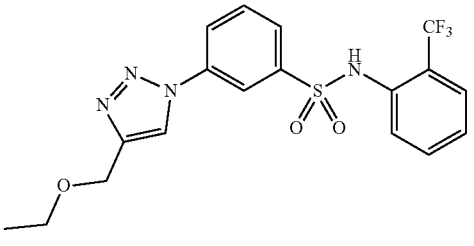 [SMILES: CCOCc1cn(-c2cccc(S(=O)(=O)Nc3ccccc3C(F)(F)F)c2)nn1] | 0.4 |
| 67d | 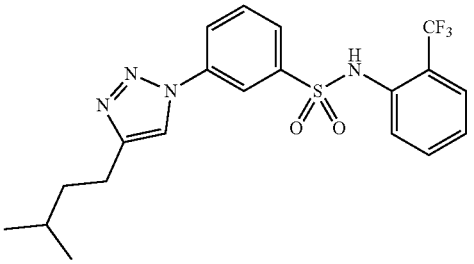 [SMILES: CC(C)CCc1cn(-c2cccc(S(=O)(=O)Nc3ccccc3C(F)(F)F)c2)nn1] | n.a |

TABLE 5-continued

Activity of representative compounds of the invention against DDX3 Helicase.

| Compound ID | Structure | ID$_{50}$ (μM)$^a$ |
|---|---|---|
| 64e | 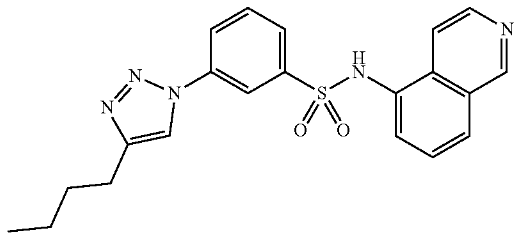 [SMILES: CCCCc1cn(-c2cccc(S(=O)(=O)Nc3cccc4cnccc34)c2)nn1] | 0.16 |
| 68e | 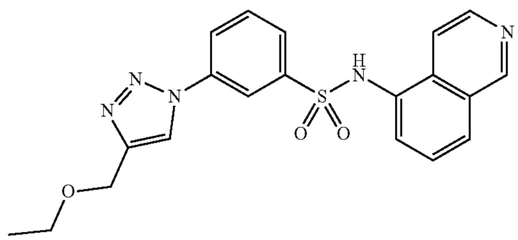 [SMILES: CCOCc1cn(-c2cccc(S(=O)(=O)Nc3cccc4cnccc34)c2)nn1] | n.d* |
| 65a | 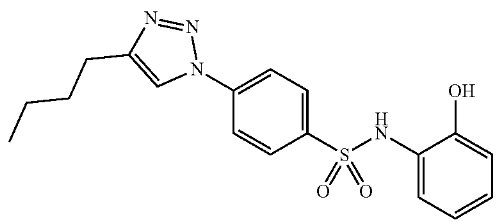 [SMILES: CCCCc1cn(-c2ccc(S(=O)(=O)Nc3ccccc3O)cc2)nn1] | 15.5 |
| 65c | 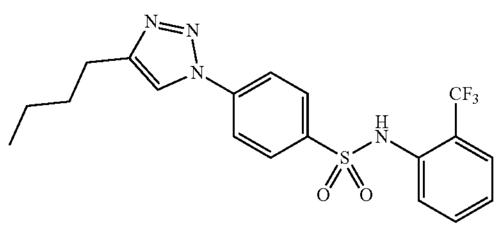 [SMILES: CCCCc1cn(-c2ccc(S(=O)(=O)Nc3ccccc3C(F)(F)F)cc2)nn1] | n.a |
| 134 | 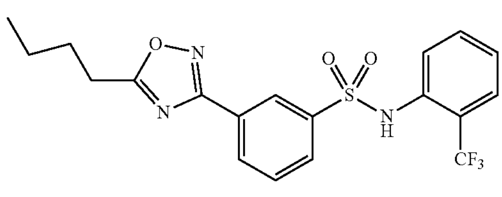 [SMILES: CCCCc1nc(-c2cccc(S(=O)(=O)Nc3ccccc3C(F)(F)F)c2)no1] | 1 |
| 112 | 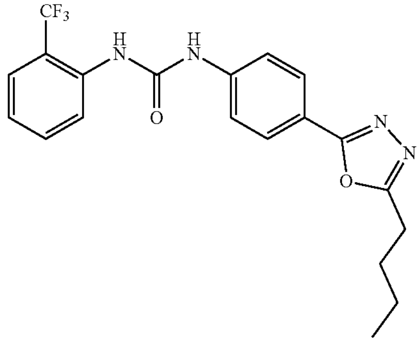 [SMILES: CCCCc1nnc(-c2ccc(NC(=O)Nc3ccccc3C(F)(F)F)cc2)o1] | 1 |

TABLE 5-continued

Activity of representative compounds of the invention against DDX3 Helicase.

| Compound ID | Structure | ID$_{50}$ (μM)$^a$ |
|---|---|---|
| 106 | 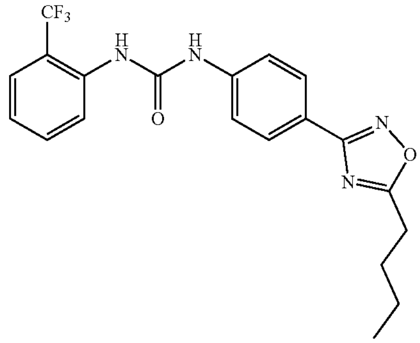 [SMILES: CCCCc1nc(-c2ccc(NC(=O)Nc3ccccc3C(F)(F)F)cc2)no1] | 0.1 |
| 8e | 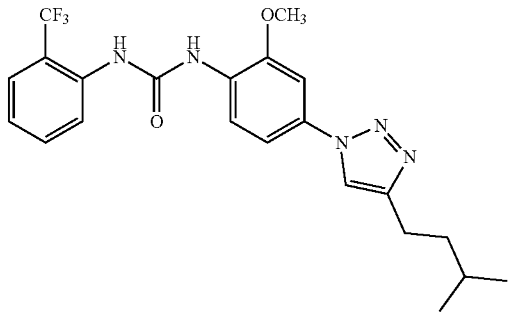 [SMILES: COc1cc(-n2cc(CCC(C)C)nn2)ccc1NC(=O)Nc1ccccc1C(F)(F)F] | 0.6 |
| 80 | 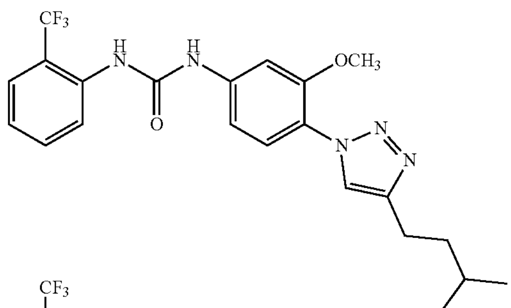 | 0.4 |
| 86 | 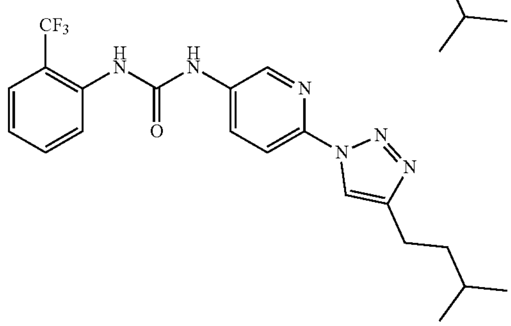 | 1 |
| 55h | 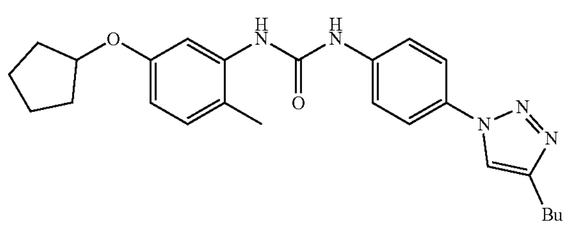 | 0.1 |

$^a$IC$_{50}$: inhibiting concentration 50 or needed dose to inhibit 50% of the enzyme, n.a. Compound not active.
*not determined Several DDX3 inhibitors of the invention showed submicromolar activity. In particular compounds 22b, 55a, 55b, 64e are approximately ten-fold more active than compound EI01D previously reported.

TABLE 6

Selectivity data on compound 20a

| ATPase DDX3 $IC_{50}$, µM | DDX1 $IC_{50}$, µM | NS3 (DENV) $IC_{50}$, µM | NS3 (HCV) $IC_{50}$, µM |
|---|---|---|---|
| >200 | >200 | >200 | 16.8 |

[a]The value >200 indicates that less than 20% of inhibition was observed at 200 µM, the highest concentration tested.

Example 26

Antiviral Activity

Selected compounds from Table 5 were tested against the viruses in which DDX3 is involved.

The antiviral potencies and toxicity of the most active compounds are summarized in the Tables 7-15 below. It is important to note that DDX3 inhibitors identified are able to inhibit the replication of different viruses such as HCV, HIV, DENV, WNV, JEV.

TABLE 7

Antiviral and cytotoxic activity of selected compounds against Hepatitis C Virus (HCV) replicon system.

| Compound ID | $EC_{50}$ (µM)[a] | $CC_{50}$ (µM)[b] |
|---|---|---|
| EI01D* | >86 | 86 |
| 20a | 0.97 | 49.77 |
| 8b | 5.73 | 100 |
| 8f | >36 | 36 |
| 8g | 36 | 295 |
| 20b | 0.8 | 189 |
| 20e | 8.55 | 51.8 |
| 20f | 28.8 | 44.4 |
| 22a | 0.3 | 200 |
| 22b | 0.67 | 46.8 |
| 35b | 28.9 | >370 |
| 35e | >125 | >125 |
| 35f | >125 | >125 |
| 35h | 43.5 | 128 |
| 35l | 19.3 | 201.7 |
| 36 | 75 | >150 |

TABLE 7-continued

Antiviral and cytotoxic activity of selected compounds against Hepatitis C Virus (HCV) replicon system.

| Compound ID | $EC_{50}$ (µM)[a] | $CC_{50}$ (µM)[b] |
|---|---|---|
| 37 | 11.7 | 179.7 |
| 38 | 0.5 | 23.2 |
| 39 | 4.3 | 28.6 |
| 41c | 0.8 | 8.6 |
| 20c | >125 | >125 |
| 81 | 1.99 | 74.16 |
| 49 | 7.16 | 11.24 |
| 50 | 22.8 | 244.9 |
| 51 | 0.6 | 6.7 |
| 55r | 7.3 | 50.7 |
| 55a | 0.4 | >340 |
| 55b | 0.2 | 183 |
| 21b | 6.11 | 42.05 |
| 55e | 1 | 245 |
| 55f | 0.9 | >312 |
| 55g | 12.4 | >278 |
| 15b | 3.65 | 180 |
| 58a | 204 | 215 |
| 66d | >58.6 | 58.6 |
| 64e | 59.1 | 201 |
| 8d | 0.67 | 290 |

[a]$EC_{50}$: Effective concentration 50 or needed concentration to inhibit 50% HCV-induced cell death, evaluated with the luciferase method in LucUbiNeo-ET cells
[b]$CC_{50}$ Cytotoxic concentration 50 or needed concentration to induce 50% death of non-infected cells, evaluated with the MMT method in LUNET cells.
*Compound previously published [6]

Data showed that compound EI01D previously reported was found completely inactive against HCV.

TABLE 8

Antiviral and cytotoxic activity of selected compounds against Hepatitis C Virus (HCV) infectious cell culture system.

| | HCV | |
|---|---|---|
| Cmpd ID | $EC_{50}$[a] | $CC_{50}$[b] |
| 20a | 3.8 | 10.1 |
| 22a | 0.6 | 94.4 |
| 20b | 30.0 | 209 |

[a] $EC_{50}$: Effective concentration 50 or needed concentration to inhibit 50% HCV Jc1 (genotype 2a virus)-induced cell death, evaluated with the immunohistochemistry (IHC) method against the HCV NS5A antigen in HuH7.5 cells.
[b]$CC_{50}$: Cytotoxic concentration 50 or needed concentration to induce 50% death of non-infected cells, evaluated with the MTT method in HuH7.5 cells.

TABLE 9

Antiviral and cytotoxic activity of selected compounds against Immunodeficiency Virus (HIV).

| | $CC_{50}$[b] PBMC | | | $EC_{50}$[a] HIV (PBMC) | SI |
|---|---|---|---|---|---|
| | 24 h | 48 h | 72 h | 72 h | (HIV/PBMC) |
| EI01D* | | | 100 | 10 | 10 |
| 49 | >1000 | >1000 | >1000 | 9.5 | >100 |
| 64d | 2131 | 332 | 197.5 | 31 | 6.3 |
| 64e | 219 | 86.96 | 63 | 9.5 | 6.6 |
| 66d | 450 | 356.8 | 703 | 26 | 27 |
| 20a | >1000 | >1000 | >1000 | 30 | >33 |

[a]$EC_{50}$: Effective concentration 50 or needed concentration to inhibit 50% HIV-induced cell death, evaluated with PBMC cells after 72 h.
PBMC: Peripheral Blood Mononuclear Cells
[b]$CC_{50}$ Concentration required to inhibit 50% of cells viability,
[c].not determined;
*Compound previously published. [6]

TABLE 10

Evaluation of the in vitro antiviral activity (EC$_{50}$) and cytotoxicity (CC$_{50}$) in the West Nile Virus (WNV) infectious cell culture system.

| Compound ID | WNV EC$_{50}$[a] | CC$_{50}$[b] |
|---|---|---|
| 20a | 16.05 | >500 |
| 58a | 7.16 | 60.9 |
| 20b | 2.83 | 62.3 |
| 22a | 0.18 | 145 |

[a]EC$_{50}$: Effective concentration 50 or needed concentration to inhibit 50% WNV-induced cell death, evaluated with Huh7 cells.
[b]CC$_{50}$ Concentration required to inhibit 50% of cells viability.

TABLE 11

Evaluation of the in vitro antiviral activity (EC$_{50}$) and cytotoxicity (CC$_{50}$) in the Dengue Virus (DENV) infectious cell culture system.

| Compound ID | DENV EC$_{50}$[a] | CC$_{50}$[b] |
|---|---|---|
| 20a | 2.55 | >787 |
| 58a | 1.1 | 99.4 |
| 20b | 0.13 | 40.4 |
| 22a | 0.12 | 178 |

[a]EC$_{50}$: Effective concentration 50 or needed concentration to inhibit 50% DV-induced cell death, evaluated with Huh7 cells.
[b]CC$_{50}$ Concentration required to inhibit 50% of cells viability.

TABLE 12

Evaluation of the in vitro antiviral activity (EC$_{50}$) and cytotoxicity (CC$_{50}$) in the JEV infectious cell culture system.

| Compound ID | JEV EC$_{50}$[a] | CC$_{50}$[b] |
|---|---|---|
| EIO1D* | 10 | >50 |
| 20a | 20 | >50 |
| 58a | 10 | >50 |
| 49 | 7.1 | >50 |
| 20e | 25 | >50 |
| 64d | 6.7 | >50 |
| 66d | 6.1 | >50 |
| 68e | 4.4 | >50 |
| 36 | 21.1 | >50 |
| 55e | 3.3 | >50 |
| 55f | 32.8 | >50 |

[a] The viral titre was determined by plaque formation assay in baby hamster kidney (BHK-21) cells
[b]CC$_{50}$ Concentration required to inhibit 50% of cells viability.
*Published reference compound[6]

TABLE 13

Evaluation of the in vitro antiviral activity (EC$_{50}$) in the PRRSV infectious cell culture system.

| Compound ID | PRRSV EC$_{50}$[a] |
|---|---|
| 64d | 30 |

[a] The viral titre was determined by plaque formation assay in MARC-145 cells

Example 27

Evaluation of Antiviral Activity on HIV-1 Strains Carrying Mutations Conferring Resistance to Drugs Currently Used to Treat HIV Infection.

MT-2 and TZM-b1 cell lines and the infectious clones used to evaluate the antiviral activity of compound 16d were all obtained through the AIDS Reagent Program (ARP, Division of AIDS, NIAID, NIH). Drugs susceptibility of NIH clones has been previously characterized through the "Phenosense" phenotypic assay (available at Quest Diagnostics, Monogram Biosciences laboratory, San Francisco, USA). The features of the reference and resistant viruses are showed in the following table:

| VIRUS (ARP CATALOGUE NUMBER) | DRUG RESISTANCE CLASS | MUTATIONS | DEGREE OF RESISTANCE TO MOST COMMON DRUGS |
|---|---|---|---|
| 114 | Wild type virus | None | Full susceptibility to all drugs |
| 11808 | PIs | Major: V32I, I54V, I84V, L90M Minor: L10F, V11I, K20T, L33F, E35G, A71I, G73S, L89V | High level resistance to atazanavir and lopinavir; intermediate resistance to darunavir |
| 7406 | NRTIs | M41L, L74V, M184V, L210W, T215Y | High level resistance to lamivudine, emtricitabine, zidovudine, abacavir; intermediate resistance to tenofovir |
|  | NNRTIs | A98G, G190C | High level resistance to efavirenz and nevirapine; low level resistance to etravirine and rilpivirine |
| 7404 | NRTIs | A62V, V75I, F77L, F116Y, Q151M | High level resistance to abacavir and zidovudine; intermediate resistance to lamivudine, emtricitabine and tenofovir |

-continued

| VIRUS (ARP CATALOGUE NUMBER) | DRUG RESISTANCE CLASS | MUTATIONS | DEGREE OF RESISTANCE TO MOST COMMON DRUGS |
|---|---|---|---|
| 12227 | NRTIs | M41L, T215Y | High level resistance to zidovudine; intermediate resistance to abacavir and tenofovir; low level to lamivudine and emtricitabine |
|  | NNRTIs | K101P, K103N | High level resistance to efavirenz, nevirapine and rilpivirine; intermediate resistance to etravirine |
| 12235 | NRTIs | M41L, D67N, T69D, L74I, L210W, T215Y | High level resistance to zidovudine, tenofovir and abacavir; intermediate resistance to lamivudine and emtricitabine |
|  | NNRTIs | A98G, K101E, Y181C, G190A | High level resistance to efavirenz, nevirapine, rilpivirine and etravirine |
| 11845 | INIs | G140S, Q148H | High level resistance to raltegravir and elvitegravir; intermediate resistance to dolutegravir |

PIs: protease inhibitors;
NRTIs: nucleoside reverse transcriptase inhibitors;
NNRTIs: non-nucleoside reverse transcriptase inhibitors;
INIs: integrase inhibitors.

The IC50 values of the HIV-1 wild-type reference strain NL4-3 and viruses carrying resistant mutations were determined in a phenotypic assay consisting in a first cycle of replication in the MT-2 cell line followed by an additional round of replication in TZM-bl cells. MT-2 cells were seeded at a concentration of 50,000 cells/well in a 96-well plate and infected with the reference strain NL4-3 in presence of five-fold dilutions of the compounds. After 48-72 hours, 50 µl of supernatant from each well, containing the virus produced in the first round of infection, were used to infect TZM-bl cells seeded in a 96-plate well at a concentration of 30,000 cells/well. Two days later, cells were lysed adding 40 µl of Glo Lysis Buffer (Promega) to each well for 5 minutes, than 40 microliters of Bright-Glo Luciferase Reagent (Promega) were added to each well for relative luminescence units (RLU) counting using Glo-Max Multi Detection System (Promega). RLU values from each well were elaborated using the GraphPad v5.0 software to calculate the IC50 of each compound.

TABLE 14

Evaluation of the in vitro antiviral activity ($EC_{50}$) in the HIV infectious cell culture system.

| Compound ID | HIV $EC_{50}$[a] |
|---|---|
| 20a | 1.1 |
| 55b | 1.8 |

TABLE 14-continued

Evaluation of the in vitro antiviral activity ($EC_{50}$) in the HIV infectious cell culture system.

| Compound ID | HIV $EC_{50}$[a] |
|---|---|
| 55o | 21.2 |
| 55h | 16.2 |
| 86 | 3.0 |
| 80 | 7.35 |
| 49 | 5.2 |
| 51 | 5.5 |
| 106 | 2.2 |
| 112 | 5.5 |
| 102 | 72.8 |
| 64d | 12.7 |
| 134 | 3.1 |
| 64e | 1.0 |
| 58a | 20.2 |

[a] $EC_{50}$: Effective concentration 50 or needed concentration to inhibit 50% HIV-induced cell death, evaluated in a phenotypic assay consisting in a first cycle of replication in the MT-2 cell line followed by an additional round of replication in TZM-bl cells.

TABLE 15

Antiviral activity of compound 20a against HIV-1 strains carrying the most common patterns of resistance mutations selected by drugs currently used to treat HIV-1 infection.

| HIV-1 strain[a] | Drug resistance class[b] | IC50 [95% CI] (µM) | Fold change[c] |
|---|---|---|---|
| 114[d] | wild type | 1.11[0.31-3.90] | / |
| 11808 | PIs | 0.23[0.08-0.65] | 0.2 |
| 7406 | NRTIs | 0.33[0.13-0.87] | 0.3 |
| 7404 | NRTIs | 0.22[0.11-0.47] | 0.2 |

TABLE 15-continued

Antiviral activity of compound 20a against HIV-1 strains carrying the most common patterns of resistance mutations selected by drugs currently used to treat HIV-1 infection.

| HIV-1 strain[a] | Drug resistance class[b] | IC50 [95% CI] (μM) | Fold change[c] |
|---|---|---|---|
| 12227 | NNRTIs | 0.94[0.21-1.34] | 0.8 |
| 12235 | NNRTIs | 0.36[0.15-0.87] | 0.3 |
| 11845 | INIs | 0.37[0.26-0.52] | 0.3 |

[a]NIH AIDS Reagent Program catalogue number (www.aidsreagent.org).
[b]PIs: protease inhibitors; NRTIs: nucleos(t)ide reverse transcriptase inhibitors; NNRTIs: non nucleos(t)ide reverse transcriptase inhibitors; INIs: integrase inhibitors.
[c]Resistant strain $IC_{50}$ to wild type strain $IC_{50}$ ratio.
[d]NL4-3 HIV-1 wild type reference strain.

Example 28

Evaluation of the In Vitro Antiviral Activity in the EBOV Infectious Cell Culture System.

Vero E6 cells were seeded in 48 well plates the day prior infection. 24 hrs after, the cells were infected with EBOV expressing GFP (EBOV/GFP) at an multiplicity of infection (MOI) of 0.1 in the presence of different compounds at 5 μM concentration in serum free medium for 1 hr at 37°, then inoculum was removed and replace by 3% FCS culture medium containing 5 μM drug, cells were then incubated 48 hrs at 37° C. Forty-eight hours afterwards, cells were detached from the plate with trypsin and fixed for 20 min with 3% PBS buffered paraformaldehyde prior to flow cytometry analysis on a Beckman Coulter Gallios apparatus (Beckman, Brea, Calif., USA). The virus input is adjusted to get 50-70% of infected cells at 48 hrs. Infected cells are identified by the expression of GFP (Ebola GFP), as GFP is inserted as a viral gene in ebola genome, GFP intensity (MFI) is related to viral replication. Neg value indicate the background level in the non infected condition. All data represents averages and SD of three independent experiments.

TABLE 16

Evaluation of the in vitro antiviral activity in the EBOV infectious cell culture system.

| Compound ID | Normalized % infected cells[a] |
|---|---|
| 51 | 60 |
| 66d | 80 |

[a]The viral titre was determined in Vero E6 cells

The results demonstrate that compounds showed anti-HIV activity in cells as well as a good inhibitory activity against group IV viruses such as anti-HCV, WNV, JEV and DENY infections. Compounds 20a, 20b, 22a, 22b, 55a and 55b showed the best activity against HCV. Results showed also that drug 20a, 22a and 20b can significantly inhibit DENV and WNV infections. Compounds 51 and 66d are able to affect EBOV replication (Group V virus), demonstrating the activity against (−)ssRNA viruses.

In conclusion, the anti-HIV activity of the compounds of the invention was evaluated by in vitro activity using a recombinant human DDX3 protein produced in E. Coli. The antiviral activity of compound 20a was also evaluated against viruses carrying resistance mutations conferring high level resistance to most of the antivirals approved to treat HIV infection. Compound 20a retained full activity against all the resistant viruses tested, confirming its novel mechanism of action and the potential to overcome HIV resistance.

The $IC_{50}$ was calculated for each molecule, and represents the concentration of the inhibitor able to reduce the DDX3 helicase activity by 50%. Enzymatic assays showed that compounds are selective inhibitors of the human helicase DDX3. The most active compounds were further optimized and tested in viral diseases.

The results obtained and reported in the Examples show that the compounds of the invention were able to:
1) Inhibit helicase activity of human DDX3 protein by interacting with the RNA binding site and interfering with the subsequent catalytic steps;
2) Suppress HIV-1 replication in infected cells without any toxicity to uninfected cells used as control;
3) Suppress HCV replication in infected cells without any toxicity to uninfected cells used as control;
4) Suppress WNV replication in infected cells without any toxicity to uninfected cells used as control;
5) Suppress DENV replication in infected cells without any toxicity to uninfected cells used as control;
6) Suppress JEV replication in infected cells without any toxicity to uninfected cells used as control;
7) Suppress PRRSV replication in infected cells without any toxicity to uninfected cells used as control;
8) Suppress HIV-1 mutant strains replication in infected cells.
9) Suppress EBOV replication in infected cells without any toxicity to uninfected cells used as control;

REFERENCES

1. Paul Ahlquist, Amine O. Noueiry, Wai-Ming Lee, David B. Kushner, and Billy T. Dye. Host factors in positive-strand RNA virus genome replication. *J. Virol.* 2003, 15, 8181-8186.
2. Andrew Prussia, Pahk Thepchatri, James P. Snyder and Richard K. Plemper. Systematic Approaches towards the Development of Host-Directed Antiviral Therapeutics. *Int. J. Mol. Sci.* 2011, 12, 4027-4052.
3. Brian M. Friedrich, Natallia Dziuba, Guangyu Li, Mark A. Endsley, James L. Murray, Monique R. Ferguson. Host factors mediating HIV-1 replication. *Virus Research* 2011, 161, 101-114.
4. Rupp D, Bartenschlager R. Targets for antiviral therapy of hepatitis C. *Semin Liver Dis.* 2014, 34, 9-21.
5. Garbelli, A., Radi, M., Falchi, F., Beermann, S., Zanoli, S., Manetti, F., Dietrich, U., Botta, M., Maga, G. Targeting the human DEAD-box polypeptide 3 (DDX3) RNA helicase as a novel strategy to inhibit viral replication. *Curr Med Chem;* 2011, 18, 3015-3027.

6. Radi, M.; Falchi, F.; Garbelli, A.; Samuele, A.; Bernardo, V.; Paolucci, S.; Baldanti, F.; Schenone, S.; Manetti, F.; Maga, G.; Botta, M. *Bioorg. Med. Chem. Lett.* 2012, 22, 2094-2098.
7. Yedavalli V S, Neuveut C, Chi Y H, Kleiman L, Jeang K T. Requirement of DDX3 DEAD box RNA helicase for HIV-1 Rev-RRE export function. *Cell* 2004; 119, 381-92.
8. Owsianka A M, Patel A H, Hepatitis C virus core protein interacts with a human DEAD box protein DDX3. *Virology* 1999, 257, 330-40,
9. Andrew Easton, Phillip Gould, Andrew Marsh Use of ddx3x inhibitors for the treatment of pneumovirus infections, WO 2015136292 A1.
10. Mamiya N, Worman H J, Hepatitis C virus core protein binds to a DEAD box RNA helicase. *J Biol Chem* 1999, 274, 15751-6.
11. You L R, Chen C M, Yeh T S, Tsai T Y, Mai R T, Lin C H. Hepatitis C virus core protein interacts with cellular putative RNA helicase. *J Virol* 1999, 73, 2841-53.
12. Ariumi Y, Kuroki M, Abe K, Dansako H, Ikeda M, Wakita T. DDX3 DEAD-box RNA helicase is required for hepatitis C virus RNA replication. *J Virol* 2007, 81, 13922-6.
13. Li C, Ge L L, Li P P, Wang Y, Dai J J, Sun M X, Huang L, Shen Z Q, Hu X C, Ishag H, Mao X. Cellular DDX3 regulates Japanese encephalitis virus replication by interacting with viral un-translated regions. *Virology,* 2014, 449, 70-81.
14. Christian G. Noble, Yen-Liang Chen, Hongping Dong, Feng Gu, Siew Pheng Lim, Wouter Schul, Qing-Yin Wang, Pei-Yong Shi. Strategies for development of Dengue virus inhibitors. *Antiviral Research* 2010, 85, 3450-462.
15. Schroder M, Baran M, Bowie A G. Viral targeting of DEAD box protein 3 reveals its role in TBK1/IKKepsilon-mediated IRF activation. *EMBO J* 2008, 17, 2147-57.
16. Vashist, Urena L, Chaudhry Y, Goodfellow I. Identification of RNA-protein interaction networks involved in the norovirus life cycle. *J Virol.* 2012, 22, 11977-90.
17. Glass R I, Parashar U D, Estes M K. Norovirus gastroenteritis. *Engl. J. Med.* 2009, 361, 1776-1785.
18. Yang Q, Jankowsky E. The DEAD-box protein Ded1 unwinds RNA duplexes by a mode distinct from translocating helicases. *Nat Struct Mol Biol* 2006; 13, 981-6.
19. Rocak S, Linder P. DEAD-box proteins: the driving forces behind RNA metabolism. *Nat Rev Mol Cell Biol* 2004, 5, 232-41.
20. Kohler A, Hurt E. Exporting RNA from the nucleus to the cytoplasm. *Nat Rev Mol Cell Biol,* 2007, 8, 761-73.
21. Mardsen S, Nardelli M, Linder P, McCarthy J E. Unwinding single RNA molecules using helicases involved in eukaryotic translation initiation. *J Mol Biol* 2006, 361, 327-35.
22. Cavignac Y, Lieber D, Laib Sampaio K, Madlung J, Lamkemeyer T, Jahn G, Nordheim A, Sinzger C. The Cellular Proteins Grb2 and DDX3 Are Increased upon Human Cytomegalovirus Infection and Act in a Proviral Fashion. *PLoS One.* 2015 Jun. 29; 10(6):e0131614.
23. Shih J W, Tsai T Y, Chao C H, Wu Lee Y H. Candidate tumor suppressor DDX3 RNA helicase specifically represses cap-dependent translation by acting as an eIF4E inhibitory protein. *Oncogene* 2008, 27, 700-14.
24. Botlagunta M, Vesuna F, Mironchik Y, Raman A, Lisok A, Winnard Jr P. Oncogenic role of DDX3 in breast cancer biogenesis. *Oncogene* 2008, 11, 3912-22
25. Kwong A D, Rao B G, Jeang K T. Viral and cellular RNA helicases as antiviral targets. *Nat Rev Drug Discov* 2005, 4, 845-53;
26. Soulat D, Burckstummer T, Westermayer S, Goncalves A, Bauch A, Stefanovic A. The DEAD-box helicase DDX3X is a critical component of the TANK-binding kinase 1-dependent innate immune response. *EMBO J* 2008, 26, 26.
27. Chang P C, Chi C W, Chau G Y, Li F Y, Tsai Y H, Wu J C. DDX3, a DEAD box RNA helicase, is deregulated in hepatitis virus-associated hepatocellular carcinoma and is involved in cell growth control. *Oncogene* 2006, 25, 1991-2003.
28. Chao C H, Chen C M, Cheng P L, Shih J W, Tsou A P, Lee Y H. DDX3, a DEAD box RNA helicase with tumor growth-suppressive property and transcriptional regulation activity of the p21waf1/cip1 promoter, is a candidate tumor suppressor. *Cancer Res* 2006, 66, 6579-88.
29. Huang J S, Chao C C, Su T L, Yeh S H, Chen D S, Chen C T Diverse cellular transformation capability of overexpressed genes in human hepatocellular carcinoma. *Biochem Biophys Res Commun* 2004, 315, 950-8.
30. Soto-Rifo R, Rubilar P S, Limousin T, de Breyne S, Decimo D, Ohlmann T. DEAD-box protein DDX3 associates with eIF4F to promote translation of selected mRNAs. *EMBO J.,* 2012, 31, 3745-56.
31. Skinner D E, Rinaldi G, Koziol U, Brehm K, Brindley P J. How might flukes and tapeworms maintain genome integrity without a canonical piRNA pathway? *Trends Parasitol.* 2014, 3, 123-9.
32. Berman J J (2012) Taxonomic guide to infectious diseases: understanding the biologic classes of pathogenic organisms London: Elsevier. 355 p.
33. Usha Kant Misra; Overview: Japanese encephalitis. *Prog Neurobiol.* 2010, 2, 108-20.
34. Tsai, I. J., Zarowiecki M, Holroyd N, Garciarrubio A, Sanchez-Flores A, Brooks K L, Tracey A, Bobes R J, Fragoso G, Sciutto E, Aslett M, Beasley H, Bennett H M, Cai J, Camicia F, Clark R, Cucher M, De Silva N, Day T A, Deplazes P, Estrada K, Fernández C, Holland P W, Hou J, Hu S, Huckvale T, Hung S S, Kamenetzky L, Keane J A, Kiss F, Koziol U, Lambert O, Liu K, Luo X, Luo Y, Macchiaroli N, Nichol S, Paps J, Parkinson J, Pouchkina-Stantcheva N, Riddiford N, Rosenzvit M, Salinas G, Wasmuth J D, Zamanian M, Zheng Y; Taenia solium Genome Consortium, Cai X, Soberón, Olson P D, Laclette J P, Brehm K, Berriman M. The genomes of four tapeworm species reveal adaptations to parasitism. *Nature* 2013, 496, 57-63.
35. Jefferson M, Donaszi-Ivanov A, Pollen S, Dalmay T, Saalbach G, Powell P P. Host factors that interact with the pestivirus N-terminal protease, Npro, are components of the ribonucleoprotein complex. *J Virol.* 2014, 18, 10340-53.
36. Berge S. M. et al., J. Pharm. Sci. 1977, 66, 1-19; Gould P. L. Int. J. Pharm 1986, 33, 201-217; and Bighley et al. Encyclopedia of Pharmaceutical Technology, Marcel Dekker Inc, New York 1996, Volume 13, page 453-497.
37. Remington "The Science and Practice of Pharmacy", Lippincott Williams & Wilkins, 2000.
38. Paolucci S, Baldanti F, Maga G, Cancio R, Zazzi M, Zavattoni M, Chiesa A, Spadari S, Gerna G. Gln145Met/Leu changes in human immunodeficiency virus type 1 reverse transcriptase confer resistance to nucleoside and nonnucleoside analogs and impair virus replication. *Antimicrob Agents Chemother.* 2004, 48,4611-7.

39. Wohnsland, F.; Faller, B. High-throughput permeability pH profile and high-throughput alkane/water log P with artificial membranes. *J. Med. Chem.* 2001 44, 923-930.
40. Sugano, K.; Hamada, H.; Machida, M.; Ushio, H. High throughput prediction of oral absorption: improvement of the composition of the lipid solution used in parallel artificial membrane permeation assay. *J. Biomol. Screen.* 2001, 6, 189-196.

The invention claimed is:

1. A compound selected from the group consisting of:

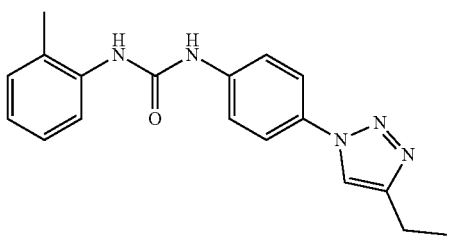
8g

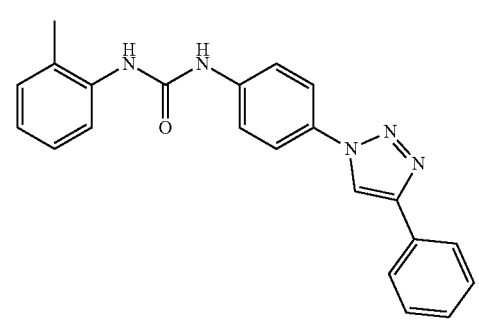
8a

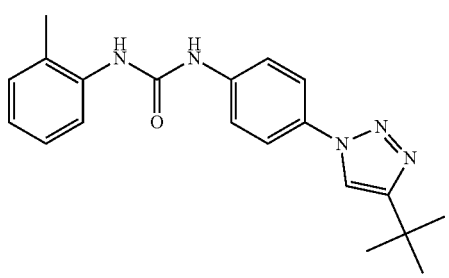
8b

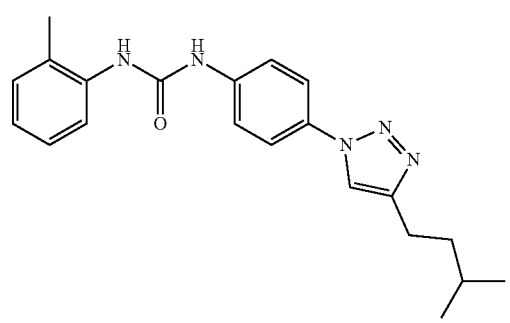
20b

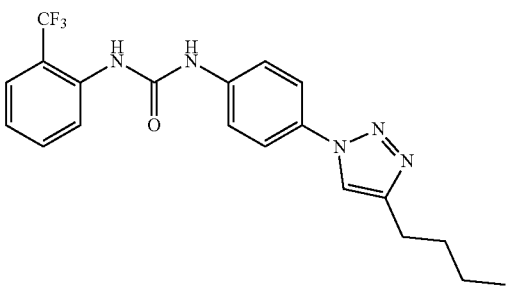
22a

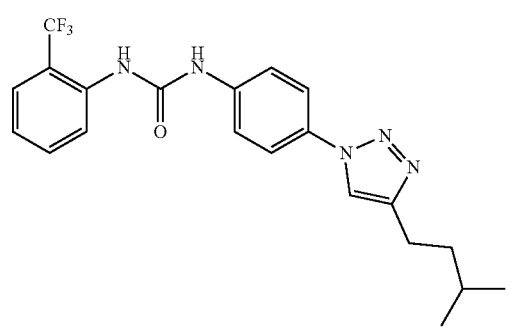
22b

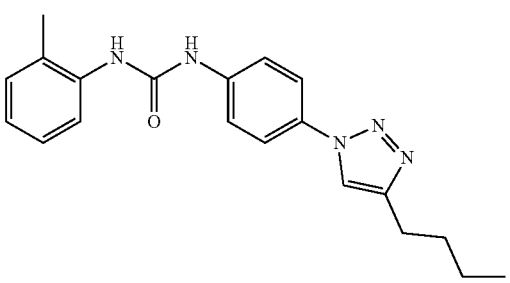
20a

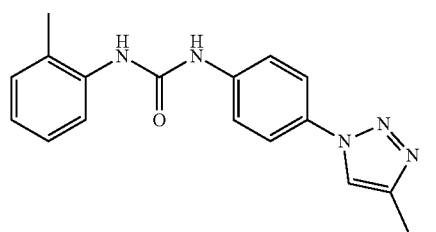
8f

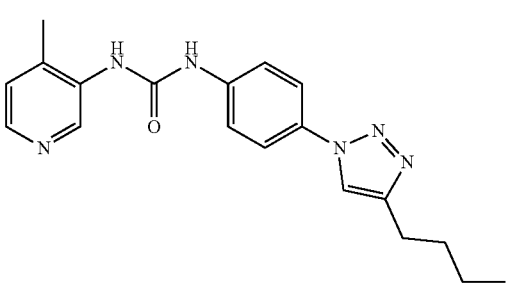
15a

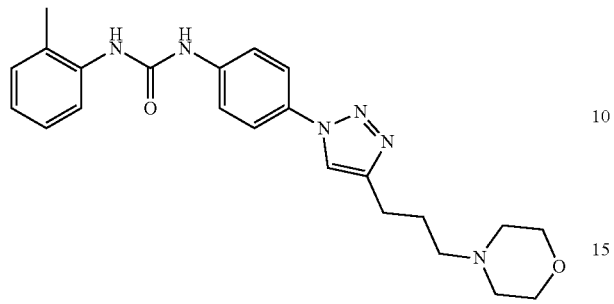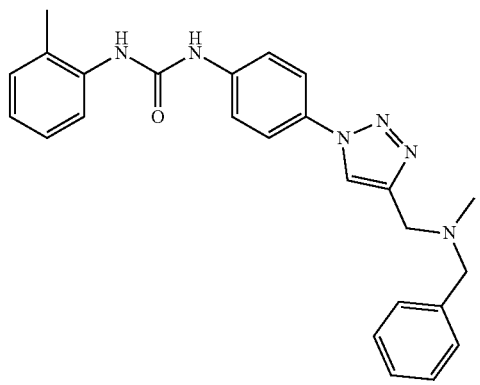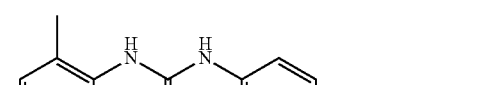

35a
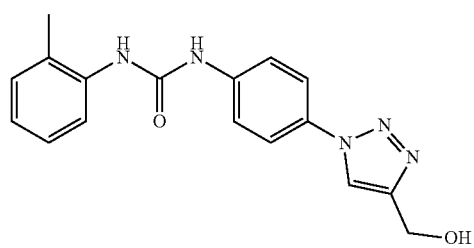
49
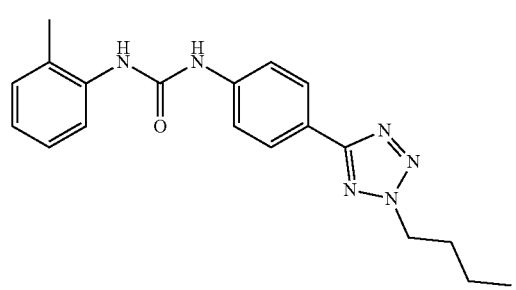
50
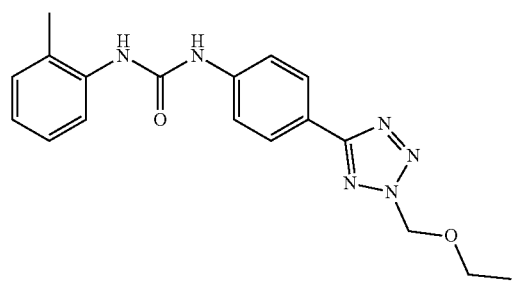
20c
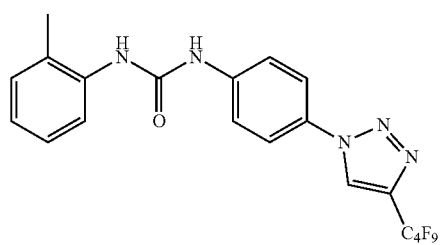
51
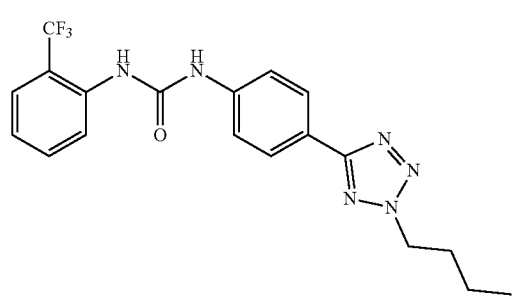
55f
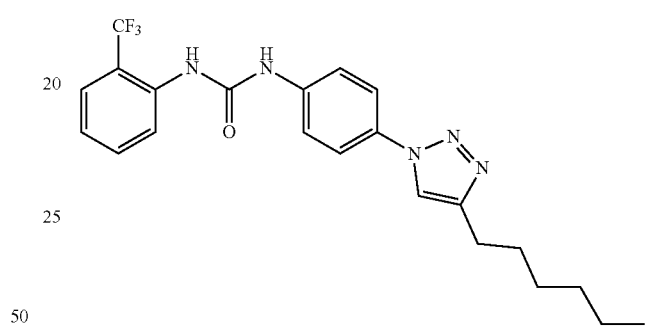
8d
86
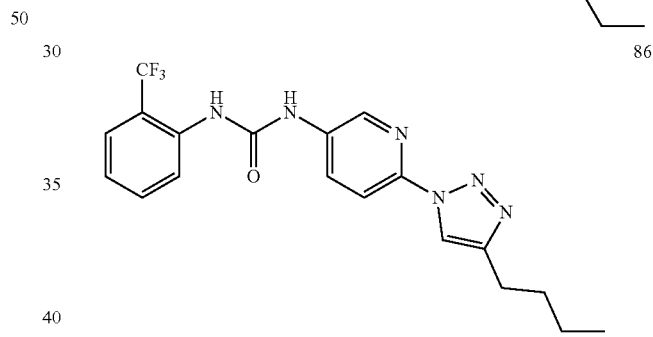
42b
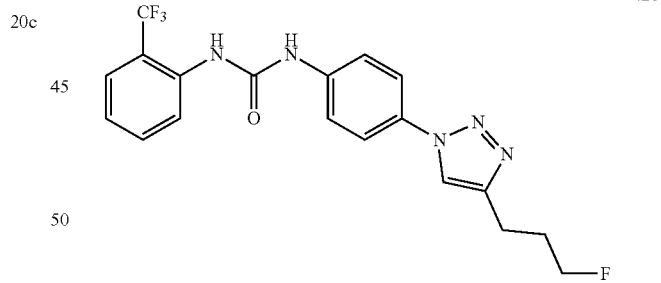
81
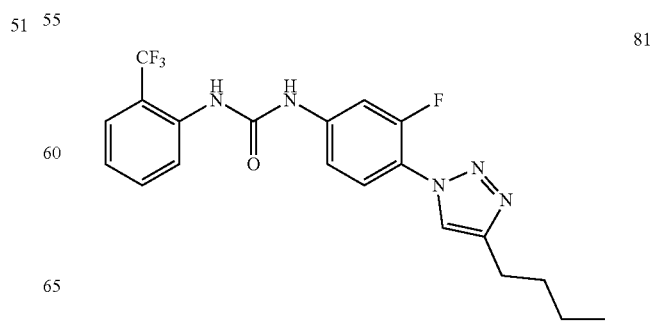

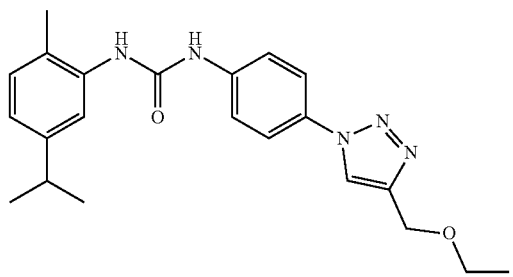
55e
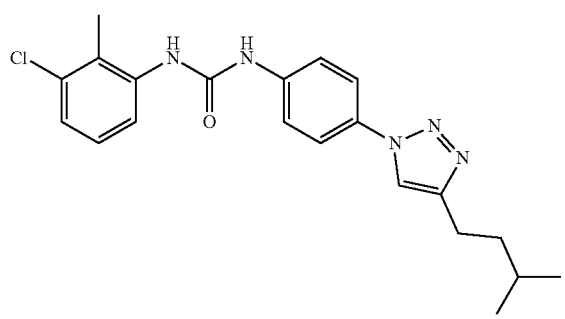
21b
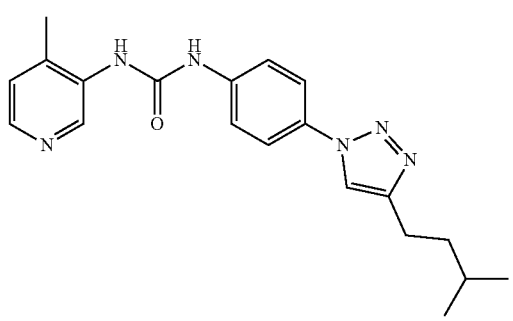
15b
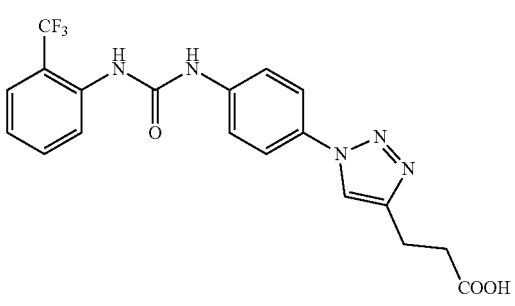
20d
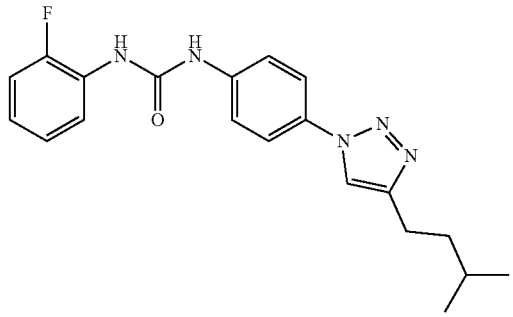
55a
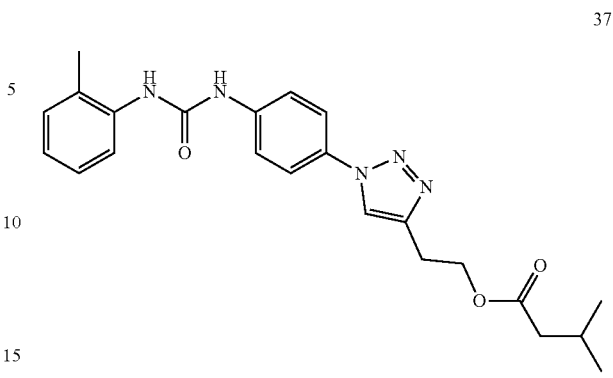
37
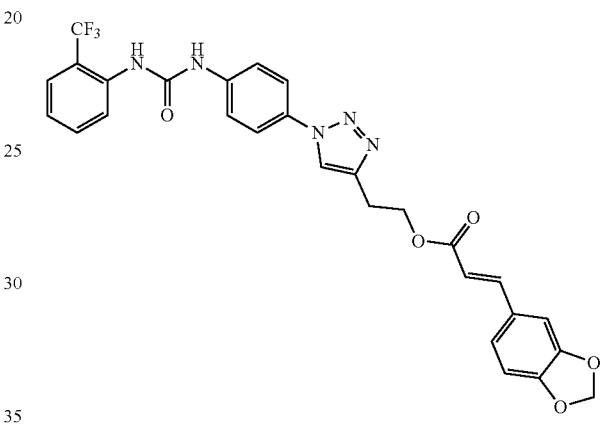
39
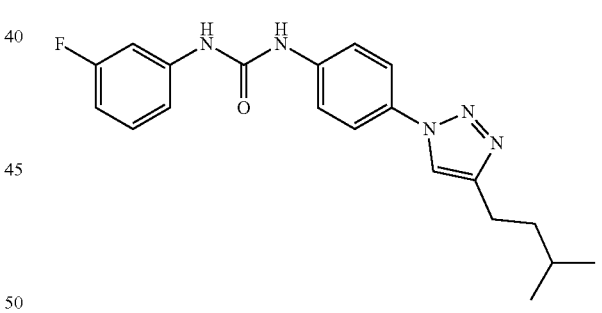
55b
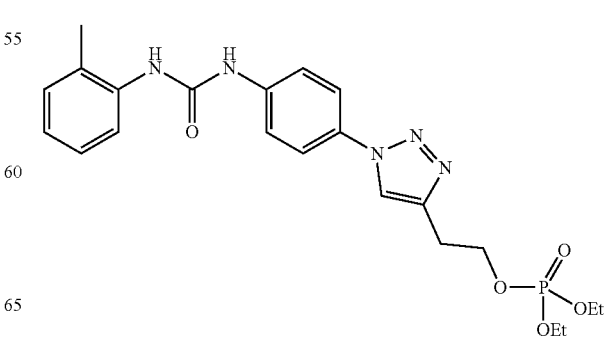
36

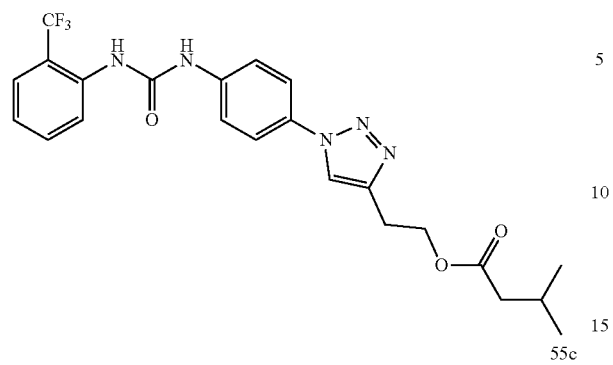
38
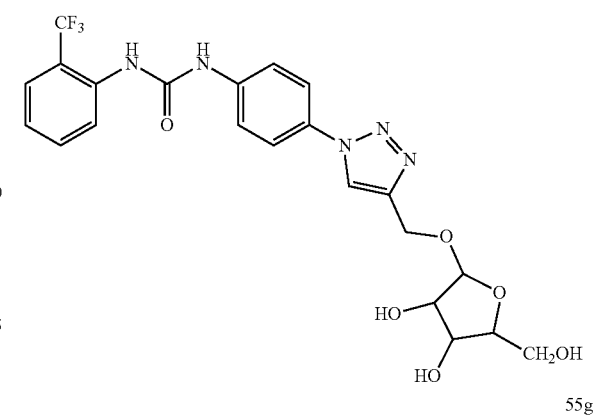
22g
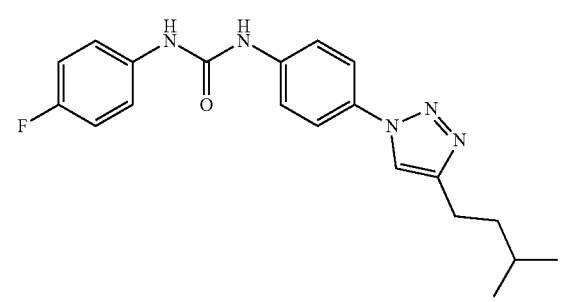
55c
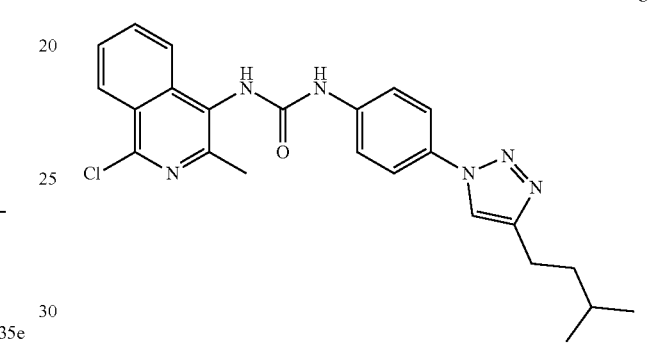
55g
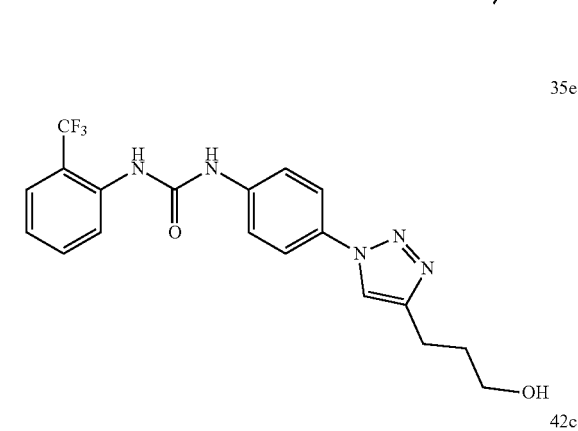
35e
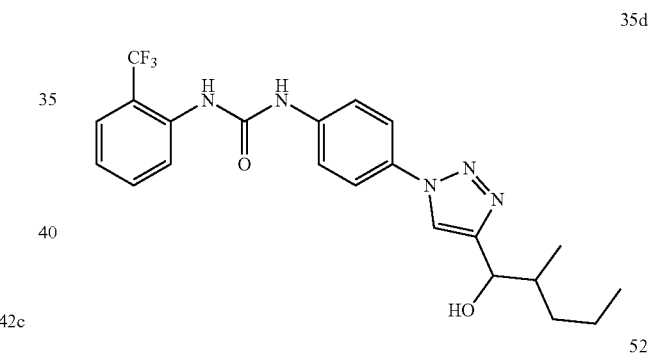
35d
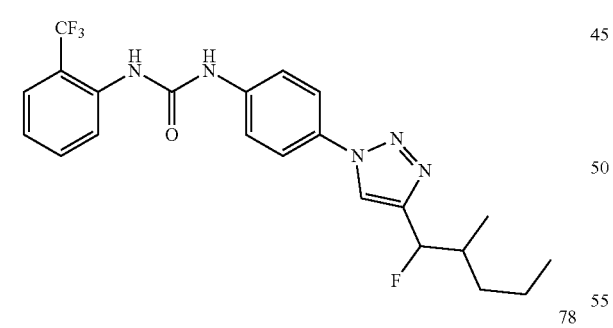
42c
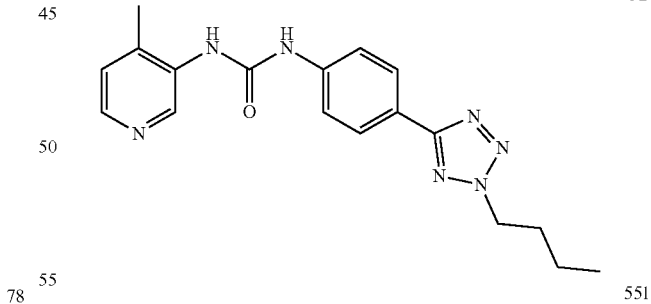
52
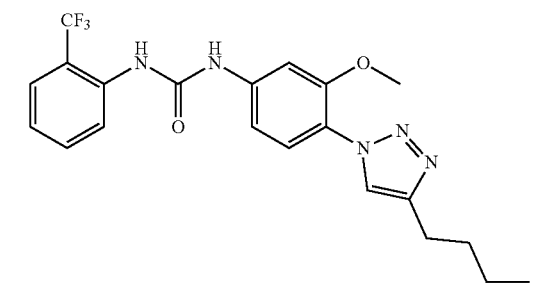
78
55l

| | |
|---|---|
| 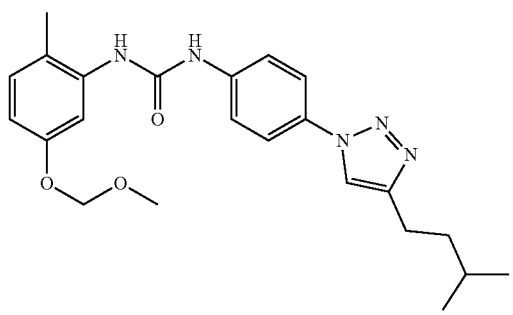 55i | 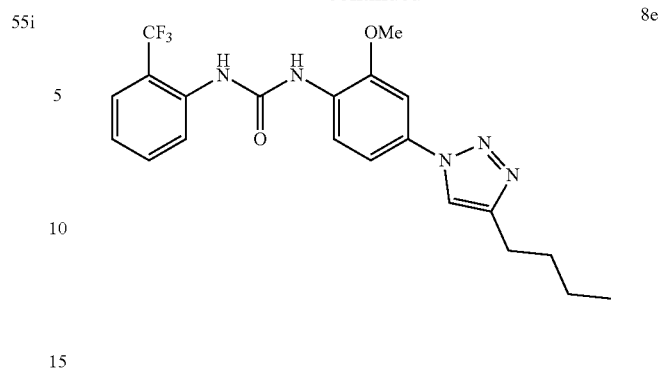 8e |
| 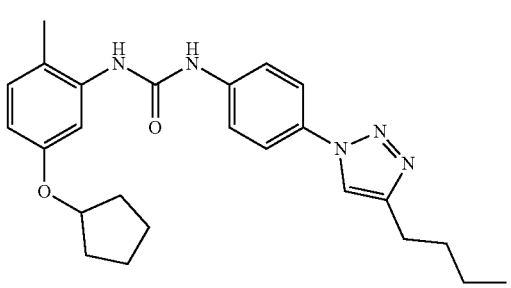 55h | 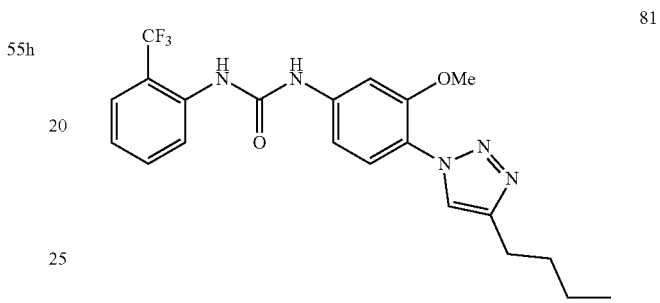 81 |
| 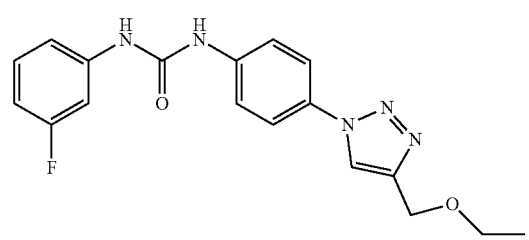 55o | 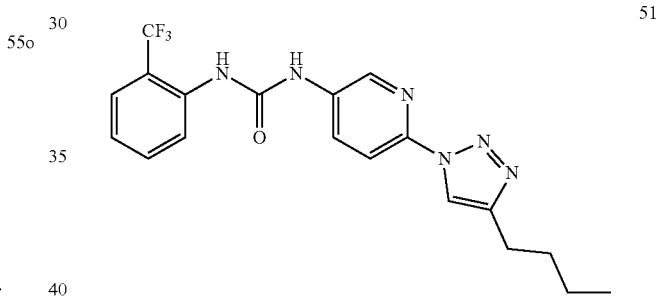 51 |
| 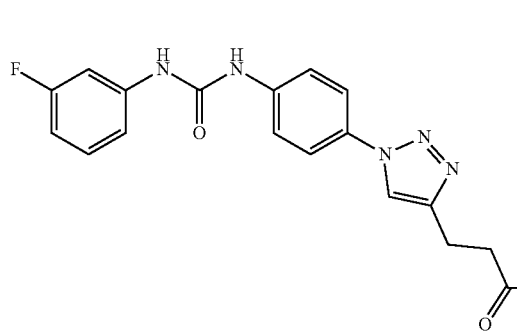 55n | 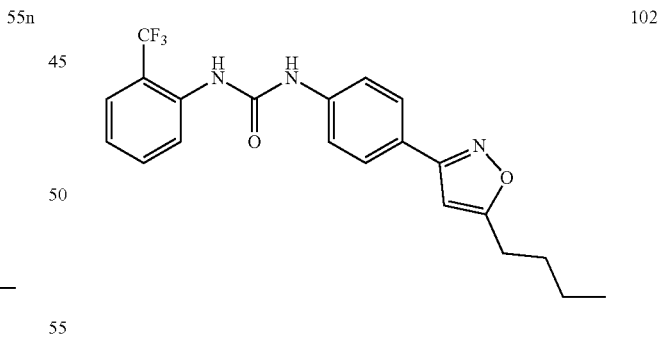 102 |
| 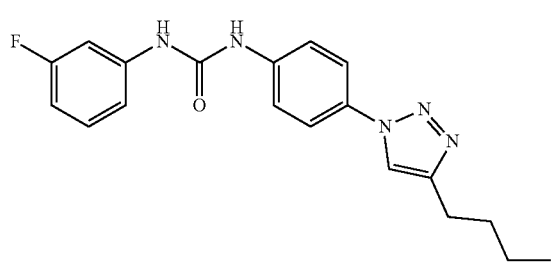 55m | 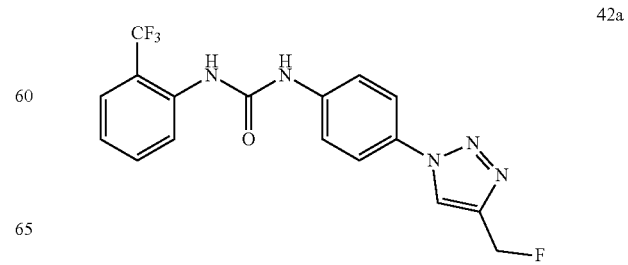 42a |

185
-continued
106
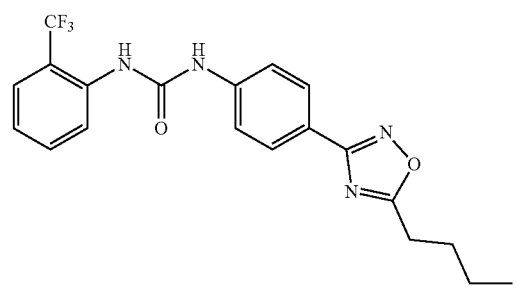
112
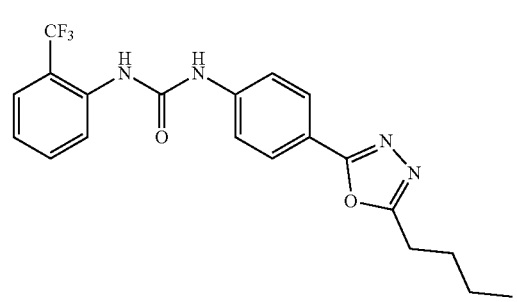
55p
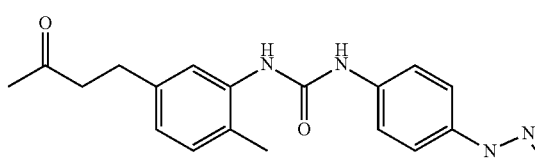
55q
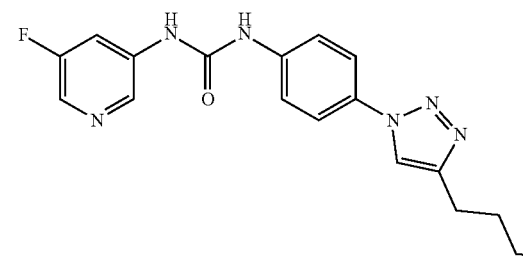
119
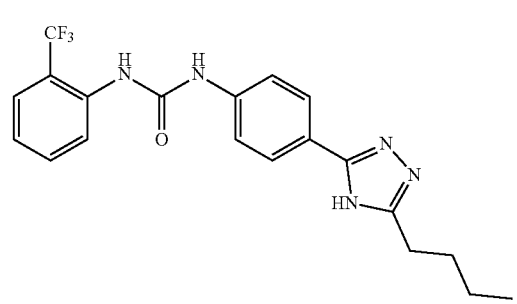
186
-continued
124
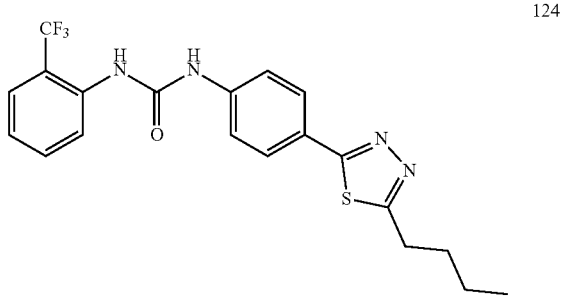
64a
64c
64d
64b
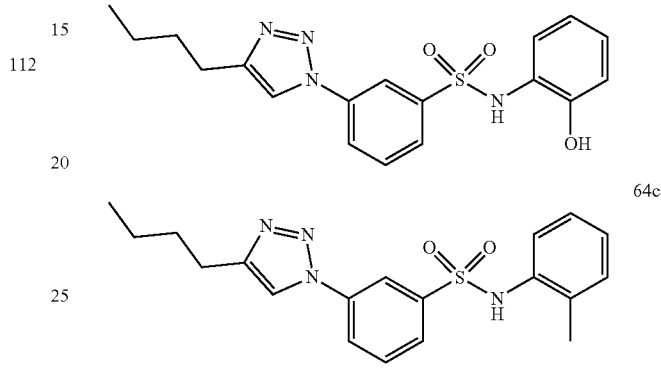
130
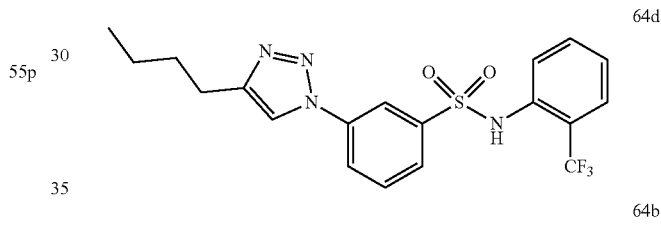
64e
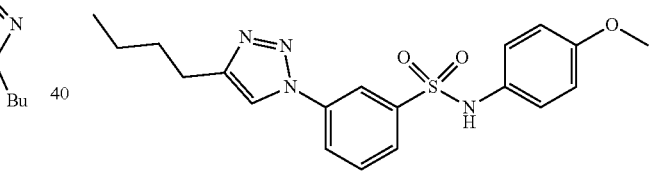
66d
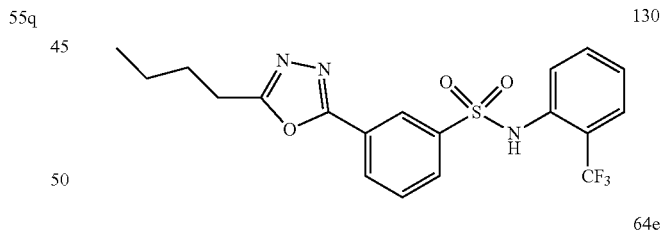

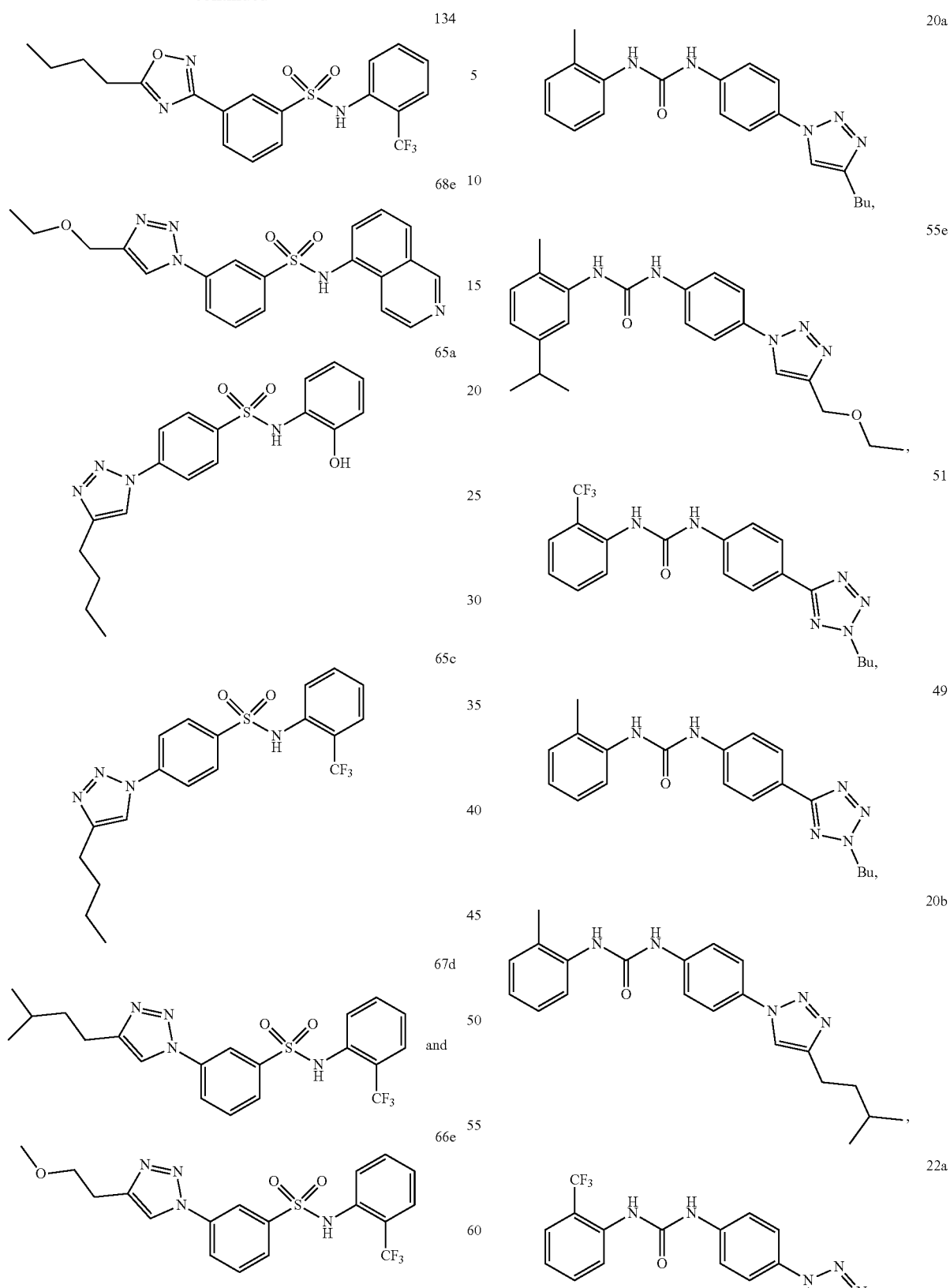
or salt, solvate, stereoisomer thereof.
2. A compound according to claim 1 selected from the group consisting of:

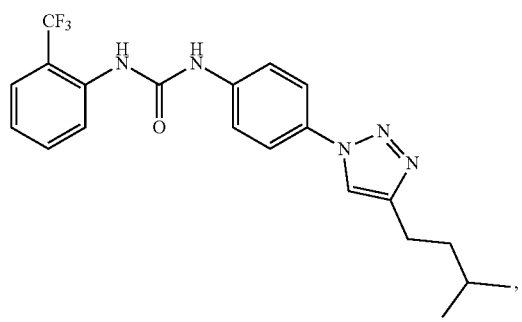

22b

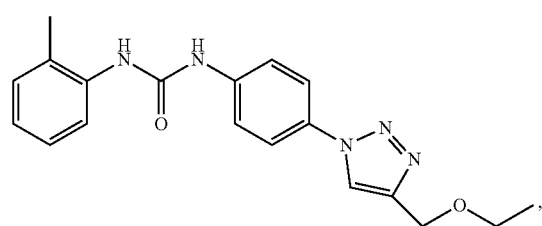

20e

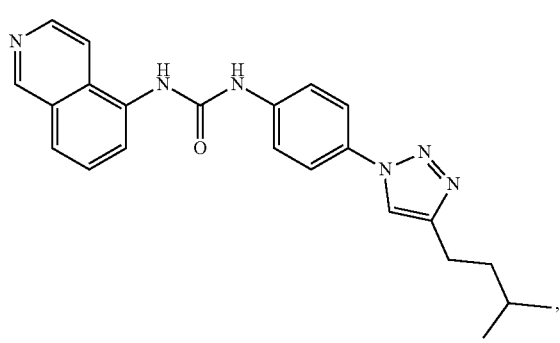

55f

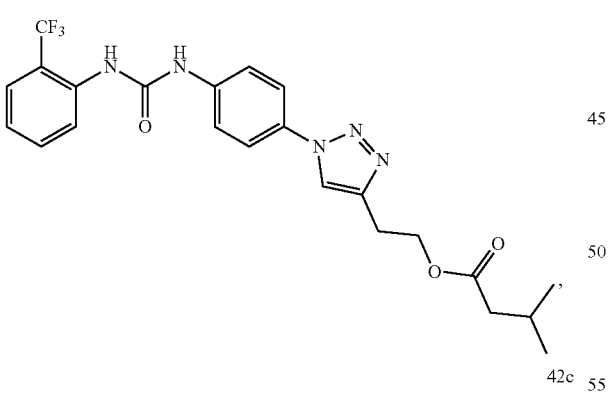

42c

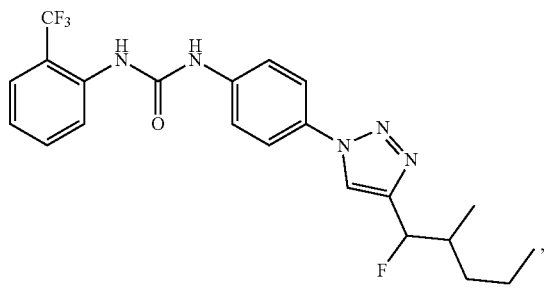

5

10

15

20

25

30

35

40

45

50

55

60

65

55a

55b

64d

66d

, and

64e or pharmaceutical acceptable salt, solvate, stereoisomer thereof.

3. A pharmaceutical composition comprising the compound according to claim 1 and a pharmaceutically acceptable excipient.

4. The pharmaceutical composition according to claim 3 further comprising at least one antiviral agent.

5. The pharmaceutical composition according to claim 4 wherein the antiviral agent is selected from the group consisting of: a nucleoside or a non-nucleoside analogue reverse-transcriptase inhibitor, a nucleotide analogue reverse-transcriptase inhibitor, a NS3/4A serine protease inhibitor, a NS5B polymerase inhibitor and interferon alpha.

6. A method for treating a viral disease comprising administering to a patient a compound or pharmaceutical acceptable salt, solvate, or stereoisomer of claim 1 to a patient in need thereof.

7. The method according to claim 6 wherein the viral disease is modulated by DDX3.

8. The method according to claim 6 wherein the viral disease is caused by a virus that is resistant to at least one compound selected from the group consisting of: protease inhibitor, nucleoside reverse transcriptase inhibitor, non-nucleoside reverse transcriptase inhibitor and integrase inhibitor.

9. The method according to claim 6 wherein the viral disease is caused by a virus selected from the group consisting of: Human Immunodeficiency Virus 1 (HIV-1), Hepatitis C Virus, Hepatitis B Virus, Eastern Equine Encephalitis Virus, Western Equine Encephalitis Virus, Venezuelan Equine Encephalitis Virus, Japanese Encephalitis Virus, Tick Borne Encephalitis Virus, Yellow Fever Virus, St. Louis Encephalitis Virus, Murray Valley Encephalitis Virus, Powassan Virus, Dengue Virus, Zika Virus, West Nile Virus, Rubella Virus, Cytomegalovirus, O'nyong'nyong Virus, Mayaro Virus, Ross River Virus, Sindbis Virus, Vaccinia Virus, Influenza Virus, Norovirus, SARS Coronavirus, Chikunguya Virus, Lassa Virus, Ebola Virus, Lujo Virus, Pneumovirus, Severe Fever With Thrombocytopenia Syndrome Virus, Porcine Reproductive And Respiratory Syndrome Virus, Poxvirus, Bovine Viral Diarrhea Virus (BVDV), Border Disease Virus (BDV) of sheep, and Classical Swine Fever Virus (CSFV).

10. The method of claim 9 wherein the virus is selected from the group consisting of: Human Immunodeficiency Virus 1 (HIV-1), Hepatitis C Virus, West Nile Virus, Dengue Virus, Japanese Encephalitis Virus, Porcine Reproductive And Respiratory Syndrome Virus, Ebola Virus, and Zika Virus.

11. The method of claim 10 wherein the virus is selected from the group consisting of: Ebola Virus and Zika Virus.

\* \* \* \* \*